US010053675B2

(12) United States Patent
Hawkes et al.

(10) Patent No.: US 10,053,675 B2
(45) Date of Patent: Aug. 21, 2018

(54) HYDROXYPHENYLPYRUVATE DIOXYGENASE POLYPEPTIDES AND METHODS OF USE

(71) Applicant: SYNGENTA PARTICIPATIONS AG, Basel (CH)

(72) Inventors: Timothy Robert Hawkes, Bracknell (GB); Michael Phillip Langford, Bracknell (GB); Russell Colin Viner, Bracknell (GB); Richard Dale, Bracknell (GB)

(73) Assignee: Syngenta Participations AG, Basel (CH)

( * ) Notice: Subject to any disclaimer, the term of this patent is extended or adjusted under 35 U.S.C. 154(b) by 221 days.

(21) Appl. No.: 15/135,692

(22) Filed: Apr. 22, 2016

(65) Prior Publication Data

US 2016/0222360 A1   Aug. 4, 2016

Related U.S. Application Data

(60) Division of application No. 12/838,387, filed on Jul. 16, 2010, now Pat. No. 9,347,046, which is a continuation-in-part of application No. 12/692,552, filed on Jan. 22, 2010, now Pat. No. 8,269,068.

(60) Provisional application No. 61/224,661, filed on Jul. 10, 2009, provisional application No. 61/146,513, filed on Jan. 22, 2009.

(51) Int. Cl.
| | |
|---|---|
| *C12N 9/02* | (2006.01) |
| *C12N 15/82* | (2006.01) |
| *C12N 15/09* | (2006.01) |
| *A01N 41/10* | (2006.01) |
| *A01N 43/40* | (2006.01) |
| *A01N 43/80* | (2006.01) |

(52) U.S. Cl.
CPC ........... *C12N 9/0069* (2013.01); *A01N 41/10* (2013.01); *A01N 43/40* (2013.01); *A01N 43/80* (2013.01); *C12N 9/0004* (2013.01); *C12N 9/0073* (2013.01); *C12N 15/09* (2013.01); *C12N 15/8274* (2013.01); *C12Y 113/11027* (2013.01)

(58) Field of Classification Search
CPC .................... C12N 9/0069; C12N 15/8274
See application file for complete search history.

(56) References Cited

U.S. PATENT DOCUMENTS

| | | | |
|---|---|---|---|
| 6,245,968 B1 | 6/2001 | Boudec et al. | |
| 7,119,255 B2 | 10/2006 | Betts et al. | |
| 7,166,770 B2 | 1/2007 | Hohn et al. | |
| 7,312,379 B2 | 12/2007 | Andrews et al. | |
| 2003/0041357 A1 | 2/2003 | Jepson et al. | |
| 2003/0200560 A1 | 10/2003 | Warner et al. | |
| 2004/0034889 A1 | 2/2004 | Khan et al. | |
| 2005/0246800 A1 | 11/2005 | Dunne et al. | |
| 2008/0076178 A1 | 3/2008 | Andrews et al. | |
| 2008/0146447 A1 | 6/2008 | Andrews et al. | |
| 2009/0011936 A1 | 1/2009 | Hawkes et al. | |
| 2009/0031442 A1 | 1/2009 | Andrews et al. | |
| 2009/0055976 A1 | 2/2009 | Andrews et al. | |
| 2009/0172831 A1 | 7/2009 | Andrews et al. | |
| 2009/0229006 A1 | 9/2009 | Jepson et al. | |

FOREIGN PATENT DOCUMENTS

| | | |
|---|---|---|
| WO | 1997049816 | 12/1997 |
| WO | 1998004685 | 2/1998 |
| WO | 1998020144 | 5/1998 |
| WO | 1999004021 | 1/1999 |
| WO | 2000032757 | 6/2000 |
| WO | 2002046387 | 6/2002 |
| WO | 2008150473 | 12/2008 |
| WO | 2009144079 | 12/2009 |

OTHER PUBLICATIONS

GenBank Accession XP_001614243, available online Aug. 16, 2007 (Year: 2007).*
Fritze et al., Plant Physiol., Apr. 2004, 134, 1388-1400.
International Search Report dated Aug. 30, 2010, issued in corresponding International Application No. PCT/US2010/021879.
NCBI Reference Sequence YP_004495319.1, first available online May 24, 2011.
NCBI Reference Sequence WP_003610392, first available online May 7, 2013.
NCBI Reference Sequence EFN83434.1, first available online Sep. 17, 2010.
NCBI Reference Sequence WP_005993660.1, first available online May 8, 2013.
NCBI Reference Sequence NP_600992.1, first available online Mar. 20, 2002.
NCBI Reference Sequence XP_001614243, first available online Aug. 16, 2007.
NCBI Reference Sequence EAZ00184.1, first available online Feb. 9, 2007.
NCBI Reference Sequence NP_607535.1, first available online Mar. 27, 2002.

(Continued)

*Primary Examiner* — Lee A Visone
(74) *Attorney, Agent, or Firm* — S. Matthew Edwards

(57) ABSTRACT

Novel hydroxyphenyl pyruvate dioxygenase (HPPD) polypeptides, variants and fragments thereof, as well as polynucleotides encoding the same, capable of conferring commercial levels of conferring HPPD herbicide resistance or tolerance to plants. Compositions include amino acid sequences, and variants and fragments thereof, for HPPD polypeptides, as well as polynucleotides encoding the same. Methods for the production and use of HPPD herbicide resistant plants that express these novel HPPD polypeptides, methods for selectively controlling weeds in a field at a crop locus, and methods for the assay, characterization, identification and selection of these novel HPPDs are also provided.

28 Claims, 4 Drawing Sheets

(56) References Cited

OTHER PUBLICATIONS

NCBI Reference Sequence BAC65397.1, first available online Mar. 15, 2003.
NCBI Reference Sequence ACJ84488.1, first available online Dec. 10, 2008.

* cited by examiner

SEQUENCE LISTING

```
<160> NUMBER OF SEQ ID NOS: 88

<210> SEQ ID NO 1
<211> LENGTH: 439
<212> TYPE: PRT
<213> ORGANISM: Avena sativa

<400> SEQUENCE: 1

Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
            20                  25                  30

Pro Arg Ser Asp Arg Phe Pro Val Leu Ser Phe His His Val Glu Leu
        35                  40                  45

Trp Cys Ala Asp Ala Ala Ser Ala Ala Gly Arg Phe Ser Phe Ala Leu
    50                  55                  60

Gly Ala Pro Leu Ala Ala Arg Ser Asp Leu Ser Thr Gly Asn Ser Ala
```

```
                65                  70                  75                  80
His Ala Ser Leu Leu Arg Ser Gly Ala Leu Ala Phe Leu Phe Thr
                    85                  90                  95

Ala Pro Tyr Ala Pro Pro Gln Glu Ala Thr Ala Ala Thr Ala
            100                 105                 110

Ser Ile Pro Ser Phe Ser Ala Asp Ala Ala Arg Thr Phe Ala Ala Ala
            115                 120                 125

His Gly Leu Ala Val Arg Ser Val Gly Val Arg Val Ala Asp Ala Ala
    130                 135                 140

Glu Ala Phe Arg Val Ser Val Ala Gly Ala Arg Pro Ala Phe Ala
145                 150                 155                 160

Pro Ala Asp Leu Gly His Gly Phe Gly Leu Ala Glu Val Glu Leu Tyr
                    165                 170                 175

Gly Asp Val Val Leu Arg Phe Val Ser Tyr Pro Asp Glu Thr Asp Leu
                180                 185                 190

Pro Phe Leu Pro Gly Phe Glu Arg Val Ser Ser Pro Gly Ala Val Asp
            195                 200                 205

Tyr Gly Leu Thr Arg Phe Asp His Val Val Gly Asn Val Pro Glu Met
        210                 215                 220

Ala Pro Val Ile Asp Tyr Met Lys Gly Phe Leu Gly Phe His Glu Phe
225                 230                 235                 240

Ala Glu Phe Thr Ala Glu Asp Val Gly Thr Thr Glu Ser Gly Leu Asn
                    245                 250                 255

Ser Val Val Leu Ala Asn Asn Ser Glu Ala Val Leu Leu Pro Leu Asn
                260                 265                 270

Glu Pro Val His Gly Thr Lys Arg Arg Ser Gln Ile Gln Thr Tyr Leu
            275                 280                 285

Glu Tyr His Gly Gly Pro Gly Val Gln His Ile Ala Leu Ala Ser Asn
        290                 295                 300

Asp Val Leu Arg Thr Leu Arg Glu Met Arg Ala Arg Thr Pro Met Gly
305                 310                 315                 320

Gly Phe Glu Phe Met Ala Pro Pro Gln Ala Lys Tyr Tyr Glu Gly Val
                    325                 330                 335

Arg Arg Ile Ala Gly Asp Val Leu Ser Glu Glu Gln Ile Lys Glu Cys
                340                 345                 350

Gln Glu Leu Gly Val Leu Val Asp Arg Asp Gln Gly Val Leu Leu
            355                 360                 365

Gln Ile Phe Thr Lys Pro Val Gly Asp Arg Pro Thr Phe Phe Leu Glu
        370                 375                 380

Met Ile Gln Arg Ile Gly Cys Met Glu Lys Asp Glu Val Gly Gln Glu
385                 390                 395                 400

Tyr Gln Lys Gly Gly Cys Gly Gly Phe Gly Lys Gly Asn Phe Ser Glu
                    405                 410                 415

Leu Phe Lys Ser Ile Glu Asp Tyr Glu Lys Ser Leu Glu Val Lys Gln
                420                 425                 430

Ser Val Val Ala Gln Lys Ser
            435

<210> SEQ ID NO 2
<211> LENGTH: 441
<212> TYPE: PRT
<213> ORGANISM: Alopecurus mycosuroides

<400> SEQUENCE: 2
```

```
Met Pro Pro Thr Thr Ala Thr Ala Thr Gly Ala Ala Ala Ala Val
1               5                   10                  15

Thr Pro Glu His Ala Ala Arg Arg Phe Pro Arg Val Val Arg Val Asn
            20                  25                  30

Pro Arg Ser Asp Arg Phe Pro Val Leu Ala Phe His His Val Glu Phe
            35                  40                  45

Trp Cys Ala Asp Ala Ala Ser Ala Ala Gly Arg Phe Ser Phe Ala Leu
    50                  55                  60

Gly Ala Pro Leu Ala Ala Arg Ser Asp Leu Ser Thr Gly Asn Ser Ser
65                  70                  75                  80

His Ala Ser His Leu Leu Arg Ser Gly Ala Leu Ala Phe Leu Phe Thr
                85                  90                  95

Ala Pro Tyr Ala Pro Pro Gln Asp Ala Ala Asp Ala Ala Ala Thr
                100                 105                 110

Ala Ser Ile Pro Ser Phe Ser Thr Glu Ala Ala Arg Thr Phe Ser Ser
            115                 120                 125

Ala His Gly Leu Ala Val Arg Ser Val Ala Ile Arg Val Ala Asp Ala
    130                 135                 140

Ala Glu Ala Phe His Thr Ser Val Ala Gly Gly Ala Arg Pro Ala Phe
145                 150                 155                 160

Ala Pro Ala Asp Leu Gly Ser Gly Phe Gly Leu Ala Glu Val Glu Leu
                165                 170                 175

Tyr Gly Asp Val Val Leu Arg Phe Val Ser His Pro Asp Gly Asp Asp
                180                 185                 190

Val Pro Phe Leu Pro Gly Phe Glu Gly Val Ser Arg Pro Gly Ala Met
            195                 200                 205

Asp Tyr Gly Leu Thr Arg Phe Asp His Val Val Gly Asn Val Pro Glu
    210                 215                 220

Met Ala Pro Val Ala Ala Tyr Met Lys Gly Phe Thr Gly Phe His Glu
225                 230                 235                 240

Phe Ala Glu Phe Thr Ala Glu Asp Val Gly Thr Ala Glu Ser Gly Leu
                245                 250                 255

Asn Ser Val Val Leu Ala Asn Asn Ser Glu Ala Val Leu Leu Pro Leu
            260                 265                 270

Asn Glu Pro Val His Gly Thr Lys Arg Arg Ser Gln Ile Gln Thr Tyr
    275                 280                 285

Leu Asp Tyr His Gly Gly Pro Gly Val Gln His Ile Ala Leu Ala Ser
    290                 295                 300

Ser Asp Val Leu Arg Thr Leu Arg Glu Met Arg Ala Arg Ser Ala Met
305                 310                 315                 320

Gly Gly Phe Glu Phe Met Ala Pro Pro Gln Ala Lys Tyr Tyr Glu Gly
                325                 330                 335

Val Arg Arg Leu Ala Gly Asp Val Leu Ser Glu Ala Gln Ile Lys Glu
            340                 345                 350

Cys Gln Glu Leu Gly Val Leu Val Asp Arg Asp Gln Gly Val Leu
            355                 360                 365

Leu Gln Ile Phe Thr Lys Pro Val Gly Asp Arg Pro Thr Phe Phe
370                 375                 380

Leu Glu Met Ile Gln Arg Ile Gly Cys Met Glu Lys Asp Glu Ile Gly
385                 390                 395                 400

Gln Glu Tyr Gln Lys Gly Gly Cys Gly Gly Phe Gly Lys Gly Asn Phe
                405                 410                 415

Ser Glu Leu Phe Lys Ser Ile Glu Asp Tyr Glu Lys Ser Leu Glu Ala
```

420                 425                 430

Lys Gln Ser Ala Val Ala Gln Gln Ser
            435                 440

<210> SEQ ID NO 3
<211> LENGTH: 440
<212> TYPE: PRT
<213> ORGANISM: Alopecurus mycosuroides

<400> SEQUENCE: 3

Met Pro Pro Thr Thr Ala Thr Ala Thr Gly Ala Ala Ala Ala Ala Val
1               5                   10                  15

Thr Pro Glu His Ala Ala Arg Arg Phe Pro Arg Val Val Arg Val Asn
                20                  25                  30

Pro Arg Ser Asp Arg Phe Pro Val Leu Ala Phe His His Val Glu Phe
            35                  40                  45

Trp Cys Ala Asp Ala Ala Ser Ala Ala Gly Arg Phe Ser Phe Ala Leu
    50                  55                  60

Gly Ala Pro Leu Ala Ala Arg Ser Asp Leu Ser Thr Gly Asn Ser Ser
65                  70                  75                  80

His Ala Ser His Leu Leu Arg Ser Gly Ala Leu Ala Phe Leu Phe Thr
                85                  90                  95

Ala Pro Tyr Ala Pro Pro Gln Asp Ala Ala Asp Ala Ala Ala Thr
            100                 105                 110

Ala Ser Ile Pro Ser Phe Ser Thr Glu Ala Ala Arg Thr Phe Ser Ser
        115                 120                 125

Ala His Gly Leu Ala Val Arg Ser Val Ala Ile Arg Val Ala Asp Ala
130                 135                 140

Ala Glu Ala Phe His Thr Ser Val Ala Gly Gly Ala Arg Pro Ala Phe
145                 150                 155                 160

Ala Pro Ala Asp Leu Gly Ser Gly Phe Gly Leu Ala Glu Val Glu Leu
                165                 170                 175

Tyr Gly Asp Val Val Leu Arg Phe Val Ser His Pro Asp Gly Asp Asp
            180                 185                 190

Val Pro Phe Leu Pro Gly Phe Glu Gly Val Ser Arg Pro Gly Ala Met
        195                 200                 205

Asp Tyr Gly Leu Thr Arg Phe Asp His Val Val Gly Asn Val Pro Glu
    210                 215                 220

Met Ala Pro Val Ala Ala Tyr Met Lys Gly Phe Thr Gly Phe His Glu
225                 230                 235                 240

Phe Ala Glu Phe Thr Ala Glu Asp Val Gly Thr Ala Glu Ser Gly Leu
                245                 250                 255

Asn Ser Val Val Leu Ala Asn Asn Ser Glu Ala Val Leu Leu Pro Leu
            260                 265                 270

Asn Glu Pro Val His Gly Thr Lys Arg Arg Ser Gln Ile Gln Thr Tyr
        275                 280                 285

Leu Asp Tyr His Gly Gly Pro Gly Val Gln His Ile Ala Leu Ala Ser
    290                 295                 300

Ser Asp Val Leu Arg Thr Leu Arg Glu Met Arg Ala Arg Ser Ala Met
305                 310                 315                 320

Gly Gly Phe Glu Phe Met Ala Pro Pro Gln Ala Lys Tyr Tyr Glu Gly
                325                 330                 335

Val Arg Arg Leu Ala Gly Asp Val Leu Ser Glu Ala Gln Ile Lys Glu
            340                 345                 350

```
Cys Gln Glu Leu Gly Val Leu Val Asp Arg Asp Gln Gly Val Leu
            355                 360                 365

Leu Gln Ile Phe Thr Lys Pro Val Gly Asp Arg Pro Thr Phe Phe Leu
        370                 375                 380

Glu Met Ile Gln Arg Ile Gly Cys Met Glu Lys Asp Glu Ile Gly Gln
385                 390                 395                 400

Glu Tyr Gln Lys Gly Gly Cys Gly Gly Phe Gly Lys Gly Asn Phe Ser
            405                 410                 415

Glu Leu Phe Lys Ser Ile Glu Asp Tyr Glu Lys Ser Leu Glu Ala Lys
        420                 425                 430

Gln Ser Ala Val Ala Gln Gln Ser
            435                 440

<210> SEQ ID NO 4
<211> LENGTH: 440
<212> TYPE: PRT
<213> ORGANISM: Sorghum halepense

<400> SEQUENCE: 4

Met Pro Pro Thr Pro Thr Thr Ala Ala Ala Thr Gly Ala Ala Val Ala
1               5                   10                  15

Ala Ala Ser Ala Glu Gln Ala Ala Phe Arg Leu Val Gly His Arg Asn
            20                  25                  30

Phe Val Arg Val Asn Pro Arg Ser Asp Arg Phe His Thr Leu Ala Phe
        35                  40                  45

His His Val Glu Leu Trp Cys Ala Asp Ala Ala Ser Ala Ala Gly Arg
    50                  55                  60

Phe Ser Phe Gly Leu Gly Ala Pro Leu Ala Ala Arg Ser Asp Leu Ser
65                  70                  75                  80

Thr Gly Asn Thr Ala His Ala Ser Leu Leu Leu Arg Ser Gly Ala Leu
                85                  90                  95

Ala Phe Leu Phe Thr Ala Pro Tyr Ala His Gly Ala Asp Ala Ala Thr
            100                 105                 110

Ala Ser Leu Pro Ser Phe Ser Ala Ala Glu Ala Arg Arg Phe Ala Ala
        115                 120                 125

Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Pro Ala Phe
145                 150                 155                 160

Glu Pro Val Glu Leu Gly Leu Gly Phe Arg Leu Ala Glu Val Glu Leu
                165                 170                 175

Tyr Gly Asp Val Val Leu Arg Tyr Val Ser Tyr Pro Asp Asp Ala Asp
            180                 185                 190

Ala Ser Phe Leu Pro Gly Phe Val Gly Val Ser Ser Pro Gly Ala Ala
        195                 200                 205

Asp Tyr Gly Leu Arg Arg Phe Asp His Ile Val Gly Asn Val Pro Glu
    210                 215                 220

Leu Ala Pro Ala Ala Tyr Phe Ala Gly Phe Thr Gly Phe His Glu
225                 230                 235                 240

Phe Ala Glu Phe Thr Ala Glu Asp Val Gly Thr Thr Glu Ser Gly Leu
                245                 250                 255

Asn Ser Met Val Leu Ala Asn Asn Ala Glu Asn Val Leu Leu Pro Leu
            260                 265                 270

Asn Glu Pro Val His Gly Thr Lys Arg Arg Ser Gln Ile Gln Thr Phe
        275                 280                 285
```

```
Leu Asp His His Gly Gly Pro Gly Val Gln His Met Ala Leu Ala Ser
    290                 295                 300

Asp Asp Val Leu Arg Thr Leu Arg Glu Met Gln Ala Cys Ser Ala Met
305                 310                 315                 320

Gly Gly Phe Glu Phe Met Ala Pro Pro Ala Pro Glu Tyr Tyr Asp Gly
                325                 330                 335

Val Arg Arg Arg Ala Gly Asp Val Leu Thr Glu Ala Gln Ile Lys Glu
                340                 345                 350

Cys Gln Glu Leu Gly Val Leu Val Asp Arg Asp Gln Gly Val Leu
                355                 360                 365

Leu Gln Ile Phe Thr Lys Pro Val Gly Asp Arg Pro Thr Phe Phe Leu
    370                 375                 380

Glu Ile Ile Gln Arg Ile Gly Cys Met Glu Lys Asp Glu Lys Gly Gln
385                 390                 395                 400

Glu Tyr Gln Lys Gly Gly Cys Gly Gly Phe Gly Lys Gly Asn Phe Ser
                405                 410                 415

Gln Leu Phe Lys Ser Ile Glu Asp Tyr Glu Lys Ser Leu Glu Ala Lys
                420                 425                 430

Gln Ala Ala Ala Gln Gly Pro
    435                 440

<210> SEQ ID NO 5
<211> LENGTH: 453
<212> TYPE: PRT
<213> ORGANISM: Sorghum halepense

<400> SEQUENCE: 5

Met Pro Pro Thr Pro Thr Thr Ala Ala Ala Thr Gly Ala Ala Val Ala
1               5                   10                  15

Ala Ala Ser Ala Glu Gln Ala Ala Phe Arg Leu Val Gly His Arg Asn
                20                  25                  30

Phe Val Arg Val Asn Pro Arg Ser Asp Arg Phe His Thr Leu Ala Phe
            35                  40                  45

His His Val Glu Leu Trp Cys Ala Asp Ala Ala Ser Ala Ala Gly Arg
        50                  55                  60

Phe Ser Phe Gly Leu Gly Ala Pro Leu Ala Ala Arg Ser Asp Leu Ser
65                  70                  75                  80

Thr Gly Asn Thr Ala His Ala Ser Leu Leu Leu Arg Ser Gly Ala Leu
                85                  90                  95

Ala Phe Leu Phe Thr Ala Pro Tyr Ala His Gly Ala Asp Ala Ala Thr
            100                 105                 110

Ala Ser Leu Pro Ser Phe Ser Ala Ala Glu Ala Arg Arg Phe Ala Ala
        115                 120                 125

Asp His Gly Leu Ala Val Arg Ala Val Ala Leu Arg Val Ala Asp Ala
    130                 135                 140

Glu Asp Ala Phe Arg Ala Ser Val Ala Ala Gly Ala Arg Pro Ala Phe
145                 150                 155                 160

Glu Pro Val Glu Leu Gly Leu Gly Phe Arg Leu Ala Glu Val Glu Leu
                165                 170                 175

Tyr Gly Asp Val Val Leu Arg Tyr Val Ser Tyr Pro Thr Thr Arg Thr
            180                 185                 190

Arg Pro Ser Cys Arg Gly Ser Trp Ala Asp Asp Ala Asp Ala Ser Phe
        195                 200                 205

Leu Pro Gly Phe Val Gly Val Thr Ser Pro Gly Ala Ala Asp Tyr Gly
```

```
                  210                 215                 220
Leu Lys Arg Phe Asp His Ile Val Gly Asn Val Pro Glu Leu Ala Pro
225                 230                 235                 240

Ala Ala Ala Tyr Phe Ala Gly Phe Thr Gly Phe His Glu Phe Ala Glu
                245                 250                 255

Phe Thr Ala Glu Asp Val Gly Thr Thr Glu Ser Gly Leu Asn Ser Met
                260                 265                 270

Val Leu Ala Asn Asn Ala Glu Asn Val Leu Pro Leu Asn Glu Pro
                275                 280                 285

Val His Gly Thr Lys Arg Arg Ser Gln Ile Gln Thr Phe Leu Asp His
                290                 295                 300

His Gly Gly Pro Gly Val Gln His Met Ala Leu Ala Ser Asp Asp Val
305                 310                 315                 320

Leu Arg Thr Leu Arg Glu Met Gln Ala Arg Ser Ala Met Gly Gly Phe
                325                 330                 335

Glu Phe Met Ala Pro Pro Ala Pro Glu Tyr Tyr Asp Gly Val Arg Arg
                340                 345                 350

Arg Ala Gly Asp Val Leu Thr Glu Ala Gln Ile Lys Glu Cys Gln Glu
                355                 360                 365

Leu Gly Val Leu Val Asp Arg Asp Gln Gly Val Leu Leu Gln Ile
                370                 375                 380

Phe Thr Lys Pro Val Gly Asp Arg Pro Thr Phe Phe Leu Glu Ile Ile
385                 390                 395                 400

Gln Arg Ile Gly Cys Met Glu Lys Asp Glu Lys Gly Gln Glu Tyr Gln
                405                 410                 415

Lys Gly Gly Cys Gly Gly Phe Gly Lys Gly Asn Phe Ser Gln Leu Phe
                420                 425                 430

Lys Ser Ile Glu Asp Tyr Glu Lys Ser Leu Glu Ala Lys Gln Ala Ala
                435                 440                 445

Ala Ala Gln Gly Pro
                450

<210> SEQ ID NO 6
<211> LENGTH: 436
<212> TYPE: PRT
<213> ORGANISM: Poa annua

<400> SEQUENCE: 6

Met Pro Pro Thr Thr Ala Thr Ala Thr Ala Ala Ala Thr Val Thr Pro
1               5                   10                  15

Glu His Ala Ala Arg Arg Phe Pro Arg Val Val Arg Val Asn Pro Arg
                20                  25                  30

Ser Asp Arg Phe Pro Val Leu Ser Phe His His Val Glu Phe Trp Cys
                35                  40                  45

Ala Asp Ala Ala Ser Ala Ala Gly Arg Phe Ser Phe Ala Leu Gly Ala
                50                  55                  60

Pro Leu Ala Ala Arg Ser Asp Leu Ser Thr Gly Asn Ser Ala His Ala
65                  70                  75                  80

Ser Leu Leu Leu Arg Ser Gly Ala Leu Ala Phe Leu Phe Thr Ala Pro
                85                  90                  95

Tyr Ala Pro Gln Pro Gln Asp Ala Asp Thr Ala Ser Ile Pro Ser Phe
                100                 105                 110

Ser Ala Asp Ala Ala Arg Ala Phe Ser Ala Ala His Gly Leu Ala Val
                115                 120                 125
```

Arg Ser Val Ala Val Arg Val Ala Asp Ala Ala Asp Ala Phe Arg Ala
        130                 135                 140

Ser Ile Ala Ala Gly Ala Arg Pro Ala Phe Ala Pro Ala Asp Leu Gly
145                 150                 155                 160

Arg Gly Phe Gly Leu Ala Glu Val Glu Leu Tyr Gly Asp Val Val Leu
                165                 170                 175

Arg Phe Val Ser His Pro Asp Ala Asp Asp Ala Pro Pro Phe Leu Pro
                180                 185                 190

Gly Phe Glu Ala Val Ser Arg Arg Pro Gly Ala Val Asp Tyr Gly Leu
            195                 200                 205

Thr Arg Phe Asp His Val Val Gly Asn Val Pro Glu Met Gly Pro Val
210                 215                 220

Ile Asp Tyr Ile Lys Gly Phe Met Gly Phe His Glu Phe Ala Glu Phe
225                 230                 235                 240

Thr Ala Glu Asp Val Gly Thr Thr Glu Ser Gly Leu Asn Ser Val Val
                245                 250                 255

Leu Ala Asn Asn Ser Glu Ala Val Leu Leu Pro Leu Asn Glu Pro Val
                260                 265                 270

His Gly Thr Lys Arg Arg Ser Gln Ile Gln Thr Tyr Leu Glu Tyr His
            275                 280                 285

Gly Gly Pro Gly Val Gln His Ile Ala Leu Ala Ser Ser Asp Val Leu
        290                 295                 300

Arg Thr Leu Arg Glu Met Gln Ala Arg Ser Ala Met Gly Gly Phe Glu
305                 310                 315                 320

Phe Met Ala Pro Pro Gln Pro Lys Tyr Tyr Glu Gly Val Arg Arg Ile
                325                 330                 335

Ala Gly Asp Val Leu Ser Glu Ala Gln Ile Lys Glu Cys Gln Glu Leu
                340                 345                 350

Gly Val Leu Val Asp Arg Asp Asp Gln Gly Val Leu Leu Gln Ile Phe
            355                 360                 365

Thr Lys Pro Val Gly Asp Arg Pro Thr Phe Phe Leu Glu Met Ile Gln
370                 375                 380

Arg Ile Gly Cys Met Glu Lys Asp Glu Arg Gly Gln Glu Tyr Gln Lys
385                 390                 395                 400

Gly Gly Cys Gly Gly Phe Gly Lys Gly Asn Phe Ser Glu Leu Phe Lys
                405                 410                 415

Ser Ile Glu Asp Tyr Glu Lys Ser Leu Glu Ala Lys Gln Ser Ala Val
                420                 425                 430

Ala Gln Gln Ser
        435

<210> SEQ ID NO 7
<211> LENGTH: 434
<212> TYPE: PRT
<213> ORGANISM: Poa annua

<400> SEQUENCE: 7

Met Pro Pro Thr Thr Ala Thr Ala Thr Ala Ala Thr Val Thr Pro
1               5                   10                  15

Glu His Ala Ala Arg Arg Phe Pro Arg Val Val Arg Val Asn Pro Arg
                20                  25                  30

Ser Asp Arg Phe Pro Val Leu Ser Phe His His Val Glu Phe Trp Cys
            35                  40                  45

Ala Asp Ala Ala Ser Ala Ala Gly Arg Phe Ser Phe Ala Leu Gly Ala
        50                  55                  60

Pro Leu Ala Ala Arg Ser Asp Leu Ser Thr Gly Asn Ser His Ala
65                  70                  75                  80

Ser Leu Leu Leu Arg Ser Gly Ala Leu Ala Phe Leu Phe Thr Ala Pro
            85                  90                  95

Tyr Ala Pro Gln Pro Gln Asp Ala Asp Thr Ala Ser Ile Pro Ser Phe
        100                 105                 110

Ser Ala Asp Ala Ala Arg Ala Phe Ser Ala Ala His Gly Leu Ala Val
    115                 120                 125

Arg Ser Val Ala Val Arg Val Ala Asp Ala Ala Asp Ala Phe Arg Ala
130                 135                 140

Ser Ile Ala Ala Gly Ala Arg Pro Ala Phe Ala Pro Ala Asp Leu Gly
145                 150                 155                 160

Arg Gly Phe Gly Leu Ala Glu Val Glu Leu Tyr Gly Asp Val Val Leu
                165                 170                 175

Arg Phe Val Ser His Pro Asp Ala Asp Ala Pro Phe Leu Pro Gly
            180                 185                 190

Phe Glu Ala Val Ser Arg Pro Gly Ala Val Asp Tyr Gly Leu Thr Arg
        195                 200                 205

Phe Asp His Val Val Gly Asn Val Pro Glu Met Gly Pro Val Ile Asp
    210                 215                 220

Tyr Ile Lys Gly Phe Met Gly Phe His Glu Phe Ala Glu Phe Thr Ala
225                 230                 235                 240

Glu Asp Val Gly Thr Thr Glu Ser Gly Leu Asn Ser Val Val Leu Ala
                245                 250                 255

Asn Asn Ser Glu Ala Val Leu Leu Pro Leu Asn Glu Pro Val His Gly
            260                 265                 270

Thr Lys Arg Arg Ser Gln Ile Gln Thr Tyr Leu Glu Tyr His Gly Gly
        275                 280                 285

Pro Gly Val Gln His Ile Ala Leu Ala Ser Ser Asp Val Leu Arg Thr
    290                 295                 300

Leu Arg Glu Met Gln Ala Arg Ser Ala Met Gly Gly Phe Glu Phe Met
305                 310                 315                 320

Ala Pro Pro Gln Pro Lys Tyr Tyr Glu Gly Val Arg Arg Ile Ala Gly
                325                 330                 335

Asp Val Leu Ser Glu Ala Gln Ile Lys Glu Cys Gln Glu Leu Gly Val
            340                 345                 350

Leu Val Asp Arg Asp Asp Gln Gly Val Leu Leu Gln Ile Phe Thr Lys
        355                 360                 365

Pro Val Gly Asp Arg Pro Thr Phe Phe Leu Glu Met Ile Gln Arg Ile
    370                 375                 380

Gly Cys Met Glu Lys Asp Glu Arg Gly Gln Glu Tyr Gln Lys Gly Gly
385                 390                 395                 400

Cys Gly Gly Phe Gly Lys Gly Asn Phe Ser Glu Leu Phe Lys Ser Ile
                405                 410                 415

Glu Asp Tyr Glu Lys Ser Leu Glu Ala Lys Gln Ser Ala Val Ala Gln
            420                 425                 430

Gln Ser

<210> SEQ ID NO 8
<211> LENGTH: 440
<212> TYPE: PRT
<213> ORGANISM: Lolium multiflorum

<400> SEQUENCE: 8

```
Met Pro Pro Thr Pro Ala Thr Ala Thr Gly Ala Ala Ala Ala Val
1               5                   10                  15

Thr Pro Glu His Ala Ala Arg Ser Phe Pro Arg Val Val Arg Val Asn
            20                  25                  30

Pro Arg Ser Asp Arg Phe Pro Val Leu Ser Phe His His Val Glu Leu
            35                  40                  45

Trp Cys Ala Asp Ala Ala Ser Ala Ala Gly Arg Phe Ser Phe Ala Leu
    50                  55                  60

Gly Ala Pro Leu Ala Ala Arg Ser Asp Leu Ser Thr Gly Asn Ser Ala
65                  70                  75                  80

His Ala Ser Leu Leu Leu Arg Ser Gly Ala Leu Ala Phe Leu Phe Thr
                85                  90                  95

Ala Pro Tyr Ala Pro Pro Gln Glu Ala Ala Thr Ala Ala Ala Thr
                100                 105                 110

Ala Ser Ile Pro Ser Phe Ser Ala Asp Ala Ala Arg Thr Phe Ala Ala
            115                 120                 125

Ala His Gly Leu Ala Val Arg Ser Val Gly Val Arg Val Ala Asp Ala
    130                 135                 140

Ala Glu Ala Phe Arg Val Ser Val Ala Gly Gly Ala Arg Pro Ala Phe
145                 150                 155                 160

Ala Pro Ala Asp Leu Gly His Gly Phe Gly Leu Ala Glu Val Glu Leu
                165                 170                 175

Tyr Gly Asp Val Val Leu Arg Phe Val Ser Tyr Pro Asp Glu Thr Asp
                180                 185                 190

Leu Pro Phe Leu Pro Gly Phe Glu Arg Val Ser Ser Pro Gly Ala Val
            195                 200                 205

Asp Tyr Gly Leu Thr Arg Phe Asp His Val Val Gly Asn Val Pro Glu
    210                 215                 220

Met Ala Pro Val Ile Asp Tyr Met Lys Gly Phe Leu Gly Phe His Glu
225                 230                 235                 240

Phe Ala Glu Phe Thr Ala Glu Asp Val Gly Thr Thr Glu Ser Gly Leu
                245                 250                 255

Asn Ser Val Val Leu Ala Asn Asn Ser Glu Asn Val Leu Leu Pro Leu
            260                 265                 270

Asn Glu Pro Val His Gly Thr Lys Arg Arg Ser Gln Ile Gln Thr Tyr
    275                 280                 285

Leu Asp Tyr His Gly Gly Pro Gly Val Gln His Ile Ala Leu Ala Ser
        290                 295                 300

Thr Asp Val Leu Arg Thr Leu Arg Glu Met Arg Ala Arg Thr Pro Met
305                 310                 315                 320

Gly Gly Phe Glu Phe Met Ala Pro Pro Gln Ala Lys Tyr Tyr Glu Gly
                325                 330                 335

Val Arg Arg Ile Ala Gly Asp Val Leu Ser Glu Glu Ile Lys Glu
            340                 345                 350

Cys Gln Glu Leu Gly Val Leu Val Asp Arg Asp Gln Gly Val Leu
    355                 360                 365

Leu Gln Ile Phe Thr Lys Pro Val Gly Asp Arg Pro Thr Phe Phe Leu
    370                 375                 380

Glu Met Ile Gln Arg Ile Gly Cys Met Glu Lys Asp Glu Val Gly Gln
385                 390                 395                 400

Glu Tyr Gln Lys Gly Gly Cys Gly Gly Phe Gly Lys Gly Asn Phe Ser
                405                 410                 415
```

Glu Leu Phe Lys Ser Ile Glu Asp Tyr Glu Lys Thr Leu Glu Ala Lys
            420                 425                 430

Gln Ser Val Val Ala Gln Lys Ser
        435                 440

<210> SEQ ID NO 9
<211> LENGTH: 444
<212> TYPE: PRT
<213> ORGANISM: Erichola villosa

<400> SEQUENCE: 9

Met Pro Pro Thr Pro Thr Pro Ala Ala Ala Pro Gly Ala Ala Ala
1               5                   10                  15

Ala Pro Pro Ala Ala Ala Glu Gln Ala Ala Phe Arg Leu Val Gly His
            20                  25                  30

Arg Ser Phe Val Arg Val Asn Pro Arg Ser Asp Arg Phe His Thr Leu
        35                  40                  45

Ala Phe His His Val Glu Leu Trp Cys Ala Asp Ala Ala Ser Ala Ala
    50                  55                  60

Gly Arg Phe Ser Phe Gly Leu Gly Ala Pro Leu Ala Ala Arg Ser Asp
65              70                  75                  80

Leu Ser Thr Gly Asn Ser Ala His Thr Ser Leu Leu Arg Ser Gly
            85                  90                  95

Ser Leu Ala Phe Leu Phe Thr Ala Pro Tyr Ala Glu His Ala Gly Ala
            100                 105                 110

Asp Ala Ala Thr Ala Ser Leu Pro Ser Phe Ser Ala Pro Thr Ala Arg
        115                 120                 125

Arg Phe Ala Ala Asp His Gly Leu Ala Val Arg Ala Ile Ala Leu Arg
    130                 135                 140

Val Ala Asp Ala Glu Asp Ala Phe Arg Ala Ser Val Ala Ala Gly Ala
145                 150                 155                 160

Arg Pro Ala Phe Glu Pro Ala Glu Leu Gly Leu Gly Phe Arg Leu Ala
                165                 170                 175

Glu Val Glu Leu Tyr Gly Glu Val Val Leu Arg Tyr Val Ser Tyr Pro
            180                 185                 190

Asp Ala Ala Gly Ser Pro Phe Leu Pro Gly Phe Glu Glu Val Arg Asn
        195                 200                 205

Pro Arg Ala Val Asp Tyr Gly Leu Lys Arg Phe Asp His Ile Val Gly
    210                 215                 220

Asn Val Pro Glu Leu Ala Pro Val Ala Ala Tyr Val Ala Gly Phe Thr
225                 230                 235                 240

Gly Phe His Glu Phe Ala Glu Phe Thr Ala Glu Asp Val Gly Thr Ala
                245                 250                 255

Glu Ser Gly Leu Asn Ser Met Val Leu Ala Asn Asn Ser Glu Thr Val
            260                 265                 270

Leu Ile Pro Leu Asn Glu Pro Val His Gly Thr Lys Arg Arg Ser Gln
        275                 280                 285

Ile Gln Thr Phe Leu Glu His His Gly Gly Pro Gly Val Gln His Ile
    290                 295                 300

Ala Leu Ala Ser Asp Asp Val Leu Arg Thr Leu Arg Glu Met Gln Ala
305                 310                 315                 320

Arg Ser Ala Met Gly Gly Phe Glu Phe Met Ala Pro Pro Pro Asp
                325                 330                 335

Tyr Tyr Asp Gly Val Arg Arg Ala Gly Asp Val Leu Ser Glu Ala
            340                 345                 350

```
Gln Ile Lys Glu Cys Gln Glu Leu Gly Val Leu Val Asp Arg Asp Asp
            355                 360                 365

Gln Gly Val Leu Leu Gln Ile Phe Thr Lys Pro Val Gly Asp Arg Pro
    370                 375                 380

Thr Phe Phe Leu Glu Ile Ile Gln Arg Ile Gly Cys Met Glu Lys Asp
385                 390                 395                 400

Glu Gln Gly Gln Glu Tyr Gln Lys Gly Cys Gly Gly Phe Gly Lys
                405                 410                 415

Gly Asn Phe Ser Gln Leu Phe Lys Ser Ile Glu Asp Tyr Glu Lys Ser
            420                 425                 430

Leu Glu Val Lys Gln Ser Val Val Ala Gln Lys Ser
            435                 440

<210> SEQ ID NO 10
<211> LENGTH: 453
<212> TYPE: PRT
<213> ORGANISM: Bidens subalternans

<400> SEQUENCE: 10

Met Gly Thr Glu Ala Asn Thr Thr Phe Thr Gly Glu Gln Gln Ser Thr
1               5                   10                  15

Gln Ala Phe Lys Leu Val Gly Phe Arg Asn Phe Ile Arg Thr Asn Pro
            20                  25                  30

Lys Ser Asp Lys Phe Thr Val Lys Arg Phe His His Val Glu Phe Trp
        35                  40                  45

Cys Ser Asp Ala Thr Asn Thr Ser Arg Arg Phe Ser Trp Gly Leu Gly
    50                  55                  60

Met Pro Ile Leu Leu Lys Ser Asp Leu Ser Thr Gly Asn Thr Val His
65                  70                  75                  80

Ala Ser Tyr Leu Ile Arg Ser Gly His Leu Asn Phe Leu Phe Thr Ala
                85                  90                  95

Pro Tyr Ser Pro Ser Ile Thr Thr Gly Ser Ser Ser Ser Ser
            100                 105                 110

Ser Ile Pro Ser Phe Ser His Thr Val Cys Arg Asp Phe Thr Gly Lys
        115                 120                 125

His Gly Leu Ala Val Arg Ala Ile Ala Val Glu Val Glu Asp Ala Glu
    130                 135                 140

Thr Ala Phe Ala Val Ser Val Ala Asn Gly Ala Lys Pro Ser Cys Thr
145                 150                 155                 160

Pro Val Thr Ile Ser Asn Asn Asn Asn Asn Asn Gln Asn Asp Val
                165                 170                 175

Val Val Val Leu Ser Glu Val Lys Leu Tyr Gly Asp Val Val Leu Arg
            180                 185                 190

Tyr Val Ser Tyr Lys Asn Pro Asn Leu Glu Thr Asn Leu Lys Phe Leu
        195                 200                 205

Pro Gly Phe Glu Pro Val Glu Ala Thr Ser Ser Phe Pro Asp Leu Asp
    210                 215                 220

Tyr Gly Ile Arg Arg Leu Asp His Ala Val Gly Asn Val Pro Glu Leu
225                 230                 235                 240

Ala Pro Ala Val Glu Tyr Val Lys Ser Phe Thr Gly Phe His Glu Phe
                245                 250                 255

Ala Glu Phe Thr Ala Glu Asp Val Gly Thr Ser Glu Ser Gly Leu Asn
        260                 265                 270

Ser Val Val Leu Ala Cys Asn Ser Glu Glu Val Leu Leu Pro Met Asn
```

-continued

```
                275                 280                 285
Glu Pro Val Tyr Gly Thr Lys Arg Lys Ser Gln Ile Gln Thr Tyr Leu
290                 295                 300
Glu His Asn Glu Gly Ala Gly Val Gln His Leu Ala Leu Ala Ser Glu
305                 310                 315                 320
Asp Ile Phe Arg Thr Leu Arg Glu Met Arg Lys Arg Ser Gly Val Gly
                325                 330                 335
Gly Phe Glu Phe Met Pro Ser Pro Pro Thr Tyr Tyr Arg Asn Leu
340                 345                 350
Lys Asn Arg Ala Gly Asp Val Leu Ser Asp Glu Gln Ile Lys Glu Cys
                355                 360                 365
Glu Glu Leu Gly Ile Leu Val Asp Arg Asp Asp Gln Gly Thr Leu Leu
370                 375                 380
Gln Ile Phe Thr Lys Pro Val Gly Asp Arg Pro Thr Ile Phe Ile Glu
385                 390                 395                 400
Ile Ile Gln Arg Val Gly Cys Met Val Lys Asp Asp Glu Gly Asn Val
                405                 410                 415
Gln Gln Lys Ala Gly Cys Gly Gly Phe Gly Lys Gly Asn Phe Ser Glu
                420                 425                 430
Leu Phe Lys Ser Ile Glu Glu Tyr Glu Lys Thr Leu Glu Ala Arg Val
                435                 440                 445
Ala Thr Ala Thr Ala
                450

<210> SEQ ID NO 11
<211> LENGTH: 456
<212> TYPE: PRT
<213> ORGANISM: Bidens pilosa

<400> SEQUENCE: 11

Met Gly Thr Glu Ala Asn Thr Thr Phe Thr Gly Glu Gln Gln Gln Gln
1               5                   10                  15
Gln Ser Thr Gln Pro Phe Lys Leu Val Gly Phe Lys Asn Phe Ile Arg
                20                  25                  30
Thr Asn Pro Lys Ser Asp Lys Phe Thr Val Lys Arg Phe His His Val
                35                  40                  45
Glu Phe Trp Cys Ser Asp Ala Thr Asn Thr Ser Arg Arg Phe Ser Trp
                50                  55                  60
Gly Leu Gly Met Pro Ile Val Leu Lys Ser Asp Leu Ser Thr Gly Asn
65                  70                  75                  80
Ser Val His Ala Ser Tyr Leu Leu Arg Ser Gly Ser Leu Asn Phe Leu
                85                  90                  95
Phe Thr Ala Pro Tyr Ser Pro Ser Ile Thr Thr Thr Gly Ser Thr Ser
                100                 105                 110
Ser Ser Ile Pro Ser Phe Ser His Thr Val Cys Arg Asp Phe Thr Gly
                115                 120                 125
Lys His Gly Leu Ala Val Arg Ala Ile Ala Val Glu Val Asp Ala
                130                 135                 140
Glu Thr Ala Phe Ala Val Ser Val Ala Asn Gly Ala Lys Pro Ser Cys
145                 150                 155                 160
Ala Pro Val Thr Ile Ser Asn Asn Asn Asn Asp Asn Gln Asn Asp
                165                 170                 175
Val Val Val Leu Ser Glu Val Lys Leu Tyr Gly Asp Val Leu Arg
                180                 185                 190
```

```
Tyr Val Ser Tyr Lys Asn Pro Asn Leu Glu Thr Asn Leu Asn Asn Leu
            195                 200                 205

Lys Ile Leu Pro Gly Phe Glu Pro Val Glu Thr Thr Ser Ser Phe Pro
210                 215                 220

Asp Leu Asp Tyr Gly Ile Arg Arg Leu Asp His Ala Val Gly Asn Val
225                 230                 235                 240

Pro Glu Leu Ala Lys Ala Val Asp Tyr Val Lys Ser Phe Thr Gly Phe
            245                 250                 255

His Glu Phe Ala Glu Phe Thr Ala Glu Asp Val Gly Thr Ser Glu Ser
            260                 265                 270

Gly Leu Asn Ser Val Val Leu Ala Cys Asn Ser Glu Glu Val Leu Ile
            275                 280                 285

Pro Met Asn Glu Pro Val Tyr Gly Thr Lys Arg Lys Ser Gln Ile Gln
290                 295                 300

Thr Tyr Leu Glu His Asn Glu Gly Ala Gly Val Gln His Leu Ala Leu
305                 310                 315                 320

Ala Ser Glu Asp Ile Phe Arg Thr Leu Arg Glu Met Arg Lys Arg Ser
            325                 330                 335

Gly Val Gly Gly Phe Glu Phe Met Pro Ser Pro Pro Thr Tyr Tyr
            340                 345                 350

Arg Asn Leu Lys Asn Arg Ala Gly Asp Val Leu Ser Asp Glu Gln Ile
            355                 360                 365

Lys Glu Cys Glu Glu Leu Gly Ile Leu Val Asp Arg Asp Gln Gly
            370                 375                 380

Thr Leu Leu Gln Ile Phe Thr Lys Pro Val Gly Asp Arg Pro Thr Ile
385                 390                 395                 400

Phe Ile Glu Ile Ile Gln Arg Val Gly Cys Met Met Lys Asp Asp Glu
                405                 410                 415

Gly Lys Val Gln Gln Lys Ala Gly Cys Gly Phe Gly Lys Gly Asn
            420                 425                 430

Phe Ser Glu Leu Phe Lys Ser Ile Glu Glu Tyr Glu Lys Thr Leu Glu
            435                 440                 445

Ala Arg Ala Thr Thr Ala Thr Ala
            450                 455

<210> SEQ ID NO 12
<211> LENGTH: 436
<212> TYPE: PRT
<213> ORGANISM: Brachypodium arbuscula

<400> SEQUENCE: 12

Met Pro Pro Pro Ala Thr Thr Ala Ala Pro Ala Ala Ala Ala Val Thr
1               5                   10                  15

Pro Glu His Ala Arg Pro Pro Arg Arg Val Ala Arg Val Asn Pro Arg
            20                  25                  30

Ser Asp Arg Phe Ser Ala Leu Ser Phe His His Val Glu Leu Trp Cys
        35                  40                  45

Ala Asp Ala Ala Ser Ala Ala Gly Arg Phe Ser Phe Ala Leu Gly Ala
    50                  55                  60

Pro Pro Ala Ala Arg Ser Asp Leu Ser Thr Gly Asn Ser Ala His Ala
65                  70                  75                  80

Ser Ile Leu Leu Arg Ser Gly Ser Leu Ala Phe Leu Phe Thr Ala Pro
                85                  90                  95

Tyr Ala Pro Ser Pro Ala Ser Asp Ser Ala Ala Ser Ile Pro Ser Phe
            100                 105                 110
```

Ser Ala Ser Ala Ala Arg Gln Phe Thr Ala Asp His Gly Gly Leu Ala
            115                 120                 125

Val Arg Ala Val Ala Leu Arg Val Ser Ser Ala Ser Asp Ala Phe His
130                 135                 140

Ala Ser Val Ser Ala Gly Ala Arg Pro Ser Phe Pro Pro Ala Asp Leu
145                 150                 155                 160

Gly Gln Gly Phe Ala Leu Ala Glu Val Glu Leu Tyr Gly Asp Val Val
            165                 170                 175

Leu Arg Phe Ile Ser His Pro Asp Glu Asn Thr Glu Ile Pro Phe Leu
            180                 185                 190

Pro Gly Phe Glu Ser Val Ser Asn Pro Gly Ala Ser Thr Tyr Gly Leu
            195                 200                 205

Thr Arg Phe Asp His Val Val Gly Asn Val Pro Ser Leu Ala Pro Val
            210                 215                 220

Ala Ala Tyr Ile Ala Gly Phe Thr Gly Phe His Glu Phe Ala Glu Phe
225                 230                 235                 240

Thr Ala Glu Asp Val Gly Thr Ala Asp Ser Gly Leu Asn Ser Val Val
            245                 250                 255

Leu Ala Asn Asn Ser Glu Arg Val Leu Leu Pro Leu Asn Glu Pro Val
            260                 265                 270

His Gly Thr Lys Arg Arg Ser Gln Ile Gln Thr Tyr Leu Asp His His
            275                 280                 285

Gly Gly Pro Gly Val Gln His Ile Ala Leu Ala Ser Asp Asp Val Leu
            290                 295                 300

Arg Thr Leu Arg Glu Met Arg Ala Arg Ser Ala Met Gly Gly Phe Glu
305                 310                 315                 320

Phe Leu Ala Pro Pro Pro Asn Tyr Tyr Asp Gly Val Arg Arg Arg
            325                 330                 335

Ala Gly Asp Val Leu Ser Glu Ala Gln Ile Lys Glu Cys Gln Glu Leu
            340                 345                 350

Gly Val Leu Val Asp Arg Asp Gln Gly Val Leu Leu Gln Ile Phe
            355                 360                 365

Thr Lys Pro Val Gly Asp Arg Pro Thr Leu Phe Leu Glu Met Ile Gln
            370                 375                 380

Arg Ile Gly Cys Met Glu Lys Asp Glu Ile Gly Gln Glu Gln Lys
385                 390                 395                 400

Gly Gly Cys Gly Gly Phe Gly Lys Gly Asn Phe Ser Glu Leu Phe Arg
            405                 410                 415

Ser Ile Glu Glu Tyr Glu Lys Ser Leu Glu Ala Lys Gln Ser Ala Val
            420                 425                 430

Val Gln Glu Ser
        435

<210> SEQ ID NO 13
<211> LENGTH: 445
<212> TYPE: PRT
<213> ORGANISM: Arabidopsis thaliana

<400> SEQUENCE: 13

Met Gly His Gln Asn Ala Ala Val Ser Glu Asn Gln Asn His Asp Asp
1               5                   10                  15

Gly Ala Ala Ser Ser Pro Gly Phe Lys Leu Val Gly Phe Ser Lys Phe
            20                  25                  30

Val Arg Lys Asn Pro Lys Ser Asp Lys Phe Lys Val Lys Arg Phe His

```
            35                  40                  45
His Ile Glu Phe Trp Cys Gly Asp Ala Thr Asn Val Ala Arg Arg Phe
    50                  55                  60

Ser Trp Gly Leu Gly Met Arg Phe Ser Ala Lys Ser Asp Leu Ser Thr
65                  70                  75                  80

Gly Asn Met Val His Ala Ser Tyr Leu Leu Thr Ser Gly Asp Leu Arg
                85                  90                  95

Phe Leu Phe Thr Ala Pro Tyr Ser Pro Ser Leu Ser Ala Gly Glu Ile
                100                 105                 110

Lys Pro Thr Thr Thr Ala Ser Ile Pro Ser Phe Asp His Gly Ser Cys
                115                 120                 125

Arg Ser Phe Phe Ser Ser His Gly Leu Gly Val Arg Ala Val Ala Ile
        130                 135                 140

Glu Val Glu Asp Ala Glu Ser Ala Phe Ser Ile Ser Val Ala Asn Gly
145                 150                 155                 160

Ala Ile Pro Ser Ser Pro Pro Ile Val Leu Asn Glu Ala Val Thr Ile
                165                 170                 175

Ala Glu Val Lys Leu Tyr Gly Asp Val Val Leu Arg Tyr Val Ser Tyr
                180                 185                 190

Lys Ala Glu Asp Thr Glu Lys Ser Glu Phe Leu Pro Gly Phe Glu Arg
        195                 200                 205

Val Glu Asp Ala Ser Ser Phe Pro Leu Asp Tyr Gly Ile Arg Arg Leu
210                 215                 220

Asp His Ala Val Gly Asn Val Pro Glu Leu Gly Pro Ala Leu Thr Tyr
225                 230                 235                 240

Val Ala Gly Phe Thr Gly Phe His Gln Phe Ala Glu Phe Thr Ala Asp
                245                 250                 255

Asp Val Gly Thr Ala Glu Ser Gly Leu Asn Ser Ala Val Leu Ala Ser
                260                 265                 270

Asn Asp Glu Met Val Leu Leu Pro Ile Asn Glu Pro Val His Gly Thr
                275                 280                 285

Lys Arg Lys Ser Gln Ile Gln Thr Tyr Leu Glu His Asn Glu Gly Ala
        290                 295                 300

Gly Leu Gln His Leu Ala Leu Met Ser Glu Asp Ile Phe Arg Thr Leu
305                 310                 315                 320

Arg Glu Met Arg Lys Arg Ser Ser Ile Gly Gly Phe Asp Phe Met Pro
                325                 330                 335

Ser Pro Pro Pro Thr Tyr Tyr Gln Asn Leu Lys Lys Arg Val Gly Asp
                340                 345                 350

Val Leu Ser Asp Asp Gln Ile Lys Glu Cys Glu Glu Leu Gly Ile Leu
                355                 360                 365

Val Asp Arg Asp Asp Gln Gly Thr Leu Leu Gln Ile Phe Thr Lys Pro
        370                 375                 380

Leu Gly Asp Arg Pro Thr Ile Phe Ile Glu Ile Ile Gln Arg Val Gly
385                 390                 395                 400

Cys Met Met Lys Asp Glu Gly Lys Ala Tyr Gln Ser Gly Gly Cys
                405                 410                 415

Gly Gly Phe Gly Lys Gly Asn Phe Ser Glu Leu Phe Lys Ser Ile Glu
                420                 425                 430

Glu Tyr Glu Lys Thr Leu Glu Ala Lys Gln Leu Val Gly
        435                 440                 445

<210> SEQ ID NO 14
```

```
<211> LENGTH: 358
<212> TYPE: PRT
<213> ORGANISM: Pseudomonas aeruginosa

<400> SEQUENCE: 14

Met Ala Asp Gln Tyr Glu Asn Pro Met Gly Leu Met Gly Phe Glu Phe
1               5                   10                  15

Ile Glu Phe Ala Ser Pro Thr Pro Gly Thr Leu Glu Pro Ile Phe Glu
            20                  25                  30

Ile Met Gly Phe Thr Lys Val Ala Thr His Arg Ser Lys Asn Val His
        35                  40                  45

Leu Tyr Arg Gln Gly Glu Ile Asn Leu Ile Leu Asn Asn Gln Pro Asp
    50                  55                  60

Ser Leu Ala Ser Tyr Phe Ala Ala Glu His Gly Pro Ser Val Cys Gly
65                  70                  75                  80

Met Ala Phe Arg Val Lys Asp Ser Gln Gln Ala Tyr Asn Arg Ala Leu
                85                  90                  95

Glu Leu Gly Ala Gln Pro Ile His Ile Glu Thr Gly Pro Met Glu Leu
            100                 105                 110

Asn Leu Pro Ala Ile Lys Gly Ile Gly Gly Ala Pro Leu Tyr Leu Ile
        115                 120                 125

Asp Arg Phe Gly Glu Gly Ser Ser Ile Tyr Asp Ile Asp Phe Val Tyr
    130                 135                 140

Leu Glu Gly Val Asp Arg Asn Pro Val Gly Ala Gly Leu Lys Val Ile
145                 150                 155                 160

Asp His Leu Thr His Asn Val Tyr Arg Gly Arg Met Ala Tyr Trp Ala
                165                 170                 175

Asn Phe Tyr Glu Lys Leu Phe Asn Phe Arg Glu Ala Arg Tyr Phe Asp
            180                 185                 190

Ile Lys Gly Glu Tyr Thr Gly Leu Thr Ser Lys Ala Met Ser Ala Pro
        195                 200                 205

Asp Gly Met Ile Arg Ile Pro Leu Asn Glu Glu Ser Ser Lys Gly Ala
    210                 215                 220

Gly Gln Ile Glu Glu Phe Leu Met Gln Phe Asn Gly Glu Gly Ile Gln
225                 230                 235                 240

His Val Ala Phe Leu Thr Glu Asp Leu Val Lys Thr Trp Asp Ala Leu
                245                 250                 255

Lys Lys Ile Gly Met Arg Phe Met Thr Ala Pro Pro Asp Thr Tyr Tyr
            260                 265                 270

Glu Met Leu Glu Gly Arg Leu Pro Asn His Gly Glu Pro Val Asp Gln
        275                 280                 285

Leu Gln Ala Arg Gly Ile Leu Leu Asp Gly Ser Ser Ile Glu Gly Asp
    290                 295                 300

Lys Arg Leu Leu Leu Gln Ile Phe Ser Glu Thr Leu Met Gly Pro Val
305                 310                 315                 320

Phe Phe Glu Phe Ile Gln Arg Lys Gly Asp Asp Gly Phe Gly Glu Gly
                325                 330                 335

Asn Phe Lys Ala Leu Phe Glu Ser Ile Glu Arg Asp Gln Val Arg Arg
            340                 345                 350

Gly Val Leu Thr Thr Asp
        355

<210> SEQ ID NO 15
<211> LENGTH: 7
<212> TYPE: PRT
```

```
<213> ORGANISM: Artificial Sequence
<220> FEATURE:
<223> OTHER INFORMATION: Sequence motif from Avena sativa derived HPPD
<220> FEAT

```
<221> NAME/KEY: VARIANT
<222> LOCATION: (6)..(6)
<223> OTHER INFORMATION: Xaa = M or L
<220> FEATURE:
<221> NAME/KEY: VARIANT
<222> LOCATION: (7)..(7)
<223> OTHER INFORMATION: Xaa = any amino acid other than A or P

<400> SEQUENCE: 18

Gly Gly Phe Xaa Phe Xaa Xaa
1               5

<210> SEQ ID NO 19
<211> LENGTH: 8
<212> TYPE: PRT
<213> ORGANISM: Artificial Sequence
<220> FEATURE:
<223> OTHER INFORMATION: Sequence motif from Avena sativa derived HPPD
<220> FEATURE:
<221> NAME/KEY: VARIANT
<222> LOCATION: (6)..(6)
<223> OTHER INFORMATION: Xaa = any amino acid other than K

<400> SEQUENCE: 19

Cys Gly Gly Phe Gly Xaa Gly Asn
1               5

<210> SEQ ID NO 20
<211> LENGTH: 439
<212> TYPE: PRT
<213> ORGANISM: Avena sativa

<400> SEQUENCE: 20

Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
                20                  25                  30

Pro Arg Ser Asp Arg Phe Pro Val Leu Ser Phe His His Val Glu Leu
            35                  40                  45

Trp Cys Ala Asp Ala Ala Ser Ala Ala Gly Arg Phe Ser Phe Ala Leu
    50                  55                  60

Gly Ala Pro Leu Ala Ala Arg Ser Asp Leu Ser Thr Gly Asn Ser Ala
65                  70                  75                  80

His Ala Ser Leu Leu Leu Arg Ser Gly Ala Leu Ala Phe Leu Phe Thr
                85                  90                  95

Ala Pro Tyr Ala Pro Pro Pro Gln Glu Ala Thr Ala Ala Thr Ala
            100                 105                 110

Ser Ile Pro Ser Phe Ser Ala Asp Ala Ala Arg Thr Phe Ala Ala Ala
        115                 120                 125

His Gly Leu Ala Val Arg Ser Val Gly Val Arg Val Ala Asp Ala Ala
    130                 135                 140

Glu Ala Phe Arg Val Ser Val Ala Gly Gly Ala Arg Pro Ala Phe Ala
145                 150                 155                 160

Pro Ala Asp Leu Gly His Gly Phe Gly Leu Ala Glu Val Glu Leu Tyr
                165                 170                 175

Gly Asp Val Val Leu Arg Phe Val Ser Tyr Pro Asp Glu Thr Asp Leu
            180                 185                 190

Pro Phe Leu Pro Gly Phe Glu Arg Val Ser Ser Pro Gly Ala Val Asp
        195                 200                 205

Tyr Gly Leu Thr Arg Phe Asp His Val Val Gly Asn Val Pro Glu Met
    210                 215                 220
```

Ala Pro Val Ile Asp Tyr Met Lys Gly Phe Leu Gly Phe His Glu Phe
225                 230                 235                 240

Ala Glu Phe Thr Ala Glu Asp Val Gly Thr Thr Glu Ser Gly Leu Asn
            245                 250                 255

Ser Val Val Leu Ala Asn Asn Ser Glu Ala Val Leu Leu Pro Leu Asn
                260                 265                 270

Glu Pro Val His Gly Thr Lys Arg Arg Ser Gln Ile Gln Thr Tyr Leu
            275                 280                 285

Glu Tyr His Gly Gly Pro Gly Val Gln His Ile Ala Leu Ala Ser Asn
        290                 295                 300

Asp Val Leu Arg Thr Leu Arg Glu Met Arg Ala Arg Thr Pro Met Gly
305                 310                 315                 320

Gly Phe Glu Phe Met Ala Pro Pro Gln Ala Lys Tyr Tyr Glu Gly Val
                325                 330                 335

Arg Arg Ile Ala Gly Asp Val Leu Ser Glu Glu Gln Ile Lys Glu Cys
            340                 345                 350

Gln Glu Leu Gly Val Met Val Asp Arg Asp Gln Gly Val Leu Leu
        355                 360                 365

Gln Ile Phe Thr Lys Pro Val Gly Asp Arg Pro Thr Phe Phe Leu Glu
    370                 375                 380

Met Ile Gln Arg Ile Gly Cys Met Glu Lys Asp Glu Val Gly Gln Glu
385                 390                 395                 400

Tyr Gln Lys Gly Gly Cys Gly Gly Phe Gly Lys Gly Asn Phe Ser Glu
                405                 410                 415

Leu Phe Lys Ser Ile Glu Asp Tyr Glu Lys Ser Leu Glu Val Lys Gln
            420                 425                 430

Ser Val Val Ala Gln Lys Ser
            435

<210> SEQ ID NO 21
<211> LENGTH: 439
<212> TYPE: PRT
<213> ORGANISM: Avena sativa

<400> SEQUENCE: 21

Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
            20                  25                  30

Pro Arg Ser Asp Arg Phe Pro Val Leu Ser Phe His His Val Glu Leu
        35                  40                  45

Trp Cys Ala Asp Ala Ala Ser Ala Ala Gly Arg Phe Ser Phe Ala Leu
    50                  55                  60

Gly Ala Pro Leu Ala Ala Arg Ser Asp Leu Ser Thr Gly Asn Ser Ala
65                  70                  75                  80

His Ala Ser Leu Leu Leu Arg Ser Gly Ala Leu Ala Phe Leu Phe Thr
                85                  90                  95

Ala Pro Tyr Ala Pro Pro Pro Gln Glu Ala Thr Ala Ala Thr Ala
            100                 105                 110

Ser Ile Pro Ser Phe Ser Ala Asp Ala Ala Arg Thr Phe Ala Ala Ala
        115                 120                 125

His Gly Leu Ala Val Arg Ser Val Gly Val Arg Val Ala Asp Ala Ala
    130                 135                 140

Glu Ala Phe Arg Val Ser Val Ala Gly Gly Ala Arg Pro Ala Phe Ala

```
            145                 150                 155                 160
        Pro Ala Asp Leu Gly His Gly Phe Gly Leu Ala Glu Val Glu Leu Tyr
                        165                 170                 175

Gly Asp Val Val Leu Arg Phe Val Ser Tyr Pro Asp Glu Thr Asp Leu
                        180                 185                 190

Pro Phe Leu Pro Gly Phe Glu Arg Val Ser Ser Pro Gly Ala Val Asp
                        195                 200                 205

Tyr Gly Leu Thr Arg Phe Asp His Ile Val Gly Asn Val Pro Glu Met
                        210                 215                 220

Ala Pro Val Ile Asp Tyr Met Lys Gly Phe Leu Gly Phe His Glu Phe
        225                 230                 235                 240

Ala Glu Phe Thr Ala Glu Asp Val Gly Thr Thr Glu Ser Gly Leu Asn
                        245                 250                 255

Ser Val Val Leu Ala Asn Asn Ser Glu Ala Val Leu Leu Pro Leu Asn
                        260                 265                 270

Glu Pro Val His Gly Thr Lys Arg Arg Ser Gln Ile Gln Thr Tyr Leu
                        275                 280                 285

Glu Tyr His Gly Gly Pro Gly Val Gln His Ile Ala Leu Ala Ser Asn
                        290                 295                 300

Asp Val Leu Arg Thr Leu Arg Glu Met Arg Ala Arg Thr Pro Met Gly
        305                 310                 315                 320

Gly Phe Glu Phe Met Ala Pro Pro Gln Ala Lys Tyr Tyr Glu Gly Val
                        325                 330                 335

Arg Arg Ile Ala Gly Asp Val Leu Ser Glu Glu Gln Ile Lys Glu Cys
                        340                 345                 350

Gln Glu Leu Gly Val Leu Val Asp Arg Asp Gln Gly Val Leu Leu
                        355                 360                 365

Gln Ile Phe Thr Lys Pro Val Gly Asp Arg Pro Thr Phe Phe Leu Glu
                        370                 375                 380

Met Ile Gln Arg Ile Gly Cys Met Glu Lys Asp Glu Val Gly Gln Glu
        385                 390                 395                 400

Tyr Gln Lys Gly Gly Cys Gly Gly Phe Gly Lys Gly Asn Phe Ser Glu
                        405                 410                 415

Leu Phe Lys Ser Ile Glu Asp Tyr Glu Lys Ser Leu Glu Val Lys Gln
                        420                 425                 430

Ser Val Val Ala Gln Lys Ser
                        435

<210> SEQ ID NO 22
<211> LENGTH: 439
<212> TYPE: PRT
<213> ORGANISM: Avena sativa

<400> SEQUENCE: 22

Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
                20                  25                  30

Pro Arg Ser Asp Arg Phe Pro Val Leu Ser Phe His His Val Glu Leu
            35                  40                  45

Trp Cys Ala Asp Ala Ala Ser Ala Ala Gly Arg Phe Ser Phe Ala Leu
        50                  55                  60

Gly Ala Pro Leu Ala Ala Arg Ser Asp Leu Ser Thr Gly Asn Ser Ala
65                  70                  75                  80
```

His Ala Ser Leu Leu Leu Arg Ser Gly Ala Leu Ala Phe Leu Phe Thr
            85                  90                  95

Ala Pro Tyr Ala Pro Pro Gln Glu Ala Ala Thr Ala Ala Thr Ala
            100                 105                 110

Ser Ile Pro Ser Phe Ser Ala Asp Ala Ala Arg Thr Phe Ala Ala Ala
            115                 120                 125

His Gly Leu Ala Val Arg Ser Val Gly Val Arg Val Ala Asp Ala Ala
            130                 135                 140

Glu Ala Phe Arg Val Ser Val Ala Gly Gly Ala Arg Pro Ala Phe Ala
145                 150                 155                 160

Pro Ala Asp Leu Gly His Gly Phe Gly Leu Ala Glu Val Glu Leu Tyr
            165                 170                 175

Gly Asp Val Val Leu Arg Phe Val Ser Tyr Pro Asp Glu Thr Asp Leu
            180                 185                 190

Pro Phe Leu Pro Gly Phe Glu Arg Val Ser Ser Pro Gly Ala Val Asp
            195                 200                 205

Tyr Gly Leu Thr Arg Phe Asp His Leu Val Gly Asn Val Pro Glu Met
            210                 215                 220

Ala Pro Val Ile Asp Tyr Met Lys Gly Phe Leu Gly Phe His Glu Phe
225                 230                 235                 240

Ala Glu Phe Thr Ala Glu Asp Val Gly Thr Thr Glu Ser Gly Leu Asn
            245                 250                 255

Ser Val Val Leu Ala Asn Asn Ser Glu Ala Val Leu Leu Pro Leu Asn
            260                 265                 270

Glu Pro Val His Gly Thr Lys Arg Arg Ser Gln Ile Gln Thr Tyr Leu
            275                 280                 285

Glu Tyr His Gly Gly Pro Gly Val Gln His Ile Ala Leu Ala Ser Asn
            290                 295                 300

Asp Val Leu Arg Thr Leu Arg Glu Met Arg Ala Arg Thr Pro Met Gly
305                 310                 315                 320

Gly Phe Glu Phe Met Ala Pro Pro Gln Ala Lys Tyr Tyr Glu Gly Val
            325                 330                 335

Arg Arg Ile Ala Gly Asp Val Leu Ser Glu Glu Gln Ile Lys Glu Cys
            340                 345                 350

Gln Glu Leu Gly Val Leu Val Asp Arg Asp Gln Gly Val Leu Leu
            355                 360                 365

Gln Ile Phe Thr Lys Pro Val Gly Asp Arg Pro Thr Phe Phe Leu Glu
            370                 375                 380

Met Ile Gln Arg Ile Gly Cys Met Glu Lys Asp Glu Val Gly Gln Glu
385                 390                 395                 400

Tyr Gln Lys Gly Gly Cys Gly Gly Phe Gly Lys Gly Asn Phe Ser Glu
            405                 410                 415

Leu Phe Lys Ser Ile Glu Asp Tyr Glu Lys Ser Leu Glu Val Lys Gln
            420                 425                 430

Ser Val Val Ala Gln Lys Ser
            435

<210> SEQ ID NO 23
<211> LENGTH: 439
<212> TYPE: PRT
<213> ORGANISM: Avena sativa

<400> SEQUENCE: 23

Met Pro Pro Thr Pro Ala Thr Ala Thr Gly Ala Ala Ala Ala Val
1               5                   10                  15

-continued

```
Thr Pro Glu His Ala Ala Arg Ser Phe Pro Arg Val Arg Val Asn
             20                  25                  30

Pro Arg Ser Asp Arg Phe Pro Val Leu Ser Phe His His Val Glu Leu
         35                  40                  45

Trp Cys Ala Asp Ala Ala Ser Ala Ala Gly Arg Phe Ser Phe Ala Leu
 50                  55                  60

Gly Ala Pro Leu Ala Ala Arg Ser Asp Leu Ser Thr Gly Asn Ser Ala
 65                  70                  75                  80

His Ala Ser Leu Leu Leu Arg Ser Gly Ala Leu Ala Phe Leu Phe Thr
                 85                  90                  95

Ala Pro Tyr Ala Pro Pro Gln Glu Ala Ala Thr Ala Ala Thr Ala
            100                 105                 110

Ser Ile Pro Ser Phe Ser Ala Asp Ala Ala Arg Thr Phe Ala Ala Ala
            115                 120                 125

His Gly Leu Ala Val Arg Ser Val Gly Val Arg Val Ala Asp Ala Ala
130                 135                 140

Glu Ala Phe Arg Val Ser Val Ala Gly Gly Ala Arg Pro Ala Phe Ala
145                 150                 155                 160

Pro Ala Asp Leu Gly His Gly Phe Gly Leu Ala Glu Val Glu Leu Tyr
                165                 170                 175

Gly Asp Val Val Leu Arg Phe Val Ser Tyr Pro Asp Glu Thr Asp Leu
            180                 185                 190

Pro Phe Leu Pro Gly Phe Glu Arg Val Ser Ser Pro Gly Ala Val Asp
            195                 200                 205

Tyr Gly Leu Thr Arg Phe Asp His Val Val Gly Asn Val Pro Glu Met
210                 215                 220

Ala Pro Val Ile Asp Tyr Met Lys Gly Phe Leu Gly Phe His Glu Phe
225                 230                 235                 240

Ala Glu Phe Thr Ala Glu Asp Val Gly Thr Thr Glu Ser Gly Leu Asn
                245                 250                 255

Ser Val Val Leu Ala Asn Asn Ser Glu Ala Val Leu Leu Pro Leu Asn
            260                 265                 270

Glu Pro Val His Gly Thr Lys Arg Arg Ser Gln Ile Gln Thr Tyr Leu
            275                 280                 285

Glu Tyr His Gly Gly Pro Gly Val Gln His Ile Ala Leu Ala Ser Asn
290                 295                 300

Asp Val Leu Arg Thr Leu Arg Glu Met Arg Ala Arg Thr Pro Met Gly
305                 310                 315                 320

Gly Phe Glu Phe Met Arg Pro Pro Gln Ala Lys Tyr Tyr Glu Gly Val
                325                 330                 335

Arg Arg Ile Ala Gly Asp Val Leu Ser Glu Glu Gln Ile Lys Glu Cys
            340                 345                 350

Gln Glu Leu Gly Val Leu Val Asp Arg Asp Gln Gly Val Leu Leu
            355                 360                 365

Gln Ile Phe Thr Lys Pro Val Gly Asp Arg Pro Thr Phe Phe Leu Glu
            370                 375                 380

Met Ile Gln Arg Ile Gly Cys Met Glu Lys Asp Glu Val Gly Gln Glu
385                 390                 395                 400

Tyr Gln Lys Gly Gly Cys Gly Gly Phe Gly Lys Gly Asn Phe Ser Glu
                405                 410                 415

Leu Phe Lys Ser Ile Glu Asp Tyr Glu Lys Ser Leu Gly Val Lys Gln
            420                 425                 430
```

Ser Val Val Ala Gln Lys Ser
            435

<210> SEQ ID NO 24
<211> LENGTH: 439
<212> TYPE: PRT
<213> ORGANISM: Avena sativa

<400> SEQUENCE: 24

Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
            20                  25                  30

Pro Arg Ser Asp Arg Phe Pro Val Leu Ser Phe His His Val Glu Leu
        35                  40                  45

Trp Cys Ala Asp Ala Ala Ser Ala Ala Gly Arg Phe Ser Phe Ala Leu
50                  55                  60

Gly Ala Pro Leu Ala Ala Arg Ser Asp Leu Ser Thr Gly Asn Ser Ala
65                  70                  75                  80

His Ala Ser Leu Leu Leu Arg Ser Gly Ala Leu Ala Phe Leu Phe Thr
                85                  90                  95

Ala Pro Tyr Ala Pro Pro Pro Gln Glu Ala Ala Thr Ala Ala Thr Ala
            100                 105                 110

Ser Ile Pro Ser Phe Ser Ala Asp Ala Ala Arg Thr Phe Ala Ala Ala
        115                 120                 125

His Gly Leu Ala Val Arg Ser Val Gly Val Arg Val Ala Asp Ala Ala
130                 135                 140

Glu Ala Phe Arg Val Ser Val Ala Gly Gly Ala Arg Pro Ala Phe Ala
145                 150                 155                 160

Pro Ala Asp Leu Gly His Gly Phe Gly Leu Ala Glu Val Glu Leu Tyr
                165                 170                 175

Gly Asp Val Val Leu Arg Phe Val Ser Tyr Pro Asp Glu Thr Asp Leu
            180                 185                 190

Pro Phe Leu Pro Gly Phe Glu Arg Val Ser Ser Pro Gly Ala Val Asp
        195                 200                 205

Tyr Gly Leu Thr Arg Phe Asp His Val Val Gly Asn Val Pro Glu Met
210                 215                 220

Ala Pro Val Ile Asp Tyr Met Lys Gly Phe Leu Gly Phe His Glu Phe
225                 230                 235                 240

Ala Glu Phe Thr Ala Glu Asp Val Gly Thr Thr Glu Ser Gly Leu Asn
                245                 250                 255

Ser Val Val Leu Ala Asn Asn Ser Glu Ala Val Leu Leu Pro Leu Asn
            260                 265                 270

Glu Pro Val His Gly Thr Lys Arg Arg Ser Gln Ile Gln Thr Tyr Leu
        275                 280                 285

Glu Tyr His Gly Gly Pro Gly Val Gln His Ile Ala Leu Ala Ser Asn
290                 295                 300

Asp Val Leu Arg Thr Leu Arg Glu Met Arg Ala Arg Thr Pro Met Gly
305                 310                 315                 320

Gly Phe Glu Phe Met Lys Pro Pro Gln Ala Lys Tyr Tyr Glu Gly Val
                325                 330                 335

Arg Arg Ile Ala Gly Asp Val Leu Ser Glu Glu Gln Ile Lys Glu Cys
            340                 345                 350

Gln Glu Leu Gly Val Leu Val Asp Arg Asp Asp Gln Gly Val Leu Leu
        355                 360                 365

```
Gln Ile Phe Thr Lys Pro Val Gly Asp Arg Pro Thr Phe Phe Leu Glu
        370                 375                 380

Met Ile Gln Arg Ile Gly Cys Met Glu Lys Asp Glu Val Gly Gln Glu
385                 390                 395                 400

Tyr Gln Lys Gly Gly Cys Gly Gly Phe Gly Lys Gly Asn Phe Ser Glu
                405                 410                 415

Leu Phe Lys Ser Ile Glu Asp Tyr Glu Lys Ser Leu Glu Val Lys Gln
            420                 425                 430

Ser Val Val Ala Gln Lys Ser
            435

<210> SEQ ID NO 25
<211> LENGTH: 439
<212> TYPE: PRT
<213> ORGANISM: Avena sativa

<400> SEQUENCE: 25

Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
            20                  25                  30

Pro Arg Ser Asp Arg Phe Pro Val Leu Ser Phe His His Val Glu Leu
        35                  40                  45

Trp Cys Ala Asp Ala Ala Ser Ala Ala Gly Arg Phe Ser Phe Ala Leu
50                  55                  60

Gly Ala Pro Leu Ala Ala Arg Ser Asp Leu Ser Thr Gly Asn Ser Ala
65                  70                  75                  80

His Ala Ser Leu Leu Leu Arg Ser Gly Ala Leu Ala Phe Leu Phe Thr
                85                  90                  95

Ala Pro Tyr Ala Pro Pro Gln Glu Ala Ala Thr Ala Ala Thr Ala
            100                 105                 110

Ser Ile Pro Ser Phe Ser Ala Asp Ala Ala Arg Thr Phe Ala Ala Ala
        115                 120                 125

His Gly Leu Ala Val Arg Ser Val Gly Val Arg Val Ala Asp Ala Ala
130                 135                 140

Glu Ala Phe Arg Val Ser Val Ala Gly Gly Ala Arg Pro Ala Phe Ala
145                 150                 155                 160

Pro Ala Asp Leu Gly His Gly Phe Gly Leu Ala Glu Val Glu Leu Tyr
                165                 170                 175

Gly Asp Val Val Leu Arg Phe Val Ser Tyr Pro Asp Glu Thr Asp Leu
            180                 185                 190

Pro Phe Leu Pro Gly Phe Glu Arg Val Ser Ser Pro Gly Ala Val Asp
        195                 200                 205

Tyr Gly Leu Thr Arg Phe Asp His Val Val Gly Asn Val Pro Glu Met
210                 215                 220

Ala Pro Val Ile Asp Tyr Met Lys Gly Phe Leu Gly Phe His Glu Phe
225                 230                 235                 240

Ala Glu Phe Thr Ala Glu Asp Val Gly Thr Thr Glu Ser Gly Leu Asn
                245                 250                 255

Ser Val Val Leu Ala Asn Asn Ser Glu Ala Val Leu Leu Pro Leu Asn
            260                 265                 270

Glu Pro Val His Gly Thr Lys Arg Arg Ser Gln Ile Gln Thr Tyr Leu
        275                 280                 285

Glu Tyr His Gly Gly Pro Gly Val Gln His Ile Ala Leu Ala Ser Asn
```

```
                290                 295                 300
Asp Val Leu Arg Thr Leu Arg Glu Met Arg Ala Arg Thr Pro Met Gly
305                 310                 315                 320

Gly Phe Glu Phe Met Ile Pro Pro Gln Ala Lys Tyr Tyr Glu Gly Val
                325                 330                 335

Arg Arg Ile Ala Gly Asp Val Leu Ser Glu Glu Ile Lys Glu Cys
                340                 345                 350

Gln Glu Leu Gly Val Leu Val Asp Arg Asp Gln Gly Val Leu Leu
            355                 360                 365

Gln Ile Phe Thr Lys Pro Val Gly Asp Arg Pro Thr Phe Phe Leu Glu
        370                 375                 380

Met Ile Gln Arg Ile Gly Cys Met Glu Lys Asp Glu Val Gly Gln Glu
385                 390                 395                 400

Tyr Gln Lys Gly Gly Cys Gly Gly Phe Gly Lys Gly Asn Phe Ser Glu
                405                 410                 415

Leu Phe Lys Ser Ile Glu Asp Tyr Glu Lys Ser Leu Glu Val Lys Gln
            420                 425                 430

Ser Val Val Ala Gln Lys Ser
        435

<210> SEQ ID NO 26
<211> LENGTH: 439
<212> TYPE: PRT
<213> ORGANISM: Avena sativa

<400> SEQUENCE: 26

Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
            20                  25                  30

Pro Arg Ser Asp Arg Phe Pro Val Leu Ser Phe His His Val Glu Leu
        35                  40                  45

Trp Cys Ala Asp Ala Ala Ser Ala Ala Gly Arg Phe Ser Phe Ala Leu
50                  55                  60

Gly Ala Pro Leu Ala Ala Arg Ser Asp Leu Ser Thr Gly Asn Ser Ala
65                  70                  75                  80

His Ala Ser Leu Leu Leu Arg Ser Gly Ala Leu Ala Phe Leu Phe Thr
                85                  90                  95

Ala Pro Tyr Ala Pro Pro Pro Gln Glu Ala Ala Thr Ala Ala Thr Ala
                100                 105                 110

Ser Ile Pro Ser Phe Ser Ala Asp Ala Ala Arg Thr Phe Ala Ala Ala
            115                 120                 125

His Gly Leu Ala Val Arg Ser Val Gly Val Arg Val Ala Asp Ala Ala
        130                 135                 140

Glu Ala Phe Arg Val Ser Val Ala Gly Ala Arg Pro Ala Phe Ala
145                 150                 155                 160

Pro Ala Asp Leu Gly His Gly Phe Gly Leu Ala Glu Val Glu Leu Tyr
                165                 170                 175

Gly Asp Val Val Leu Arg Phe Val Ser Tyr Pro Asp Glu Thr Asp Leu
            180                 185                 190

Pro Phe Leu Pro Gly Phe Glu Arg Val Ser Ser Pro Gly Ala Val Asp
        195                 200                 205

Tyr Gly Leu Thr Arg Phe Asp His Val Val Gly Asn Val Pro Glu Met
    210                 215                 220
```

```
Ala Pro Val Ile Asp Tyr Met Lys Gly Phe Leu Gly Phe His Glu Phe
225                 230                 235                 240

Ala Glu Phe Thr Ala Glu Asp Val Gly Thr Thr Glu Ser Gly Leu Asn
            245                 250                 255

Ser Val Val Leu Ala Asn Asn Ser Glu Ala Val Leu Leu Pro Leu Asn
        260                 265                 270

Glu Pro Val His Gly Thr Lys Arg Arg Ser Gln Ile Gln Thr Tyr Leu
    275                 280                 285

Glu Tyr His Gly Gly Pro Val Gln His Ile Ala Leu Ala Ser Asn
290                 295                 300

Asp Val Leu Arg Thr Leu Arg Glu Met Arg Ala Arg Thr Pro Met Gly
305                 310                 315                 320

Gly Phe Glu Phe Met Ala Pro Pro Gln Ala Lys Tyr Tyr Glu Gly Val
                325                 330                 335

Arg Arg Glu Ala Gly Asp Val Leu Ser Glu Glu Gln Ile Lys Glu Cys
                340                 345                 350

Gln Glu Leu Gly Val Leu Val Asp Arg Asp Gln Gly Val Leu Leu
        355                 360                 365

Gln Ile Phe Thr Lys Pro Val Gly Asp Arg Pro Thr Phe Phe Leu Glu
370                 375                 380

Met Ile Gln Arg Ile Gly Cys Met Glu Lys Asp Glu Val Gly Gln Glu
385                 390                 395                 400

Tyr Gln Lys Gly Gly Cys Gly Gly Phe Gly Lys Gly Asn Phe Ser Glu
                405                 410                 415

Leu Phe Lys Ser Ile Glu Asp Tyr Glu Lys Ser Leu Glu Val Lys Gln
            420                 425                 430

Ser Val Val Ala Gln Lys Ser
        435

<210> SEQ ID NO 27
<211> LENGTH: 439
<212> TYPE: PRT
<213> ORGANISM: Avena sativa

<400> SEQUENCE: 27

Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
            20                  25                  30

Pro Arg Ser Asp Arg Phe Pro Val Leu Ser Phe His His Val Glu Leu
        35                  40                  45

Trp Cys Ala Asp Ala Ala Ser Ala Ala Gly Arg Phe Ser Phe Ala Leu
50                  55                  60

Gly Ala Pro Leu Ala Ala Arg Ser Asp Leu Ser Thr Gly Asn Ser Ala
65                  70                  75                  80

His Ala Ser Leu Leu Leu Arg Ser Gly Ala Leu Ala Phe Leu Phe Thr
                85                  90                  95

Ala Pro Tyr Ala Pro Pro Pro Gln Glu Ala Ala Thr Ala Ala Thr Ala
            100                 105                 110

Ser Ile Pro Ser Phe Ser Ala Asp Ala Ala Arg Thr Phe Ala Ala Ala
        115                 120                 125

His Gly Leu Ala Val Arg Ser Val Gly Val Arg Val Ala Asp Ala Ala
    130                 135                 140

Glu Ala Phe Arg Val Ser Val Ala Gly Gly Ala Arg Pro Ala Phe Ala
145                 150                 155                 160
```

```
Pro Ala Asp Leu Gly His Gly Phe Gly Leu Ala Glu Val Glu Leu Tyr
                165                 170                 175

Gly Asp Val Val Leu Arg Phe Val Ser Tyr Pro Asp Glu Thr Asp Leu
            180                 185                 190

Pro Phe Leu Pro Gly Phe Glu Arg Val Ser Pro Gly Ala Val Asp
            195                 200                 205

Tyr Gly Leu Thr Arg Phe Asp His Val Val Gly Asn Val Pro Glu Met
        210                 215                 220

Ala Pro Val Ile Asp Tyr Met Lys Gly Phe Leu Gly Phe His Glu Phe
225                 230                 235                 240

Ala Glu Phe Thr Ala Glu Asp Val Gly Thr Thr Glu Ser Gly Leu Asn
                245                 250                 255

Ser Val Val Leu Ala Asn Asn Ser Glu Ala Val Leu Leu Pro Leu Asn
            260                 265                 270

Glu Pro Val His Gly Thr Lys Arg Arg Ser Gln Ile Gln Thr Tyr Leu
        275                 280                 285

Glu Tyr His Gly Gly Pro Gly Val Gln His Ile Ala Leu Ala Ser Asn
        290                 295                 300

Asp Val Leu Arg Thr Leu Arg Glu Met Arg Ala Arg Thr Pro Met Gly
305                 310                 315                 320

Gly Phe Glu Phe Met Ala Pro Pro Gln Ala Lys Tyr Tyr Glu Gly Val
                325                 330                 335

Arg Arg Asp Ala Gly Asp Val Leu Ser Glu Glu Gln Ile Lys Glu Cys
            340                 345                 350

Gln Glu Leu Gly Val Leu Val Asp Arg Asp Gln Gly Val Leu Leu
        355                 360                 365

Gln Ile Phe Thr Lys Pro Val Gly Asp Arg Pro Thr Phe Phe Leu Glu
        370                 375                 380

Met Ile Gln Arg Ile Gly Cys Met Glu Lys Asp Glu Val Gly Gln Glu
385                 390                 395                 400

Tyr Gln Lys Gly Gly Cys Gly Gly Phe Gly Lys Gly Asn Phe Ser Glu
                405                 410                 415

Leu Phe Lys Ser Ile Glu Asp Tyr Glu Lys Ser Leu Glu Val Lys Gln
            420                 425                 430

Ser Val Val Ala Gln Lys Ser
        435

<210> SEQ ID NO 28
<211> LENGTH: 439
<212> TYPE: PRT
<213> ORGANISM: Avena sativa

<400> SEQUENCE: 28

Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
                20                  25                  30

Pro Arg Ser Asp Arg Phe Pro Val Leu Ser Phe His His Val Glu Leu
            35                  40                  45

Trp Cys Ala Asp Ala Ala Ser Ala Ala Gly Arg Phe Ser Phe Ala Leu
        50                  55                  60

Gly Ala Pro Leu Ala Ala Arg Ser Asp Leu Ser Thr Gly Asn Ser Ala
65                  70                  75                  80

His Ala Ser Leu Leu Leu Arg Ser Gly Ala Leu Ala Phe Leu Phe Thr
```

```
                    85                  90                  95
Ala Pro Tyr Ala Pro Pro Gln Glu Ala Thr Ala Ala Thr Ala
            100                 105                 110

Ser Ile Pro Ser Phe Ser Ala Asp Ala Ala Arg Thr Phe Ala Ala Ala
            115                 120                 125

His Gly Leu Ala Val Arg Ser Val Gly Val Arg Val Ala Asp Ala Ala
            130                 135                 140

Glu Ala Phe Arg Val Ser Val Ala Gly Ala Arg Pro Ala Phe Ala
145                 150                 155                 160

Pro Ala Asp Leu Gly His Gly Phe Gly Leu Ala Glu Val Glu Leu Tyr
            165                 170                 175

Gly Asp Val Val Leu Arg Phe Val Ser Tyr Pro Asp Glu Thr Asp Leu
            180                 185                 190

Pro Phe Leu Pro Gly Phe Glu Arg Val Ser Ser Pro Gly Ala Val Asp
            195                 200                 205

Tyr Gly Leu Thr Arg Phe Asp His Val Val Gly Asn Val Pro Glu Met
            210                 215                 220

Ala Pro Val Ile Asp Tyr Met Lys Gly Phe Leu Gly Phe His Glu Phe
225                 230                 235                 240

Ala Glu Phe Thr Ala Glu Asp Val Gly Thr Thr Glu Ser Gly Leu Asn
            245                 250                 255

Ser Val Val Leu Ala Asn Asn Ser Glu Ala Val Leu Leu Pro Leu Asn
            260                 265                 270

Glu Pro Val His Gly Thr Lys Arg Arg Ser Gln Ile Gln Thr Tyr Leu
            275                 280                 285

Glu Tyr His Gly Gly Pro Gly Val Gln His Ile Ala Leu Ala Ser Asn
            290                 295                 300

Asp Val Leu Arg Thr Leu Arg Glu Met Arg Ala Arg Thr Pro Met Gly
305                 310                 315                 320

Gly Phe Glu Phe Met Ala Pro Pro Gln Ala Lys Tyr Tyr Glu Gly Val
            325                 330                 335

Arg Arg Cys Ala Gly Asp Val Leu Ser Glu Glu Gln Ile Lys Glu Cys
            340                 345                 350

Gln Glu Leu Gly Val Leu Val Asp Arg Asp Gln Gly Val Leu Leu
            355                 360                 365

Gln Ile Phe Thr Lys Pro Val Gly Asp Arg Pro Thr Phe Phe Leu Glu
            370                 375                 380

Met Ile Gln Arg Ile Gly Cys Met Glu Lys Asp Glu Val Gly Gln Glu
385                 390                 395                 400

Tyr Gln Lys Gly Gly Cys Gly Gly Phe Gly Lys Gly Asn Phe Ser Glu
            405                 410                 415

Leu Phe Lys Ser Ile Glu Asp Tyr Glu Lys Ser Leu Glu Val Lys Gln
            420                 425                 430

Ser Val Val Ala Gln Lys Ser
            435

<210> SEQ ID NO 29
<211> LENGTH: 439
<212> TYPE: PRT
<213> ORGANISM: Avena sativa

<400> SEQUENCE: 29

Met Pro Pro Thr Pro Ala Thr Thr Gly Ala Ala Ala Ala Val
1               5                   10                  15
```

-continued

```
Thr Pro Glu His Ala Ala Arg Ser Phe Pro Arg Val Val Arg Val Asn
             20                  25                  30
Pro Arg Ser Asp Arg Phe Pro Val Leu Ser Phe His His Val Glu Leu
         35                  40                  45
Trp Cys Ala Asp Ala Ala Ser Ala Ala Gly Arg Phe Ser Phe Ala Leu
     50                  55                  60
Gly Ala Pro Leu Ala Ala Arg Ser Asp Leu Ser Thr Gly Asn Ser Ala
 65                  70                  75                  80
His Ala Ser Leu Leu Leu Arg Ser Gly Ala Leu Ala Phe Leu Phe Thr
                 85                  90                  95
Ala Pro Tyr Ala Pro Pro Gln Glu Ala Ala Thr Ala Ala Thr Ala
            100                 105                 110
Ser Ile Pro Ser Phe Ser Ala Asp Ala Ala Arg Thr Phe Ala Ala Ala
        115                 120                 125
His Gly Leu Ala Val Arg Ser Val Gly Val Arg Val Ala Asp Ala Ala
    130                 135                 140
Glu Ala Phe Arg Val Ser Val Ala Gly Ala Arg Pro Ala Phe Ala
145                 150                 155                 160
Pro Ala Asp Leu Gly His Gly Phe Gly Leu Ala Glu Val Glu Leu Tyr
                165                 170                 175
Gly Asp Val Val Leu Arg Phe Val Ser Tyr Pro Asp Glu Thr Asp Leu
            180                 185                 190
Pro Phe Leu Pro Gly Phe Glu Arg Val Ser Ser Pro Gly Ala Val Asp
        195                 200                 205
Tyr Gly Leu Thr Arg Phe Asp His Val Val Gly Asn Val Pro Glu Met
    210                 215                 220
Ala Pro Val Ile Asp Tyr Met Lys Gly Phe Leu Gly Phe His Glu Phe
225                 230                 235                 240
Ala Glu Phe Thr Ala Glu Asp Val Gly Thr Thr Glu Ser Gly Leu Asn
                245                 250                 255
Ser Val Val Leu Ala Asn Asn Ser Glu Ala Val Leu Leu Pro Leu Asn
            260                 265                 270
Glu Pro Val His Gly Thr Lys Arg Arg Ser Gln Ile Gln Thr Tyr Leu
        275                 280                 285
Glu Tyr His Gly Gly Pro Gly Val Gln His Ile Ala Leu Ala Ser Asn
    290                 295                 300
Asp Val Leu Arg Thr Leu Arg Glu Met Arg Ala Arg Thr Pro Met Gly
305                 310                 315                 320
Gly Phe Glu Phe Met Ala Pro Pro Gln Ala Lys Tyr Tyr Glu Gly Val
                325                 330                 335
Arg Arg Ile Ala Gly Asp Val Leu Ser Glu Glu Gln Ile Lys Glu Cys
            340                 345                 350
Gln Glu Leu Gly Val Leu Val Asp Arg Asp Gln Gly Val Leu Leu
        355                 360                 365
Gln Ile Phe Thr Lys Pro Val Gly Asp Arg Pro Thr Phe Phe Leu Glu
    370                 375                 380
Met Ile Gln Arg Ile Gly Cys Met Glu Lys Asp Glu Val Gly Gln Glu
385                 390                 395                 400
Tyr Gln Lys Gly Gly Cys Gly Arg Phe Gly Lys Gly Asn Phe Ser Glu
                405                 410                 415
Leu Phe Lys Ser Ile Glu Asp Tyr Glu Lys Ser Leu Glu Val Lys Gln
            420                 425                 430
Ser Val Val Ala Gln Lys Ser
```

435

<210> SEQ ID NO 30
<211> LENGTH: 439
<212> TYPE: PRT
<213> ORGANISM: Avena sativa

<400> SEQUENCE: 30

```
Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
            20                  25                  30

Pro Arg Ser Asp Arg Phe Pro Val Leu Ser Phe His Val Glu Leu
        35                  40                  45

Trp Cys Ala Asp Ala Ala Ser Ala Ala Gly Arg Phe Ser Phe Ala Leu
    50                  55                  60

Gly Ala Pro Leu Ala Ala Arg Ser Asp Leu Ser Thr Gly Asn Ser Ala
65                  70                  75                  80

His Ala Ser Leu Leu Leu Arg Ser Gly Ala Leu Ala Phe Leu Phe Thr
                85                  90                  95

Ala Pro Tyr Ala Pro Pro Gln Glu Ala Ala Thr Ala Ala Thr Ala
            100                 105                 110

Ser Ile Pro Ser Phe Ser Ala Asp Ala Ala Arg Thr Phe Ala Ala Ala
            115                 120                 125

His Gly Leu Ala Val Arg Ser Val Gly Val Arg Val Ala Asp Ala Ala
        130                 135                 140

Glu Ala Phe Arg Val Ser Val Ala Gly Gly Ala Arg Pro Ala Phe Ala
145                 150                 155                 160

Pro Ala Asp Leu Gly His Gly Phe Gly Leu Ala Glu Val Glu Leu Tyr
                165                 170                 175

Gly Asp Val Val Leu Arg Phe Val Ser Tyr Pro Asp Glu Thr Asp Leu
            180                 185                 190

Pro Phe Leu Pro Gly Phe Glu Arg Val Ser Ser Pro Gly Ala Val Asp
        195                 200                 205

Tyr Gly Leu Thr Arg Phe Asp His Val Val Gly Asn Val Pro Glu Met
    210                 215                 220

Ala Pro Val Ile Asp Tyr Met Lys Gly Phe Leu Gly Phe His Glu Phe
225                 230                 235                 240

Ala Glu Phe Thr Ala Glu Asp Val Gly Thr Thr Glu Ser Gly Leu Asn
                245                 250                 255

Ser Val Val Leu Ala Asn Asn Ser Glu Ala Val Leu Leu Pro Leu Asn
            260                 265                 270

Glu Pro Val His Gly Thr Lys Arg Arg Ser Gln Ile Gln Thr Tyr Leu
        275                 280                 285

Glu Tyr His Gly Gly Pro Gly Val Gln His Ile Ala Leu Ala Ser Asn
    290                 295                 300

Asp Val Leu Arg Thr Leu Arg Glu Met Arg Ala Arg Thr Pro Met Gly
305                 310                 315                 320

Gly Phe Glu Phe Met Arg Pro Pro Gln Ala Lys Tyr Tyr Glu Gly Val
                325                 330                 335

Arg Arg Ile Ala Gly Asp Val Leu Ser Glu Glu Gln Ile Lys Glu Cys
            340                 345                 350

Gln Glu Leu Gly Val Met Val Asp Arg Asp Asp Gln Gly Val Leu Leu
        355                 360                 365
```

```
Gln Ile Phe Thr Lys Pro Val Gly Asp Arg Pro Thr Phe Phe Leu Glu
    370                 375                 380

Met Ile Gln Arg Ile Gly Cys Met Glu Lys Asp Glu Val Gly Gln Glu
385                 390                 395                 400

Tyr Gln Lys Gly Gly Cys Gly Gly Phe Gly Lys Gly Asn Phe Ser Glu
                405                 410                 415

Leu Phe Lys Ser Ile Glu Asp Tyr Glu Lys Ser Leu Glu Val Lys Gln
                420                 425                 430

Ser Val Val Ala Gln Lys Ser
                435

<210> SEQ ID NO 31
<211> LENGTH: 439
<212> TYPE: PRT
<213> ORGANISM: Avena sativa

<400> SEQUENCE: 31

Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
                20                  25                  30

Pro Arg Ser Asp Arg Phe Pro Val Leu Ser Phe His His Val Glu Leu
            35                  40                  45

Trp Cys Ala Asp Ala Ala Ser Ala Ala Gly Arg Phe Ser Phe Ala Leu
        50                  55                  60

Gly Ala Pro Leu Ala Ala Arg Ser Asp Leu Ser Thr Gly Asn Ser Ala
65                  70                  75                  80

His Ala Ser Leu Leu Leu Arg Ser Gly Ala Leu Ala Phe Leu Phe Thr
                85                  90                  95

Ala Pro Tyr Ala Pro Pro Gln Glu Ala Ala Thr Ala Ala Thr Ala
            100                 105                 110

Ser Ile Pro Ser Phe Ser Ala Asp Ala Ala Arg Thr Phe Ala Ala Ala
        115                 120                 125

His Gly Leu Ala Val Arg Ser Val Gly Val Arg Val Ala Asp Ala Ala
130                 135                 140

Glu Ala Phe Arg Val Ser Val Ala Gly Gly Ala Arg Pro Ala Phe Ala
145                 150                 155                 160

Pro Ala Asp Leu Gly His Gly Phe Gly Leu Ala Glu Val Glu Leu Tyr
                165                 170                 175

Gly Asp Val Val Leu Arg Phe Val Ser Tyr Pro Asp Glu Thr Asp Leu
            180                 185                 190

Pro Phe Leu Pro Gly Phe Glu Arg Val Ser Ser Pro Gly Ala Val Asp
        195                 200                 205

Tyr Gly Leu Thr Arg Phe Asp His Ile Val Gly Asn Val Pro Glu Met
    210                 215                 220

Ala Pro Val Ile Asp Tyr Met Lys Gly Phe Leu Gly Phe His Glu Phe
225                 230                 235                 240

Ala Glu Phe Thr Ala Glu Asp Val Gly Thr Thr Glu Ser Gly Leu Asn
                245                 250                 255

Ser Val Val Leu Ala Asn Asn Ser Glu Ala Val Leu Leu Pro Leu Asn
            260                 265                 270

Glu Pro Val His Gly Thr Lys Arg Arg Ser Gln Ile Gln Thr Tyr Leu
        275                 280                 285

Glu Tyr His Gly Gly Pro Gly Val Gln His Ile Ala Leu Ala Ser Asn
    290                 295                 300
```

-continued

```
Asp Val Leu Arg Thr Leu Arg Glu Met Arg Ala Arg Thr Pro Met Gly
305                 310                 315                 320

Gly Phe Glu Phe Met Arg Pro Pro Gln Ala Lys Tyr Tyr Glu Gly Val
            325                 330                 335

Arg Arg Ile Ala Gly Asp Val Leu Ser Glu Glu Gln Ile Lys Glu Cys
        340                 345                 350

Gln Glu Leu Gly Val Met Val Asp Arg Asp Gln Gly Val Leu Leu
    355                 360                 365

Gln Ile Phe Thr Lys Pro Val Gly Asp Arg Pro Thr Phe Phe Leu Glu
370                 375                 380

Met Ile Gln Arg Ile Gly Cys Met Glu Lys Asp Glu Val Gly Gln Glu
385                 390                 395                 400

Tyr Gln Lys Gly Gly Cys Gly Gly Phe Gly Lys Gly Asn Phe Ser Glu
                405                 410                 415

Leu Phe Lys Ser Ile Glu Asp Tyr Glu Lys Ser Leu Glu Val Lys Gln
            420                 425                 430

Ser Val Val Ala Gln Lys Ser
        435

<210> SEQ ID NO 32
<211> LENGTH: 439
<212> TYPE: PRT
<213> ORGANISM: Avena sativa

<400> SEQUENCE: 32

Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
            20                  25                  30

Pro Arg Ser Asp Arg Phe Pro Val Leu Ser Phe His His Val Glu Leu
        35                  40                  45

Trp Cys Ala Asp Ala Ala Ser Ala Ala Gly Arg Phe Ser Phe Ala Leu
    50                  55                  60

Gly Ala Pro Leu Ala Ala Arg Ser Asp Leu Ser Thr Gly Asn Ser Ala
65                  70                  75                  80

His Ala Ser Leu Leu Leu Arg Ser Gly Ala Leu Ala Phe Leu Phe Thr
                85                  90                  95

Ala Pro Tyr Ala Pro Pro Pro Gln Glu Ala Ala Thr Ala Ala Thr Ala
            100                 105                 110

Ser Ile Pro Ser Phe Ser Ala Asp Ala Ala Arg Thr Phe Ala Ala Ala
        115                 120                 125

His Gly Leu Ala Val Arg Ser Val Gly Val Arg Val Ala Asp Ala Ala
    130                 135                 140

Glu Ala Phe Arg Val Ser Val Ala Gly Ala Arg Pro Ala Phe Ala
145                 150                 155                 160

Pro Ala Asp Leu Gly His Gly Phe Gly Leu Ala Glu Val Glu Leu Tyr
                165                 170                 175

Gly Asp Val Val Leu Arg Phe Val Ser Tyr Pro Asp Glu Thr Asp Leu
            180                 185                 190

Pro Phe Leu Pro Gly Phe Glu Arg Val Ser Ser Pro Gly Ala Val Asp
        195                 200                 205

Tyr Gly Leu Thr Arg Phe Asp His Ile Val Gly Asn Val Pro Glu Met
    210                 215                 220

Ala Pro Val Ile Asp Tyr Met Lys Gly Phe Leu Gly Phe His Glu Phe
```

```
                        225                 230                 235                 240
    Ala Glu Phe Thr Ala Glu Asp Val Gly Thr Thr Glu Ser Gly Leu Asn
                        245                 250                 255

Ser Val Val Leu Ala Asn Asn Ser Glu Ala Val Leu Leu Pro Leu Asn
                        260                 265                 270

Glu Pro Val His Gly Thr Lys Arg Arg Ser Gln Ile Gln Thr Tyr Leu
                        275                 280                 285

Glu Tyr His Gly Gly Pro Gly Val Gln His Ile Ala Leu Ala Ser Asn
                        290                 295                 300

Asp Val Leu Arg Thr Leu Arg Glu Met Arg Ala Arg Thr Pro Met Gly
    305                 310                 315                 320

Gly Phe Glu Phe Met Ala Pro Pro Gln Ala Lys Tyr Tyr Glu Gly Val
                        325                 330                 335

Arg Arg Ile Ala Gly Asp Val Leu Ser Glu Gln Ile Lys Glu Cys
                        340                 345                 350

Gln Glu Leu Gly Val Met Val Asp Arg Asp Gln Gly Val Leu Leu
                        355                 360                 365

Gln Ile Phe Thr Lys Pro Val Gly Asp Arg Pro Thr Phe Phe Leu Glu
                        370                 375                 380

Met Ile Gln Arg Ile Gly Cys Met Glu Lys Asp Glu Val Gly Gln Glu
    385                 390                 395                 400

Tyr Gln Lys Gly Gly Cys Gly Gly Phe Gly Lys Gly Asn Phe Ser Glu
                        405                 410                 415

Leu Phe Lys Ser Ile Glu Asp Tyr Glu Lys Ser Leu Glu Val Lys Gln
                        420                 425                 430

Ser Val Val Ala Gln Lys Ser
                        435

<210> SEQ ID NO 33
<211> LENGTH: 439
<212> TYPE: PRT
<213> ORGANISM: Avena sativa

<400> SEQUENCE: 33

Met Pro Pro Thr Pro Ala Thr Ala Thr Gly Ala Ala Ala Ala Ala Val
    1               5                   10                  15

Thr Pro Glu His Ala Ala Arg Ser Phe Pro Arg Val Val Arg Val Asn
                        20                  25                  30

Pro Arg Ser Asp Arg Phe Pro Val Leu Ser Phe His His Val Glu Leu
                        35                  40                  45

Trp Cys Ala Asp Ala Ala Ser Ala Ala Gly Arg Phe Ser Phe Ala Leu
                        50                  55                  60

Gly Ala Pro Leu Ala Ala Arg Ser Asp Leu Ser Thr Gly Asn Ser Ala
    65                  70                  75                  80

His Ala Ser Leu Leu Leu Arg Ser Gly Ala Leu Ala Phe Leu Phe Thr
                        85                  90                  95

Ala Pro Tyr Ala Pro Pro Gln Glu Ala Ala Thr Ala Thr Ala
                        100                 105                 110

Ser Ile Pro Ser Phe Ser Ala Asp Ala Ala Arg Thr Phe Ala Ala Ala
                        115                 120                 125

His Gly Leu Ala Val Arg Ser Val Gly Val Arg Val Ala Asp Ala Ala
                        130                 135                 140

Glu Ala Phe Arg Val Ser Val Ala Gly Gly Ala Arg Pro Ala Phe Ala
    145                 150                 155                 160
```

```
Pro Ala Asp Leu Gly His Gly Phe Gly Leu Ala Glu Val Glu Leu Tyr
                165                 170                 175
Gly Asp Val Val Leu Arg Phe Val Ser Tyr Pro Asp Glu Thr Asp Leu
            180                 185                 190
Pro Phe Leu Pro Gly Phe Glu Arg Val Ser Ser Pro Gly Ala Val Asp
        195                 200                 205
Tyr Gly Leu Thr Arg Phe Asp His Ile Val Gly Asn Val Pro Glu Met
    210                 215                 220
Ala Pro Val Ile Asp Tyr Met Lys Gly Phe Leu Gly Phe His Glu Phe
225                 230                 235                 240
Ala Glu Phe Thr Ala Glu Asp Val Gly Thr Thr Glu Ser Gly Leu Asn
                245                 250                 255
Ser Val Val Leu Ala Asn Asn Ser Glu Ala Val Leu Leu Pro Leu Asn
            260                 265                 270
Glu Pro Val His Gly Thr Lys Arg Ser Gln Ile Gln Thr Tyr Leu
        275                 280                 285
Glu Tyr His Gly Gly Pro Gly Val Gln His Ile Ala Leu Ala Ser Asn
    290                 295                 300
Asp Val Leu Arg Thr Leu Arg Glu Met Arg Ala Arg Thr Pro Met Gly
305                 310                 315                 320
Gly Phe Glu Phe Met Arg Pro Pro Gln Ala Lys Tyr Tyr Glu Gly Val
                325                 330                 335
Arg Arg Ile Ala Gly Asp Val Leu Ser Glu Glu Gln Ile Lys Glu Cys
            340                 345                 350
Gln Glu Leu Gly Val Leu Val Asp Arg Asp Gln Gly Val Leu Leu
        355                 360                 365
Gln Ile Phe Thr Lys Pro Val Gly Asp Arg Pro Thr Phe Phe Leu Glu
    370                 375                 380
Met Ile Gln Arg Ile Gly Cys Met Glu Lys Asp Glu Val Gly Gln Glu
385                 390                 395                 400
Tyr Gln Lys Gly Gly Cys Gly Gly Phe Gly Lys Gly Asn Phe Ser Glu
                405                 410                 415
Leu Phe Lys Ser Ile Glu Asp Tyr Glu Lys Ser Leu Glu Val Lys Gln
            420                 425                 430
Ser Val Val Ala Gln Lys Ser
        435

<210> SEQ ID NO 34
<211> LENGTH: 439
<212> TYPE: PRT
<213> ORGANISM: Avena sativa

<400> SEQUENCE: 34

Met Pro Pro Thr Pro Ala Thr Ala Thr Gly Ala Ala Ala Ala Ala Val
1               5                   10                  15
Thr Pro Glu His Ala Ala Arg Ser Phe Pro Arg Val Val Arg Val Asn
                20                  25                  30
Pro Arg Ser Asp Arg Phe Pro Val Leu Ser Phe His His Val Glu Leu
            35                  40                  45
Trp Cys Ala Asp Ala Ala Ser Ala Ala Gly Arg Phe Ser Phe Ala Leu
        50                  55                  60
Gly Ala Pro Leu Ala Ala Arg Ser Asp Leu Thr Gly Asn Ser Ala
65                  70                  75                  80
His Ala Ser Leu Leu Leu Arg Ser Gly Ala Leu Ala Phe Leu Phe Thr
                85                  90                  95
```

```
Ala Pro Tyr Ala Pro Pro Gln Glu Ala Ala Thr Ala Ala Thr Ala
            100                 105                 110

Ser Ile Pro Ser Phe Ser Ala Asp Ala Ala Arg Thr Phe Ala Ala Ala
        115                 120                 125

His Gly Leu Ala Val Arg Ser Val Gly Val Arg Val Ala Asp Ala Ala
    130                 135                 140

Glu Ala Phe Arg Val Ser Val Ala Gly Gly Ala Arg Pro Ala Phe Ala
145                 150                 155                 160

Pro Ala Asp Leu Gly His Gly Phe Gly Leu Ala Glu Val Glu Leu Tyr
                165                 170                 175

Gly Asp Val Val Leu Arg Phe Val Ser Tyr Pro Asp Glu Thr Asp Leu
            180                 185                 190

Pro Phe Leu Pro Gly Phe Glu Arg Val Ser Ser Pro Gly Ala Val Asp
        195                 200                 205

Tyr Gly Leu Thr Arg Phe Asp His Ile Val Gly Asn Val Pro Glu Met
    210                 215                 220

Ala Pro Val Ile Asp Tyr Met Lys Gly Phe Leu Gly Phe His Glu Phe
225                 230                 235                 240

Ala Glu Phe Thr Ala Glu Asp Val Gly Thr Thr Glu Ser Gly Leu Asn
                245                 250                 255

Ser Val Val Leu Ala Asn Asn Ser Glu Ala Val Leu Leu Pro Leu Asn
            260                 265                 270

Glu Pro Val His Gly Thr Lys Arg Arg Ser Gln Ile Gln Thr Tyr Leu
        275                 280                 285

Glu Tyr His Gly Gly Pro Gly Val Gln His Ile Ala Leu Ala Ser Asn
    290                 295                 300

Asp Val Leu Arg Thr Leu Arg Glu Met Arg Ala Arg Thr Pro Met Gly
305                 310                 315                 320

Gly Phe Glu Phe Met Lys Pro Pro Gln Ala Lys Tyr Tyr Glu Gly Val
                325                 330                 335

Arg Arg Ile Ala Gly Asp Val Leu Ser Glu Glu Ile Lys Glu Cys
            340                 345                 350

Gln Glu Leu Gly Val Met Val Asp Arg Asp Gln Gly Val Leu Leu
        355                 360                 365

Gln Ile Phe Thr Lys Pro Val Gly Asp Arg Pro Thr Phe Phe Leu Glu
    370                 375                 380

Met Ile Gln Arg Ile Gly Cys Met Glu Lys Asp Glu Val Gly Gln Glu
385                 390                 395                 400

Tyr Gln Lys Gly Gly Cys Gly Gly Phe Gly Lys Gly Asn Phe Ser Glu
                405                 410                 415

Leu Phe Lys Ser Ile Glu Asp Tyr Glu Lys Ser Leu Glu Val Lys Gln
            420                 425                 430

Ser Val Val Ala Gln Lys Ser
        435

<210> SEQ ID NO 35
<211> LENGTH: 439
<212> TYPE: PRT
<213> ORGANISM: Avena sativa

<400> SEQUENCE: 35

Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
```

```
            20              25              30
Pro Arg Ser Asp Arg Phe Pro Val Leu Ser Phe His His Val Glu Leu
        35              40              45
Trp Cys Ala Asp Ala Ala Ser Ala Ala Gly Arg Phe Ser Phe Ala Leu
        50              55              60
Gly Ala Pro Leu Ala Ala Arg Ser Asp Leu Ser Thr Gly Asn Ser Ala
65              70              75              80
His Ala Ser Leu Leu Leu Arg Ser Gly Ala Leu Ala Phe Leu Phe Thr
                85              90              95
Ala Pro Tyr Ala Pro Pro Gln Glu Ala Ala Thr Ala Ala Thr Ala
                100             105             110
Ser Ile Pro Ser Phe Ser Ala Asp Ala Ala Arg Thr Phe Ala Ala Ala
                115             120             125
His Gly Leu Ala Val Arg Ser Val Gly Val Arg Val Ala Asp Ala Ala
                130             135             140
Glu Ala Phe Arg Val Ser Val Ala Gly Ala Arg Pro Ala Phe Ala
145             150             155             160
Pro Ala Asp Leu Gly His Gly Phe Gly Leu Ala Glu Val Glu Leu Tyr
                165             170             175
Gly Asp Val Val Leu Arg Phe Val Ser Tyr Pro Asp Glu Thr Asp Leu
                180             185             190
Pro Phe Leu Pro Gly Phe Glu Arg Val Ser Ser Pro Gly Ala Val Asp
                195             200             205
Tyr Gly Leu Thr Arg Phe Asp His Leu Val Gly Asn Val Pro Glu Met
                210             215             220
Ala Pro Val Ile Asp Tyr Met Lys Gly Phe Leu Gly Phe His Glu Phe
225             230             235             240
Ala Glu Phe Thr Ala Glu Asp Val Gly Thr Thr Glu Ser Gly Leu Asn
                245             250             255
Ser Val Val Leu Ala Asn Asn Ser Glu Ala Val Leu Leu Pro Leu Asn
                260             265             270
Glu Pro Val His Gly Thr Lys Arg Arg Ser Gln Ile Gln Thr Tyr Leu
                275             280             285
Glu Tyr His Gly Gly Pro Gly Val Gln His Ile Ala Leu Ala Ser Asn
                290             295             300
Asp Val Leu Arg Thr Leu Arg Glu Met Arg Ala Arg Thr Pro Met Gly
305             310             315             320
Gly Phe Glu Phe Met Arg Pro Pro Gln Ala Lys Tyr Tyr Glu Gly Val
                325             330             335
Arg Arg Ile Ala Gly Asp Val Leu Ser Glu Glu Gln Ile Lys Glu Cys
                340             345             350
Gln Glu Leu Gly Val Met Val Asp Arg Asp Gln Gly Val Leu Leu
                355             360             365
Gln Ile Phe Thr Lys Pro Val Gly Asp Arg Pro Thr Phe Phe Leu Glu
                370             375             380
Met Ile Gln Arg Ile Gly Cys Met Glu Lys Asp Glu Val Gly Gln Glu
385             390             395             400
Tyr Gln Lys Gly Gly Cys Gly Phe Gly Lys Gly Asn Phe Ser Glu
                405             410             415
Leu Phe Lys Ser Ile Glu Asp Tyr Glu Lys Ser Leu Glu Val Lys Gln
                420             425             430
Ser Val Val Ala Gln Lys Ser
                435
```

<210> SEQ ID NO 36
<211> LENGTH: 439
<212> TYPE: PRT
<213> ORGANISM: Avena sativa

<400> SEQUENCE: 36

```
Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
                20                  25                  30

Pro Arg Ser Asp Arg Phe Pro Val Leu Ser Phe His His Val Glu Leu
            35                  40                  45

Trp Cys Ala Asp Ala Ala Ser Ala Ala Gly Arg Phe Ser Phe Ala Leu
        50                  55                  60

Gly Ala Pro Leu Ala Ala Arg Ser Asp Leu Ser Thr Gly Asn Ser Ala
65                  70                  75                  80

His Ala Ser Leu Leu Leu Arg Ser Gly Ala Leu Ala Phe Leu Phe Thr
                85                  90                  95

Ala Pro Tyr Ala Pro Pro Gln Glu Ala Thr Ala Ala Thr Ala
                100                 105                 110

Ser Ile Pro Ser Phe Ser Ala Asp Ala Ala Arg Thr Phe Ala Ala Ala
            115                 120                 125

His Gly Leu Ala Val Arg Ser Val Gly Val Arg Val Ala Asp Ala Ala
        130                 135                 140

Glu Ala Phe Arg Val Ser Val Ala Gly Gly Ala Arg Pro Ala Phe Ala
145                 150                 155                 160

Pro Ala Asp Leu Gly His Gly Phe Gly Leu Ala Glu Val Glu Leu Tyr
                165                 170                 175

Gly Asp Val Val Leu Arg Phe Val Ser Tyr Pro Asp Glu Thr Asp Leu
            180                 185                 190

Pro Phe Leu Pro Gly Phe Glu Arg Val Ser Ser Pro Gly Ala Val Asp
        195                 200                 205

Tyr Gly Leu Thr Arg Phe Asp His Ile Val Gly Asn Val Pro Glu Met
210                 215                 220

Ala Pro Val Ile Asp Tyr Met Lys Gly Phe Leu Gly Phe His Glu Phe
225                 230                 235                 240

Ala Glu Phe Thr Ala Glu Asp Val Gly Thr Thr Glu Ser Gly Leu Asn
                245                 250                 255

Ser Val Val Leu Ala Asn Asn Ser Glu Ala Val Leu Leu Pro Leu Asn
            260                 265                 270

Glu Pro Val His Gly Thr Lys Arg Ser Gln Ile Gln Thr Tyr Leu
        275                 280                 285

Glu Tyr His Gly Gly Pro Gly Val Gln His Ile Ala Leu Ala Ser Asn
290                 295                 300

Asp Val Leu Arg Thr Leu Arg Glu Met Arg Ala Arg Thr Pro Met Gly
305                 310                 315                 320

Gly Phe Glu Phe Met Arg Pro Pro Gln Ala Lys Tyr Tyr Glu Gly Val
                325                 330                 335

Arg Arg Glu Ala Gly Asp Val Leu Ser Glu Gln Ile Lys Glu Cys
            340                 345                 350

Gln Glu Leu Gly Val Met Val Asp Arg Asp Gln Gly Val Leu Leu
        355                 360                 365

Gln Ile Phe Thr Lys Pro Val Gly Asp Arg Pro Thr Phe Phe Leu Glu
```

-continued

```
                370                 375                 380
Met Ile Gln Arg Ile Gly Cys Met Glu Lys Asp Glu Val Gly Gln Glu
385                 390                 395                 400

Tyr Gln Lys Gly Gly Cys Gly Gly Phe Gly Lys Gly Asn Phe Ser Glu
                405                 410                 415

Leu Phe Lys Ser Ile Glu Asp Tyr Glu Lys Ser Leu Glu Val Lys Gln
                420                 425                 430

Ser Val Val Ala Gln Lys Ser
                435

<210> SEQ ID NO 37
<211> LENGTH: 439
<212> TYPE: PRT
<213> ORGANISM: Avena sativa

<400> SEQUENCE: 37

Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
                20                  25                  30

Pro Arg Ser Asp Arg Phe Pro Val Leu Ser Phe His His Val Glu Leu
            35                  40                  45

Trp Cys Ala Asp Ala Ala Ser Ala Ala Gly Arg Phe Ser Phe Ala Leu
50                  55                  60

Gly Ala Pro Leu Ala Ala Arg Ser Asp Leu Ser Thr Gly Asn Ser Ala
65                  70                  75                  80

His Ala Ser Leu Leu Leu Arg Ser Gly Ala Leu Ala Phe Leu Phe Thr
                85                  90                  95

Ala Pro Tyr Ala Pro Pro Gln Glu Ala Ala Thr Ala Ala Thr Ala
            100                 105                 110

Ser Ile Pro Ser Phe Ser Ala Asp Ala Ala Arg Thr Phe Ala Ala Ala
            115                 120                 125

His Gly Leu Ala Val Arg Ser Val Gly Val Arg Val Ala Asp Ala Ala
130                 135                 140

Glu Ala Phe Arg Val Ser Val Ala Gly Ala Arg Pro Ala Phe Ala
145                 150                 155                 160

Pro Ala Asp Leu Gly His Gly Phe Gly Leu Ala Glu Val Glu Leu Tyr
                165                 170                 175

Gly Asp Val Val Leu Arg Phe Val Ser Tyr Pro Asp Glu Thr Asp Leu
            180                 185                 190

Pro Phe Leu Pro Gly Phe Glu Arg Val Ser Ser Pro Gly Ala Val Asp
            195                 200                 205

Tyr Gly Leu Thr Arg Phe Asp His Leu Val Gly Asn Val Pro Glu Met
210                 215                 220

Ala Pro Val Ile Asp Tyr Met Lys Gly Phe Leu Gly Phe His Glu Phe
225                 230                 235                 240

Ala Glu Phe Thr Ala Glu Asp Val Gly Thr Thr Glu Ser Gly Leu Asn
                245                 250                 255

Ser Val Val Leu Ala Asn Asn Ser Glu Ala Val Leu Leu Pro Leu Asn
            260                 265                 270

Glu Pro Val His Gly Thr Lys Arg Arg Ser Gln Ile Gln Thr Tyr Leu
            275                 280                 285

Glu Tyr His Gly Gly Pro Gly Val Gln His Ile Ala Leu Ala Ser Asn
            290                 295                 300
```

```
Asp Val Leu Arg Thr Leu Arg Glu Met Arg Ala Arg Thr Pro Met Gly
305                 310                 315                 320

Gly Phe Glu Phe Met Arg Pro Pro Gln Ala Lys Tyr Tyr Glu Gly Val
            325                 330                 335

Arg Arg Glu Ala Gly Asp Val Leu Ser Glu Glu Gln Ile Lys Glu Cys
        340                 345                 350

Gln Glu Leu Gly Val Met Val Asp Arg Asp Gln Gly Val Leu Leu
    355                 360                 365

Gln Ile Phe Thr Lys Pro Val Gly Asp Arg Pro Thr Phe Phe Leu Glu
    370                 375                 380

Met Ile Gln Arg Ile Gly Cys Met Glu Lys Asp Glu Val Gly Gln Glu
385                 390                 395                 400

Tyr Gln Lys Gly Gly Cys Gly Gly Phe Gly Lys Gly Asn Phe Ser Glu
                405                 410                 415

Leu Phe Lys Ser Ile Glu Asp Tyr Glu Lys Ser Leu Glu Val Lys Gln
                420                 425                 430

Ser Val Val Ala Gln Lys Ser
                435

<210> SEQ ID NO 38
<211> LENGTH: 434
<212> TYPE: PRT
<213> ORGANISM: Poa annua

<400> SEQUENCE: 38

Met Pro Pro Thr Thr Ala Thr Ala Thr Ala Ala Thr Val Thr Pro
1               5                   10                  15

Glu His Ala Ala Arg Arg Phe Pro Arg Val Val Arg Val Asn Pro Arg
                20                  25                  30

Ser Asp Arg Phe Pro Val Leu Ser Phe His His Val Glu Phe Trp Cys
            35                  40                  45

Ala Asp Ala Ala Ser Ala Ala Gly Arg Phe Ser Phe Ala Leu Gly Ala
        50                  55                  60

Pro Leu Ala Ala Arg Ser Asp Leu Ser Thr Gly Asn Ser Ala His Ala
65                  70                  75                  80

Ser Leu Leu Leu Arg Ser Gly Ala Leu Ala Phe Leu Phe Thr Ala Pro
                85                  90                  95

Tyr Ala Pro Gln Pro Gln Asp Ala Asp Thr Ala Ser Ile Pro Ser Phe
                100                 105                 110

Ser Ala Asp Ala Ala Arg Ala Phe Ser Ala Ala His Gly Leu Ala Val
            115                 120                 125

Arg Ser Val Ala Val Arg Val Ala Asp Ala Ala Asp Ala Phe Arg Ala
        130                 135                 140

Ser Ile Ala Ala Gly Ala Arg Pro Ala Phe Pro Ala Asp Leu Gly
145                 150                 155                 160

Arg Gly Phe Gly Leu Ala Glu Val Glu Leu Tyr Gly Asp Val Val Leu
                165                 170                 175

Arg Phe Val Ser His Pro Asp Ala Asp Asp Ala Pro Phe Leu Pro Gly
            180                 185                 190

Phe Glu Ala Val Ser Arg Pro Gly Ala Val Asp Tyr Gly Leu Thr Arg
        195                 200                 205

Phe Asp His Val Val Gly Asn Val Pro Glu Met Gly Pro Val Ile Asp
    210                 215                 220

Tyr Ile Lys Gly Phe Met Gly Phe His Glu Phe Ala Glu Phe Thr Ala
225                 230                 235                 240
```

```
Glu Asp Val Gly Thr Thr Glu Ser Gly Leu Asn Ser Val Val Leu Ala
            245                 250                 255

Asn Asn Ser Glu Ala Val Leu Leu Pro Leu Asn Glu Pro Val His Gly
            260                 265                 270

Thr Lys Arg Arg Ser Gln Ile Gln Thr Tyr Leu Glu Tyr His Gly Gly
            275                 280                 285

Pro Gly Val Gln His Ile Ala Leu Ala Ser Ser Asp Val Leu Arg Thr
    290                 295                 300

Leu Arg Glu Met Gln Ala Arg Ser Ala Met Gly Gly Phe Glu Phe Met
305                 310                 315                 320

Arg Pro Pro Gln Pro Lys Tyr Tyr Glu Gly Val Arg Ile Ala Gly
                325                 330                 335

Asp Val Leu Ser Glu Ala Gln Ile Lys Glu Cys Gln Glu Leu Gly Val
                340                 345                 350

Met Val Asp Arg Asp Asp Gln Gly Val Leu Leu Gln Ile Phe Thr Lys
            355                 360                 365

Pro Val Gly Asp Arg Pro Thr Phe Phe Leu Glu Met Ile Gln Arg Ile
    370                 375                 380

Gly Cys Met Glu Lys Asp Glu Arg Gly Gln Glu Tyr Gln Lys Gly Gly
385                 390                 395                 400

Cys Gly Gly Phe Gly Lys Gly Asn Phe Ser Glu Leu Phe Lys Ser Ile
                405                 410                 415

Glu Asp Tyr Glu Lys Ser Leu Glu Ala Lys Gln Ser Ala Val Ala Gln
            420                 425                 430

Gln Ser

<210> SEQ ID NO 39
<211> LENGTH: 434
<212> TYPE: PRT
<213> ORGANISM: Poa annua

<400> SEQUENCE: 39

Met Pro Pro Thr Thr Ala Thr Ala Thr Ala Ala Thr Val Thr Pro
1               5                   10                  15

Glu His Ala Ala Arg Arg Phe Pro Arg Val Val Arg Val Asn Pro Arg
                20                  25                  30

Ser Asp Arg Phe Pro Val Leu Ser Phe His His Val Glu Phe Trp Cys
            35                  40                  45

Ala Asp Ala Ala Ser Ala Ala Gly Arg Phe Ser Phe Ala Leu Gly Ala
    50                  55                  60

Pro Leu Ala Ala Arg Ser Asp Leu Ser Thr Gly Asn Ser Ala His Ala
65                  70                  75                  80

Ser Leu Leu Leu Arg Ser Gly Ala Leu Ala Phe Leu Phe Thr Ala Pro
                85                  90                  95

Tyr Ala Pro Gln Pro Gln Asp Ala Asp Thr Ala Ser Ile Pro Ser Phe
                100                 105                 110

Ser Ala Asp Ala Ala Arg Ala Phe Ser Ala Ala His Gly Leu Ala Val
            115                 120                 125

Arg Ser Val Ala Val Arg Val Ala Asp Ala Ala Asp Ala Phe Arg Ala
    130                 135                 140

Ser Ile Ala Ala Gly Ala Arg Pro Ala Phe Pro Ala Asp Leu Gly
145                 150                 155                 160

Arg Gly Phe Gly Leu Ala Glu Val Glu Leu Tyr Gly Asp Val Val Leu
                165                 170                 175
```

```
Arg Phe Val Ser His Pro Asp Ala Asp Ala Pro Phe Leu Pro Gly
            180                 185                 190

Phe Glu Ala Val Ser Arg Pro Gly Ala Val Asp Tyr Gly Leu Thr Arg
        195                 200                 205

Phe Asp His Ile Val Gly Asn Val Pro Glu Met Gly Pro Val Ile Asp
        210                 215                 220

Tyr Ile Lys Gly Phe Met Gly Phe His Glu Phe Ala Glu Phe Thr Ala
225                 230                 235                 240

Glu Asp Val Gly Thr Thr Glu Ser Gly Leu Asn Ser Val Val Leu Ala
                245                 250                 255

Asn Asn Ser Glu Ala Val Leu Leu Pro Leu Asn Glu Pro Val His Gly
                260                 265                 270

Thr Lys Arg Arg Ser Gln Ile Gln Thr Tyr Leu Glu Tyr His Gly Gly
            275                 280                 285

Pro Gly Val Gln His Ile Ala Leu Ala Ser Ser Asp Val Leu Arg Thr
        290                 295                 300

Leu Arg Glu Met Gln Ala Arg Ser Ala Met Gly Gly Phe Glu Phe Met
305                 310                 315                 320

Arg Pro Pro Gln Pro Lys Tyr Tyr Glu Gly Val Arg Arg Ile Ala Gly
                325                 330                 335

Asp Val Leu Ser Glu Ala Gln Ile Lys Glu Cys Gln Glu Leu Gly Val
            340                 345                 350

Met Val Asp Arg Asp Gln Gly Val Leu Leu Gln Ile Phe Thr Lys
            355                 360                 365

Pro Val Gly Asp Arg Pro Thr Phe Phe Leu Glu Met Ile Gln Arg Ile
        370                 375                 380

Gly Cys Met Glu Lys Asp Glu Arg Gly Gln Glu Tyr Gln Lys Gly Gly
385                 390                 395                 400

Cys Gly Gly Phe Gly Lys Gly Asn Phe Ser Glu Leu Phe Lys Ser Ile
                405                 410                 415

Glu Asp Tyr Glu Lys Ser Leu Glu Ala Lys Gln Ser Ala Val Ala Gln
            420                 425                 430

Gln Ser

<210> SEQ ID NO 40
<211> LENGTH: 440
<212> TYPE: PRT
<213> ORGANISM: Alopecurus mycosuroides

<400> SEQUENCE: 40

Met Pro Pro Thr Thr Ala Thr Ala Thr Gly Ala Ala Ala Ala Ala Val
1               5                   10                  15

Thr Pro Glu His Ala Ala Arg Arg Phe Pro Arg Val Val Arg Val Asn
            20                  25                  30

Pro Arg Ser Asp Arg Phe Pro Val Leu Ala Phe His His Val Glu Phe
        35                  40                  45

Trp Cys Ala Asp Ala Ala Ser Ala Ala Gly Arg Phe Ser Phe Ala Leu
    50                  55                  60

Gly Ala Pro Leu Ala Ala Arg Ser Asp Leu Ser Thr Gly Asn Ser Ser
65                  70                  75                  80

His Ala Ser His Leu Leu Arg Ser Gly Ala Leu Ala Phe Leu Phe Thr
                85                  90                  95

Ala Pro Tyr Ala Pro Pro Gln Asp Ala Ala Asp Ala Ala Ala Thr
            100                 105                 110
```

Ala Ser Ile Pro Ser Phe Ser Thr Glu Ala Ala Arg Thr Phe Ser Ser
            115                 120                 125

Ala His Gly Leu Ala Val Arg Ser Val Ala Ile Arg Val Ala Asp Ala
        130                 135                 140

Ala Glu Ala Phe His Thr Ser Val Ala Gly Ala Arg Pro Ala Phe
145                 150                 155                 160

Ala Pro Ala Asp Leu Gly Ser Gly Phe Gly Leu Ala Glu Val Glu Leu
            165                 170                 175

Tyr Gly Asp Val Val Leu Arg Phe Val Ser His Pro Asp Gly Asp Asp
            180                 185                 190

Val Pro Phe Leu Pro Gly Phe Glu Gly Val Ser Arg Pro Gly Ala Met
            195                 200                 205

Asp Tyr Gly Leu Thr Arg Phe Asp His Val Val Gly Asn Val Pro Glu
            210                 215                 220

Met Ala Pro Val Ala Ala Tyr Met Lys Gly Phe Thr Gly Phe His Glu
225                 230                 235                 240

Phe Ala Glu Phe Thr Ala Glu Asp Val Gly Thr Ala Glu Ser Gly Leu
            245                 250                 255

Asn Ser Val Val Leu Ala Asn Asn Ser Glu Ala Val Leu Leu Pro Leu
            260                 265                 270

Asn Glu Pro Val His Gly Thr Lys Arg Arg Ser Gln Ile Gln Thr Tyr
            275                 280                 285

Leu Asp Tyr His Gly Gly Pro Gly Val Gln His Ile Ala Leu Ala Ser
            290                 295                 300

Ser Asp Val Leu Arg Thr Leu Arg Glu Met Arg Ala Arg Ser Ala Met
305                 310                 315                 320

Gly Gly Phe Glu Phe Met Arg Pro Pro Gln Ala Lys Tyr Tyr Glu Gly
            325                 330                 335

Val Arg Arg Leu Ala Gly Asp Val Leu Ser Glu Ala Gln Ile Lys Glu
            340                 345                 350

Cys Gln Glu Leu Gly Val Met Val Asp Arg Asp Gln Gly Val Leu
            355                 360                 365

Leu Gln Ile Phe Thr Lys Pro Val Gly Asp Arg Pro Thr Phe Leu
            370                 375                 380

Glu Met Ile Gln Arg Ile Gly Cys Met Glu Lys Asp Glu Ile Gly Gln
385                 390                 395                 400

Glu Tyr Gln Lys Gly Gly Cys Gly Gly Phe Gly Lys Gly Asn Phe Ser
            405                 410                 415

Glu Leu Phe Lys Ser Ile Glu Asp Tyr Glu Lys Ser Leu Glu Ala Lys
            420                 425                 430

Gln Ser Ala Val Ala Gln Gln Ser
            435                 440

<210> SEQ ID NO 41
<211> LENGTH: 440
<212> TYPE: PRT
<213> ORGANISM: Alopecurus mycosuroides

<400> SEQUENCE: 41

Met Pro Pro Thr Thr Ala Thr Ala Thr Gly Ala Ala Ala Ala Ala Val
1               5                   10                  15

Thr Pro Glu His Ala Ala Arg Arg Phe Pro Arg Val Val Arg Val Asn
            20                  25                  30

Pro Arg Ser Asp Arg Phe Pro Val Leu Ala Phe His His Val Glu Phe

```
            35                  40                  45
Trp Cys Ala Asp Ala Ala Ser Ala Ala Gly Arg Phe Ser Phe Ala Leu
 50                  55                  60

Gly Ala Pro Leu Ala Ala Arg Ser Asp Leu Ser Thr Gly Asn Ser Ser
 65                  70                  75                  80

His Ala Ser His Leu Leu Arg Ser Gly Ala Leu Ala Phe Leu Phe Thr
                 85                  90                  95

Ala Pro Tyr Ala Pro Pro Gln Asp Ala Ala Asp Ala Ala Ala Thr
                100                 105                 110

Ala Ser Ile Pro Ser Phe Ser Thr Glu Ala Ala Arg Thr Phe Ser Ser
                115                 120                 125

Ala His Gly Leu Ala Val Arg Ser Val Ala Ile Arg Val Ala Asp Ala
            130                 135                 140

Ala Glu Ala Phe His Thr Ser Val Ala Gly Ala Arg Pro Ala Phe
145                 150                 155                 160

Ala Pro Ala Asp Leu Gly Ser Gly Phe Gly Leu Ala Glu Val Glu Leu
                165                 170                 175

Tyr Gly Asp Val Val Leu Arg Phe Val Ser His Pro Asp Gly Asp Asp
                180                 185                 190

Val Pro Phe Leu Pro Gly Phe Glu Gly Val Ser Arg Pro Gly Ala Met
            195                 200                 205

Asp Tyr Gly Leu Thr Arg Phe Asp His Ile Val Gly Asn Val Pro Glu
210                 215                 220

Met Ala Pro Val Ala Ala Tyr Met Lys Gly Phe Thr Gly Phe His Glu
225                 230                 235                 240

Phe Ala Glu Phe Thr Ala Glu Asp Val Gly Thr Ala Glu Ser Gly Leu
                245                 250                 255

Asn Ser Val Val Leu Ala Asn Asn Ser Glu Ala Val Leu Leu Pro Leu
                260                 265                 270

Asn Glu Pro Val His Gly Thr Lys Arg Arg Ser Gln Ile Gln Thr Tyr
            275                 280                 285

Leu Asp Tyr His Gly Gly Pro Gly Val Gln His Ile Ala Leu Ala Ser
290                 295                 300

Ser Asp Val Leu Arg Thr Leu Arg Glu Met Arg Ala Arg Ser Ala Met
305                 310                 315                 320

Gly Gly Phe Glu Phe Met Arg Pro Pro Gln Ala Lys Tyr Tyr Glu Gly
                325                 330                 335

Val Arg Arg Leu Ala Gly Asp Val Leu Ser Glu Ala Gln Ile Lys Glu
                340                 345                 350

Cys Gln Glu Leu Gly Val Met Val Asp Arg Asp Gln Gly Val Leu
            355                 360                 365

Leu Gln Ile Phe Thr Lys Pro Val Gly Asp Arg Pro Thr Phe Phe Leu
            370                 375                 380

Glu Met Ile Gln Arg Ile Gly Cys Met Glu Lys Asp Glu Ile Gly Gln
385                 390                 395                 400

Glu Tyr Gln Lys Gly Gly Cys Gly Gly Phe Gly Lys Gly Asn Phe Ser
                405                 410                 415

Glu Leu Phe Lys Ser Ile Glu Asp Tyr Glu Lys Ser Leu Glu Ala Lys
                420                 425                 430

Gln Ser Ala Val Ala Gln Gln Ser
            435                 440

<210> SEQ ID NO 42
```

<211> LENGTH: 439
<212> TYPE: PRT
<213> ORGANISM: Avena sativa

<400> SEQUENCE: 42

Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
            20                  25                  30

Pro Arg Ser Asp Arg Phe Pro Val Leu Ser Phe His His Val Glu Leu
        35                  40                  45

Trp Cys Ala Asp Ala Ala Ser Ala Ala Gly Arg Phe Ser Phe Ala Leu
    50                  55                  60

Gly Ala Pro Leu Ala Ala Arg Ser Asp Leu Ser Thr Gly Asn Ser Ala
65                  70                  75                  80

His Ala Ser Leu Leu Leu Arg Ser Gly Ala Leu Ala Phe Leu Phe Thr
                85                  90                  95

Ala Pro Tyr Ala Pro Pro Gln Glu Ala Ala Thr Ala Ala Thr Ala
            100                 105                 110

Ser Ile Pro Ser Phe Ser Ala Asp Ala Ala Arg Thr Phe Ala Ala Ala
        115                 120                 125

His Gly Leu Ala Val Arg Ser Val Gly Val Arg Val Ala Asp Ala Ala
130                 135                 140

Glu Ala Phe Arg Val Ser Val Ala Gly Gly Ala Arg Pro Ala Phe Ala
145                 150                 155                 160

Pro Ala Asp Leu Gly His Gly Phe Gly Leu Ala Glu Val Glu Leu Tyr
                165                 170                 175

Gly Asp Val Val Leu Arg Phe Val Ser Tyr Pro Asp Glu Thr Asp Leu
            180                 185                 190

Pro Phe Leu Pro Gly Phe Glu Arg Val Ser Ser Pro Gly Ala Val Asp
        195                 200                 205

Tyr Gly Leu Thr Arg Phe Asp His Val Val Gly Asn Val Pro Glu Met
    210                 215                 220

Ala Pro Val Ile Asp Tyr Met Lys Gly Phe Leu Gly Phe His Glu Phe
225                 230                 235                 240

Ala Glu Phe Thr Ala Glu Asp Val Gly Thr Thr Glu Ser Gly Leu Asn
                245                 250                 255

Ser Val Val Leu Ala Asn Asn Ser Glu Ala Val Leu Leu Pro Leu Asn
            260                 265                 270

Glu Pro Val His Gly Thr Lys Arg Arg Ser Gln Ile Gln Thr Tyr Leu
        275                 280                 285

Glu Tyr His Gly Gly Pro Gly Val Gln His Ile Ala Leu Ala Ser Asn
    290                 295                 300

Asp Val Leu Arg Thr Leu Arg Glu Met Arg Ala Arg Thr Pro Met Gly
305                 310                 315                 320

Gly Phe Glu Phe Met Ala Pro Pro Gln Ala Lys Tyr Tyr Glu Gly Val
                325                 330                 335

Arg Arg Ile Ala Gly Asp Val Leu Ser Glu Glu Gln Ile Lys Glu Cys
            340                 345                 350

Gln Glu Leu Gly Val Leu Val Asp Arg Asp Gln Gly Val Leu Leu
        355                 360                 365

Gln Ile Phe Thr Lys Pro Val Gly Asp Arg Pro Thr Phe Phe Leu Glu
    370                 375                 380

Met Ile Gln Arg Ile Gly Cys Met Glu Lys Asp Glu Val Gly Gln Glu

```
385                 390                 395                 400
Tyr Gln Lys Gly Gly Cys Gly Gly Phe Gly Lys His Asn Phe Ser Glu
                405                 410                 415

Leu Phe Lys Ser Ile Glu Asp Tyr Glu Lys Ser Leu Glu Val Lys Gln
                420                 425                 430

Ser Val Ala Gln Lys Ser
        435

<210> SEQ ID NO 43
<211> LENGTH: 439
<212> TYPE: PRT
<213> ORGANISM: Avena sativa

<400> SEQUENCE: 43

Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
                20                  25                  30

Pro Arg Ser Asp Arg Phe Pro Val Leu Ser Phe His His Val Glu Leu
            35                  40                  45

Trp Cys Ala Asp Ala Ala Ser Ala Ala Gly Arg Phe Ser Phe Ala Leu
50                  55                  60

Gly Ala Pro Leu Ala Ala Arg Ser Asp Leu Ser Thr Gly Asn Ser Ala
65                  70                  75                  80

His Ala Ser Leu Leu Leu Arg Ser Gly Ala Leu Ala Phe Leu Phe Thr
                85                  90                  95

Ala Pro Tyr Ala Pro Pro Gln Glu Ala Ala Thr Ala Ala Thr Ala
            100                 105                 110

Ser Ile Pro Ser Phe Ser Ala Asp Ala Ala Arg Thr Phe Ala Ala Ala
        115                 120                 125

His Gly Leu Ala Val Arg Ser Val Gly Val Arg Val Ala Asp Ala Ala
130                 135                 140

Glu Ala Phe Arg Val Ser Val Ala Gly Gly Ala Arg Pro Ala Phe Ala
145                 150                 155                 160

Pro Ala Asp Leu Gly His Gly Phe Gly Leu Ala Glu Val Glu Leu Tyr
                165                 170                 175

Gly Asp Val Val Leu Arg Phe Val Ser Tyr Pro Asp Glu Thr Asp Leu
            180                 185                 190

Pro Phe Leu Pro Gly Phe Glu Arg Val Ser Ser Pro Gly Ala Val Asp
        195                 200                 205

Tyr Gly Leu Thr Arg Phe Asp His Val Val Gly Asn Val Pro Glu Met
210                 215                 220

Ala Pro Val Ile Asp Tyr Met Lys Gly Phe Leu Gly Phe His Glu Phe
225                 230                 235                 240

Ala Glu Phe Thr Ala Glu Asp Val Gly Thr Thr Glu Ser Gly Leu Asn
                245                 250                 255

Ser Val Val Leu Ala Asn Asn Ser Glu Ala Val Leu Leu Pro Leu Asn
            260                 265                 270

Glu Pro Val His Gly Thr Lys Arg Ser Gln Ile Gln Thr Tyr Leu
        275                 280                 285

Glu Tyr His Gly Gly Pro Gly Val Gln His Ile Ala Leu Ala Ser Asn
290                 295                 300

Asp Val Leu Arg Thr Leu Arg Glu Met Arg Ala Arg Thr Pro Met Gly
305                 310                 315                 320
```

Gly Phe Glu Phe Met Ala Pro Pro Gln Ala Lys Tyr Tyr Glu Gly Val
                325                 330                 335

Arg Arg Ile Ala Gly Asp Val Leu Ser Glu Glu Gln Ile Lys Glu Cys
            340                 345                 350

Gln Glu Leu Gly Val Leu Val Asp Arg Asp Gln Gly Val Leu Leu
        355                 360                 365

Gln Ile Phe Thr Lys Pro Val Gly Asp Arg Pro Thr Phe Phe Leu Glu
370                 375                 380

Met Ile Gln Arg Ile Gly Cys Met Glu Lys Asp Glu Val Gly Gln Glu
385                 390                 395                 400

Tyr Gln Lys Gly Gly Cys Gly Gly Phe Gly Lys Cys Asn Phe Ser Glu
                405                 410                 415

Leu Phe Lys Ser Ile Glu Asp Tyr Glu Lys Ser Leu Glu Val Lys Gln
            420                 425                 430

Ser Val Val Ala Gln Lys Ser
            435

<210> SEQ ID NO 44
<211> LENGTH: 439
<212> TYPE: PRT
<213> ORGANISM: Avena sativa

<400> SEQUENCE: 44

Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
            20                  25                  30

Pro Arg Ser Asp Arg Phe Pro Val Leu Ser Phe His His Val Glu Leu
        35                  40                  45

Trp Cys Ala Asp Ala Ala Ser Ala Ala Gly Arg Phe Ser Phe Ala Leu
    50                  55                  60

Gly Ala Pro Leu Ala Ala Arg Ser Asp Leu Ser Thr Gly Asn Ser Ala
65                  70                  75                  80

His Ala Ser Leu Leu Leu Arg Ser Gly Ala Leu Ala Phe Leu Phe Thr
                85                  90                  95

Ala Pro Tyr Ala Pro Pro Gln Glu Ala Ala Thr Ala Ala Thr Ala
            100                 105                 110

Ser Ile Pro Ser Phe Ser Ala Asp Ala Ala Arg Thr Phe Ala Ala Ala
        115                 120                 125

His Gly Leu Ala Val Arg Ser Val Gly Val Arg Val Ala Asp Ala Ala
    130                 135                 140

Glu Ala Phe Arg Val Ser Val Ala Gly Gly Ala Arg Pro Ala Phe Ala
145                 150                 155                 160

Pro Ala Asp Leu Gly His Gly Phe Gly Leu Ala Glu Val Glu Leu Tyr
                165                 170                 175

Gly Asp Val Val Leu Arg Phe Val Ser Tyr Pro Asp Glu Thr Asp Leu
            180                 185                 190

Pro Phe Leu Pro Gly Phe Glu Arg Val Ser Ser Pro Gly Ala Val Asp
        195                 200                 205

Tyr Gly Leu Thr Arg Phe Asp His Val Val Gly Asn Val Pro Glu Met
    210                 215                 220

Ala Pro Val Ile Asp Tyr Met Lys Gly Phe Leu Gly Phe His Glu Phe
225                 230                 235                 240

Ala Glu Phe Thr Ala Glu Asp Val Gly Thr Thr Glu Ser Gly Leu Asn
                245                 250                 255

```
Ser Val Val Leu Ala Asn Asn Ser Glu Ala Val Leu Leu Pro Leu Asn
            260                 265                 270

Glu Pro Val His Gly Thr Lys Arg Arg Ser Gln Ile Gln Thr Tyr Leu
        275                 280                 285

Glu Tyr His Gly Gly Pro Gly Val Ala His Ile Ala Leu Ala Ser Asn
    290                 295                 300

Asp Val Leu Arg Thr Leu Arg Glu Met Arg Ala Arg Thr Pro Met Gly
305                 310                 315                 320

Gly Phe Glu Phe Met Ala Pro Pro Gln Ala Lys Tyr Tyr Glu Gly Val
                325                 330                 335

Arg Arg Ile Ala Gly Asp Val Leu Ser Glu Glu Gln Ile Lys Glu Cys
            340                 345                 350

Gln Glu Leu Gly Val Leu Val Asp Arg Asp Asp Gln Gly Val Leu Leu
        355                 360                 365

Gln Ile Phe Thr Lys Pro Val Gly Asp Arg Pro Thr Phe Phe Leu Glu
    370                 375                 380

Met Ile Gln Arg Ile Gly Cys Met Glu Lys Asp Glu Val Gly Gln Glu
385                 390                 395                 400

Tyr Gln Lys Gly Gly Cys Gly Gly Phe Gly Lys Gly Asn Phe Ser Glu
                405                 410                 415

Leu Phe Lys Ser Ile Glu Asp Tyr Glu Lys Ser Leu Glu Val Lys Gln
            420                 425                 430

Ser Val Val Ala Gln Lys Ser
        435

<210> SEQ ID NO 45
<211> LENGTH: 439
<212> TYPE: PRT
<213> ORGANISM: Avena sativa

<400> SEQUENCE: 45

Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
            20                  25                  30

Pro Arg Ser Asp Arg Phe Pro Val Leu Ser Phe His His Val Glu Leu
        35                  40                  45

Trp Cys Ala Asp Ala Ala Ser Ala Ala Gly Arg Phe Ser Phe Ala Leu
    50                  55                  60

Gly Ala Pro Leu Ala Ala Arg Ser Asp Leu Ser Thr Gly Asn Ser Ala
65                  70                  75                  80

His Ala Ser Leu Leu Leu Arg Ser Gly Ala Leu Ala Phe Leu Phe Thr
                85                  90                  95

Ala Pro Tyr Ala Pro Pro Pro Gln Glu Ala Ala Thr Ala Ala Thr Ala
            100                 105                 110

Ser Ile Pro Ser Phe Ser Ala Asp Ala Ala Arg Thr Phe Ala Ala Ala
        115                 120                 125

His Gly Leu Ala Val Arg Ser Val Gly Val Arg Val Ala Asp Ala Ala
    130                 135                 140

Glu Ala Phe Arg Val Ser Val Ala Gly Gly Arg Pro Ala Phe Ala
145                 150                 155                 160

Pro Ala Asp Leu Gly His Gly Phe Gly Leu Ala Glu Val Glu Leu Tyr
                165                 170                 175

Gly Asp Val Val Leu Arg Phe Val Ser Tyr Pro Asp Glu Thr Asp Leu
```

```
                180                 185                 190
Pro Phe Leu Pro Gly Phe Glu Arg Val Ser Ser Pro Gly Ala Val Asp
            195                 200                 205

Tyr Gly Leu Thr Arg Phe Asp His Val Val Gly Asn Val Pro Glu Met
            210                 215                 220

Ala Pro Val Ile Asp Tyr Met Lys Gly Phe Leu Gly Phe His Glu Phe
225                 230                 235                 240

Ala Glu Phe Thr Ala Glu Asp Val Gly Thr Thr Glu Ser Gly Leu Asn
                245                 250                 255

Ser Val Val Leu Ala Asn Asn Ser Glu Ala Val Leu Leu Pro Leu Asn
            260                 265                 270

Glu Pro Val His Gly Thr Lys Arg Arg Ser Asn Ile Gln Thr Tyr Leu
            275                 280                 285

Glu Tyr His Gly Gly Pro Gly Val Gln His Ile Ala Leu Ala Ser Asn
            290                 295                 300

Asp Val Leu Arg Thr Leu Arg Glu Met Arg Ala Arg Thr Pro Met Gly
305                 310                 315                 320

Gly Phe Glu Phe Met Ala Pro Pro Gln Ala Lys Tyr Tyr Glu Gly Val
                325                 330                 335

Arg Arg Ile Ala Gly Asp Val Leu Ser Glu Glu Gln Ile Lys Glu Cys
            340                 345                 350

Gln Glu Leu Gly Val Leu Val Asp Arg Asp Gln Gly Val Leu Leu
            355                 360                 365

Gln Ile Phe Thr Lys Pro Val Gly Asp Arg Pro Thr Phe Phe Leu Glu
            370                 375                 380

Met Ile Gln Arg Ile Gly Cys Met Glu Lys Asp Glu Val Gly Gln Glu
385                 390                 395                 400

Tyr Gln Lys Gly Gly Cys Gly Gly Phe Gly Lys Gly Asn Phe Ser Glu
                405                 410                 415

Leu Phe Lys Ser Ile Glu Asp Tyr Glu Lys Ser Leu Glu Val Lys Gln
            420                 425                 430

Ser Val Val Ala Gln Lys Ser
            435

<210> SEQ ID NO 46
<211> LENGTH: 439
<212> TYPE: PRT
<213> ORGANISM: Avena sativa

<400> SEQUENCE: 46

Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
                20                  25                  30

Pro Arg Ser Asp Arg Phe Pro Val Leu Ser Phe His His Val Glu Leu
            35                  40                  45

Trp Cys Ala Asp Ala Ala Ser Ala Ala Gly Arg Phe Ser Phe Ala Leu
        50                  55                  60

Gly Ala Pro Leu Ala Ala Arg Ser Asp Leu Ser Thr Gly Asn Ser Ala
65                  70                  75                  80

His Ala Ser Leu Leu Leu Arg Ser Gly Ala Leu Ala Phe Leu Phe Thr
                85                  90                  95

Ala Pro Tyr Ala Pro Pro Gln Glu Ala Ala Thr Ala Ala Thr Ala
            100                 105                 110
```

```
Ser Ile Pro Ser Phe Ser Ala Asp Ala Ala Arg Thr Phe Ala Ala Ala
            115                 120                 125

His Gly Leu Ala Val Arg Ser Val Gly Val Arg Val Ala Asp Ala Ala
        130                 135                 140

Glu Ala Phe Arg Val Ser Val Ala Gly Gly Ala Arg Pro Ala Phe Ala
145                 150                 155                 160

Pro Ala Asp Leu Gly His Gly Phe Gly Leu Ala Glu Val Glu Leu Tyr
                165                 170                 175

Gly Asp Val Val Leu Arg Phe Val Ser Tyr Pro Asp Glu Thr Asp Leu
            180                 185                 190

Pro Phe Leu Pro Gly Phe Glu Arg Val Ser Ser Pro Gly Ala Val Asp
        195                 200                 205

Tyr Gly Leu Thr Arg Phe Asp His Val Val Gly Asn Val Pro Glu Met
    210                 215                 220

Ala Pro Val Ile Asp Tyr Met Lys Gly Phe Leu Gly Phe His Glu Phe
225                 230                 235                 240

Ala Glu Phe Thr Ala Glu Asp Val Gly Thr Thr Glu Ser Gly Leu Asn
                245                 250                 255

Ser Val Val Leu Ala Asn Asn Ser Glu Ala Val Leu Leu Pro Leu Asn
            260                 265                 270

Glu Pro Val His Gly Thr Lys Arg Arg Ser Gln Ile Gln Thr Tyr Leu
        275                 280                 285

Glu Tyr His Gly Gly Pro Gly Val Gly His Ile Ala Leu Ala Ser Asn
    290                 295                 300

Asp Val Leu Arg Thr Leu Arg Glu Met Arg Ala Arg Thr Pro Met Gly
305                 310                 315                 320

Gly Phe Glu Phe Met Ala Pro Pro Gln Ala Lys Tyr Tyr Glu Gly Val
                325                 330                 335

Arg Arg Ile Ala Gly Asp Val Leu Ser Glu Glu Gln Ile Lys Glu Cys
            340                 345                 350

Gln Glu Leu Gly Val Leu Val Asp Arg Asp Gln Gly Val Leu Leu
        355                 360                 365

Gln Ile Phe Thr Lys Pro Val Gly Asp Arg Pro Thr Phe Phe Leu Glu
    370                 375                 380

Met Ile Gln Arg Ile Gly Cys Met Glu Lys Asp Glu Val Gly Gln Glu
385                 390                 395                 400

Tyr Gln Lys Gly Gly Cys Gly Gly Phe Gly Lys Gly Asn Phe Ser Glu
                405                 410                 415

Leu Phe Lys Ser Ile Glu Asp Tyr Glu Lys Ser Leu Glu Val Lys Gln
            420                 425                 430

Ser Val Val Ala Gln Lys Ser
        435

<210> SEQ ID NO 47
<211> LENGTH: 439
<212> TYPE: PRT
<213> ORGANISM: Avena sativa

<400> SEQUENCE: 47

Met Pro Pro Thr Pro Ala Thr Ala Thr Gly Ala Ala Ala Ala Ala Val
1               5                   10                  15

Thr Pro Glu His Ala Ala Arg Ser Phe Pro Arg Val Val Arg Val Asn
                20                  25                  30

Pro Arg Ser Asp Arg Phe Pro Val Leu Ser Phe His His Val Glu Leu
            35                  40                  45
```

Trp Cys Ala Asp Ala Ala Ser Ala Gly Arg Phe Ser Phe Ala Leu
 50                  55                  60

Gly Ala Pro Leu Ala Ala Arg Ser Asp Leu Ser Thr Gly Asn Ser Ala
 65                  70                  75                  80

His Ala Ser Leu Leu Arg Ser Gly Ala Leu Ala Phe Leu Phe Thr
                 85                  90                  95

Ala Pro Tyr Ala Pro Pro Gln Glu Ala Thr Ala Ala Thr Ala
             100                 105                 110

Ser Ile Pro Ser Phe Ser Ala Asp Ala Ala Arg Thr Phe Ala Ala Ala
             115                 120                 125

His Gly Leu Ala Val Arg Ser Val Gly Val Arg Val Ala Asp Ala Ala
             130                 135                 140

Glu Ala Phe Arg Val Ser Val Ala Gly Ala Arg Pro Ala Phe Ala
145                 150                 155                 160

Pro Ala Asp Leu Gly His Gly Phe Gly Leu Ala Glu Val Glu Leu Tyr
                 165                 170                 175

Gly Asp Val Val Leu Arg Phe Val Ser Tyr Pro Asp Glu Thr Asp Leu
                 180                 185                 190

Pro Phe Leu Pro Gly Phe Glu Arg Val Ser Ser Pro Gly Ala Val Asp
             195                 200                 205

Tyr Gly Leu Thr Arg Phe Asp His Val Val Gly Asn Val Pro Glu Met
210                 215                 220

Ala Pro Val Ile Asp Tyr Met Lys Gly Phe Leu Gly Phe His Glu Phe
225                 230                 235                 240

Ala Glu Phe Thr Ala Glu Asp Val Gly Thr Thr Glu Ser Gly Leu Asn
                 245                 250                 255

Ser Val Val Leu Ala Asn Asn Ser Glu Ala Val Leu Leu Pro Leu Asn
             260                 265                 270

Glu Pro Val His Gly Thr Lys Arg Arg Ser Gln Ile Gln Thr Tyr Leu
             275                 280                 285

Glu Tyr His Gly Gly Pro Gly Val Gln His Ile Ala Leu Ala Ser Asn
             290                 295                 300

Asp Val Leu Arg Thr Leu Arg Glu Met Arg Ala Arg Thr Pro Met Gly
305                 310                 315                 320

Gly Phe Glu Phe Met Ala Pro Pro Gln Ala Lys Tyr Tyr Glu Gly Val
                 325                 330                 335

Arg Arg Ile Ala Gly Asp Val Leu Ser Glu Glu Gln Ile Lys Glu Cys
             340                 345                 350

Gln Glu Leu Gly Val Ala Val Asp Arg Asp Gln Gly Val Leu Leu
             355                 360                 365

Gln Ile Phe Thr Lys Pro Val Gly Asp Arg Pro Thr Phe Phe Leu Glu
             370                 375                 380

Met Ile Gln Arg Ile Gly Cys Met Glu Lys Asp Glu Val Gly Gln Glu
385                 390                 395                 400

Tyr Gln Lys Gly Gly Cys Gly Gly Phe Gly Lys Gly Asn Phe Ser Glu
                 405                 410                 415

Leu Phe Lys Ser Ile Glu Asp Tyr Glu Lys Ser Leu Glu Val Lys Gln
             420                 425                 430

Ser Val Val Ala Gln Lys Ser
             435

<210> SEQ ID NO 48
<211> LENGTH: 72

<212> TYPE: PRT
<213> ORGANISM: Petunia x hybrida

<400> SEQUENCE: 48

Met Ala Gln Ile Asn Asn Met Ala Gln Gly Ile Gln Thr Leu Asn Pro
1               5                   10                  15

Asn Ser Asn Phe His Lys Pro Gln Val Pro Lys Ser Ser Phe Leu
            20                  25                  30

Val Phe Gly Ser Lys Lys Leu Lys Asn Ser Ala Asn Ser Met Leu Val
        35                  40                  45

Leu Lys Lys Asp Ser Ile Phe Met Gln Lys Phe Cys Ser Phe Arg Ile
    50                  55                  60

Ser Ala Ser Val Ala Thr Ala Cys
65                  70

<210> SEQ ID NO 49
<211> LENGTH: 440
<212> TYPE: PRT
<213> ORGANISM: Avena sativa

<400> SEQUENCE: 49

Met Pro Pro Thr Pro Ala Thr Ala Thr Gly Ala Ala Ala Ala Val
1               5                   10                  15

Thr Pro Glu His Ala Ala Arg Ser Phe Pro Arg Val Val Arg Val Asn
            20                  25                  30

Pro Arg Ser Asp Arg Phe Pro Val Leu Ser Phe His His Val Glu Leu
        35                  40                  45

Trp Cys Ala Asp Ala Ala Ser Ala Ala Gly Arg Phe Ser Phe Ala Leu
    50                  55                  60

Gly Ala Pro Leu Ala Ala Arg Ser Asp Leu Ser Thr Gly Asn Ser Ala
65                  70                  75                  80

His Ala Ser Leu Leu Leu Arg Ser Gly Ala Leu Ala Phe Leu Phe Thr
                85                  90                  95

Ala Pro Tyr Ala Pro Pro Pro Gln Glu Ala Ala Thr Ala Ala Ala Thr
            100                 105                 110

Ala Ser Ile Pro Ser Phe Ser Ala Asp Ala Ala Arg Thr Phe Ala Ala
        115                 120                 125

Ala His Gly Leu Ala Val Arg Ser Val Gly Val Arg Val Ala Asp Ala
    130                 135                 140

Ala Glu Ala Phe Arg Val Ser Val Ala Gly Ala Arg Pro Ala Phe
145                 150                 155                 160

Ala Pro Ala Asp Leu Gly His Gly Phe Gly Leu Ala Glu Val Glu Leu
                165                 170                 175

Tyr Gly Asp Val Val Leu Arg Phe Val Ser Tyr Pro Asp Glu Thr Asp
            180                 185                 190

Leu Pro Phe Leu Pro Gly Phe Glu Arg Val Ser Ser Pro Gly Ala Val
        195                 200                 205

Asp Tyr Gly Leu Thr Arg Phe Asp His Ile Val Gly Asn Val Pro Glu
    210                 215                 220

Met Ala Pro Val Ile Asp Tyr Met Lys Gly Phe Leu Gly Phe His Glu
225                 230                 235                 240

Phe Ala Glu Phe Thr Ala Glu Asp Val Gly Thr Thr Glu Ser Gly Leu
                245                 250                 255

Asn Ser Val Val Leu Ala Asn Asn Ser Glu Ala Val Leu Leu Pro Leu
            260                 265                 270

```
Asn Glu Pro Val His Gly Thr Lys Arg Arg Ser Gln Ile Gln Thr Tyr
            275                 280                 285

Leu Glu Tyr His Gly Gly Pro Gly Val Gln His Ile Ala Leu Ala Ser
    290                 295                 300

Asn Asp Val Leu Arg Thr Leu Arg Glu Met Arg Ala Arg Thr Pro Met
305                 310                 315                 320

Gly Gly Phe Glu Phe Met Arg Pro Pro Gln Ala Lys Tyr Tyr Glu Gly
                325                 330                 335

Val Arg Arg Ile Ala Gly Asp Val Leu Ser Glu Glu Gln Ile Lys Glu
            340                 345                 350

Cys Gln Glu Leu Gly Val Met Val Asp Arg Asp Gln Gly Val Leu
            355                 360                 365

Leu Gln Ile Phe Thr Lys Pro Val Gly Asp Arg Pro Thr Phe Phe Leu
    370                 375                 380

Glu Met Ile Gln Arg Ile Gly Cys Met Glu Lys Asp Glu Val Gly Gln
385                 390                 395                 400

Glu Tyr Gln Lys Gly Gly Cys Gly Gly Phe Lys Gly Asn Phe Ser
                405                 410                 415

Glu Leu Phe Lys Ser Ile Glu Asp Tyr Glu Lys Ser Leu Glu Val Lys
            420                 425                 430

Gln Ser Val Val Ala Gln Lys Ser
            435                 440

<210> SEQ ID NO 50
<211> LENGTH: 439
<212> TYPE: PRT
<213> ORGANISM: Alopecurus mycosuroides

<400> SEQUENCE: 50

Pro Pro Thr Thr Ala Thr Ala Thr Gly Ala Ala Ala Ala Ala Val Thr
1               5                   10                  15

Pro Glu His Ala Ala Arg Arg Phe Pro Arg Val Val Arg Val Asn Pro
            20                  25                  30

Arg Ser Asp Arg Phe Pro Val Leu Ala Phe His His Val Glu Phe Trp
        35                  40                  45

Cys Ala Asp Ala Ala Ser Ala Ala Gly Arg Phe Ser Phe Ala Leu Gly
    50                  55                  60

Ala Pro Leu Ala Ala Arg Ser Asp Leu Ser Thr Gly Asn Ser Ser His
65                  70                  75                  80

Ala Ser His Leu Leu Arg Ser Gly Ala Leu Ala Phe Leu Phe Thr Ala
                85                  90                  95

Pro Tyr Ala Pro Pro Gln Asp Ala Ala Asp Ala Ala Ala Thr Ala
            100                 105                 110

Ser Ile Pro Ser Phe Ser Thr Glu Ala Ala Arg Thr Phe Ser Ser Ala
        115                 120                 125

His Gly Leu Ala Val Arg Ser Val Ala Ile Arg Val Ala Asp Ala Ala
    130                 135                 140

Glu Ala Phe His Thr Ser Val Ala Gly Gly Ala Arg Pro Ala Phe Ala
145                 150                 155                 160

Pro Ala Asp Leu Gly Ser Gly Phe Gly Leu Ala Glu Val Glu Leu Tyr
                165                 170                 175

Gly Asp Val Val Leu Arg Phe Val Ser His Pro Asp Gly Asp Val
            180                 185                 190

Pro Phe Leu Pro Gly Phe Glu Gly Val Ser Arg Pro Gly Ala Met Asp
        195                 200                 205
```

-continued

```
Tyr Gly Leu Thr Arg Phe Asp His Leu Val Gly Asn Val Pro Glu Met
        210                 215                 220

Ala Pro Val Ala Ala Tyr Met Lys Gly Phe Thr Gly Phe His Glu Phe
225                 230                 235                 240

Ala Glu Phe Thr Ala Glu Asp Val Gly Thr Ala Glu Ser Gly Leu Asn
            245                 250                 255

Ser Val Val Leu Ala Asn Asn Ser Glu Ala Val Leu Leu Pro Leu Asn
        260                 265                 270

Glu Pro Val His Gly Thr Lys Arg Arg Ser Gln Ile Gln Thr Tyr Leu
    275                 280                 285

Asp Tyr His Gly Gly Pro Gly Val Gln His Ile Ala Leu Ala Ser Ser
290                 295                 300

Asp Val Leu Arg Thr Leu Arg Glu Met Arg Ala Arg Ser Ala Met Gly
305                 310                 315                 320

Gly Phe Glu Phe Met Arg Pro Pro Gln Ala Lys Tyr Tyr Glu Gly Val
                325                 330                 335

Arg Arg Glu Ala Gly Asp Val Leu Ser Glu Ala Gln Ile Lys Glu Cys
            340                 345                 350

Gln Glu Leu Gly Val Met Val Asp Arg Asp Gln Gly Val Leu Leu
        355                 360                 365

Gln Ile Phe Thr Lys Pro Val Gly Asp Arg Pro Thr Phe Phe Leu Glu
    370                 375                 380

Met Ile Gln Arg Ile Gly Cys Met Glu Lys Asp Glu Ile Gly Gln Glu
385                 390                 395                 400

Tyr Gln Lys Gly Gly Cys Gly Gly Phe Gly Lys Gly Asn Phe Ser Glu
                405                 410                 415

Leu Phe Lys Ser Ile Glu Asp Tyr Glu Lys Ser Leu Glu Ala Lys Gln
            420                 425                 430

Ser Ala Val Ala Gln Gln Ser
        435

<210> SEQ ID NO 51
<211> LENGTH: 11208
<212> TYPE: DNA
<213> ORGANISM: Artificial Sequence
<220> FEATURE:
<223> OTHER INFORMATION: Expression cassette

<400> SEQUENCE: 51
attcctgtgg ttggcatgca catacaaatg gacgaacgga taaacctttt cacgcccttt      60
taaatatccg attattctaa taaacgctct tttctcttag gtttacccgc caatatatcc     120
tgtcaaacac tgatagttta aactgaaggc gggaaacgac aatctgatca tgagcggaga     180
attaagggag tcacgttatg accccgccg atgacgcggg acaagccgtt ttacgtttgg      240
aactgacaga accgcaacgc tgcaggaatt ggccgcagcg gccatttaaa tcaattgggc     300
gcgtacgtag cactagtgaa ttccggaccc aagcttgcat gcctgcagga attggccgca     360
gcggccattt aaatcaattg ggcgcgtgcg gccgcagctg cttgtgggga ccagacaaaa     420
aaggaatggt gcagaattgt taggcgcacc taccaaaagc atctttgcct ttattgcaaa     480
gataaagcag attcctctag tacaagtggg gaacaaaata acgtggaaaa gagctgtcct     540
gacagcccac tcactaatgc gtatgacgaa cgcagtgacg accacaaaac tcgagacttt     600
tcaacaaagg gtaatatccg gaaacctcct cggattccat tgcccagcta tctgtcactt     660
tattgtgaag atagtggaaa aggaaggtgg ctcctacaaa tgccatcatt gcgataaagg     720
```

```
aaaggctatc gttgaagatg cctctgccga cagtggtccc aaagatggac ccccacccac    780
gaggagcatc gtggaaaaag aagacgttcc aaccacgtct tcaaagcaag tggattgatg    840
tgatatctcc actgacgtaa gggatgacga acaatcccac tatccttctg caggtcgact    900
ctagaggatc ctataaatag gaagttcatt tcatttggag aggaaacctc gagtattttt    960
acaacaatta ccaacaacaa caaacaacaa acaacattac aattactatt tacaattaca   1020
catatgccac caactactgc tactgctaca ggtgctgctg ctgcagctgt tactccagaa   1080
catgctgcta gaaggttccc aagagttgtt agagttaacc caaggtctga taggttccca   1140
gttcttgctt tccatcatgt tgagttttgg tgtgctgatg ctgcttctgc tgctggaaga   1200
ttttcttttg ctcttggtgc tccacttgct gctagatctg atttgtctac tggaaactct   1260
tctcacgctt ctcaccttt gagatctggt gctcttgctt cctttcac tgctccttat     1320 gctccaccac cacaagatgc tgcagatgca gcagctactg cttctattcc atcttttca   1380 actgaggctg ctaggacttt ctcttctgct catggattgg ctgttagatc tgtggctatt   1440
agagttgcag atgctgcaga ggcttccat acttctgttg ctggtggtgc tagaccagct   1500
tttgctccag ctgatcttgg atctggattt ggacttgctg aggttgagct ttacggtgat   1560
gttgttctta gattcgtgtc tcacccagat ggtgatgatg ttccatttct tccaggattc   1620
gagggtgtta gtagaccagg tgctatggat tatggactca ctaggttcga tcaccttgtg   1680
ggaaatgttc cagaaatggc tccagttgct gcttacatga agggattcac tggatttcat   1740
gagttcgctg agttcactgc tgaggatgtt ggaactgctg agtctggact taactctgtt   1800
gtgcttgcta caactctga ggctgttctt ttgccactta atgagccagt tcacggcact   1860
aagagaagat ctcagattca gacttacctc gattaccatg gtggaccagg tgttcaacat   1920
attgctcttg cttcatctga tgtgcttagg actcttagag agatgagagc tagatctgct   1980
atgggaggat ttgagtttat gagaccacca caagctaagt attacgaagg tgttagaagg   2040
gaggctggtg atgttctttc tgaggctcaa atcaaagagt gccaagagct tggagttatg   2100
gtggatagag atgatcaggg tgtgcttctc cagattttca ctaagccagt tggagatagg   2160
ccaacattct tcttggagat gattcagagg atcggctgca tggaaaagga tgagattgga   2220
caagagtacc aaaagggcgg atgtggtgga tttggaaagg gaaatttctc cgagcttttc   2280
aagtccatcg aggattacga gaagtctctt gaggctaagc aatctgctgt tgctcaacag   2340
tcttgagagc tcttcatatg acgatcgttc aaacatttgg caataaagtt tcttaagatt   2400
gaatcctgtt gccggtcttg cgatgattat catataattt ctgttgaatt acgttaagca   2460
tgtaataatt aacatgtaat gcatgacgtt atttatgaga tgggttttta tgattagagt   2520
cccgcaatta tacatttaat acgcgataga aacaaaata tagcgcgcaa actaggataa   2580
attatcgcgc gcggtgtcat ctatgttact agatcgcgga ccgaagcttg catgcctgca   2640
ggtcgactct agaggatctg ggacccagtc aaagattcaa atagaggacc taacagaact   2700
cgccgtaaag actggcgaac agttcataca gagtctctta cgactcaatg caagaagaa   2760 aatcttcgtc aacatggtgg agcacgacac gcttgtctac tccaaaaata tcaaagatac   2820
agtctcagaa gaccaaaggg caattgagac ttttcaacaa gggtaatat ccggaaacct   2880 cctcggattc cattgcccag ctatctgtca ctttattgtg aagatagtgg aaaaggaagg   2940
tggctcctac aaatgccatc attgcgataa aggaaaggcc atcgttgaag atgcctctgc   3000
cgacagtggt cccaaagatg gacccccacc cacgaggagc atcgtggaaa agaagacgt    3060
```

```
tccaaccacg tcttcaaagc aagtggattg atgtgatatc tccactgacg taagggatga    3120
cgcacaatcc cactatcctt cgcaagaccc ttcctctata taaggaagtt catttcattt    3180
ggagaggaca cgctgaaatc actagtccac catgtctccg gagaggagac cagttgagat    3240
taggccagct acagcagctg atatggccgc ggtttgtgat atcgttaacc attacattga    3300
gacgtctaca gtgaacttta ggacagagcc acaaacacca caagagtgga ttgatgatct    3360
agagaggttg caagatagat acccttggtt ggttgctgag gttgagggtg ttgtggctgg    3420
tattgcttac gctgggccct ggaaggctag gaacgcttac gattggacag ttgagagtac    3480
tgtttacgtg tcacataggc atcaaaggtt gggcctagga tccacattgt acacacattt    3540
gcttaagtct atggaggcgc aaggttttaa gtctgtggtt gctgttatag gccttccaaa    3600
cgatccatct gttaggttgc atgaggcttt gggatacaca gcccgggta cattgcgcgc    3660 agctggatac aagcatggtg gatggcatga tgttggtttt tggcaaaggg attttgagtt    3720
gccagctcct ccaaggccag ttaggccagt tacccagatc tgaactagtg atatcggcgc    3780
catgggtcga cctgcagatc gttcaaacat ttggcaataa agtttcttaa gattgaatcc    3840
tgttgccggt cttgcgatga ttatcatata atttctgttg aattacgtta agcatgtaat    3900
aattaacatg taatgcatga cgttatttat gagatgggtt tttatgatta gagtcccgca    3960
attatacatt taatacgcga tagaaaacaa aatatagcgc gcaaactagg ataaattatc    4020
gcgcgcggtg tcatctatgt tactagatcc ggacccagct gcttgtgggg accagacaaa    4080
aaaggaatgg tgcagaattg ttaggcgcac ctaccaaaag catctttgcc tttattgcaa    4140
agataaagca gattcctcta gtacaagtgg ggaacaaaat aacgtggaaa agagctgtcc    4200
tgacagccca ctcactaatg cgtatgacga acgcagtgac gaccacaaaa ctcgagactt    4260 tcaacaaag ggtaatatcc ggaaacctcc tcggattcca ttgcccagct atctgtcact    4320
ttattgtgaa gatagtggaa aaggaaggtg gctcctacaa atgccatcat gcgataaag    4380 gaaaggctat cgttgaagat gcctctgccg acagtggtcc caaagatgga cccccaccca    4440
cgaggagcat cgtggaaaaa gaagacgttc caaccacgtc ttcaaagcaa gtggattgat    4500
gtgatatctc cactgacgta agggatgacg aacaatccca ctatccttct gccgaccct    4560 catgagcgga gaattaaggg agtcacgtta tgaccccgc cgatgacgcg gacaagccg    4620 ttttacgttt ggaactgaca gaaccgcaac gaagctttgg cagacaaagt ggcagacata    4680
ctgtcccaca aatgaagatg gaatctgtaa aagaaacgc gtgaaataat gcgtctgaca    4740
aaggttaggt cggctgcctt taatcaatac caaagtggtc cctaccacga tggaaaaact    4800
gtgcagtcgg tttggctttt tctgacgaac aaataagatt cgtggccgac aggtggggt    4860 ccaccatgtg aagcatctt cagactccaa taatggagca atgacgtaag gcttacgaa    4920 ataagtaagg gtagtttggg aaatgtccac tcacccgtca gtctataaat acttagcccc    4980
tccctcattg ttaagggagc aaaatctcag agagatagtc ctagagagag aaagagagca    5040
agtagcctag aagtggatcc caccatgtct ccggagagga gaccagttga gattaggcca    5100
gctacagcag ctgatatggc cgcggtttgt gatatcgtta accattacat tgagacgtct    5160
acagtgaact ttaggacaga gccacaaaca ccacaagagt ggattgatga tctagagagg    5220
ttgcaagata gatacccttg gttggttgct gaggttgagg gtgttgtggc tggtattgct    5280
tacgctgggc cctggaaggc taggaacgct tacgattgga cagttgagag tactgtttac    5340
gtgtcacata ggcatcaaag gttgggccta ggatctacat tgtacacaca tttgcttaag    5400
tctatggagg cgcaaggttt taagtctgtg gttgctgtta taggccttcc aaacgatcca    5460
```

-continued

```
tctgttaggt tgcatgaggc tttgggatac acagcccggg gtacattgcg cgcagctgga    5520
tacaagcatg gtggatggca tgatgttggt ttttggcaaa gggattttga gttgccagct    5580
cctccaaggc cagttaggcc agttacccag atatgagtcg agctctagat ccccgaattt    5640
ccccgatcgt tcaaacattt ggcaataaag tttcttaaga ttgaatcctg ttgccggtct    5700
tgcgatgatt atcatataat ttctgttgaa ttacgttaag catgtaataa ttaacatgta    5760
atgcatgacg ttatttatga gatgggtttt tatgattaga gtcccgcaat tatacattta    5820
atacgcgata gaaaacaaaa tatagcgcgc aaactaggat aaattatcgc gcgcggtgtc    5880
atctatgtta ctagatcggg aattgggtac catgcccggg cggccagcat ggccgtatcc    5940
gcaatgtgtt attaagttgt ctaagcgtca atttgtttac accacaatat atcctgccac    6000
cagccagcca acagctcccc gaccggcagc tcggcacaaa atcaccactc gatacaggca    6060
gcccatcaga attaattctc atgtttgaca gcttatcatc gactgcacgg tgcaccaatg    6120
cttctggcgt caggcagcca tcggaagctg tggtatggct gtgcaggtcg taaatcactg    6180
cataattcgt gtcgctcaag gcgcactccc gttctggata atgttttttg cgccgacatc    6240
ataacggttc tggcaaatat tctgaaatga gctgttgaca attaatcatc cggctcgtat    6300
aatgtgtgga attgtgagcg gataacaatt tcacacagga aacagaccat gagggaagcg    6360
ttgatcgccg aagtatcgac tcaactatca gaggtagttg gcgtcatcga gcgccatctc    6420
gaaccgacgt tgctggccgt acatttgtac ggctccgcag tggatggcgg cctgaagcca    6480
cacagtgata ttgatttgct ggttacggtg accgtaaggc ttgatgaaac aacgcggcga    6540
gctttgatca acgaccttt ggaaacttcg gcttccctg gagagagcga gattctccgc    6600
gctgtagaag tcaccattgt tgtgcacgac gacatcattc cgtggcgtta tccagctaag    6660
cgcgaactgc aatttggaga atggcagcgc aatgacattc ttgcaggtat cttcgagcca    6720
gccacgatcg acattgatct ggctatcttg ctgacaaaag caagagaaca tagcgttgcc    6780
ttggtaggtc cagcggcgga ggaactcttt gatccggttc ctgaacagga tctatttgag    6840
gcgctaaatg aaaccttaac gctatggaac tcgccgcccg actgggctgg cgatgagcga    6900
aatgtagtgc ttacgttgtc ccgcatttgg tacagcgcag taaccggcaa aatcgcgccg    6960
aaggatgtcg ctgccgactg ggcaatggag cgcctgccgg cccagtatca gcccgtcata    7020
cttgaagcta ggcaggctta tcttggacaa gaagatcgct tggcctcgcg cgcagatcag    7080
ttggaagaat ttgttcacta cgtgaaaggc gagatcacca agtagtcgg caaataaagc    7140 tctagtggat ctccgtaccc ggggatctgg ctcgcggcgg acgcacgacg ccggggcgag    7200
accataggcg atctcctaaa tcaatagtag ctgtaacctc gaagcgtttc acttgtaaca    7260
acgattgaga attttgtca taaaattgaa atacttggtt cgcattttg tcatccgcgg    7320 tcagccgcaa ttctgacgaa ctgcccattt agctggagat gattgtacat ccttcacgtg    7380
aaaatttctc aagcgctgtg aacaagggtt cagattttag attgaaaggt gagccgttga    7440
aacacgttct tcttgtcgat gacgacgtcg ctatgcggca tcttattatt gaataccta    7500 cgatccacgc cttcaaagtg accgcggtag ccgacagcac ccagttcaca agagtactct    7560
cttccgcgac ggtcgatgtc gtggttgttg atctagattt aggtcgtgaa gatgggctcg    7620
agatcgttcg taatctggcg gcaaagtctg atattccaat cataattatc agtggcgacc    7680
gccttgagga gacggataaa gttgttgcac tcgagctagg agcaagtgat tttatcgcta    7740
agccgttcag tatcagagag tttctagcac gcattcgggt tgccttgcgc gtgcgcccca    7800
```

```
acgttgtccg ctccaaagac cgacggtctt tttgttttac tgactggaca cttaatctca   7860
ggcaacgtcg cttgatgtcc gaagctggcg gtgaggtgaa acttacgca ggtgagttca    7920
atcttctcct cgcgttttta gagaaacccc gcgacgttct atcgcgcgag caacttctca   7980
ttgccagtcg agtacgcgac gaggaggttt atgacaggag tatagatgtt ctcattttga   8040
ggctgcgccg caaacttgag gcagatccgt caagccctca actgataaaa acagcaagag   8100
gtgccggtta tttcttttgac gcggacgtgc aggtttcgca cggggggacg atggcagcct  8160
gagccaattc ccagatcccc gaggaatcgg cgtgagcggt cgcaaaccat ccggcccggt   8220
acaaatcggc gcggcgctgg gtgatgacct ggtggagaag ttgaaggccg cgcaggccgc   8280
ccagcggcaa cgcatcgagg cagaagcacg ccccggtgaa tcgtggcaag cggccgctga   8340
tcgaatccgc aaagaatccc ggcaaccgcc ggcagccggt cgccgtcga ttaggaagcc    8400
gcccaagggc gacgagcaac cagattttt cgttccgatg ctctatgacg tgggcacccg    8460
cgatagtcgc agcatcatgg acgtggccgt tttccgtctg tcgaagcgtg accgacgagc   8520
tggcgaggtg atccgctacg agcttccaga cgggcacgta gaggtttccg cagggccggc   8580
cggcatggcc agtgtgtggg attacgacct ggtactgatg gcggtttccc atctaaccga   8640
atccatgaac cgataccggg aagggaaggg agacaagccc ggccgcgtgt tccgtccaca   8700
cgttgcggac gtactcaagt tctgccggcg agccgatggc ggaaagcaga aagacgacct   8760
ggtagaaacc tgcattcggt taaacaccac gcacgttgcc atgcagcgta cgaagaaggc   8820
caagaacggc cgcctggtga cggtatccga gggtgaagcc ttgattagcc gctacaagat   8880
cgtaaagagc gaaaccgggc ggccggagta catcgagatc gagctagctg attggatgta   8940
ccgcgagatc acagaaggca agaacccgga cgtgctgacg gttcaccccg attactttt   9000
gatcgatccc ggcatcggcc gttttctcta ccgcctggca cgccgcgccg caggcaaggc   9060
agaagccaga tggttgttca agacgatcta cgaacgcagt ggcagcgccg gagagttcaa   9120
gaagttctgt ttcaccgtgc gcaagctgat cgggtcaaat gacctgccgg agtacgattt   9180
gaaggaggag gcggggcagg ctggcccgat cctagtcatg cgctaccgca acctgatcga   9240
gggcgaagca tccgccggtt cctaatgtac ggagcagatg ctagggcaaa ttgccctagc   9300
aggggaaaaa ggtcgaaaag gtctcttcc tgtggatagc acgtacattg ggaacccaaa    9360
gccgtacatt gggaaccgga acccgtacat tgggaaccca aagccgtaca ttgggaaccg   9420
gtcacacatg taagtgactg atataaaaga gaaaaaggc gattttccg cctaaaactc     9480
tttaaactt attaaaactc ttaaaacccg cctggcctgt gcataactgt ctggccagcg    9540
cacagccgaa gagctgcaaa aagcgcctac ccttcggtcg ctgcgctccc tacgccccgc   9600
cgcttcgcgt cggcctatcg cggccgctgg ccgctcaaaa atggctggcc tacggccagg   9660
caatctacca gggcgcggac aagccgcgcc gtcgccactc gaccgccggc gctgaggtct   9720
gcctcgtgaa gaaggtgttg ctgactcata ccaggcctga atcgcccat catccagcca    9780
gaaagtgagg gagccacggt tgatgagagc tttgttgtag gtggaccagt tggtgatttt   9840
gaacttttgc tttgccacgg aacggtctgc gttgtcggga agatgcgtga tctgatcctt   9900
caactcagca aaagttcgat ttattcaaca aagccgccgt cccgtcaagt cagcgtaatg   9960
ctctgccagt gttacaacca attaaccaat tctgattaga aaaactcatc gagcatcaaa   10020
tgaaactgca atttattcat atcaggatta tcaataccat attttgaaa aagccgtttc    10080
tgtaatgaag gagaaaactc accgaggcag ttccatagga tggcaagatc ctggtatcgg   10140
tctgcgattc cgactcgtcc aacatcaata caacctatta atttcccctc gtcaaaaata   10200
```

```
aggttatcaa gtgagaaatc accatgagtg acgactgaat ccggtgagaa tggcaaaagc    10260
tctgcattaa tgaatcggcc aacgcgcggg gagaggcggt ttgcgtattg ggcgctcttc    10320
cgcttcctcg ctcactgact cgctgcgctc ggtcgttcgg ctgcggcgag cggtatcagc    10380
tcactcaaag gcggtaatac ggttatccac agaatcaggg gataacgcag gaaagaacat    10440
gtgagcaaaa ggccagcaaa aggccaggaa ccgtaaaaag gccgcgttgc tggcgttttt    10500
ccataggctc cgcccccctg acgagcatca caaaaatcga cgctcaagtc agaggtggcg    10560
aaacccgaca ggactataaa gataccaggc gtttccccct ggaagctccc tcgtgcgctc    10620
tcctgttccg accctgccgc ttaccggata cctgtccgcc tttctccctt cgggaagcgt    10680
ggcgctttct catagctcac gctgtaggta tctcagttcg gtgtaggtcg ttcgctccaa    10740
gctgggctgt gtgcacgaac cccccgttca gcccgaccgc tgcgccttat ccggtaacta    10800
tcgtcttgag tccaacccgg taagacacga cttatcgcca ctggcagcag ccactggtaa    10860
caggattagc agagcgaggt atgtaggcgg tgctacagag ttcttgaagt ggtggcctaa    10920
ctacggctac actagaagaa cagtatttgg tatctgcgct ctgctgaagc cagttacctt    10980
cggaaaaaga gttggtagct cttgatccgg caaacaaacc accgctggta gcggtggttt    11040
ttttgtttgc aagcagcaga ttacgcgcag aaaaaaagga tctcaagaag atcctttgat    11100
cttttctacg gggtctgacg ctcagtggaa cgaaaactca cgttaaggga ttttggtcat    11160
gagattatca aaaaggatct tcacctagat ccttttgatc cggaatta                11208
```

<210> SEQ ID NO 52
<211> LENGTH: 11208
<212> TYPE: DNA
<213> ORGANISM: Artificial Sequence
<220> FEATURE:
<223> OTHER INFORMATION: Expression cassette

<400> SEQUENCE: 52

```
attcctgtgg ttggcatgca catacaaatg gacgaacgga taaaccttttt cacgcccttt      60 taaatatccg attattctaa taaacgctct tttctcttag gtttaccccgc caatatatcc     120 tgtcaaacac tgatagttta aactgaaggc gggaaacgac aatctgatca tgagcggaga     180
attaagggag tcacgttatg accccccgccg atgacgcggg acaagccgtt ttacgtttgg     240
aactgacaga accgcaacgc tgcaggaatt ggccgcagcg gccatttaaa tcaattgggc     300
gcgtacgtag cactagtgaa ttccggaccc aagcttgcat gcctgcagga attggccgca     360
gcggccattt aaatcaattg gcgcgtgcg gccgcagctg cttgtgggga ccagacaaaa     420
aaggaatggt gcagaattgt taggcgcacc taccaaaagc atctttgcct ttattgcaaa     480
gataaagcag attcctctag tacaagtggg gaacaaaata acgtggaaaa gagctgtcct     540
gacagcccac tcactaatgc gtatgacgaa cgcagtgacg accacaaaac tcgagacttt     600
tcaacaaagg gtaatatccg gaaacctcct cggattccat tgcccagcta tctgtcactt     660
tattgtgaag atagtggaaa aggaaggtgg ctcctacaaa tgccatcatt gcgataaagg     720
aaaggctatc gttgaagatg cctctgccga cagtggtccc aaagatggac ccccacccac     780
gaggagcatc gtggaaaaag aagacgttcc aaccacgtct tcaaagcaag tggattgatg     840
tgatatctcc actgacgtaa gggatgacga caatcccac tatccttctg caggtcgact     900
ctagaggatc ctataaatag gaagttcatt tcatttggag aggaaacctc gagtattttt     960
acaacaatta ccaacaacaa caacaacaa acaacattac aattactatt tacaattaca    1020
```

```
catatgccac caactactgc tactgctaca ggtgctgctg ctgcagctgt tactccagaa    1080
catgctgcta gaaggttccc aagagttgtt agagttaacc caaggtctga taggttccca    1140
gttcttgctt tccatcatgt tgagttttgg tgtgctgatg ctgcttctgc tgctggaaga    1200
tttctttttg ctcttggtgc tccacttgct gctagatctg atttgtctac tggaaactct    1260
tctcacgctt ctcaccttt  gagatctggt gctcttgctt tccttttcac tgctccttat    1320
gctccaccac cacaagatgc tgcagatgca gcagctactg cttctattcc atctttttca    1380
actgaggctg ctaggacttt ctcttctgct catggattgg ctgttagatc tgtggctatt    1440
agagttgcag atgctgcaga ggcttttcat acttctgttg ctggtggtgc tagaccagct    1500
tttgctccag ctgatcttgg atctggattt ggacttgctg aggttgagct ttacggtgat    1560
gttgttctta gattcgtgtc tcacccagat ggtgatgatg ttccatttct tccaggattc    1620
gagggtgtta gtagaccagg tgctatggat tatggactca ctaggttcga tcaccttgtg    1680
ggaaatgttc cagaaatggc tccagttgct gcttacatga agggattcac tggatttcat    1740
gagttcgctg agttcactgc tgaggatgtt ggaactgctg agtctggact taactctgtt    1800
gtgcttgcta caactctgga ggctgttctt ttgccactta atgagccagt tcacggcact    1860
aagagaagat ctcagattca gacttacctc gattaccatg tggaccaggt gttcaacat     1920 attgctcttg cttcatctga tgtgcttagg actcttagag atgagagc   tagatctgct    1980 atgggaggat ttgagtttat gagaccacca caagctaagt attacgaagg tgttagaagg    2040
gaggctggtg atgttctttc tgaggctcaa atcaaagagt gccaagagct tggagttatg    2100
gtggatagag atgatcaggg tgtgcttctc cagattttca ctaagccagt tggagatagg    2160
ccaacattct tcttggagat gattcagagg atcggctgca tggaaaagga tgagattgga    2220
caagagtacc aaaagggcgg atgtggtgga tttggaaagg gaaatttctc cgagcttttc    2280
aagtccatcg aggattacga gaagtctctt gaggctaagc aatctgctgt tgctcaacag    2340
tcttgagagc tcttcatatg acgatcgttc aaacatttgg caataaagtt tcttaagatt    2400
gaatcctgtt gccggtcttg cgatgattat catataattt ctgttgaatt acgttaagca    2460
tgtaataatt aacatgtaat gcatgacgtt atttatgaga tgggttttta tgattagagt    2520
cccgcaatta tacatttaat acgcgataga aaacaaaata tagcgcgcaa actaggataa    2580
attatcgcgc gcggtgtcat ctatgttact agatcgcgga ccgaagcttg catgcctgca    2640
ggtcgactct agaggatctg ggacccagtc aaagattcaa atagaggacc taacagaact    2700
cgccgtaaag actggcgaac agttcataca gagtctctta cgactcaatg acaagaagaa    2760
aatcttcgtc aacatggtgg agcacgacac gcttgtctac tccaaaaata tcaaagatac    2820
agtctcagaa gaccaaaggg caattgagac ttttcaacaa agggtaatat ccggaaacct    2880
cctcggattc cattgcccag ctatctgtca ctttattgtg aagatagtgg aaaaggaagg    2940
tggctcctac aaatgccatc attgcgataa aggaaaggcc atcgttgaag atgcctctgc    3000
cgacagtggt cccaaagatg gacccccacc cacgaggagc atcgtggaaa agaagacgt     3060 tccaaccacg tcttcaaagc aagtggattg atgtgatatc tccactgacg taagggatga    3120
cgcacaatcc cactatcctt cgcaagaccc ttcctctata taaggaagtt catttcattt    3180
ggagaggaca cgctgaaatc actagtccac catgtctccg gagaggagac cagttgagat    3240
taggccagct acagcagctg atatggccgc ggtttgtgat atcgttaacc attacattga    3300
gacgtctaca gtgaactta  ggacagagcc acaaacacca caagagtgga ttgatgatct    3360
agagaggttg caagatagat acccttggtt ggttgctgag gttgagggtg ttgtggctgg    3420
```

```
tattgcttac gctgggccct ggaaggctag gaacgcttac gattggacag ttgagagtac   3480
tgtttacgtg tcacataggc atcaaaggtt gggcctagga tccacattgt acacacattt   3540
gcttaagtct atggaggcgc aaggttttaa gtctgtggtt gctgttatag gccttccaaa   3600
cgatccatct gttaggttgc atgaggcttt gggatacaca gcccggggta cattgcgcgc   3660
agctggatac aagcatggtg gatggcatga tgttggtttt tggcaaaggg attttgagtt   3720
gccagctcct ccaaggccag ttaggccagt tacccagatc tgaactagtg atatcggcgc   3780
catgggtcga cctgcagatc gttcaaacat ttggcaataa agtttcttaa gattgaatcc   3840
tgttgccggt cttgcgatga ttatcatata atttctgttg aattacgtta agcatgtaat   3900
aattaacatg taatgcatga cgttatttat gagatgggtt tttatgatta gagtcccgca   3960
attatacatt taatacgcga tagaaaacaa aatatagcgc gcaaactagg ataaattatc   4020
gcgcgcggtg tcatctatgt tactagatcc ggacccagct gcttgtgggg accagacaaa   4080
aaaggaatgg tgcagaattg ttaggcgcac ctaccaaaag catctttgcc tttattgcaa   4140
agataaagca gattcctcta gtacaagtgg ggaacaaaat aacgtggaaa agagctgtcc   4200
tgacagccca ctcactaatg cgtatgacga acgcagtgac gaccacaaaa ctcgagactt   4260
ttcaacaaag ggtaatatcc ggaaacctcc tcggattcca ttgcccagct atctgtcact   4320
ttattgtgaa gatagtggaa aaggaaggtg gctcctacaa atgccatcat tgcgataaag   4380
gaaaggctat cgttgaagat gcctctgccg acagtggtcc caaagatgga cccccaccca   4440
cgaggagcat cgtggaaaaa gaagacgttc caaccacgtc ttcaaagcaa gtggattgat   4500
gtgatatctc cactgacgta agggatgacg aacaatccca ctatccttct gccggaccct   4560
catgagcgga gaattaaggg agtcacgtta tgaccccgc cgatgacgcg gacaagccg    4620 ttttacgttt ggaactgaca gaaccgcaac gaagctttgg cagacaaagt ggcagacata   4680
ctgtcccaca aatgaagatg gaatctgtaa agaaaacgc gtgaaataat gcgtctgaca    4740
aaggttaggt cggctgcctt taatcaatac caaagtggtc cctaccacga tggaaaaact   4800
gtgcagtcgg tttggctttt tctgacgaac aaataagatt cgtggccgac aggtgggggt   4860
ccaccatgtg aaggcatctt cagactccaa taatggagca atgacgtaag ggcttacgaa   4920
ataagtaagg gtagtttggg aaatgtccac tcacccgtca gtctataaat acttagcccc   4980
tccctcattg ttaagggagc aaaatctcag agagatagtc ctagagagag aaagagagca   5040
agtagcctag aagtggatcc caccatgtct ccggagagga gaccagttga gattaggcca   5100
gctacagcag ctgatatggc cgcggtttgt gatatcgtta accattacat tgagacgtct   5160
acagtgaact ttaggacaga gccacaaaca ccacaagagt ggattgatga tctagagagg   5220
ttgcaagata gataccccttg gttggttgct gaggttgagg gtgttgtggc tggtattgct   5280
tacgctgggc cctggaaggc taggaacgct tacgattgga cagttgagag tactgtttac   5340
gtgtcacata ggcatcaaag gttgggccta ggatctacat tgtacacaca tttgcttaag   5400
tctatggagg cgcaaggttt taagtctgtg gttgctgtta taggccttcc aaacgatcca   5460
tctgttaggt tgcatgaggc tttgggatac acagcccggg gtacattgcg cgcagctgga   5520
tacaagcatg gtggatggca tgatgttggt ttttggcaaa gggattttga gttgccagct   5580
cctccaaggc cagttaggcc agttacccag atatgagtcg agctctagat ccccgaattt   5640
ccccgatcgt tcaaacattt ggcaataaag tttcttaaga ttgaatcctg ttgccggtct   5700
tgcgatgatt atcatataat ttctgttgaa ttacgttaag catgtaataa ttaacatgta   5760
```

```
atgcatgacg ttatttatga gatgggtttt tatgattaga gtcccgcaat tatacattta   5820
atacgcgata gaaaacaaaa tatagcgcgc aaactaggat aaattatcgc gcgcggtgtc   5880
atctatgtta ctagatcggg aattgggtac catgcccggg cggccagcat ggccgtatcc   5940
gcaatgtgtt attaagttgt ctaagcgtca atttgtttac accacaatat atcctgccac   6000
cagccagcca acagctcccc gaccggcagc tcggcacaaa atcaccactc gatacaggca   6060
gcccatcaga attaattctc atgtttgaca gcttatcatc gactgcacgg tgcaccaatg   6120
cttctggcgt caggcagcca tcggaagctg tggtatggct gtgcaggtcg taaatcactg   6180
cataattcgt gtcgctcaag gcgcactccc gttctggata atgttttttg cgccgacatc   6240
ataacggttc tggcaaatat tctgaaatga gctgttgaca attaatcatc cggctcgtat   6300
aatgtgtgga attgtgagcg gataacaatt tcacacagga aacagaccat gagggaagcg   6360
ttgatcgccg aagtatcgac tcaactatca gaggtagttg gcgtcatcga gcgccatctc   6420
gaaccgacgt tgctggccgt acatttgtac ggctccgcag tggatggcgg cctgaagcca   6480
cacagtgata ttgatttgct ggttacggtg accgtaaggc ttgatgaaac aacgcggcga   6540
gctttgatca acgacctttt ggaaacttcg gcttcccctg agagagcga gattctccgc   6600 gctgtagaag tcaccattgt tgtgcacgac gacatcattc cgtggcgtta ccagctaag   6660 cgcgaactgc aatttggaga atggcagcgc aatgacattc ttgcaggtat cttcgagcca   6720
gccacgatcg acattgatct ggctatcttg ctgacaaaag caagagaaca tagcgttgcc   6780
ttggtaggtc cagcggcgga ggaactcttt gatccggttc ctgaacagga tctatttgag   6840
gcgctaaatg aaaaccttaac gctatggaac tcgccgccg actgggctgg cgatgagcga   6900
aatgtagtgc ttacgttgtc ccgcattttgg tacagcgcag taaccggcaa aatcgcgccg   6960
aaggatgtcg ctgccgactg ggcaatggag cgcctgccgg cccagtatca gcccgtcata   7020
cttgaagcta ggcaggctta tcttggacaa gaagatcgct tggcctcgcg cgcagatcag   7080
ttggaagaat tgttcacta cgtgaaaggc gagatcacca agtagtcgg caaataaagc   7140 tctagtggat ctccgtaccc ggggatctgg ctcgcggcgg acgcacgacg ccggggcgag   7200
accataggcg atctcctaaa tcaatagtag ctgtaacctc gaagcgtttc acttgtaaca   7260
acgattgaga atttttgtca taaaattgaa atacttggtt cgcatttttg tcatccgcgg   7320
tcagccgcaa ttctgacgaa ctgcccattt agctggagat gattgtacat ccttcacgtg   7380
aaaatttctc aagcgctgtg aacaagggtt cagatttag attgaaaggt gagccgttga   7440
aacacgttct tcttgtcgat gacgacgtcg ctatgcggca tcttattatt gaatacctta   7500
cgatccacgc cttcaaagtg accgcggtag ccgacagcac ccagttcaca agagtactct   7560
cttccgcgac ggtcgatgtc gtggttgttg atctagattt aggtcgtgaa gatgggctcg   7620
agatcgttcg taatctggcg gcaaagtctg atattccaat cataattatc agtggcgacc   7680
gccttgagga gacggataaa gttgttgcac tcgagctagg agcaagtgat tttatcgcta   7740
agccgttcag tatcagagag tttctagcac gcattcgggt tgccttgcgc gtgcgcccca   7800
acgttgtccg ctccaaagac cgacggtctt tttgtttac tgactggaca cttaatctca   7860
ggcaacgtcg cttgatgtcc gaagctggcg gtgaggtgaa acttacggca ggtgagttca   7920
atcttctcct cgcgttttta gagaaacccc gcgacgttct atcgcgcgag caacttctca   7980
ttgccagtcg agtacgcgac gaggaggttt atgacaggag tatagatgtt ctcattttga   8040
ggctgcgccg caaacttgag gcagatccgt caagccctca actgataaaa acagcaagag   8100
gtgccggtta tttctttgac gcggacgtgc aggtttcgca cggggggacg atggcagcct   8160
```

```
gagccaattc ccagatcccc gaggaatcgg cgtgagcggt cgcaaaccat ccggcccggt    8220
acaaatcggc gcggcgctgg gtgatgacct ggtggagaag ttgaaggccg cgcaggccgc    8280
ccagcggcaa cgcatcgagg cagaagcacg ccccggtgaa tcgtggcaag cggccgctga    8340
tcgaatccga aaagaatccc ggcaaccgcc ggcagccggt gcgccgtcga ttaggaagcc    8400
gcccaagggc gacgagcaac cagatttttt cgttccgatg ctctatgacg tgggcacccg    8460
cgatagtcgc agcatcatgg acgtggccgt tttccgtctg tcgaagcgtg accgacgagc    8520
tggcgaggtg atccgctacg agcttccaga cgggcacgta gaggtttccg cagggccggc    8580
cggcatggcc agtgtgtggg attacgacct ggtactgatg gcggtttccc atctaaccga    8640
atccatgaac cgataccggg aagggaaggg agacaagccc ggccgcgtgt ccgtccaca     8700 cgttgcggac gtactcaagt tctgccggcg agccgatggc ggaaagcaga aagacgacct    8760
ggtagaaacc tgcattcggt taaacaccac gcacgttgcc atgcagcgta cgaagaaggc    8820
caagaacggc cgcctggtga cggtatccga gggtgaagcc ttgattagcc gctacaagat    8880
cgtaaagagc gaaaccgggc ggccggagta catcgagatc gagctagctg attggatgta    8940
ccgcgagatc acagaaggca agaacccgga cgtgctgacg gttcaccccg attactttt    9000 gatcgatccc ggcatcggcc gttttctcta ccgcctggca cgccgcgccg caggcaaggc    9060
agaagccaga tggttgttca agacgatcta cgaacgcagt ggcagcgccg gagagttcaa    9120
gaagttctgt ttcaccgtgc gcaagctgat cgggtcaaat gacctgccgg agtacgattt    9180
gaaggaggag gcggggcagg ctggcccgat cctagtcatg cgctaccgca acctgatcga    9240
gggcgaagca tccgccggtt cctaatgtac ggagcagatg ctagggcaaa ttgccctagc    9300
aggggaaaaa ggtcgaaaag gtctctttcc tgtggatagc acgtacattg gaacccaaa    9360 gccgtacatt gggaaccgga acccgtacat tgggaaccca aagccgtaca ttgggaaccg    9420
gtcacacatg taagtgactg atataaaaga gaaaaaaggc gattttttccg cctaaaactc    9480 tttaaaactt attaaaactc ttaaaacccg cctggcctgt gcataactgt ctggccagcg    9540
cacagccgaa gagctgcaaa aagcgcctac ccttcggtcg ctgcgctccc tacgcccgc    9600 cgcttcgcgt cggcctatcg cggccgctgg ccgctcaaaa atggctggcc tacggccagg    9660
caatctacca gggcgcggac aagccgcgcc gtcgccactc gaccgccggc gctgaggtct    9720
gcctcgtgaa gaaggtgttg ctgactcata ccaggcctga atcgccccat catccagcca    9780
gaaagtgagg gagccacggt tgatgagagc tttgttgtag gtggaccagt tggtgatttt    9840
gaacttttgc tttgccacgg aacggtctgc gttgtcggga agatgcgtga tctgatcctt    9900
caactcagca aaagttcgat ttattcaaca aagccgccgt cccgtcaagt cagcgtaatg    9960
ctctgccagt gttacaacca attaaccaat tctgattaga aaactcatc gagcatcaaa   10020 tgaaactgca atttattcat atcaggatta tcaataccat attttttgaaa aagccgtttc   10080 tgtaatgaag gagaaaactc accgaggcag ttccatagga tggcaagatc ctggtatcgg   10140
tctgcgattc cgactcgtcc aacatcaata caacctatta atttcccctc gtcaaaaata   10200
aggttatcaa gtgagaaatc accatgagtg acgactgaat ccggtgagaa tggcaaaagc   10260
tctgcattaa tgaatcggcc aacgcgcggg gagaggcggt ttgcgtattg ggcgctcttc   10320
cgcttcctcg ctcactgact cgctgcgctc ggtcgttcgg ctgcggcgag cggtatcagc   10380
tcactcaaag gcggtaatac ggttatccac agaatcaggg gataacgcag gaaagaacat   10440
gtgagcaaaa ggccagcaaa aggccaggaa ccgtaaaaag gccgcgttgc tggcgttttt   10500
```

```
ccataggctc cgccccctg acgagcatca caaaaatcga cgctcaagtc agaggtggcg    10560
aaacccgaca ggactataaa gataccaggc gtttccccct ggaagctccc tcgtgcgctc    10620
tcctgttccg accctgccgc ttaccggata cctgtccgcc tttctccctt cgggaagcgt    10680
ggcgctttct catagctcac gctgtaggta tctcagttcg gtgtaggtcg ttcgctccaa    10740
gctgggctgt gtgcacgaac ccccgttca gcccgaccgc tgcgccttat ccggtaacta    10800
tcgtcttgag tccaacccgg taagacacga cttatcgcca ctggcagcag ccactggtaa    10860
caggattagc agagcgaggt atgtaggcgg tgctacagag ttcttgaagt ggtggcctaa    10920
ctacggctac actagaagaa cagtatttgg tatctgcgct ctgctgaagc cagttacctt    10980
cggaaaaaga gttggtagct cttgatccgg caaacaaacc accgctggta gcggtggttt    11040
ttttgtttgc aagcagcaga ttacgcgcag aaaaaaagga tctcaagaag atcctttgat    11100
cttttctacg gggtctgacg ctcagtggaa cgaaaactca cgttaaggga ttttggtcat    11160
gagattatca aaaaggatct tcacctagat ccttttgatc cggaatta              11208
```

<210> SEQ ID NO 53
<211> LENGTH: 1320
<212> TYPE: DNA
<213> ORGANISM: Avena sativa

<400> SEQUENCE: 53

```
atgccaccaa ctccagctac tgctactggt gctgctgctg cagctgttac tccagaacat      60
gctgctagat cttttccaag ggttgtgaga gttaacccaa ggtctgatag gttcccagtt     120
cttctcttcc accacgttga actttggtgt gctgatgcag cttctgctgc tggaagattt     180
tcttttgctc ttggtgctcc acttgctgct aggtctgatt tgtctactgg aaattctgct     240
cacgcttctt gcttttgag gtcggtgct cttgctttcc tttttactgc tccttatgct     300
ccaccaccac aagaagctgc tacagctgct actgcttcta ttccatcttt ttcagctgat     360
gctgcaagga ctttttgctgc tgctcatgga cttgctgtta gatctgttgg agttagagtt     420
gctgatgcag ctgaggcttt cagagtttct gttgctggtg gtgctagacc agcttttgct     480
ccagctgatc ttggacatgg atttggactt gctgaggttg agcttaccgg tgatgttgtt     540
cttcgtttcg tgtcttaccc agatgagact gatcttccat tccttccagg atttgagagg     600
gtttcatctc caggtgctgt tgattatgga ctcactaggt tcgatcacgt tgtgggaaat     660
gttccagaaa tggctccagt gatcgattac atgaagggat tccttggatt ccatgagttc     720
gctgagttta ctgctgagga tgttggaact actgagtctg gacttaactc tgttgtgctt     780
gctaacaact ctgaggctgt tcttttgcca cttaatgagc cagttcacgg cactaagaga     840
agatctcaga ttcagactta ccttgagtac catggtggac caggtgttca acatattgct     900
cttgcttcta cgatgtgct taggactctt agagagatga gagctagaac tccaatggga     960
ggatttgagt ttatggctcc accacaagct aagtattacg agggtgttag aaggattgct    1020
ggtgatgttc tttccgagga acagatcaaa gagtgtcaag agcttggagt tctcgtggat    1080
agagatgatc agggtgtgct tctccagatt tcactaagc cagttggaga taggccaaca    1140
ttcttcttgg agatgattca gaggatcggc tgcatggaaa aggatgaagt tggacaagag    1200
taccaaaagg gcggatgtgg tggatttgga aagggaaatt tctccgagct tttcaagtcc    1260
atcgaggatt acgagaagtc tcttgaggtt aagcagtctg ttgtggctca gaagtcttga    1320
```

<210> SEQ ID NO 54
<211> LENGTH: 1326

```
<212> TYPE: DNA
<213> ORGANISM: Alopecurus mycosuroides

<400> SEQUENCE: 54
atgcctccga ccaccgcaac cgcaaccggt gctgcagcag cagccgttac accggaacat      60
gcagcacgtc gttttccgcg tgttgttcgt gttaatccgc gtagcgatcg ttttccggtt     120
ctggcatttc atcatgttga attttggtgt gccgatgcag caagcgcagc aggtcgtttt     180
agctttgcac tgggtgcacc gctggcagca cgtagcgatc tgagcaccgg taatagcagc     240
catgcaagcc atctgctgcg tagtggtgca ctggcatttc tgtttaccgc accgtatgca     300
ccgcctccgc aggatgcagc agatgcagcc gctaccgcca gcattccgag ctttagcacc     360
gaagcagcac gtacctttag cagcgcacat ggtctggcag ttcgtagcgt tgcaattcgt     420
gttgcagatg ccgcagaagc atttcatacc agcgttgcgg gtggtgcacg tccggcattt     480
gcaccggcag atctgggtag cggttttggt ctggccgaag ttgaactgta tggtgatgtt     540
gttctgcgtt ttgttagtca tccggatggt gatgatgttc cgtttctgcc gggttttgaa     600
ggtgttagcc gtccgggtgc aatggattat ggtctgaccc gttttgatca tgttgttggt     660
aatgttccgg aaatggcacc ggttgcagca tatatgaaag ttttaccgg ctttcatgaa     720
tttgccgaat ttaccgcaga agatgttggc accgcagaaa gcggtctgaa tagcgttgtt     780
ctggcaaata tagcgaagc agttctgctg ccgctgaatg aaccggtgca tggcaccaaa     840
cgtcgtagcc agattcagac ctatctggat tatcatggtg gtccgggtgt tcagcatatt     900
gcactggcaa gcagtgatgt tctgcgtacc ctgcgtgaaa tgcgtgcacg tagcgcaatg     960
ggtggttttg aatttatggc accgccgcag gcaaaatatt atgaaggtgt tcgtcgtctg    1020
gctggtgatg ttctgagcga agcacagatt aaagaatgtc aggaactggg cgttctggtt    1080
gatcgtgatg atcagggtgt tctgctgcag attttttacca aaccggttgg tgatcgtcgt    1140
ccgaccttt ttctggaaat gattcagcgt attggctgca tggaaaaaga tgaaattggc    1200
caggaatatc agaaaggcgg ctgtggtggt tttggtaaag gtaattttag cgaactgttt    1260
aaaagcattg aagattatga aaaaagcctg gaagccaaac agagcgcagt tgcacagcag    1320
agctaa                                                               1326

<210> SEQ ID NO 55
<211> LENGTH: 1323
<212> TYPE: DNA
<213> ORGANISM: Alopecurus mycosuroides

<400> SEQUENCE: 55
atgccaccaa ctactgctac tgctacaggt gctgctgctg cagctgttac tccagaacat      60
gctgctagaa ggttcccaag agttgttaga gttaacccaa ggtctgatag gttcccagtt     120
cttgctttcc atcatgttga gttttggtgt gctgatgctg cttctgctgc tggaagattt     180
tcttttgctc ttggtgctcc acttgctgct agatctgatt tgtctactgg aaactcttct     240
cacgcttctc acctttgag atctggtgct cttgctttcc ttttcactgc tccttatgct     300
ccaccaccac aagatgctgc agatgcagca gctactgctt ctattccatc ttttcaact     360
gaggctgcta ggactttctc ttctgctcat ggattggctg ttagatctgt ggctattaga     420
gttgcagatg ctgcagaggc tttccatact tctgttgctg gtggtgctag accagctttt     480
gctccagctg atcttggatc tggatttgga cttgctgagg ttgagcttta cggtgatgtt     540
gttcttagat tcgtgtctca cccagatggt gatgatgttc catttcttcc aggattcgag     600
```

| | |
|---|---|
| ggtgttagta gaccaggtgc tatggattat ggactcacta ggttcgatca cgttgtggga | 660 |
| aatgttccag aaatggctcc agttgctgct tacatgaagg gattcactgg atttcatgag | 720 |
| ttcgctgagt tcactgctga ggatgttgga actgctgagt ctggacttaa ctctgttgtg | 780 |
| cttgctaaca actctgaggc tgttcttttg ccacttaatg agccagttca cggcactaag | 840 |
| agaagatctc agattcagac ttacctcgat taccatggtg gaccaggtgt tcaacatatt | 900 |
| gctcttgctt catctgatgt gcttaggact cttagagaga tgagagctag atctgctatg | 960 |
| ggaggatttg agtttatggc tccaccacaa gctaagtatt acgaaggtgt tagaaggctt | 1020 |
| gctggtgatg ttcttctga ggctcaaatc aaagagtgcc aagagcttgg agttcttgtg | 1080 |
| gatagagatg atcagggtgt gcttctccag attttcacta agccagttgg agataggcca | 1140 |
| acattcttct tggagatgat tcagaggatc ggctgcatgg aaaaggatga gattggacaa | 1200 |
| gagtaccaaa agggcggatg tggtggattt ggaaagggaa atttctccga gcttttcaag | 1260 |
| tccatcgagg attacgagaa gtctcttgag gctaagcaat ctgctgttgc tcaacagtct | 1320 |
| tga | 1323 |

<210> SEQ ID NO 56
<211> LENGTH: 1323
<212> TYPE: DNA
<213> ORGANISM: Sorghum halepense

<400> SEQUENCE: 56

| | |
|---|---|
| atgcctccga ccccgaccac cgcagcagca acaggtgccg cagttgcagc agcaagcgca | 60 |
| gaacaggcag catttcgtct ggttggtcat cgtaattttg ttcgtgttaa tccgcgtagc | 120 |
| gatcgttttc ataccctggc atttcatcat gttgaactgt ggtgtgccga tgcagccagc | 180 |
| gcagcaggtc gttttagctt tggtctgggt gcaccgctgg cagcacgtag cgatctgagc | 240 |
| accggtaata ccgcacatgc aagcctgctg ctgcgttcag gtgcactggc atttctgttt | 300 |
| accgcaccgt atgcccatgg tgctgatgca gcaaccgcaa gcctgccgag ctttagcgca | 360 |
| gcagaagcac gtcgttttgc agcagatcat ggtctggcag ttcgtgccgt tgcactgcgt | 420 |
| gttgcagatg ccgaagatgc atttcgtgca agcgttgcag ccggtgcacg tccggcattt | 480 |
| gaaccggttg aactgggtct gggttttcgt ctggccgaag ttgaactgta tggtgatgtt | 540 |
| gttctgcgtt atgttagcta tccggatgat gcagatgcaa gctttctgcc gggttttgtt | 600 |
| ggtgttagca gtccgggtgc ggcagattat ggcctgcgtc gttttgatca tattgtgggt | 660 |
| aatgttccgg aactggcacc ggcagcggca tattttgcag gttttaccgg ctttcatgaa | 720 |
| tttgcagaat ttaccgcaga agatgttggc accaccgaaa gcggtctgaa tagcatggtt | 780 |
| ctggcaaata tgccgaaaaa tgttctgctg ccgctgaatg aaccggtgca tggcaccaaa | 840 |
| cgtcgtagcc agattcagac cttcctggat catcatggtg gtccgggtgt tcagcacatg | 900 |
| gcactggcaa gtgatgatgt gctgcgtacc ctgcgtgaaa tgcaggcatg tagtgcaatg | 960 |
| ggtggttttg aatttatggc accgccggca ccggaatatt atgatggtgt tcgtcgtcgt | 1020 |
| gccggtgatg ttctgaccga agcacagatt aaagaatgtc aggaactggg cgttctggtt | 1080 |
| gatcgtgatg atcagggtgt tctgctgcag atttttacca agccggttgg tgatcgcccg | 1140 |
| accttttttc tggaaattat tcagcgtatt ggttgcatgg aaaaagatga aaaaggccag | 1200 |
| gaatatcaga aaggcggttg tggtggtttt ggtaaaggta attttagcca gctgtttaaa | 1260 |
| agcattgaag attatgaaaa aagcctggaa gcaaaacagg cagctgcagc acagggtccg | 1320 |
| taa | 1323 |

<210> SEQ ID NO 57
<211> LENGTH: 1323
<212> TYPE: DNA
<213> ORGANISM: Sorghum halepense

<400> SEQUENCE: 57

| | | | | | |
|---|---|---|---|---|---|
| atgcctccga | ccccgaccac | cgcagcagca | acaggtgccg | cagttgcagc | agcaagcgca | 60 |
| gaacaggcag | catttcgtct | ggttggtcat | cgtaattttg | ttcgtgttaa | tccgcgtagc | 120 |
| gatcgttttc | ataccctggc | atttcatcat | gttgaactgt | ggtgtgccga | tgcagccagc | 180 |
| gcagcaggtc | gttttagctt | tggtctgggt | gcaccgctgg | cagcacgtag | cgatctgagc | 240 |
| accggtaata | ccgcacatgc | aagcctgctg | ctgcgttcag | gtgcactggc | atttctgttt | 300 |
| accgcaccgt | atgcccatgg | tgctgatgca | gcaaccgcaa | gcctgccgag | ctttagcgca | 360 |
| gcagaagcac | gtcgttttgc | agcagatcat | ggtctggcag | ttcgtgccgt | tgcactgcgt | 420 |
| gttgcagatg | ccgaagatgc | atttcgtgca | agcgttgcag | ccggtgcacg | tccggcattt | 480 |
| gaaccggttg | aactgggtct | gggttttcgt | ctggccgaag | ttgaactgta | tggtgatgtt | 540 |
| gttctgcgtt | atgttagcta | tccggatgat | gcagatgcaa | gctttctgcc | gggttttgtt | 600 |
| ggtgttacca | gtccgggtgc | ggcagattat | ggcctgaaac | gttttgatca | tattgtgggt | 660 |
| aatgttccgg | aactggcacc | ggcagcggca | tattttgcag | ttttaccgg | ctttcatgaa | 720 |
| tttgcagaat | ttaccgcaga | gatgttggc | accaccgaaa | gcggtctgaa | tagcatggtt | 780 |
| ctggcaaata | tgccgaaaaa | tgttctgctg | ccgctgaatg | aaccggtgca | tggcaccaaa | 840 |
| cgtcgtagcc | agattcagac | ctttctggat | catcatggtg | gtccgggtgt | tcagcacatg | 900 |
| gcactggcaa | gtgatgatgt | gctgcgtacc | ctgcgtgaaa | tgcaggcacg | tagtgcaatg | 960 |
| ggtggttttg | aatttatggc | accgccggca | ccggaatatt | atgatggtgt | tcgtcgtcgt | 1020 |
| gccggtgatg | ttctgaccga | agcacagatt | aaagaatgtc | aggaactggg | cgttctggtt | 1080 |
| gatcgtgatg | atcagggtgt | tctgctgcag | attttacca | aaccggttgg | tgatcgcccg | 1140 |
| acctttttc | tggaaattat | tcagcgtatt | ggttgcatgg | aaaaagatga | aaaaggccag | 1200 |
| gaatatcaga | aaggcggttg | tggtggtttt | ggtaaaggta | attttagcca | gctgtttaaa | 1260 |
| agcattgaag | attatgaaaa | aagcctggaa | gcaaaacagg | cagctgcagc | acagggtccg | 1320 |
| taa | | | | | | 1323 |

<210> SEQ ID NO 58
<211> LENGTH: 1311
<212> TYPE: DNA
<213> ORGANISM: Poa annua

<400> SEQUENCE: 58

| | | | | | |
|---|---|---|---|---|---|
| atgcctccga | ccaccgcaac | cgccaccgca | gcagcaaccg | ttacaccgga | acatgcagca | 60 |
| cgtcgttttc | cgcgtgttgt | tcgtgttaat | ccgcgtagcg | atcgttttcc | ggttctgagc | 120 |
| tttcatcatg | ttgaattttg | gtgtgccgat | gcagcaagcg | cagcaggtcg | ttttagcttt | 180 |
| gcactgggtg | caccgctggc | agcacgtagc | gatctgagca | ccggtaatag | cgcacatgca | 240 |
| agcctgctgc | tgcgttcagg | tgcactggca | tttctgttta | ccgcaccgta | tgcaccgcag | 300 |
| ccgcaggatg | cagataccgc | aagcattccg | agctttagcg | cagatgcagc | acgtgcattt | 360 |
| agcgcagcac | atggtctggc | agttcgtagc | gttgcagttc | gtgttgcaga | tgccgcagat | 420 |
| gcatttcgtg | caagcattgc | agccggtgca | cgtccggcat | ttgcaccggc | agatctgggt | 480 |

| | |
|---|---|
| cgtggttttg gtctggccga agttgaactg tatggtgatg ttgttctgcg ttttgttagc | 540 |
| catccggatg cagatgatgc accgccgttt ctgccgggtt ttgaagcagt tagccgtcgt | 600 |
| ccgggtgccg ttgattatgg tctgacccgt tttgatcatg ttgttggtaa tgttccggaa | 660 |
| atgggtccgg tgattgatta tattaaaggc tttatgggct ttcatgaatt tgccgaattt | 720 |
| accgcagaag atgttggcac caccgaaagc ggtctgaata gcgttgttct ggcaaataat | 780 |
| agcgaagcag ttctgctgcc gctgaatgaa ccggtgcatg gcaccaaacg tcgtagccag | 840 |
| attcagacct atctggaata tcatggtggt ccgggtgttc agcatattgc actggcaagc | 900 |
| agtgatgttc tgcgtaccct gcgtgaaatg caggcacgtt cagcaatggg tggttttgaa | 960 |
| tttatggcac cgccgcagcc gaaatattat gaaggtgttc gtcgtattgc cggtgatgtt | 1020 |
| ctgagcgaag cacagattaa agaatgtcag gaactgggcg ttctggttga tcgtgatgat | 1080 |
| cagggtgttc tgctgcagat ttttaccaaa ccggttggtg atcgtccgac cttttttctg | 1140 |
| gaaatgattc agcgtattgg ctgcatgaaa aaagatgaac gtggtcagga atatcagaaa | 1200 |
| ggcggttgtg gcggttttgg taaaggtaat tttagcgaac tgtttaaaag cattgaagat | 1260 |
| tatgaaaaaa gcctggaagc caaacagagc gcagttgcac agcagagcta a | 1311 |

<210> SEQ ID NO 59
<211> LENGTH: 1305
<212> TYPE: DNA
<213> ORGANISM: Poa annua

<400> SEQUENCE: 59

| | |
|---|---|
| atgccaccaa ctactgctac tgctacagct gctgctactg ttactccaga acatgctgct | 60 |
| agaaggttcc caagagttgt tagagttaac ccaaggtctg ataggttccc agttctttct | 120 |
| ttccaccacg ttgaattttg gtgtgctgat gctgcttctg ctgctggaag attttctttt | 180 |
| gctcttggtg ctccacttgc tgctagatct gatttgtcta ctggaaattc tgctcacgct | 240 |
| tctttgcttt tgaggtctgg tgctcttgct ttccttttta ctgctcccta tgctccacaa | 300 |
| ccacaggatg ctgatactgc atcaattcca tctttctcag ctgatgctgc aagggctttt | 360 |
| tctgctgctc atggattggc tgttagatct gttgctgtta gagttgctga tgcagctgat | 420 |
| gctttcagag cttctattgc tgcaggtgct agaccagctt ttgctccagc tgatcttgga | 480 |
| agaggatttg gacttgctga ggttgagctt acggtgatg ttgttcttag attcgtgtct | 540 |
| cacccagatg ctgatgatgc tccatttctt ccaggatttg aggctgtttc tagaccaggt | 600 |
| gctgttgatt atggactcac taggttcgat cacgttgtgg gaaatgttcc agaaatggga | 660 |
| ccagtgatcg attacatcaa gggattcatg ggattccatg agttcgctga gtttactgct | 720 |
| gaggatgttg gaactactga gtctggactt aactctgttg tgcttgctaa caactctgag | 780 |
| gctgttcttt tgccacttaa tgagccagtt cacggcacta agagaagatc tcagattcag | 840 |
| acttaccttg agtaccatgg tggaccaggt gttcaacata ttgctcttgc ttcatctgat | 900 |
| gtgcttagga ctcttagaga gatgcaagct agatctgcta tgggaggatt tgagtttatg | 960 |
| gctccaccac aacctaagta ttacgagggt gttagaagga ttgctggtga tgttcttccc | 1020 |
| gaggctcaaa tcaaagagtg tcaagagctt ggagtgcttg tggatagaga tgatcagggt | 1080 |
| gtgcttctcc agattttcac taagccagtt ggagataggc caacattctt cttggagatg | 1140 |
| attcagagga tcggctgcat ggaaaaggat gagagaggtc aagagtatca aaagggcgga | 1200 |
| tgtggtggat ttgaaagggg aaatttctcc gagcttttca gtccatcga ggattacgag | 1260 |
| aagtctcttg aggctaagca atctgctgtt gctcaacagt cttga | 1305 |

<210> SEQ ID NO 60
<211> LENGTH: 1323
<212> TYPE: DNA
<213> ORGANISM: Lolium multiflorum

<400> SEQUENCE: 60

| | |
|---|---|
| atgcctccga caccggcaac cgcaaccggt gctgcagcag cagcagttac accggaacat | 60 |
| gcagcacgta gctttccgcg tgttgttcgt gttaatccgc gtagcgatcg ttttccggtt | 120 |
| ctgagctttc atcatgttga actgtggtgt gccgatgcag caagcgcagc aggtcgtttt | 180 |
| agctttgcac tgggtgctcc gctggcagcc cgtagcgatc tgagcaccgg taatagcgca | 240 |
| catgcaagcc tgctgctgcg tagcggtgca ctggcatttc tgtttaccgc accgtatgca | 300 |
| ccgcctccgc aggaagcagc aaccgcagct gcaaccgcaa gcattccgag ctttagcgca | 360 |
| gatgcagccc gtacctttgc agcagcacat ggtctggcag ttcgtagcgt tggtgttcgt | 420 |
| gttgccgatg cagcggaagc atttcgtgtt agcgttgccg gtggtgcacg tccggcattt | 480 |
| gcaccggcag atctgggtca tggttttggt ctggccgaag ttgaactgta tggtgatgtt | 540 |
| gttctgcgtt ttgttagcta tccggatgaa accgatctgc cgtttctgcc gggttttgaa | 600 |
| cgtgttagca gtccgggtgc cgttgattat ggtctgaccc gttttgatca tgttgttggt | 660 |
| aatgttccgg aaatggcacc ggttattgat tatatgaaag ctttctggg ctttcatgaa | 720 |
| tttgcagaat ttaccgcaga agatgttggc accaccgaaa gcggtctgaa tagcgttgtt | 780 |
| ctggcaaata tagcgaaaa tgttctgctg ccgctgaatg aaccggtgca tggcaccaaa | 840 |
| cgtcgtagcc agattcagac ctatctggat tatcatggtg gtccgggtgt tcagcatatt | 900 |
| gcactggcaa gcaccgatgt tctgcgtacc ctgcgtgaaa tgcgtgcacg taccccgatg | 960 |
| ggtggttttg aatttatggc accgccgcag gcaaaatatt atgaaggtgt tcgtcgtatt | 1020 |
| gccggtgatg ttctgagcga agaacaaatt aaagaatgtc aggaactggg cgttctggtt | 1080 |
| gatcgtgatg atcagggtgt tctgctgcag attttttacca aaccggttgg tgatcgtccg | 1140 |
| accttttttc tggaaatgat tcagcgtatt ggctgcatgg aaaaagatga agttggtcag | 1200 |
| gaatatcaga aaggcggttg tggtggtttt ggtaaaggta ttttagcga actgtttaaa | 1260 |
| agcattgaag attatgaaaa aaccctggaa gccaaacaga gcgttgttgc acagaaaagc | 1320 |
| taa | 1323 |

<210> SEQ ID NO 61
<211> LENGTH: 1320
<212> TYPE: DNA
<213> ORGANISM: Avena sativa

<400> SEQUENCE: 61

| | |
|---|---|
| atgccaccaa ctccagctac tgctactggt gctgctgctg cagctgttac tccagaacat | 60 |
| gctgctagat cttttccaag ggttgtgaga gttaacccaa ggtctgatag gttcccagtt | 120 |
| ctttctttcc accacgttga actttggtgt gctgatgcag cttctgctgc tggaagattt | 180 |
| tcttttgctc ttggtgctcc acttgctgct aggtctgatt tgtctactgg aaattctgct | 240 |
| cacgcttctt tgcttttgag gtctggtgct cttgctttcc tttttactgc tccttatgct | 300 |
| ccaccaccac aagaagctgc tacagctgct actgcttcta ttccatcttt ttcagctgat | 360 |
| gctgcaagga cttttgctgc tgctcatgga cttgctgtta gatctgttgg agttagagtt | 420 |
| gctgatgcag ctgaggcttt cagagtttct gttgctggtg gtgctagacc agcttttgct | 480 |

```
ccagctgatc ttggacatgg atttggactt gctgaggttg agctttacgg tgatgttgtt        540
cttcgtttcg tgtcttaccc agatgagact gatcttccat tccttccagg atttgagagg        600
gttcatctc caggtgctgt tgattatgga ctcactaggt tcgatcacgt tgtgggaaat         660
gttccagaaa tggctccagt gatcgattac atgaagggat tccttggatt ccatgagttc        720
gctgagttta ctgctgagga tgttggaact actgagtctg gacttaactc tgttgtgctt        780
gctaacaact ctgaggctgt tcttttgcca cttaatgagc cagttcacgg cactaagaga        840
agatctcaga ttcagactta ccttgagtac catggtggac caggtgttca acatattgct        900
cttgcttcta acgatgtgct taggactctt agagagatga gagctagaac tccaatggga        960
ggatttgagt ttatggctcc accacaagct aagtattacg agggtgttag aaggattgct       1020
ggtgatgttc tttccgagga acagatcaaa gagtgtcaag agcttggagt tatggtggat       1080
agagatgatc agggtgtgct tctccagatt ttcactaagc cagttggaga taggccaaca       1140
ttcttcttgg agatgattca gaggatcggc tgcatggaaa aggatgaagt tggacaagag       1200
taccaaaagg gcggatgtgg tggatttgga aagggaaatt tctccgagct tttcaagtcc       1260
atcgaggatt acgagaagtc tcttgaggtt aagcagtctg ttgtggctca gaagtcttga       1320
```

<210> SEQ ID NO 62
<211> LENGTH: 1320
<212> TYPE: DNA
<213> ORGANISM: Avena sativa

<400> SEQUENCE: 62

```
atgccaccaa ctccagctac tgctactggt gctgctgctg cagctgttac tccagaacat         60
gctgctagat cttttccaag ggttgtgaga gttaacccaa ggtctgatag gttcccagtt        120
cttctttccc accacgttga actttggtgt gctgatgcag cttctgctgc tggaagattt        180
tcttttgctc ttggtgctcc acttgctgct aggtctgatt tgtctactgg aaattctgct        240
cacgcttctt tgcttttgag gtctggtgct cttgctttcc tttttactgc tccttatgct        300
ccaccaccac aagaagctgc tacagctgct actgcttcta ttccatcttt ttcagctgat        360
gctgcaagga cttttgctgc tgctcatgga cttgctgtta gatctgttgg agttagagtt        420
gctgatgcag ctgaggcttt cagagtttct gttgctggtg gtgctagacc agcttttgct        480
ccagctgatc ttggacatgg atttggactt gctgaggttg agctttacgg tgatgttgtt        540
cttcgtttcg tgtcttaccc agatgagact gatcttccat tccttccagg atttgagagg        600
gttcatctc caggtgctgt tgattatgga ctcactaggt tcgatcacat tgtgggaaat         660
gttccagaaa tggctccagt gatcgattac atgaagggat tccttggatt ccatgagttc        720
gctgagttta ctgctgagga tgttggaact actgagtctg gacttaactc tgttgtgctt        780
gctaacaact ctgaggctgt tcttttgcca cttaatgagc cagttcacgg cactaagaga        840
agatctcaga ttcagactta ccttgagtac catggtggac caggtgttca acatattgct        900
cttgcttcta acgatgtgct taggactctt agagagatga gagctagaac tccaatggga        960
ggatttgagt ttatggctcc accacaagct aagtattacg agggtgttag aaggattgct       1020
ggtgatgttc tttccgagga acagatcaaa gagtgtcaag agcttggagt tctcgtggat       1080
agagatgatc agggtgtgct tctccagatt ttcactaagc cagttggaga taggccaaca       1140
ttcttcttgg agatgattca gaggatcggc tgcatggaaa aggatgaagt tggacaagag       1200
taccaaaagg gcggatgtgg tggatttgga aagggaaatt tctccgagct tttcaagtcc       1260
atcgaggatt acgagaagtc tcttgaggtt aagcagtctg ttgtggctca gaagtcttga       1320
```

<210> SEQ ID NO 63
<211> LENGTH: 1320
<212> TYPE: DNA
<213> ORGANISM: Avena sativa

<400> SEQUENCE: 63

| | | | | | |
|---|---|---|---|---|---|
| atgccaccaa | ctccagctac | tgctactggt | gctgctgctg | cagctgttac | tccagaacat | 60 |
| gctgctagat | cttttccaag | ggttgtgaga | gttaacccaa | ggtctgatag | gttcccagtt | 120 |
| ctttctttcc | accacgttga | actttggtgt | gctgatgcag | cttctgctgc | tggaagattt | 180 |
| tcttttgctc | ttggtgctcc | acttgctgct | aggtctgatt | tgtctactgg | aaattctgct | 240 |
| cacgcttctt | tgcttttgag | gtctggtgct | cttgctttcc | ttttactgc | tccttatgct | 300 |
| ccaccaccac | aagaagctgc | tacagctgct | actgcttcta | ttccatcttt | ttcagctgat | 360 |
| gctgcaagga | cttttgctgc | tgctcatgga | cttgctgtta | gatctgttgg | agttagagtt | 420 |
| gctgatgcag | ctgaggcttt | cagagtttct | gttgctggtg | gtgctagacc | agcttttgct | 480 |
| ccagctgatc | ttggacatgg | atttggactt | gctgaggttg | agctttacgg | tgatgttgtt | 540 |
| cttcgtttcg | tgtcttaccc | agatgagact | gatcttccat | tccttccagg | atttgagagg | 600 |
| gtttcatctc | caggtgctgt | tgattatgga | ctcactaggt | tcgatcacct | tgtgggaaat | 660 |
| gttccagaaa | tggctccagt | gatcgattac | atgaagggat | tccttggatt | ccatgagttc | 720 |
| gctgagttta | ctgctgagga | tgttggaact | actgagtctg | gacttaactc | tgttgtgctt | 780 |
| gctaacaact | tgaggctgt | tcttttgcca | cttaatgagc | cagttcacgg | cactaagaga | 840 |
| agatctcaga | ttcagactta | ccttgagtac | catggtggac | caggtgttca | acatattgct | 900 |
| cttgcttcta | cgatgtgct | taggactctt | agagagatga | gagctagaac | tccaatggga | 960 |
| ggatttgagt | ttatggctcc | accacaagct | aagtattacg | agggtgttag | aaggattgct | 1020 |
| ggtgatgttc | tttccgagga | acagatcaaa | gagtgtcaag | agcttggagt | tctcgtggat | 1080 |
| agagatgatc | agggtgtgct | tctccagatt | ttcactaagc | cagttggaga | taggccaaca | 1140 |
| ttcttcttgg | agatgattca | gaggatcggc | tgcatggaaa | aggatgaagt | tggacaagag | 1200 |
| taccaaaagg | gcggatgtgg | tggatttgga | aagggaaatt | tctccgagct | tttcaagtcc | 1260 |
| atcgaggatt | acgagaagtc | tcttgaggtt | aagcagtctg | ttgtggctca | gaagtcttga | 1320 |

<210> SEQ ID NO 64
<211> LENGTH: 1320
<212> TYPE: DNA
<213> ORGANISM: Avena sativa

<400> SEQUENCE: 64

| | | | | | |
|---|---|---|---|---|---|
| atgccaccaa | ctccagctac | tgctactggt | gctgctgctg | cagctgttac | tccagaacat | 60 |
| gctgctagat | cttttccaag | ggttgtgaga | gttaacccaa | ggtctgatag | gttcccagtt | 120 |
| ctttctttcc | accacgttga | actttggtgt | gctgatgcag | cttctgctgc | tggaagattt | 180 |
| tcttttgctc | ttggtgctcc | acttgctgct | aggtctgatt | tgtctactgg | aaattctgct | 240 |
| cacgcttctt | tgcttttgag | gtctggtgct | cttgctttcc | ttttactgc | tccttatgct | 300 |
| ccaccaccac | aagaagctgc | tacagctgct | actgcttcta | ttccatcttt | ttcagctgat | 360 |
| gctgcaagga | cttttgctgc | tgctcatgga | cttgctgtta | gatctgttgg | agttagagtt | 420 |
| gctgatgcag | ctgaggcttt | cagagtttct | gttgctggtg | gtgctagacc | agcttttgct | 480 |
| ccagctgatc | ttggacatgg | atttggactt | gctgaggttg | agctttacgg | tgatgttgtt | 540 |

```
cttcgtttcg tgtcttaccc agatgagact gatcttccat tccttccagg atttgagagg    600
gtttcatctc caggtgctgt tgattatgga ctcactaggt tcgatcacgt tgtgggaaat    660
gttccagaaa tggctccagt gatcgattac atgaagggat tccttggatt ccatgagttc    720
gctgagttta ctgctgagga tgttggaact actgagtctg gacttaactc tgttgtgctt    780
gctaacaact ctgaggctgt tcttttgcca cttaatgagc cagttcacgg cactaagaga    840
agatctcaga ttcagactta ccttgagtac catggtggac caggtgttca acatattgct    900
cttgcttcta acgatgtgct taggactctt agagagatga gagctagaac tccaatggga    960
ggatttgagt ttatgagacc accacaagct aagtattacg agggtgttag aaggattgct   1020
ggtgatgttc tttccgagga acagatcaaa gagtgtcaag agcttggagt tctcgtggat   1080
agagatgatc agggtgtgct ctccagatt ttcactaagc cagttggaga taggccaaca   1140
ttcttcttgg agatgattca gaggatcggc tgcatggaaa aggatgaagt tggacaagag   1200
taccaaaagg gcggatgtgg tggatttgga aagggaaatt tctccgagct tttcaagtcc   1260
atcgaggatt acgagaagtc tcttgaggtt aagcagtctg ttgtggctca gaagtcttga   1320
```

<210> SEQ ID NO 65
<211> LENGTH: 1320
<212> TYPE: DNA
<213> ORGANISM: Avena sativa

<400> SEQUENCE: 65

```
atgccaccaa ctccagctac tgctactggt gctgctgctg cagctgttac tccagaacat     60
gctgctagat cttttccaag ggttgtgaga gttaacccaa ggtctgatag gttcccagtt    120
cttcttttcc accacgttga actttggtgt gctgatgcag cttctgctgc tggaagattt    180
tcttttgctc ttggtgctcc acttgctgct aggtctgatt tgtctactgg aaattctgct    240
cacgcttctt tgcttttgag gtctggtgct cttgctttcc tttttactgc tccttatgct    300
ccaccaccac aagaagctgc tacagctgct actgcttcta ttccatcttt ttcagctgat    360
gctgcaagga cttttgctgc tgctcatgga cttgctgtta gatctgttgg agttagagtt    420
gctgatgcag ctgaggcttt cagagtttct gttgctggtg gtgctagacc agcttttgct    480
ccagctgatc ttggacatgg atttggactt gctgaggttg agctttacgg tgatgttgtt    540
cttcgtttcg tgtcttaccc agatgagact gatcttccat tccttccagg atttgagagg    600
gtttcatctc caggtgctgt tgattatgga ctcactaggt tcgatcacgt tgtgggaaat    660
gttccagaaa tggctccagt gatcgattac atgaagggat tccttggatt ccatgagttc    720
gctgagttta ctgctgagga tgttggaact actgagtctg gacttaactc tgttgtgctt    780
gctaacaact ctgaggctgt tcttttgcca cttaatgagc cagttcacgg cactaagaga    840
agatctcaga ttcagactta ccttgagtac catggtggac caggtgttca acatattgct    900
cttgcttcta acgatgtgct taggactctt agagagatga gagctagaac tccaatggga    960
ggatttgagt ttatgaagcc accacaagct aagtattacg agggtgttag aaggattgct   1020
ggtgatgttc tttccgagga acagatcaaa gagtgtcaag agcttggagt tctcgtggat   1080
agagatgatc agggtgtgct ctccagatt ttcactaagc cagttggaga taggccaaca   1140
ttcttcttgg agatgattca gaggatcggc tgcatggaaa aggatgaagt tggacaagag   1200
taccaaaagg gcggatgtgg tggatttgga aagggaaatt tctccgagct tttcaagtcc   1260
atcgaggatt acgagaagtc tcttgaggtt aagcagtctg ttgtggctca gaagtcttga   1320
```

<210> SEQ ID NO 66
<211> LENGTH: 1320
<212> TYPE: DNA
<213> ORGANISM: Avena sativa

<400> SEQUENCE: 66

| | | | | | |
|---|---|---|---|---|---|
| atgccaccaa | ctccagctac | tgctactggt | gctgctgctg | cagctgttac | tccagaacat | 60 |
| gctgctagat | cttttccaag | ggttgtgaga | gttaacccaa | ggtctgatag | gttcccagtt | 120 |
| ctttctttcc | accacgttga | actttggtgt | gctgatgcag | cttctgctgc | tggaagattt | 180 |
| tcttttgctc | ttggtgctcc | acttgctgct | aggtctgatt | tgtctactgg | aaattctgct | 240 |
| cacgcttctt | gcttttgag | gtctggtgct | cttgctttcc | tttttactgc | tccttatgct | 300 |
| ccaccaccac | aagaagctgc | tacagctgct | actgcttcta | ttccatcttt | ttcagctgat | 360 |
| gctgcaagga | cttttgctgc | tgctcatgga | cttgctgtta | gatctgttgg | agttagagtt | 420 |
| gctgatgcag | ctgaggcttt | cagagtttct | gttgctggtg | gtgctagacc | agcttttgct | 480 |
| ccagctgatc | ttggacatgg | atttggactt | gctgaggttg | agcttacgg | tgatgttgtt | 540 |
| cttcgtttcg | tgtcttaccc | agatgagact | gatcttccat | tccttccagg | atttgagagg | 600 |
| gtttcatctc | caggtgctgt | tgattatgga | ctcactaggt | tcgatcacgt | tgtgggaaat | 660 |
| gttccagaaa | tggctccagt | gatcgattac | atgaagggat | tccttggatt | ccatgagttc | 720 |
| gctgagttta | ctgctgagga | tgttggaact | actgagtctg | gacttaactc | tgttgtgctt | 780 |
| gctaacaact | ctgaggctgt | tcttttgcca | cttaatgagc | cagttcacgg | cactaagaga | 840 |
| agatctcaga | ttcagactta | ccttgagtac | catggtggac | caggtgttca | acatattgct | 900 |
| cttgcttcta | acgatgtgct | taggactctt | agagagatga | gagctagaac | tccaatggga | 960 |
| ggatttgagt | ttatgattcc | accacaagct | aagtattacg | agggtgttag | aaggattgct | 1020 |
| ggtgatgttc | tttccgagga | acagatcaaa | gagtgtcaag | agcttggagt | tctcgtggat | 1080 |
| agagatgatc | agggtgtgct | tctccagatt | ttcactaagc | cagttggaga | taggccaaca | 1140 |
| ttcttcttgg | agatgattca | gaggatcggc | tgcatggaaa | aggatgaagt | tggacaagag | 1200 |
| taccaaaagg | gcggatgtgg | tggatttgga | aagggaaatt | tctccgagct | tttcaagtcc | 1260 |
| atcgaggatt | acgagaagtc | tcttgaggtt | aagcagtctg | ttgtggctca | gaagtcttga | 1320 |

<210> SEQ ID NO 67
<211> LENGTH: 1320
<212> TYPE: DNA
<213> ORGANISM: Avena sativa

<400> SEQUENCE: 67

| | | | | | |
|---|---|---|---|---|---|
| atgccaccaa | ctccagctac | tgctactggt | gctgctgctg | cagctgttac | tccagaacat | 60 |
| gctgctagat | cttttccaag | ggttgtgaga | gttaacccaa | ggtctgatag | gttcccagtt | 120 |
| ctttctttcc | accacgttga | actttggtgt | gctgatgcag | cttctgctgc | tggaagattt | 180 |
| tcttttgctc | ttggtgctcc | acttgctgct | aggtctgatt | tgtctactgg | aaattctgct | 240 |
| cacgcttctt | gcttttgag | gtctggtgct | cttgctttcc | tttttactgc | tccttatgct | 300 |
| ccaccaccac | aagaagctgc | tacagctgct | actgcttcta | ttccatcttt | ttcagctgat | 360 |
| gctgcaagga | cttttgctgc | tgctcatgga | cttgctgtta | gatctgttgg | agttagagtt | 420 |
| gctgatgcag | ctgaggcttt | cagagtttct | gttgctggtg | gtgctagacc | agcttttgct | 480 |
| ccagctgatc | ttggacatgg | atttggactt | gctgaggttg | agcttacgg | tgatgttgtt | 540 |
| cttcgtttcg | tgtcttaccc | agatgagact | gatcttccat | tccttccagg | atttgagagg | 600 |

|  |  |  |  |  |
|---|---|---|---|---|
| gtttcatctc | caggtgctgt | tgattatgga | ctcactaggt tcgatcacgt | tgtgggaaat | 660 |
| gttccagaaa | tggctccagt | gatcgattac | atgaagggat tccttggatt | ccatgagttc | 720 |
| gctgagttta | ctgctgagga | tgttggaact | actgagtctg gacttaactc | tgttgtgctt | 780 |
| gctaacaact | ctgaggctgt | tcttttgcca | cttaatgagc cagttcacgg | cactaagaga | 840 |
| agatctcaga | ttcagactta | ccttgagtac | catggtggac caggtgttca | acatattgct | 900 |
| cttgcttcta | acgatgtgct | taggactctt | agagagatga gagctagaac | tccaatggga | 960 |
| ggatttgagt | ttatggctcc | accacaagct | aagtattacg agggtgttag | aagggaggct | 1020 |
| ggtgatgttc | tttccgagga | acagatcaaa | gagtgtcaag agcttggagt | tctcgtggat | 1080 |
| agagatgatc | agggtgtgct | tctccagatt | ttcactaagc cagttggaga | taggccaaca | 1140 |
| ttcttcttgg | agatgattca | gaggatcggc | tgcatgaaaa aggatgaagt | tggacaagag | 1200 |
| taccaaaagg | gcggatgtgg | tggatttgga | aagggaaatt tctccgagct | tttcaagtcc | 1260 |
| atcgaggatt | acgagaagtc | tcttgaggtt | aagcagtctg ttgtggctca | gaagtcttga | 1320 |

<210> SEQ ID NO 68
<211> LENGTH: 1320
<212> TYPE: DNA
<213> ORGANISM: Avena sativa

<400> SEQUENCE: 68

|  |  |  |  |  |
|---|---|---|---|---|
| atgccaccaa | ctccagctac | tgctactggt | gctgctgctg cagctgttac | tccagaacat | 60 |
| gctgctagat | cttttccaag | ggttgtgaga | gttaacccaa ggtctgatag | gttcccagtt | 120 |
| cttctttcc | accacgttga | actttggtgt | gctgatgcag cttctgctgc | tggaagattt | 180 |
| tcttttgctc | ttggtgctcc | acttgctgct | aggtctgatt tgtctactgg | aaattctgct | 240 |
| cacgcttctt | tgcttttgag | gtcggtgct | cttgctttcc ttttactgc | tccttatgct | 300 |
| ccaccaccac | aagaagctgc | tacagctgct | actgcttcta ttccatcttt | ttcagctgat | 360 |
| gctgcaagga | cttttgctgc | tgctcatgga | cttgctgtta gatctgttgg | agttagagtt | 420 |
| gctgatgcag | ctgaggcttt | cagagtttct | gttgctggtg gtgctagacc | agcttttgct | 480 |
| ccagctgatc | ttggacatgg | atttggactt | gctgaggttg agcttacgg | tgatgttgtt | 540 |
| cttcgtttcg | tgtcttaccc | agatgagact | gatcttccat tccttccagg | atttgagagg | 600 |
| gtttcatctc | caggtgctgt | tgattatgga | ctcactaggt tcgatcacgt | tgtgggaaat | 660 |
| gttccagaaa | tggctccagt | gatcgattac | atgaagggat tccttggatt | ccatgagttc | 720 |
| gctgagttta | ctgctgagga | tgttggaact | actgagtctg gacttaactc | tgttgtgctt | 780 |
| gctaacaact | ctgaggctgt | tcttttgcca | cttaatgagc cagttcacgg | cactaagaga | 840 |
| agatctcaga | ttcagactta | ccttgagtac | catggtggac caggtgttca | acatattgct | 900 |
| cttgcttcta | acgatgtgct | taggactctt | agagagatga gagctagaac | tccaatggga | 960 |
| ggatttgagt | ttatggctcc | accacaagct | aagtattacg agggtgttag | aagggatgct | 1020 |
| ggtgatgttc | tttccgagga | acagatcaaa | gagtgtcaag agcttggagt | tctcgtggat | 1080 |
| agagatgatc | agggtgtgct | tctccagatt | ttcactaagc cagttggaga | taggccaaca | 1140 |
| ttcttcttgg | agatgattca | gaggatcggc | tgcatgaaaa aggatgaagt | tggacaagag | 1200 |
| taccaaaagg | gcggatgtgg | tggatttgga | aagggaaatt tctccgagct | tttcaagtcc | 1260 |
| atcgaggatt | acgagaagtc | tcttgaggtt | aagcagtctg ttgtggctca | gaagtcttga | 1320 |

<210> SEQ ID NO 69
<211> LENGTH: 1320

```
<212> TYPE: DNA
<213> ORGANISM: Avena sativa

<400> SEQUENCE: 69
atgccaccaa ctccagctac tgctactggt gctgctgctg cagctgttac tccagaacat      60
gctgctagat cttttccaag ggttgtgaga gttaacccaa ggtctgatag gttcccagtt     120
ctttctttcc accacgttga actttggtgt gctgatgcag cttctgctgc tggaagattt     180
tcttttgctc ttggtgctcc acttgctgct aggtctgatt tgtctactgg aaattctgct     240
cacgcttctt tgcttttgag gtctggtgct cttgctttcc tttttactgc tccttatgct     300
ccaccaccac aagaagctgc tacagctgct actgcttcta ttccatcttt ttcagctgat     360
gctgcaagga cttttgctgc tgctcatgga cttgctgtta gatctgttgg agttagagtt     420
gctgatgcag ctgaggcttt cagagtttct gttgctggtg gtgctagacc agcttttgct     480
ccagctgatc ttggacatgg atttggactt gctgaggttg agctttacgg tgatgttgtt     540
cttcgtttcg tgtcttaccc agatgagact gatcttccat tccttccagg atttgagagg     600
gtttcatctc caggtgctgt tgattatgga ctcactaggt tcgatcacgt tgtgggaaat     660
gttccagaaa tggctccagt gatcgattac atgaagggat tccttggatt ccatgagttc     720
gctgagttta ctgctgagga tgttggaact actgagtctg gacttaactc tgttgtgctt     780
gctaacaact ctgaggctgt tcttttgcca cttaatgagc cagttcacgg cactaagaga     840
agatctcaga ttcagactta ccttgagtac catggtggac caggtgttca acatattgct     900
cttgcttcta cgatgtgct taggactctt agagagatga gagctagaac tccaatggga     960
ggatttgagt ttatggctcc accacaagct aagtattacg agggtgttag aaggtgcgct    1020
ggtgatgttc tttccgagga acagatcaaa gagtgtcaag agcttggagt tctcgtggat    1080
agagatgatc agggtgtgct tctccagatt ttcactaagc cagttggaga taggccaaca    1140
ttcttcttgg agatgattca gaggatcggc tgcatgaaaa aggatgaagt tggacaagag    1200
taccaaaagg gcggatgtgg tggatttgga aagggaaatt tctccgagct tttcaagtcc    1260
atcgaggatt acgagaagtc tcttgaggtt aagcagtctg ttgtggctca gaagtcttga    1320

<210> SEQ ID NO 70
<211> LENGTH: 1320
<212> TYPE: DNA
<213> ORGANISM: Avena sativa

<400> SEQUENCE: 70
atgccaccaa ctccagctac tgctactggt gctgctgctg cagctgttac tccagaacat      60
gctgctagat cttttccaag ggttgtgaga gttaacccaa ggtctgatag gttcccagtt     120
ctttctttcc accacgttga actttggtgt gctgatgcag cttctgctgc tggaagattt     180
tcttttgctc ttggtgctcc acttgctgct aggtctgatt tgtctactgg aaattctgct     240
cacgcttctt tgcttttgag gtctggtgct cttgctttcc tttttactgc tccttatgct     300
ccaccaccac aagaagctgc tacagctgct actgcttcta ttccatcttt ttcagctgat     360
gctgcaagga cttttgctgc tgctcatgga cttgctgtta gatctgttgg agttagagtt     420
gctgatgcag ctgaggcttt cagagtttct gttgctggtg gtgctagacc agcttttgct     480
ccagctgatc ttggacatgg atttggactt gctgaggttg agctttacgg tgatgttgtt     540
cttcgtttcg tgtcttaccc agatgagact gatcttccat tccttccagg atttgagagg     600
gtttcatctc caggtgctgt tgattatgga ctcactaggt tcgatcacgt tgtgggaaat     660
```

```
gttccagaaa tggctccagt gatcgattac atgaagggat tccttggatt ccatgagttc    720
gctgagttta ctgctgagga tgttggaact actgagtctg gacttaactc tgttgtgctt    780
gctaacaact ctgaggctgt tcttttgcca cttaatgagc cagttcacgg cactaagaga    840
agatctcaga ttcagactta ccttgagtac catggtggac caggtgttca acatattgct    900
cttgcttcta acgatgtgct taggactctt agagagatga gagctagaac tccaatggga    960
ggatttgagt ttatggctcc accacaagct aagtattacg agggtgttag aaggattgct   1020
ggtgatgttc tttccgagga acagatcaaa gagtgtcaag agcttggagt tctcgtggat   1080
agagatgatc agggtgtgct tctccagatt ttcactaagc cagttggaga taggccaaca   1140
ttcttcttgg agatgattca gaggatcggc tgcatggaaa aggatgaagt tggacaagag   1200
taccaaaagg gcggatgtgg tagatttgga aagggaaatt tctccgagct tttcaagtcc   1260
atcgaggatt acgagaagtc tcttgaggtt aagcagtctg ttgtggctca gaagtcttga   1320
```

<210> SEQ ID NO 71
<211> LENGTH: 1320
<212> TYPE: DNA
<213> ORGANISM: Avena sativa

<400> SEQUENCE: 71

```
atgccaccaa ctccagctac tgctactggt gctgctgctg cagctgttac tccagaacat     60
gctgctagat cttttccaag ggttgtgaga gttaacccaa ggtctgatag gttcccagtt    120 cttctttcc accacgttga actttggtgt gctgatgcag cttctgctgc tggaagattt    180
tcttttgctc ttggtgctcc acttgctgct aggtctgatt tgtctactgg aaattctgct    240
cacgcttctt tgcttttgag gtctggtgct cttgctttcc tttttactgc tccttatgct    300
ccaccaccac aagaagctgc tacagctgct actgcttcta ttccatcttt ttcagctgat    360
gctgcaagga cttttgctgc tgctcatgga cttgctgtta gatctgttgg agttagagtt    420
gctgatgcag ctgaggcttt cagagtttct gttgctggtg gtgctagacc agcttttgct    480
ccagctgatc ttggacatgg atttggactt gctgaggttg agctttacgg tgatgttgtt    540
cttcgtttcg tgtcttaccc agatgagact gatcttccat tccttccagg atttgagagg    600
gtttcatctc caggtgctgt tgattatgga ctcactaggt tcgatcacgt tgtgggaaat    660
gttccagaaa tggctccagt gatcgattac atgaagggat tccttggatt ccatgagttc    720
gctgagttta ctgctgagga tgttggaact actgagtctg gacttaactc tgttgtgctt    780
gctaacaact ctgaggctgt tcttttgcca cttaatgagc cagttcacgg cactaagaga    840
agatctcaga ttcagactta ccttgagtac catggtggac caggtgttca acatattgct    900
cttgcttcta acgatgtgct taggactctt agagagatga gagctagaac tccaatggga    960
ggatttgagt ttatgagacc accacaagct aagtattacg agggtgttag aaggattgct   1020
ggtgatgttc tttccgagga acagatcaaa gagtgtcaag agcttggagt tatggtggat   1080
agagatgatc agggtgtgct tctccagatt ttcactaagc cagttggaga taggccaaca   1140
ttcttcttgg agatgattca gaggatcggc tgcatggaaa aggatgaagt tggacaagag   1200
taccaaaagg gcggatgtgg tggatttgga aagggaaatt tctccgagct tttcaagtcc   1260
atcgaggatt acgagaagtc tcttgaggtt aagcagtctg ttgtggctca gaagtcttga   1320
```

<210> SEQ ID NO 72
<211> LENGTH: 1320
<212> TYPE: DNA
<213> ORGANISM: Avena sativa

<400> SEQUENCE: 72

```
atgccaccaa ctccagctac tgctactggt gctgctgctg cagctgttac tccagaacat    60
gctgctagat cttttccaag ggttgtgaga gttaacccaa ggtctgatag gttcccagtt   120
ctttctttcc accacgttga actttggtgt gctgatgcag cttctgctgc tggaagattt   180
tcttttgctc ttggtgctcc acttgctgct aggtctgatt tgtctactgg aaattctgct   240
cacgcttctt tgcttttgag gtctggtgct cttgctttcc ttttactgc tccttatgct    300
ccaccaccac aagaagctgc tacagctgct actgcttcta ttccatcttt ttcagctgat   360
gctgcaagga cttttgctgc tgctcatgga cttgctgtta gatctgttgg agttagagtt   420
gctgatgcag ctgaggcttt cagagtttct gttgctggtg gtgctagacc agcttttgct   480
ccagctgatc ttggacatgg atttggactt gctgaggttg agctttacgg tgatgttgtt   540
cttcgtttcg tgtcttaccc agatgagact gatcttccat tccttccagg atttgagagg   600
gtttcatctc caggtgctgt tgattatgga ctcactaggt tcgatcacat tgtgggaaat   660
gttccagaaa tggctccagt gatcgattac atgaagggat tccttggatt ccatgagttc   720
gctgagttta ctgctgagga tgttggaact actgagtctg gacttaactc tgttgtgctt   780
gctaacaact ctgaggctgt tcttttgcca cttaatgagc cagttcacgg cactaagaga   840
agatctcaga ttcagactta ccttgagtac catggtggac caggtgttca acatattgct   900
cttgcttcta acgatgtgct taggactctt agagagatga gagctagaac tccaatggga   960
ggatttgagt ttatgagacc accacaagct aagtattacg agggtgttag aaggattgct  1020
ggtgatgttc tttccgagga acagatcaaa gagtgtcaag agcttggagt tatggtggat  1080
agagatgatc agggtgtgct ctccagattt tcactaagc cagttggaga taggccaaca  1140
ttcttcttgg agatgattca gaggatcggc tgcatggaaa aggatgaagt tggacaagag  1200
taccaaaagg gcggatgtgg tggatttgga aagggaaatt ctccgagct tttcaagtcc   1260
atcgaggatt acgagaagtc tcttgaggtt aagcagtctg ttgtggctca gaagtcttga  1320
```

<210> SEQ ID NO 73
<211> LENGTH: 1320
<212> TYPE: DNA
<213> ORGANISM: Avena sativa

<400> SEQUENCE: 73

```
atgccaccaa ctccagctac tgctactggt gctgctgctg cagctgttac tccagaacat    60
gctgctagat cttttccaag ggttgtgaga gttaacccaa ggtctgatag gttcccagtt   120
ctttctttcc accacgttga actttggtgt gctgatgcag cttctgctgc tggaagattt   180
tcttttgctc ttggtgctcc acttgctgct aggtctgatt tgtctactgg aaattctgct   240
cacgcttctt tgcttttgag gtctggtgct cttgctttcc ttttactgc tccttatgct    300
ccaccaccac aagaagctgc tacagctgct actgcttcta ttccatcttt ttcagctgat   360
gctgcaagga cttttgctgc tgctcatgga cttgctgtta gatctgttgg agttagagtt   420
gctgatgcag ctgaggcttt cagagtttct gttgctggtg gtgctagacc agcttttgct   480
ccagctgatc ttggacatgg atttggactt gctgaggttg agctttacgg tgatgttgtt   540
cttcgtttcg tgtcttaccc agatgagact gatcttccat tccttccagg atttgagagg   600
gtttcatctc caggtgctgt tgattatgga ctcactaggt tcgatcacat tgtgggaaat   660
gttccagaaa tggctccagt gatcgattac atgaagggat tccttggatt ccatgagttc   720
```

```
gctgagttta ctgctgagga tgttggaact actgagtctg gacttaactc tgttgtgctt      780
gctaacaact ctgaggctgt tcttttgcca cttaatgagc cagttcacgg cactaagaga      840
agatctcaga ttcagactta ccttgagtac catggtggac caggtgttca acatattgct      900
cttgcttcta acgatgtgct taggactctt agagagatga gagctagaac tccaatggga      960
ggatttgagt ttatggctcc accacaagct aagtattacg agggtgttag aaggattgct     1020
ggtgatgttc tttccgagga acagatcaaa gagtgtcaag agcttggagt tatggtggat     1080
agagatgatc agggtgtgct tctccagatt ttcactaagc cagttggaga taggccaaca     1140
ttcttcttgg agatgattca gaggatcggc tgcatggaaa aggatgaagt tggacaagag     1200
taccaaaagg gcggatgtgg tggatttgga aagggaaatt tctccgagct tttcaagtcc     1260
atcgaggatt acgagaagtc tcttgaggtt aagcagtctg ttgtggctca gaagtcttga     1320
```

<210> SEQ ID NO 74
<211> LENGTH: 1320
<212> TYPE: DNA
<213> ORGANISM: Avena sativa

<400> SEQUENCE: 74

```
atgccaccaa ctccagctac tgctactggt gctgctgctg cagctgttac tccagaacat       60
gctgctagat cttttccaag ggttgtgaga gttaacccaa ggtctgatag gttcccagtt      120 cttctttcc accacgttga actttggtgt gctgatgcag cttctgctgc tggaagattt       180
tcttttgctc ttggtgctcc acttgctgct aggtctgatt tgtctactgg aaattctgct      240
cacgcttctt tgcttttgag gtctggtgct cttgcttttcc ttttactgc tccttatgct      300 ccaccaccac aagaagctgc tacagctgct actgcttcta ttccatcttt ttcagctgat      360
gctgcaagga cttttgctgc tgctcatgga cttgctgtta gatctgttgg agttagagtt      420
gctgatgcag ctgaggcttt cagagtttct gttgctggtg gtgctagacc agcttttgct      480
ccagctgatc ttggacatgg atttggactt gctgaggttg agctttacgg tgatgttgtt      540
cttcgtttcg tgtcttaccc agatgagact gatcttccat tccttccagg atttgagagg      600
gtttcatctc caggtgctgt tgattatgga ctcactaggt tcgatcacat tgtgggaaat      660
gttccagaaa tggctccagt gatcgattac atgaagggat tccttggatt ccatgagttc      720
gctgagttta ctgctgagga tgttggaact actgagtctg gacttaactc tgttgtgctt      780
gctaacaact ctgaggctgt tcttttgcca cttaatgagc cagttcacgg cactaagaga      840
agatctcaga ttcagactta ccttgagtac catggtggac caggtgttca acatattgct      900
cttgcttcta acgatgtgct taggactctt agagagatga gagctagaac tccaatggga      960
ggatttgagt ttatgagacc accacaagct aagtattacg agggtgttag aaggattgct     1020
ggtgatgttc tttccgagga acagatcaaa gagtgtcaag agcttggagt tctcgtggat     1080
agagatgatc agggtgtgct tctccagatt ttcactaagc cagttggaga taggccaaca     1140
ttcttcttgg agatgattca gaggatcggc tgcatggaaa aggatgaagt tggacaagag     1200
taccaaaagg gcggatgtgg tggatttgga aagggaaatt tctccgagct tttcaagtcc     1260
atcgaggatt acgagaagtc tcttgaggtt aagcagtctg ttgtggctca gaagtcttga     1320
```

<210> SEQ ID NO 75
<211> LENGTH: 1320
<212> TYPE: DNA
<213> ORGANISM: Avena sativa

<400> SEQUENCE: 75

```
atgccaccaa ctccagctac tgctactggt gctgctgctg cagctgttac tccagaacat    60
gctgctagat cttttccaag ggttgtgaga gttaacccaa ggtctgatag gttcccagtt   120
ctttctttcc accacgttga actttggtgt gctgatgcag cttctgctgc tggaagattt   180
tcttttgctc ttggtgctcc acttgctgct aggtctgatt tgtctactgg aaattctgct   240
cacgcttctt tgcttttgag gtctggtgct cttgctttcc ttttactgc tccttatgct    300 ccaccaccac aagaagctgc tacagctgct actgcttcta ttccatcttt ttcagctgat   360
gctgcaagga cttttgctgc tgctcatgga cttgctgtta gatctgttgg agttagagtt   420
gctgatgcag ctgaggcttt cagagtttct gttgctggtg gtgctagacc agcttttgct   480
ccagctgatc ttggacatgg atttggactt gctgaggttg agcttacgg tgatgttgtt    540 cttcgtttcg tgtcttaccc agatgagact gatcttccat ccttccagg atttgagagg    600 gtttcatctc caggtgctgt tgattatgga ctcactaggt tcgatcacat tgtgggaaat   660
gttccagaaa tggctccagt gatcgattac atgaagggat tccttggatt ccatgagttc   720
gctgagttta ctgctgagga tgttggaact actgagtctg gacttaactc tgttgtgctt   780
gctaacaact ctgaggctgt tcttttgcca cttaatgagc cagttcacgg cactaagaga   840
agatctcaga ttcagactta ccttgagtac catggtggac caggtgttca acatattgct   900
cttgcttcta cgatgtgct taggactctt agagagatga gagctagaac tccaatggga    960
ggatttgagt ttatgaagcc accacaagct aagtattacg agggtgttag aaggattgct  1020
ggtgatgttc tttccgagga acagatcaaa gagtgtcaag agcttggagt tatggtggat  1080
agagatgatc agggtgtgct tctccagatt ttcactaagc cagttggaga taggccaaca  1140
ttcttcttgg agatgattca gaggatcggc tgcatggaaa aggatgaagt tggacaagag  1200
taccaaaagg gcggatgtgg tggatttgga aagggaaatt tctccgagct tttcaagtcc  1260
atcgaggatt acgagaagtc tcttgaggtt aagcagtctg ttgtggctca gaagtcttga  1320
```

<210> SEQ ID NO 76
<211> LENGTH: 1320
<212> TYPE: DNA
<213> ORGANISM: Avena sativa

<400> SEQUENCE: 76

```
atgccaccaa ctccagctac tgctactggt gctgctgctg cagctgttac tccagaacat    60
gctgctagat cttttccaag ggttgtgaga gttaacccaa ggtctgatag gttcccagtt   120
ctttctttcc accacgttga actttggtgt gctgatgcag cttctgctgc tggaagattt   180
tcttttgctc ttggtgctcc acttgctgct aggtctgatt tgtctactgg aaattctgct   240
cacgcttctt tgcttttgag gtctggtgct cttgctttcc ttttactgc tccttatgct    300 ccaccaccac aagaagctgc tacagctgct actgcttcta ttccatcttt ttcagctgat   360
gctgcaagga cttttgctgc tgctcatgga cttgctgtta gatctgttgg agttagagtt   420
gctgatgcag ctgaggcttt cagagtttct gttgctggtg gtgctagacc agcttttgct   480
ccagctgatc ttggacatgg atttggactt gctgaggttg agcttacgg tgatgttgtt    540 cttcgtttcg tgtcttaccc agatgagact gatcttccat ccttccagg atttgagagg    600 gtttcatctc caggtgctgt tgattatgga ctcactaggt tcgatcacct tgtgggaaat   660
gttccagaaa tggctccagt gatcgattac atgaagggat tccttggatt ccatgagttc   720
gctgagttta ctgctgagga tgttggaact actgagtctg gacttaactc tgttgtgctt   780
```

| | | | | |
|---|---|---|---|---|
| gctaacaact | ctgaggctgt | tctttttgcca | cttaatgagc | cagttcacgg cactaagaga | 840 |
| agatctcaga | ttcagactta | ccttgagtac | catggtggac | caggtgttca acatattgct | 900 |
| cttgcttcta | acgatgtgct | taggactctt | agagagatga | gagctagaac tccaatggga | 960 |
| ggatttgagt | ttatgagacc | accacaagct | aagtattacg | agggtgttag aaggattgct | 1020 |
| ggtgatgttc | tttccgagga | acagatcaaa | gagtgtcaag | agcttggagt tatggtggat | 1080 |
| agagatgatc | agggtgtgct | tctccagatt | ttcactaagc | cagttggaga taggccaaca | 1140 |
| ttcttcttgg | agatgattca | gaggatcggc | tgcatggaaa | aggatgaagt tggacaagag | 1200 |
| taccaaaagg | gcggatgtgg | tggatttgga | aagggaaatt | tctccgagct tttcaagtcc | 1260 |
| atcgaggatt | acgagaagtc | tcttgaggtt | aagcagtctg | ttgtggctca gaagtcttga | 1320 |

<210> SEQ ID NO 77
<211> LENGTH: 1320
<212> TYPE: DNA
<213> ORGANISM: Avena sativa

<400> SEQUENCE: 77

| | | | | |
|---|---|---|---|---|
| atgccaccaa | ctccagctac | tgctactggt | gctgctgctg | cagctgttac tccagaacat | 60 |
| gctgctagat | cttttccaag | ggttgtgaga | gttaacccaa | ggtctgatag gttcccagtt | 120 |
| ctttctttcc | accacgttga | actttggtgt | gctgatgcag | cttctgctgc tggaagattt | 180 |
| tcttttgctc | ttggtgctcc | acttgctgct | aggtctgatt | tgtctactgg aaattctgct | 240 |
| cacgcttctt | tgcttttgag | gtctggtgct | cttgctttcc | tttttactgc tccttatgct | 300 |
| ccaccaccac | aagaagctgc | tacagctgct | actgcttcta | ttccatcttt ttcagctgat | 360 |
| gctgcaagga | cttttgctgc | tgctcatgga | cttgctgtta | gatctgttgg agttagagtt | 420 |
| gctgatgcag | ctgaggcttt | cagagtttct | gttgctggtg | gtgctagacc agcttttgct | 480 |
| ccagctgatc | ttggacatgg | atttggactt | gctgaggttg | agctttacgg tgatgttgtt | 540 |
| cttcgtttcg | tgtcttaccc | agatgagact | gatcttccat | tccttccagg atttgagagg | 600 |
| gtttcatctc | caggtgctgt | tgattatgga | ctcactaggt | tcgatcacat tgtgggaaat | 660 |
| gttccagaaa | tggctccagt | gatcgattac | atgaagggat | tccttggatt ccatgagttc | 720 |
| gctgagttta | ctgctgagga | tgttggaact | actgagtctg | gacttaactc tgttgtgctt | 780 |
| gctaacaact | ctgaggctgt | tctttttgcca | cttaatgagc | cagttcacgg cactaagaga | 840 |
| agatctcaga | ttcagactta | ccttgagtac | catggtggac | caggtgttca acatattgct | 900 |
| cttgcttcta | acgatgtgct | taggactctt | agagagatga | gagctagaac tccaatggga | 960 |
| ggatttgagt | ttatgagacc | accacaagct | aagtattacg | agggtgttag aagggaggct | 1020 |
| ggtgatgttc | tttccgagga | acagatcaaa | gagtgtcaag | agcttggagt tatggtggat | 1080 |
| agagatgatc | agggtgtgct | tctccagatt | ttcactaagc | cagttggaga taggccaaca | 1140 |
| ttcttcttgg | agatgattca | gaggatcggc | tgcatggaaa | aggatgaagt tggacaagag | 1200 |
| taccaaaagg | gcggatgtgg | tggatttgga | aagggaaatt | tctccgagct tttcaagtcc | 1260 |
| atcgaggatt | acgagaagtc | tcttgaggtt | aagcagtctg | ttgtggctca gaagtcttga | 1320 |

<210> SEQ ID NO 78
<211> LENGTH: 1320
<212> TYPE: DNA
<213> ORGANISM: Avena sativa

<400> SEQUENCE: 78

| | | | | |
|---|---|---|---|---|
| atgccaccaa | ctccagctac | tgctactggt | gctgctgctg | cagctgttac tccagaacat | 60 |

```
gctgctagat cttttccaag ggttgtgaga gttaacccaa ggtctgatag gttcccagtt      120 cttctttcc accacgttga actttggtgt gctgatgcag cttctgctgc tggaagattt       180
tcttttgctc ttggtgctcc acttgctgct aggtctgatt tgtctactgg aaattctgct     240
cacgcttctt tgcttttgag gtctggtgct cttgctttcc tttttactgc tccttatgct    300
ccaccaccac aagaagctgc tacagctgct actgcttcta ttccatcttt ttcagctgat    360
gctgcaagga cttttgctgc tgctcatgga cttgctgtta gatctgttgg agttagagtt     420
gctgatgcag ctgaggcttt cagagtttct gttgctggtg gtgctagacc agcttttgct    480
ccagctgatc ttggacatgg atttggactt gctgaggttg agctttacgg tgatgttgtt     540
cttcgtttcg tgtcttaccc agatgagact gatcttccat tccttccagg atttgagagg     600
gtttcatctc caggtgctgt tgattatgga ctcactaggt tcgatcacct tgtgggaaat     660
gttccagaaa tggctccagt gatcgattac atgaagggat ccttggatt ccatgagttc     720 gctgagttta ctgctgagga tgttggaact actgagtctg gacttaactc tgttgtgctt    780
gctaacaact ctgaggctgt tcttttgcca cttaatgagc cagttcacgg cactaagaga    840
agatctcaga ttcagactta ccttgagtac catggtggac caggtgttca acatattgct     900
cttgcttcta acgatgtgct taggactctt agagagatga gagctagaac tccaatggga    960
ggatttgagt ttatgagacc accacaagct aagtattacg agggtgttag aagggaggct   1020
ggtgatgttc tttccgagga acagatcaaa gagtgtcaag agcttggagt tatggtggat   1080
agagatgatc agggtgtgct tctccagatt ttcactaagc cagttggaga taggccaaca   1140
ttcttcttgg agatgattca gaggatcggc tgcatggaaa aggatgaagt tggacaagag   1200
taccaaaagg gcggatgtgg tggatttgga aagggaaatt tctccgagct tttcaagtcc   1260
atcgaggatt acgagaagtc tcttgaggtt aagcagtctg ttgtggctca gaagtcttga   1320
```

```
<210> SEQ ID NO 79
<211> LENGTH: 1305
<212> TYPE: DNA
<213> ORGANISM: Poa annua

<400> SEQUENCE: 79
```

```
atgccaccaa ctactgctac tgctacagct gctgctactg ttactccaga acatgctgct      60
agaaggttcc caagagttgt tagagttaac ccaaggtctg ataggttccc agttctttct     120
ttccaccacg ttgaattttg gtgtgctgat gctgcttctg ctgctggaag atttctttt     180 gctcttggtg ctccacttgc tgctagatct gatttgtcta ctggaaattc tgctcacgct    240
tctttgcttt tgaggtctgg tgctcttgct ttccttttta ctgctcctta tgctccacaa    300
ccacaggatg ctgatactgc atcaattcca tcttttctcag ctgatgctgc aagggctttt   360
tctgctgctc atgattggc tgttagatct gttgctgtta gagttgctga tgcagctgat    420
gctttcagag cttctattgc tgcaggtgct agaccagctt ttgctccagc tgatcttgga    480
agaggatttg gacttgctga ggttgagctt tacggtgatg ttgttcttag attcgtgtct    540
cacccagatg ctgatgatgc tccatttctt ccaggatttg aggctgtttc tagaccaggt     600
gctgttgatt atggactcac taggttcgat cacgttgtgg aaatgttcc agaaatggga    660 ccagtgatcg attacatcaa gggattcatg ggattccatg agttcgctga gtttactgct    720
gaggatgttg aactactga gtctggactt aactctgttg tgcttgctaa caactctgag    780
gctgttcttt tgccacttaa tgagccagtt cacggcacta agagaagatc tcagattcag    840
```

| acttaccttg agtaccatgg tggaccaggt gttcaacata ttgctcttgc ttcatctgat | 900 |
| gtgcttagga ctcttagaga gatgcaagct agatctgcta tgggaggatt tgagtttatg | 960 |
| aggccaccac aacctaagta ttacgagggt gttagaagga ttgctggtga tgttctttcc | 1020 |
| gaggctcaaa tcaaagagtg tcaagagctt ggagtgatgg tggatagaga tgatcagggt | 1080 |
| gtgcttctcc agattttcac taagccagtt ggagataggc caacattctt cttggagatg | 1140 |
| attcagagga tcggctgcat ggaaaaggat gagagaggtc aagagtatca aaagggcgga | 1200 |
| tgtggtggat ttggaaaggg aaatttctcc gagcttttca gtccatcga ggattacgag | 1260 |
| aagtctcttg aggctaagca atctgctgtt gctcaacagt cttga | 1305 |

<210> SEQ ID NO 80
<211> LENGTH: 1305
<212> TYPE: DNA
<213> ORGANISM: Poa annua

<400> SEQUENCE: 80

| atgccaccaa ctactgctac tgctacagct gctgctactg ttactccaga acatgctgct | 60 |
| agaaggttcc caagagttgt tagagttaac ccaaggtctg ataggttccc agttctttct | 120 |
| ttccaccacg ttgaattttg gtgtgctgat gctgcttctg ctgctggaag attttctttt | 180 |
| gctcttggtg ctccacttgc tgctagatct gatttgtcta ctggaaattc tgctcacgct | 240 |
| tctttgcttt tgaggtctgg tgctcttgct ttccttttta ctgctcctta tgctccacaa | 300 |
| ccacaggatg ctgatactgc atcaattcca tctttctcag ctgatgctgc aagggctttt | 360 |
| tctgctgctc atggattggc tgttagatct gttgctgtta gagttgctga tgcagctgat | 420 |
| gctttcagag cttctattgc tgcaggtgct agaccagctt ttgctccagc tgatcttgga | 480 |
| agaggatttg gacttgctga ggttgagctt tacggtgatg ttgttcttag attcgtgtct | 540 |
| cacccagatg ctgatgatgc tccatttctt ccaggatttg aggctgtttc tagaccaggt | 600 |
| gctgttgatt atggactcac taggttcgat cacattgtgg gaaatgttcc agaaatggga | 660 |
| ccagtgatcg attacatcaa gggattcatg ggattccatg agttcgctga gtttactgct | 720 |
| gaggatgttg gaactactga gtctggactt aactctgttg tgcttgctaa caactctgag | 780 |
| gctgttcttt tgccacttaa tgagccagtt cacggcacta agagaagatc tcagattcag | 840 |
| acttaccttg agtaccatgg tggaccaggt gttcaacata ttgctcttgc ttcatctgat | 900 |
| gtgcttagga ctcttagaga gatgcaagct agatctgcta tgggaggatt tgagtttatg | 960 |
| aggccaccac aacctaagta ttacgagggt gttagaagga ttgctggtga tgttctttcc | 1020 |
| gaggctcaaa tcaaagagtg tcaagagctt ggagtgatgg tggatagaga tgatcagggt | 1080 |
| gtgcttctcc agattttcac taagccagtt ggagataggc caacattctt cttggagatg | 1140 |
| attcagagga tcggctgcat ggaaaaggat gagagaggtc aagagtatca aaagggcgga | 1200 |
| tgtggtggat ttggaaaggg aaatttctcc gagcttttca gtccatcga ggattacgag | 1260 |
| aagtctcttg aggctaagca atctgctgtt gctcaacagt cttga | 1305 |

<210> SEQ ID NO 81
<211> LENGTH: 1323
<212> TYPE: DNA
<213> ORGANISM: Alopecurus mycosuroides

<400> SEQUENCE: 81

| atgccaccaa ctactgctac tgctacaggt gctgctgctg cagctgttac tccagaacat | 60 |
| gctgctagaa ggttcccaag agttgttaga gttaacccaa ggtctgatag gttcccagtt | 120 |

```
cttgctttcc atcatgttga gttttggtgt gctgatgctg cttctgctgc tggaagattt      180
tcttttgctc ttggtgctcc acttgctgct agatctgatt tgtctactgg aaactcttct      240
cacgcttctc acctttttgag atctggtgct cttgctttcc ttttcactgc tccttatgct     300
ccaccaccac aagatgctgc agatgcagca gctactgctt ctattccatc tttttcaact      360
gaggctgcta ggactttctc ttctgctcat ggattggctg ttagatctgt ggctattaga      420
gttgcagatg ctgcagaggc tttccatact tctgttgctg gtggtgctag accagctttt      480
gctccagctg atcttggatc tggatttgga cttgctgagg ttgagcttta cggtgatgtt      540
gttcttagat tcgtgtctca cccagatggt gatgatgttc catttcttcc aggattcgag      600
ggtgttagta gaccaggtgc tatggattat ggactcacta ggttcgatca cgttgtggga     660
aatgttccag aaatggctcc agttgctgct tacatgaagg gattcactgg atttcatgag     720
ttcgctgagt tcactgctga ggatgttgga actgctgagt ctggacttaa ctctgttgtg     780
cttgctaaca actctgaggc tgttcttttg ccacttaatg agccagttca cggcactaag      840
agaagatctc agattcagac ttacctcgat taccatggtg gaccaggtgt tcaacatatt     900
gctcttgctt catctgatgt gcttaggact cttagagaga tgagagctag atctgctatg     960
ggaggatttg agtttatgag accaccacaa gctaagtatt acgaaggtgt tagaaggctt     1020
gctggtgatg ttcttttctga ggctcaaatc aaagagtgcc aagagcttgg agttatggtg    1080
gatagagatg atcagggtgt gcttctccag attttcacta gccagttgg agataggcca     1140 acattcttct tggagatgat tcagaggatc ggctgcatgg aaaaggatga gattggacaa    1200
gagtaccaaa agggcggatg tggtggattt ggaaagggaa atttctccga gcttttcaag    1260
tccatcgagg attacgagaa gtctcttgag gctaagcaat ctgctgttgc tcaacagtct    1320
tga                                                                    1323
```

<210> SEQ ID NO 82
<211> LENGTH: 1323
<212> TYPE: DNA
<213> ORGANISM: Alopecurus mycosuroides

<400> SEQUENCE: 82

```
atgccaccaa ctactgctac tgctacaggt gctgctgctg cagctgttac tccagaacat      60
gctgctagaa ggttcccaag agttgttaga gttaacccaa ggtctgatag gttcccagtt     120
cttgctttcc atcatgttga gttttggtgt gctgatgctg cttctgctgc tggaagattt      180
tcttttgctc ttggtgctcc acttgctgct agatctgatt tgtctactgg aaactcttct      240
cacgcttctc acctttttgag atctggtgct cttgctttcc ttttcactgc tccttatgct     300
ccaccaccac aagatgctgc agatgcagca gctactgctt ctattccatc tttttcaact      360
gaggctgcta ggactttctc ttctgctcat ggattggctg ttagatctgt ggctattaga      420
gttgcagatg ctgcagaggc tttccatact tctgttgctg gtggtgctag accagctttt      480
gctccagctg atcttggatc tggatttgga cttgctgagg ttgagcttta cggtgatgtt      540
gttcttagat tcgtgtctca cccagatggt gatgatgttc catttcttcc aggattcgag      600
ggtgttagta gaccaggtgc tatggattat ggactcacta ggttcgatca cattgtggga     660
aatgttccag aaatggctcc agttgctgct tacatgaagg gattcactgg atttcatgag     720
ttcgctgagt tcactgctga ggatgttgga actgctgagt ctggacttaa ctctgttgtg     780
cttgctaaca actctgaggc tgttcttttg ccacttaatg agccagttca cggcactaag      840
```

```
agaagatctc agattcagac ttacctcgat taccatggtg gaccaggtgt tcaacatatt    900
gctcttgctt catctgatgt gcttaggact cttagagaga tgagagctag atctgctatg    960
ggaggatttg agtttatgag accaccacaa gctaagtatt acgaaggtgt tagaaggctt   1020
gctggtgatg ttcttttctga ggctcaaatc aaagagtgcc aagagcttgg agttatggtg   1080
gatagagatg atcagggtgt gcttctccag attttcacta agccagttgg agataggcca   1140
acattcttct tggagatgat tcagaggatc ggctgcatgg aaaaggatga gattggacaa   1200
gagtaccaaa agggcggatg tggtggattt ggaaagggaa atttctccga gcttttcaag   1260
tccatcgagg attacgagaa gtctcttgag gctaagcaat ctgctgttgc tcaacagtct   1320
tga                                                                 1323

<210> SEQ ID NO 83
<211> LENGTH: 217
<212> TYPE: DNA
<213> ORGANISM: Petunia x hybrida

<400> SEQUENCE: 83
atggcacaaa ttaacaacat ggcacaaggg atacaaaccc ttaatcccaa ttccaatttc     60
cataaacccc aagttcctaa atcttcaagt tttcttgttt ttggatctaa aaaactgaaa    120
aattcagcaa attctatgtt ggttttgaaa aagattcaa ttttatgca aagttttgt     180 tcctttagga tttcagcatc agtggctaca gcctgcc                            217

<210> SEQ ID NO 84
<211> LENGTH: 1323
<212> TYPE: DNA
<213> ORGANISM: Avena sativa

<400> SEQUENCE: 84
atgccaccaa ctccagctac tgctactggt gctgctgctg cagctgttac tccagaacat     60
gctgctagat cttttccaag ggttgtgaga gttaacccaa ggtctgatag gttcccagtt    120 cttttctttcc accacgttga actttggtgt gctgatgcag cttctgctgc tggaagattt    180
tcttttgctc ttggtgctcc acttgctgct aggtctgatt tgtctactgg aaattctgct    240
cacgcttctt tgcttttgag gtctggtgct cttgctttcc tttttactgc tccttatgct    300
ccaccaccac aagaagctgc tacagctgca gctactgctt ctattccatc ttttttcagct   360 gatgctgcaa ggacttttgc tgctgctcat ggacttgctg ttagatctgt tggagttaga    420
gttgctgatg cagctgaggc tttcagagtt tctgttgctg gtggtgctag accagctttt    480
gctccagctg atcttggaca tggatttgga cttgctgagg ttgagctta cggtgatgtt    540 gttcttcgtt tcgtgtctta cccagatgag actgatcttc cattccttcc aggatttgag    600
agggtttcat ctccaggtgc tgttgattat ggactcacta ggttcgatca cattgtggga    660
aatgttccag aaatggctcc agtgatcgat tacatgaagg gattccttgg attccatgag    720
ttcgctgagt ttactgctga ggatgttgga actactgagt ctggacttaa ctctgttgtg    780
cttgctaaca actctgaggc tgttcttttg ccacttaatg agccagttca cggcactaag    840
agaagatctc agattcagac ttaccttgag taccatggtg gaccaggtgt tcaacatatt    900
gctcttgctt ctaacgatgt gcttaggact cttagagaga tgagagctag aactccaatg    960
ggaggatttg agtttatgag accaccacaa gctaagtatt acgagggtgt tagaaggatt   1020
gctggtgatg ttcttttccga ggaacagatc aaagagtgtc aagagcttgg agttatggtg   1080
gatagagatg atcagggtgt gcttctccag attttcacta agccagttgg agataggcca   1140
```

```
acattcttct tggagatgat tcagaggatc ggctgcatgg aaaaggatga agttggacaa    1200
gagtaccaaa agggcggatg tggtggattt ggaaagggaa atttctccga gcttttcaag    1260
tccatcgagg attacgagaa gtctcttgag gttaagcagt ctgttgtggc tcagaagtct    1320
tga                                                                  1323

<210> SEQ ID NO 85
<211> LENGTH: 1323
<212> TYPE: DNA
<213> ORGANISM: Alopecurus mycosuroides

<400> SEQUENCE: 85
atgccaccaa ctactgctac tgctacaggt gctgctgctg cagctgttac tccagaacat      60
gctgctagaa ggttcccaag agttgttaga gttaacccaa ggtctgatag gttcccagtt     120
cttgctttcc atcatgttga gttttggtgt gctgatgctg cttctgctgc tggaagattt     180
tcttttgctc ttggtgctcc acttgctgct agatctgatt tgtctactgg aaactcttct     240
cacgcttctc accttttgag atctggtgct cttgctttcc ttttcactgc tccttatgct     300
ccaccaccac aagatgctgc agatgcagca gctactgctt ctattccatc tttttcaact     360
gaggctgcta ggactttctc ttctgctcat ggattggctg ttagatctgt ggctattaga     420
gttgcagatg ctgcagaggc tttccatact tctgttgctg gtggtgctag accagctttt     480
gctccagctg atcttggatc tggatttgga cttgctgagg ttgagcttta cggtgatgtt     540
gttcttagat cgtgtctca cccagatggt gatgatgttc catttcttcc aggattcgag     600
ggtgttagta gaccaggtgc tatggattat ggactcacta ggttcgatca ccttgtggga     660
aatgttccag aaatggctcc agttgctgct tacatgaagg gattcactgg atttcatgag     720
ttcgctgagt tcactgctga ggatgttgga actgctgagt ctggacttaa ctctgttgtg     780
cttgctaaca actctgaggc tgttcttttg ccacttaatg agccagttca cggcactaag     840
agaagatctc agattcagac ttacctcgat taccatggtg gaccaggtgt tcaacatatt     900
gctcttgctt catctgatgt gcttaggact cttagagaga tgagagctag atctgctatg     960
ggaggatttg agtttatgag accaccacaa gctaagtatt acgaaggtgt tagaagggag    1020
gctggtgatg ttcttttctga ggctcaaatc aaagagtgcc aagagcttgg agttatggtg    1080
gatagagatg atcagggtgt gcttctccag atttttcacta gccagttgg agataggcca    1140 acattcttct tggagatgat tcagaggatc ggctgcatgg aaaaggatga gattggacaa    1200
gagtaccaaa agggcggatg tggtggattt ggaaagggaa atttctccga gcttttcaag    1260
tccatcgagg attacgagaa gtctcttgag gctaagcaat ctgctgttgc tcaacagtct    1320
tga                                                                  1323

<210> SEQ ID NO 86
<211> LENGTH: 70
<212> TYPE: DNA
<213> ORGANISM: Tobacco mosaic virus

<400> SEQUENCE: 86
tatttttaca acaattacca acaacaacaa acaacaaaca acattacaat tactatttac      60
aattacacat                                                            70

<210> SEQ ID NO 87
<211> LENGTH: 744
<212> TYPE: DNA
```

<213> ORGANISM: Artificial Sequence
<220> FEATURE:
<223> OTHER INFORMATION: Double 35S promoter DNA sequence

<400> SEQUENCE: 87

```
aacatggtgg agcacgacac acttgtctac tccaaaaata tcaaagatac agtctcagaa      60
gaccaaaggg caattgagac ttttcaacaa agggtaatat ccggaaacct cctcggattc     120
cattgcccag ctatctgtca ctttattgtg aagatagtgg aaaaggaagg tggctcctac     180
aaatgccatc attgcgataa aggaaaggcc atcgttgaag atgcctctgc cgacagtggt     240
cccaaagatg gacccccacc cacgaggagc atcgtggaaa aagaagacgt tccaaccacg     300
tcttcaaagc aagtggattg atgtgataac atggtggagc acgacacact tgtctactcc     360
aaaaatatca aagatacagt ctcagaagac caaagggcaa ttgagacttt tcaacaaagg     420
gtaatatccg gaaacctcct cggattccat gcccagcta tctgtcactt tattgtgaag     480
atagtggaaa aggaaggtgg ctcttacaaa tgccatcatt gcgataaagg aaaggccatc     540
gttgaagatg cctctgccga cagtggtccc aaagatggac ccccacccac gaggagcatc     600
gtggaaaaag aagacgttcc aaccacgtct tcaaagcaag tggattgatg tgatatctcc     660
actgacgtaa gggatgacgc acaatcccac tatccttcgc aagacccttc ctctatataa     720
ggaagttcat ttcatttgga gagg                                           744
```

<210> SEQ ID NO 88
<211> LENGTH: 255
<212> TYPE: DNA
<213> ORGANISM: Artificial Sequence
<220> FEATURE:
<223> OTHER INFORMATION: Nos-terminator DNA sequence

<400> SEQUENCE: 88

```
cgatcgttca acatttggc aataaagttt cttaagattg aatcctgttg ccggtcttgc      60
gatgattatc atataatttc tgttgaatta cgttaagcat gtaataatta acatgtaatg    120
catgacgtta tttatgagat gggtttttat gattagagtc ccgcaattat acatttaata    180
cgcgatagaa aacaaaatat agcgcgcaaa ctaggataaa ttatcgcgcg cggtgtcatc    240
tatgttacta gatcg                                                     255
```

HYDROXYPHENYLPYRUVATE DIOXYGENASE POLYPEPTIDES AND METHODS OF USE

CROSS-REFERENCE TO RELATED APPLICATIONS

This application is a divisional of U.S. patent application Ser. No. 12/838,387, filed Jul. 16, 2010, which is a continuation-in-part of U.S. patent application Ser. No. 12/692,552, filed Jan. 22, 2010, which claims priority to U.S. Provisional Application No. 61/224,661, filed Jul. 10, 2009, and to U.S. Provisional Application No. 61/146,513, filed Jan. 22, 2009, each of which are incorporated herein by reference in their entirety.

TECHNICAL FIELD OF THE INVENTION

The present invention relates to novel hydroxyphenyl pyruvate dioxygenase (HPPD) polypeptides that confer herbicide resistance or tolerance to plants and the nucleic acid sequences that encode them. Methods of the invention relate to the production and use of plants that express these mutant HPPD polypeptides and that are resistant to HPPD herbicides.

BACKGROUND OF THE INVENTION

The hydroxyphenylpyruvate dioxygenases (HPPDs) are enzymes that catalyze the reaction in which para-hydroxyphenylpyruvate (HPP) is transformed into homogentisate. This reaction takes place in the presence of enzyme-bound iron ($Fe^{2+}$) and oxygen. Herbicides that act by inhibiting HPPD are well known, and include isoxazoles, diketonitriles, triketones, and pyrazolinates (Hawkes "Hydroxyphenylpyruvate Dioxygenase (HPPD)—The Herbicide Target." In *Modern Crop Protection Compounds*. Eds. Krämer and Schirmer. Weinheim, Germany: Wiley-VCH, 2007. Ch. 4.2, pp. 211-220). Inhibition of HPPD blocks the biosynthesis of plastoquinone (PQ) from tyrosine. PQ is an essential cofactor in the biosynthesis of carotenoid pigments which are essential for photoprotection of the photosynthetic centres. HPPD-inhibiting herbicides are phloem-mobile bleachers which cause the light-exposed new meristems and leaves to emerge white. In the absence of carotenoids, chlorophyll is photo-destroyed and becomes itself an agent of photo-destruction via the photo-generation of singlet oxygen.

Methods for providing plants that are tolerant to HPPD herbicides are also known. These methods have included: 1) overexpressing the HPPD enzyme so as to produce quantities of HPPD enzyme in the plant that are sufficient in relation to a given herbicide so as to have enough of the functional enzyme available for the plant to thrive despite the presence of the herbicide; and 2) mutating a particular HPPD enzyme into an enzyme that is less sensitive to inhibition by herbicides. Methods for mutating HPPD enzymes for improved HPPD herbicide tolerance have been described (see, e.g., PCT Application Nos. WO 99/24585 and WO 2009/144079), and some particular mutations of plant HPPD enzymes (e.g., mutation of G422 in the *Arabidopsis* HPPD sequence) are purportedly capable of providing some measure of tolerance to mesotrione and other triketone herbicides. However, the enzyme kinetic and whole plant data reported thus far are insufficient to conclude whether the reported mutational changes confer commercially significant benefits over the corresponding wild type enzyme(s).

Furthermore, while a particular HPPD enzyme may provide a useful level of tolerance to some HPPD-inhibitor herbicides, the same HPPD may be quite inadequate to provide commercial levels of tolerance to a different, more desirable HPPD-inhibitor herbicide (See, e.g., U.S. Patent Application Publication No. 20040058427; PCT Publication Nos. WO 98/20144 and WO 02/46387; see also U.S. Patent Application Publication No. 20050246800 relating to the identification and labelling of soybean varieties as being relatively HPPD tolerant). Moreover, mutated versions of HPPDs from cool-climate grasses with improved resistance to triketone-type herbicides have yet to be reported. Such mutants would be highly desirable, as HPPDs from cool-climate grasses are preferable to other types (see, e.g., PCT Application No. WO 02/46387 and Hawkes et al. 2001 in *Proc. Brit. Crop Prot. Conf. Weeds* 2, 563). Accordingly, new methods and compositions for conferring commercial levels of HPPD herbicide tolerance upon various crops and crop varieties are needed.

BRIEF SUMMARY OF THE INVENTION

Compositions and methods for conferring hydroxyphenyl pyruvate dioxygenase (HPPD) herbicide resistance or tolerance to plants are provided. The compositions include nucleotide and amino acid sequences for HPPD polypeptides. In certain embodiments, the polypeptides of the invention are novel HPPDs that derive from plants and that confer resistance or tolerance when expressed heterologously in other plants to certain classes of herbicides that inhibit HPPD. In particular embodiments, these HPPDs comprise amino acid sequences set forth in SEQ ID NOs: 2-12, particularly SEQ ID NOs: 2-8, and polypeptides having at least about 99, 98, 97, 96, 95, 94, 93, 92, 91 or 90% sequence identity to SEQ ID NOs: 2-12 that exhibit HPPD enzyme activity.

Preferred novel HPPDs are likewise those that, in comparison with HPPD enzymes of the prior art, exhibit superior tolerance to one or more types of HPPD herbicide and where tolerance is characterised in vitro by the numerical value of the parameter ($k_{off} \times k_{cat}/K_{m\ HPP}$) and where $k_{off}$ is the rate constant governing the dissociation rate of the complex of the HPPD enzyme with herbicide and $k_{cat}/K_{m\ HPP}$ is the catalytic turnover number divided by the $K_m$ value for the substrate HPP (4-hydroxyphenyl pyruvate).

In a further embodiment of the current invention there is therefore also provided an in vitro method for characterising and selecting HPPDs that confer superior levels of tolerance to HPPD herbicides based on measuring and comparing values of $k_{cat}/K_m$ HPP and $k_{off}$ or functional equivalents of these parameters.

In further embodiments the polypeptides of the invention are catalytically active mutant HPPDs that derive from plants and that, relative to the like unmutated enzyme, confer superior levels of resistance or tolerance to certain classes of herbicides that inhibit HPPD. In particular embodiments these mutant HPPD polypeptides comprise one or more amino acid sequences selected from SEQ ID NOs: 15-19, wherein SEQ ID NOs: 15-19 have one or more amino acid substitutions described as follows:

With respect to the sequence (L,I,R)(V,A)(G,A)DVL(S,T) (SEQ ID NO: 15), the first L, the I, or the R is replaced with any other amino acid, particularly E, D, G, C, N, Q, S, and A, and more particularly E, C, A and D.

With respect to the sequence G(I,V)LVD(R,K) (SEQ ID NO: 16), the L is replaced with any other amino acid, particularly M, F, Y, I, A, W, and V, and more particularly M.

With respect to the sequence DH(V, I, M)VGN (SEQ ID NO: 17), the first V, the I or the M is replaced with any other amino acid, particularly L, A and I, and more particularly L and I.

With respect to the sequence GGF(E,D)F(M,L)(A,P) (SEQ ID NO: 18), the A or the P is replaced with any other amino acid, particularly R, K, H, N, I, L, T, S and Q, and more particularly R, I, L, H and K.

With respect to the sequence CGGFGKGN (SEQ ID NO: 19), the second G or the K is replaced with any other amino acid. In certain embodiments, the second G is replaced with an R, K, H, E, D, N, Q, A, S, T, and more particularly R, S, T, H and K. In other embodiments, the K is replaced with an S and T, and more particularly a T.

In some embodiments the polypeptides are singly, doubly, triply, quadruply, quintuply or sextuply mutant HPPDs that combine more than one of the above mutations in the various permutations (for example, 2+3, 2+4, 2+1; 3+4, 3+1; 4+1; 3+4+1, 2+3+4, 2+4+1, 2+3+1; 2+3+4+1; 1+2+3+4+5 etc.).

In further embodiments the mutant HPPD is derived from a monocot plant and, in particular, a cool climate grass species such as wheat, barley, oats or rye. In particular embodiments the mutant HPPD is derived from *Lolium, Avena, Poa, Alopecurus* or *Sorghum* species and, more particularly, is derived from one or more of the HPPD polypeptides of SEQ ID NOs: 1-8.

Exemplary HPPD polypeptides and mutant HPPD polypeptides according to the invention correspond to the amino acid sequences set forth in SEQ ID NOs: 2-8, 20-41, 49 and 50 and variants and fragments thereof. Nucleic acid molecules comprising polynucleotide sequences that encode these particular mutant HPPD polypeptides of the invention are further provided, e.g., SEQ ID NOs: 53-82, 84 and 85. Compositions also include expression cassettes comprising a promoter operably linked to a nucleotide sequence that encodes an HPPD polypeptide of the invention, alone or in combination with one or more additional nucleic acid molecules encoding polypeptides that confer desirable traits. Transformed plants, plant cells, and seeds comprising an expression cassette of the invention are further provided.

The compositions of the invention are useful in methods directed to conferring herbicide resistance or tolerance to plants, particularly resistance or tolerance to certain classes of herbicides that inhibit HPPD. In particular embodiments, the methods comprise introducing into a plant at least one expression cassette comprising a promoter operably linked to a nucleotide sequence that encodes an HPPD polypeptide of the invention. As a result, the HPPD polypeptide is expressed in the plant, and since the HPPD is selected on the basis that it is less sensitive to HPPD-inhibiting herbicides, this leads to the plant exhibiting substantially improved resistance or tolerance to HPPD-inhibiting herbicides.

Methods of the present invention also comprise selectively controlling weeds in a field at a crop locus. In one embodiment, such methods involve over-the-top pre- or postemergence application of weed-controlling amounts of HPPD herbicides in a field at a crop locus that contains plants expressing the HPPD polypeptides of the invention. In other embodiments, methods are also provided for the assay, characterization, identification, and selection of the HPPDs of the current invention.

DETAILED DESCRIPTION OF THE INVENTION

Figure 1:
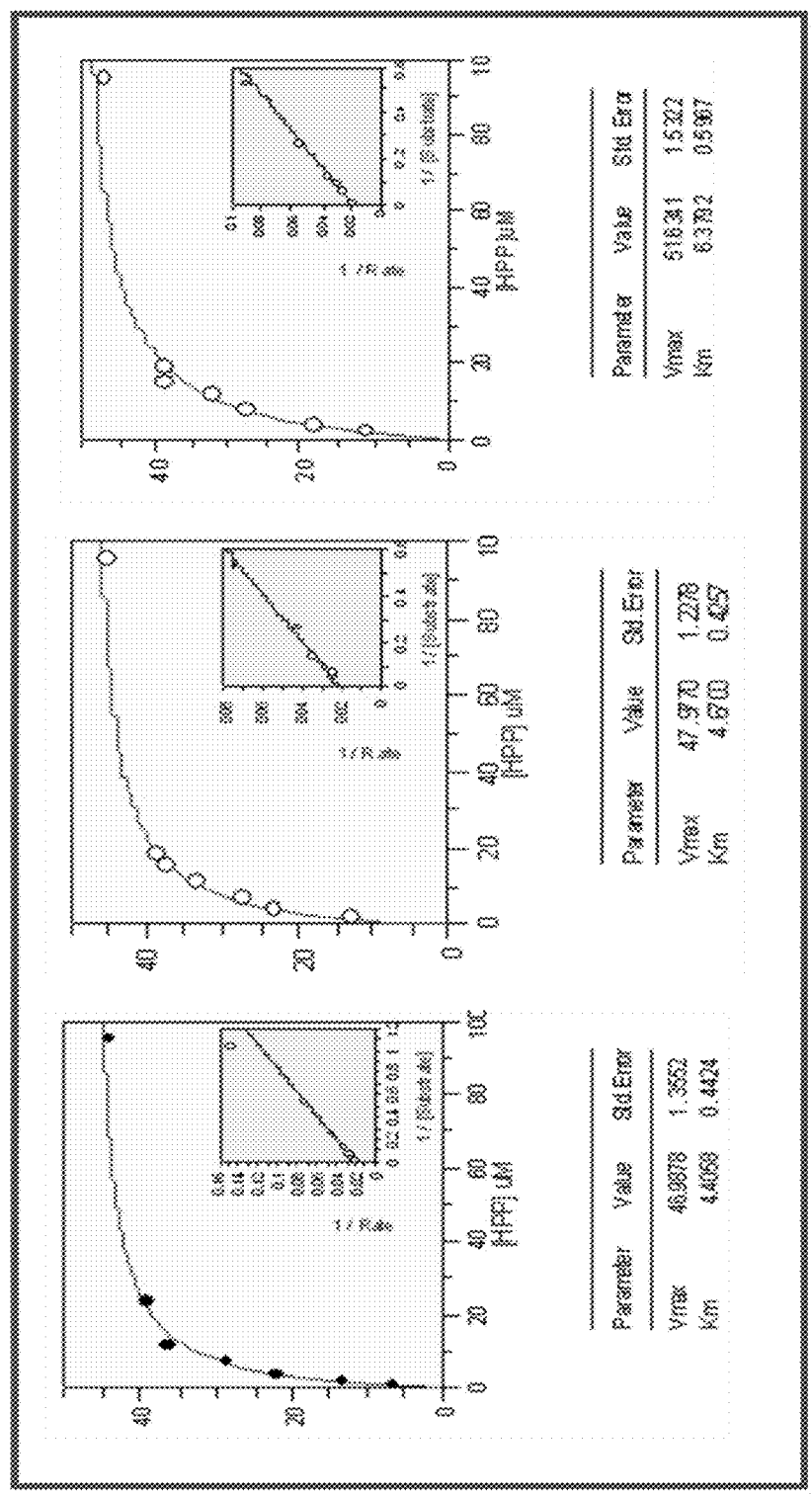
FIG. 1 depicts data from $K_m$ and $V_{max}$ determinations of the *Avena*-derived HPPD polypeptide corresponding to the amino acid sequence set forth in SEQ ID NO: 1.
Figure 2:
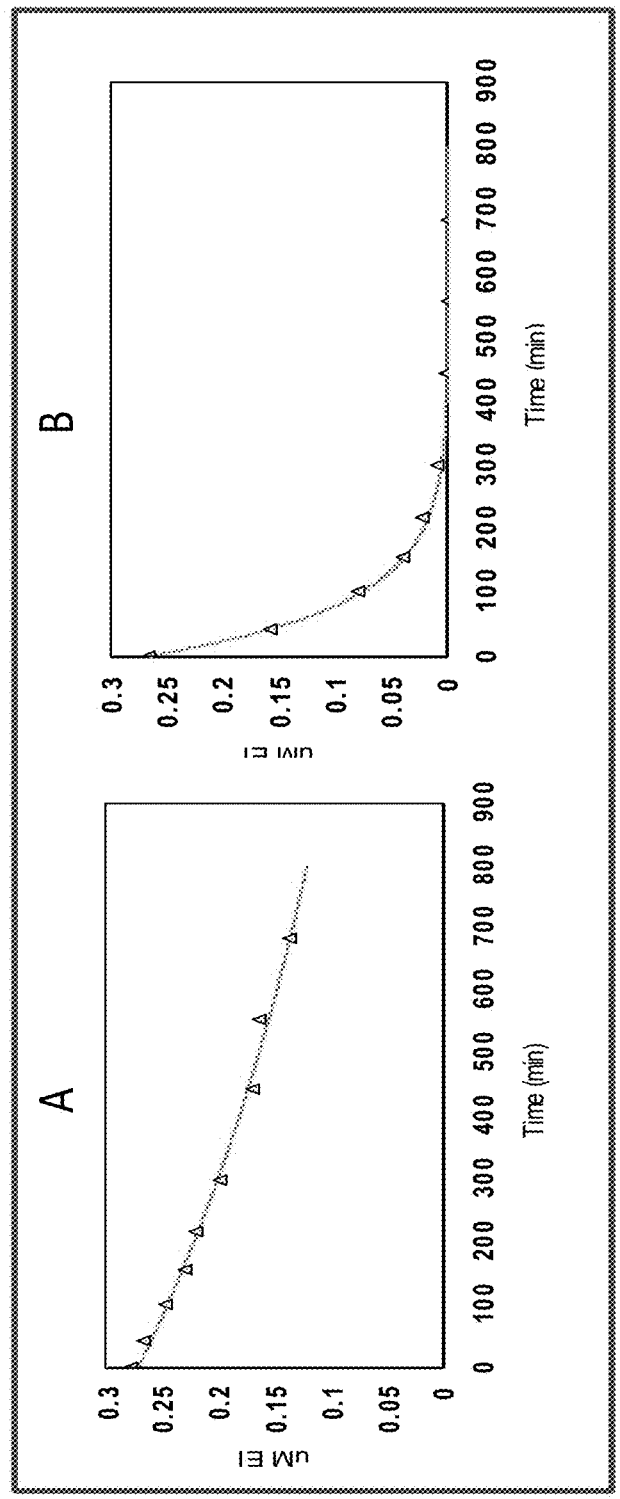
FIG. 2 depicts data from inhibitor exchange experiments at ice temperature to determine the off rate ($k_{off}$) values governing dissociation of the complex of structure B (mesotrione) with the HPPD polypeptide corresponding to A) the amino acid sequence set forth in SEQ ID NO: 1 and B) the amino acid sequence set forth in SEQ ID NO: 41.

The present invention provides compositions and methods directed to conferring hydroxyphenyl pyruvate dioxygenase (HPPD) herbicide resistance or tolerance to plants. Compositions include amino acid sequences for native and mutant HPPD polypeptides having HPPD enzymatic activity, and variants and fragments thereof. Nucleic acids that encode the mutant HPPD polypeptides of the invention are also provided. Methods for conferring herbicide resistance or tolerance to plants, particularly resistance or tolerance to certain classes of herbicides that inhibit HPPD, are further provided. Methods are also provided for selectively controlling weeds in a field at a crop locus and for the assay, characterization, identification and selection of the mutant HPPDs of the current invention that provide herbicide tolerance.

Within the context of the present invention the terms hydroxy phenyl pyruvate dioxygenase (HPPD), 4-hydroxy phenyl pyruvate dioxygenase (4-HPPD) and p-hydroxy phenyl pyruvate dioxygenase (p-HPPD) are synonymous.

"HPPD herbicides" are herbicides that are bleachers and whose primary site of action is HPPD. Many are well known and described elsewhere herein and in the lature (Hawkes "Hydroxyphenylpyruvate Dioxygenase (HPPD)—The Herbicide Target." In *Modern Crop Protection Compounds*. Eds. Krämer and Schirmer. Weinheim, Germany: Wiley-VCH, 2007. Ch. 4.2, pp. 211-220; Edmunds "Hydroxyphenylpyruvate dioxygenase (HPPD) Inhibitors: Triketones." In *Modern Crop Protection Compounds*. Eds. Krämer and Schirmer. Weinheim, Germany: Wiley-VCH, 2007. Ch. 4.2, pp. 221-242). As used herein, the term "HPPD herbicides" refers to herbicides that act either directly or indirectly to inhibit HPPD, where the herbicides are bleachers and where inhibition of HPPD is at least part of the herbicide's mode of action on plants.

As used herein, plants which are substantially "tolerant" to a herbicide exhibit, when treated with said herbicide, a dose/response curve which is shifted to the right when compared with that exhibited by similarly subjected non tolerant like plants. Such dose/response curves have "dose" plotted on the x-axis and "percentage kill or damage", "herbicidal effect" etc. plotted on the y-axis. Tolerant plants will typically require at least twice as much herbicide as non tolerant like plants in order to produce a given herbicidal effect. Plants which are substantially "resistant" to the herbicide exhibit few, if any, necrotic, lytic, chlorotic or other lesions or, at least, none that impact significantly on yield, when subjected to the herbicide at concentrations and rates which are typically employed by the agricultural community to kill weeds in the field.

As used herein, "non-transgenic-like plants" are plants that are similar or the same as transgenic plants but that do not contain a transgene conferring herbicide resistance.

As used herein, the term "confer" refers to providing a characteristic or trait, such as herbicide tolerance or resistance and/or other desirable traits to a plant.

As described elsewhere herein, the term "heterologous" means from another source. In the context of DNA, "heterologous" refers to any foreign "non-self" DNA including that from another plant of the same species. For example, in the present application a soybean HPPD gene that was transgenically expressed back into a soybean plant would still be described as "heterologous" DNA.

The article "a" and "an" are used herein to refer to one or more than one (i.e., to at least one) of the grammatical object of the article. By way of example, "an element" means one or more element. Throughout the specification the word "comprising," or variations such as "comprises" or "comprising," will be understood to imply the inclusion of a stated element, integer or step, or group of elements, integers or steps, but not the exclusion of any other element, integer or step, or group of elements, integers or steps.

A variety of additional terms are defined or otherwise characterized herein.

HPPD Sequences

The compositions of the invention include isolated or substantially purified native and mutant HPPD polynucleotides and polypeptides as well as host cells comprising the HPPD polynucleotides. Specifically, the present invention provides HPPD polypeptides that have HPPD enzymatic activity and that confer resistance or tolerance in plants to certain classes of herbicides that inhibit HPPD, and variants and fragments thereof. Nucleic acids that encode the native and mutant HPPD polypeptides of the invention are also provided.

Mutant HPPD polypeptides of the presenting invention have amino acid changes at one or more positions relative to the starting wild type sequence from which they are derived, and exhibit enhanced tolerance to one or more HPPD inhibitor herbicides. HPPD enzymes that exhibit enhanced tolerance to an HPPD herbicide may do so by virtue of exhibiting, relative to the like unmutated starting enzyme:

a) a lower $K_m$ value for the natural substrate, 4-hydroxyphenylpyruvate;

b) a higher $k_{cat}$ value for converting 4-hydroxyphenylpyruvate to homogentisate;

c) a lower value of the apparent rate constant, $k_{on}$, governing formation of an enzyme: HPPD inhibitor herbicide complex;

d) an increased value of the rate constant, $k_{off}$, governing dissociation of an enzyme: HPPD inhibitor herbicide complex; and/or e) as a result of changes in one or both of c) and d), an increased value of the equilibrium constant, $K_i$ (also called $K_d$), governing dissociation of an enzyme: HPPD inhibitor herbicide complex. DNA sequences encoding such improved mutated HPPDs are used in the provision of HPPD plants, crops, plant cells and seeds of the current invention that offer enhanced tolerance or resistance to one or more HPPD herbicides as compared to like plants likewise expressing the unmutated starting enzyme.

Here it is found that increases in the value of $k_{off}$ are of particular value in improving the ability of an HPPD to confer resistance to a HPPD herbicide whereas, at least in the range above 5000 $s^{-1} M^{-1}$ at 25° C. changes in $k_m$, have relatively little impact. So, for example, compounds B and C exhibit similar Kd values in respect of the HPPD of SEQ ID NO: 1 but $k_{off}$ values that are about 10 fold different in respect of B and C. Accordingly, transgenic plants expressing the HPPD of SEQ ID NO: 1 exhibit superior resistance to compound B than to compound C.

Thus preferred HPPDs are selected as those that, in comparison with other HPPD enzymes, exhibit superior tolerance to one or more types of HPPD herbicide and where tolerance is characterised in vitro by the numerical value of the parameter ($k_{off} \times k_{cat}/K_{m\ HPP}$) and where $k_{off}$ is the rate constant governing the dissociation rate of the complex of the HPPD enzyme with herbicide and $k_{cat}/K_{m\ HPP}$ is the catalytic turnover number divided by the $K_m$ value for the substrate HPP (4-hydroxyphenylpyruvate).

Thus in one embodiment of the current invention there is provided an in vitro method for characterising and selecting HPPDs that confer superior levels of tolerance to HPPD herbicides based on measuring and comparing values of $k_{cat}/K_m$ HPP and $k_{off}$ or functional equivalents of these parameters.

Site-directed mutations of genes encoding HPPDs are selected so as to encode amino acid changes selected from those listed here either singly or preferably in combination. Genes encoding such mutant forms of HPPDs are useful for making crop plants resistant to herbicides that inhibit HPPD. HPPD genes so modified are especially suitable for use in transgenic plants in order to confer herbicide tolerance or resistance upon crop plants. In a preferred embodiment the HPPDs derive from plants.

Many HPPD sequences are known in the art and can be used to generate mutant HPPD sequences by making amino acid substitutions corresponding to those described herein. For example, a known or suspected HPPD sequence can be inspected for the presence of the amino acid motifs SEQ ID NOs: 15-19 and the corresponding changes described herein made. Alternatively, in the case of HPPDs not deriving from plants the equivalent changes to those indicated here can be made on the basic of sequence line ups and similarity to the motifs specified here. Alternatively, the sequence to be improved by mutation can be aligned with, for example, SEQ ID NO: 1 using standard sequence alignment tools, and the corresponding amino acid substitutions described herein with respect to SEQ ID NO: 1 can be made at the corresponding positions in the reference sequence.

In particular embodiments, the compositions of the invention comprise a mutant HPPD polypeptide having at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to SEQ ID NO: 1 (the HPPD amino acid sequence of *Avena sativa*) or to SEQ ID NO: 2, or to SEQ ID NO: 3 or to SEQ ID NO: 4 or to SEQ ID NO: 5 or to SEQ ID NO: 6 or to SEQ ID NO: 7 or to SEQ ID NO: 8, where the polypeptide has HPPD enzymatic activity, and where the polypeptide contains one or more substitution(s) corresponding to the amino acid positions listed in column 1 of Table 1.

TABLE 1

Exemplary HPPD mutations

| Mutable amino acid position relative to SEQ ID NO: 1 | Substitution or addition |
| --- | --- |
| 217 | A, I, L, |
| 326 | R, K, H, N, I, L, T, S, Q |

TABLE 1-continued

Exemplary HPPD mutations

| Mutable amino acid position relative to SEQ ID NO: 1 | Substitution or addition |
|---|---|
| 339 | E, D, G, C, N, Q, S, A, L |
| 358 | M, F, Y, I, A, W, V |
| 408 | R, K, H, E, D, N, Q, A, S, T |
| 411 | S, T |

In various embodiments, an amino acid at one or more position(s) listed in column 1 is replaced with any other amino acid. In another embodiment, the polypeptide comprises one or more amino acid substitutions, additions, or deletions corresponding to the amino acid substitution(s) or deletion(s) listed in column 2 of Table 1. In yet another embodiment, the polypeptide comprises one or more substitutions corresponding to a conservative variant of the amino acids listed in column 2 of Table 1.

For example, the polypeptide may comprise a mutation corresponding to amino acid position 339 of SEQ ID NO: 1, wherein that amino acid is replaced with a glutamate or a conservative substitution of glutamate.

In particular embodiments, the amino acid sequence of the mutant HPPD polypeptide of the invention is selected from the group consisting of SEQ ID NOs: 20, 21, 22, 23, 24, 25, 26, 27, 28, 29, 30, 31, 31, 33, 34, 35, 36, 37, 38, 39, 40, 41, 49 and 50.

The terms "polypeptide," "peptide," and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers. Polypeptides of the invention can be produced either from a nucleic acid disclosed herein, or by the use of standard molecular biology techniques. For example, a truncated protein of the invention can be produced by expression of a recombinant nucleic acid of the invention in an appropriate host cell, or alternatively by a combination of ex vivo procedures, such as protease digestion and purification.

Accordingly, the present invention also provides nucleic acid molecules comprising polynucleotide sequences that encode mutant HPPD polypeptides that have HPPD enzymatic activity and that confer resistance or tolerance in plants to certain classes of herbicides that inhibit HPPD, and variants and fragments thereof. In general, the invention includes any polynucleotide sequence that encodes any of the mutant HPPD polypeptides described herein, as well as any polynucleotide sequence that encodes HPPD polypeptides having one or more conservative amino acid substitutions relative to the mutant HHPD polypeptides described herein. Conservative substitution tables providing functionally similar amino acids are well known in the art. The following five groups each contain amino acids that are conservative substitutions for one another: Aliphatic: Glycine (G), Alanine (A), Valine (V), Leucine (L), Isoleucine (I); Aromatic: Phenylalanine (F), Tyrosine (Y), Tryptophan (W); Sulfur-containing: Methionine (M), Cysteine (C); Basic: Arginine I, Lysine (K), Histidine (H); Acidic: Aspartic acid (D), Glutamic acid (E), Asparagine (N), Glutamine (Q).

In one embodiment, the present invention provides a polynucleotide sequence encoding an amino acid sequence having at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to SEQ ID NOs: 1, 2, 3, 4, 5, 6, 7 or 8 where the HPPD amino acid sequence derives from a plant, where the polypeptide has HPPD enzymatic activity, and where the polypeptide contains one or more substitutions, additions or deletions as discussed infra.

In another embodiment, the present invention provides a polynucleotide sequence selected from the group consisting of SEQ ID NOs: 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 84 and 85.

As used herein, "nucleic acid" includes reference to a deoxyribonucleotide or ribonucleotide polymer in either single- or double-stranded form, and unless otherwise limited, encompasses known analogues (e.g., peptide nucleic acids) having the essential nature of natural nucleotides in that they hybridize to single-stranded nucleic acids in a manner similar to naturally occurring nucleotides.

As used herein, the terms "encoding" or "encoded" when used in the context of a specified nucleic acid mean that the nucleic acid comprises the requisite information to direct translation of the nucleotide sequence into a specified protein. The information by which a protein is encoded is specified by the use of codons. A nucleic acid encoding a protein may comprise non-translated sequences (e.g., introns) within translated regions of the nucleic acid or may lack such intervening non-translated sequences (e.g., as in cDNA).

The invention encompasses isolated or purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material, or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A protein that is substantially free of interfering enzyme activities and that is capable being characterized in respect of its catalytic, kinetic and molecular properties includes quite crude preparations of protein (for example recombinantly produced in cell extracts) having less than about 98%, 95% 90%, 80%, 70%, 60% or 50% (by dry weight) of contaminating protein as well as preparations further purified by methods known in the art to have 40%, 30%, 20%, 10%, 5%, or 1% (by dry weight) of contaminating protein.

The proteins of the invention may be altered in various ways including amino acid substitutions, deletions, truncations, and insertions. Methods for such manipulations are generally known in the art. For example, amino acid sequence variants and fragments of the mutant HPPD proteins can be prepared by mutations in the DNA. Methods for mutagenesis and polynucleotide alterations are well known in the art. See, for example, Kunkel (1985) *Proc. Natl. Acad.*

Sci. USA 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that often do not affect biological activity of the protein of interest may be found in the model of Dayhoff et al. (1978) *Atlas of Protein Sequence and Structure* (Natl. Biomed. Res. Found., Washington, D.C.). Conservative substitutions, such as exchanging one amino acid with another having similar properties, may be optimal.

The polynucleotides of the invention can also be used to isolate corresponding sequences from other organisms, particularly other plants. In this manner, methods such as PCR, hybridization, and the like can be used to identify such sequences based on their sequence homology to the sequences set forth herein.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art. See, for example, Sambrook et al. (1989) *Molecular Cloning: A Laboratory Manual* (2d ed., Cold Spring Harbor Laboratory Press, Plainview, N.Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York).

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Methods for preparation of probes for hybridization and for construction of cDNA and genomic libraries are generally known in the art and are disclosed in Sambrook et al. (1989) *Molecular Cloning: A Laboratory Manual* ($2^{nd}$ ed., Cold Spring Harbor Laboratory Press, Plainview, N.Y.).

By "hybridizing to" or "hybridizing specifically to" refers to the binding, duplexing, or hybridizing of a molecule only to a particular nucleotide sequence under stringent conditions when that sequence is present in a complex mixture (e.g., total cellular) DNA or RNA. "Bind(s) substantially" refers to complementary hybridization between a probe nucleic acid and a target nucleic acid and embraces minor mismatches that can be accommodated by reducing the stringency of the hybridization media to achieve the desired detection of the target nucleic acid sequence.

"Stringent hybridization conditions" and "stringent hybridization wash conditions" in the context of nucleic acid hybridization experiments such as Southern and Northern hybridizations are sequence dependent, and are different under different environmental parameters. Longer sequences hybridize specifically at higher temperatures. An extensive guide to the hybridization of nucleic acids is found in Tijssen (1993) *Laboratory Techniques in Biochemistry and Molecular Biology—Hybridization with Nucleic Acid Probes* part I chapter 2 "Overview of principles of hybridization and the strategy of nucleic acid probe assays" Elsevier, New York. Generally, highly stringent hybridization and wash conditions are selected to be about 5° C. lower than the thermal melting point ($T_m$) for the specific sequence at a defined ionic strength and pH. Typically, under "stringent conditions" a probe will hybridize to its target subsequence, but to no other sequences.

The $T_m$ is the temperature (under defined ionic strength and pH) at which 50% of the target sequence hybridizes to a perfectly matched probe. Very stringent conditions are selected to be equal to the $T_m$ for a particular probe. An example of stringent hybridization conditions for hybridization of complementary nucleic acids which have more than 100 complementary residues on a filter in a Southern or northern blot is 50% formamide with 1 mg of heparin at 42° C., with the hybridization being carried out overnight. An example of highly stringent wash conditions is 0.1 5M NaCl at 72° C. for about 15 minutes. An example of stringent wash conditions is a 0.2×SSC wash at 65° C. for 15 minutes (see, Sambrook, infra, for a description of SSC buffer). Often, a high stringency wash is preceded by a low stringency wash to remove background probe signal. An example medium stringency wash for a duplex of, e.g., more than 100 nucleotides, is 1×SSC at 45° C. for 15 minutes. An example low stringency wash for a duplex of, e.g., more than 100 nucleotides, is 4-6×SSC at 40° C. for 15 minutes. For short probes (e.g., about 10 to 50 nucleotides), stringent conditions typically involve salt concentrations of less than about 1.0 M Na ion, typically about 0.01 to 1.0 M Na ion concentration (or other salts) at pH 7.0 to 8.3, and the temperature is typically at least about 30° C. Stringent conditions can also be achieved with the addition of destabilizing agents such as formamide. In general, a signal to noise ratio of 2× (or higher) than that observed for an unrelated probe in the particular hybridization assay indicates detection of a specific hybridization. Nucleic acids that do not hybridize to each other under stringent conditions are still substantially identical if the proteins that they encode are substantially identical. This occurs, e.g., when a copy of a nucleic acid is created using the maximum codon degeneracy permitted by the genetic code.

The following are examples of sets of hybridization/wash conditions that may be used to clone nucleotide sequences that are homologues of reference nucleotide sequences of the present invention: a reference nucleotide sequence preferably hybridizes to the reference nucleotide sequence in 7% sodium dodecyl sulfate (SDS), 0.5 M NaPO$_4$, 1 mM EDTA at 50° C. with washing in 2×SSC, 0.1% SDS at 50° C., more desirably in 7% sodium dodecyl sulfate (SDS), 0.5 M NaPO$_4$, 1 mM EDTA at 50° C. with washing in 1×SSC, 0.1% SDS at 50° C., more desirably still in 7% sodium dodecyl sulfate (SDS), 0.5 M NaPO$_4$, 1 mM EDTA at 50° C. with washing in 0.5×SSC, 0.1% SDS at 50° C., preferably in 7% sodium dodecyl sulfate (SDS), 0.5 M NaPO$_4$, 1 mM EDTA at 50° C. with washing in 0.1×SSC, 0.1% SDS at 50° C., more preferably in 7% sodium dodecyl sulfate (SDS), 0.5 M NaPO$_4$, 1 mM EDTA at 50° C. with washing in 0.1×SSC, 0.1% SDS at 65° C.

Fragments and variants of the disclosed nucleotide sequences and proteins encoded thereby are also encompassed by the present invention. "Fragment" is intended to mean a portion of the nucleotide sequence or a portion of the amino acid sequence and hence protein encoded thereby. Fragments of a nucleotide sequence may encode protein fragments that retain the biological activity of the mutant HPPD protein and hence have HPPD enzymatic activity. Alternatively, fragments of a nucleotide sequence that are useful as hybridization probes or in mutagenesis and shuffling reactions to generate yet further HPPD variants generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the polypeptides of the invention.

A fragment of a nucleotide sequence that encodes a biologically active portion of a mutant HPPD protein of the invention will encode at least 15, 25, 30, 40, 50, 60, 70, 80, 90, 100, 110, 120, 150, 180, 200, 250, 300, 350 contiguous amino acids, or up to the total number of amino acids present in a full-length mutant HPPD polypeptide of the invention. Fragments of a nucleotide sequence that are useful as hybridization probes or PCR primers generally need not encode a biologically active portion of an HPPD protein.

As used herein, "full-length sequence" in reference to a specified polynucleotide means having the entire nucleic acid sequence of a native or mutated HPPD sequence. "Native sequence" is intended to mean an endogenous sequence, i.e., a non-engineered sequence found in an organism's genome.

Thus, a fragment of a nucleotide sequence of the invention may encode a biologically active portion of a mutant HPPD polypeptide, or it may be a fragment that can be used as a hybridization probe etc. or PCR primer using methods disclosed below. A biologically active portion of a mutant HPPD polypeptide can be prepared by isolating a portion of one of the nucleotide sequences of the invention, expressing the encoded portion of the mutant HPPD protein (e.g., by recombinant expression in vitro), and assessing the activity of the encoded portion of the mutant HPPD protein. Nucleic acid molecules that are fragments of a nucleotide sequence of the invention comprise at least 15, 20, 50, 75, 100, 150, 200, 300, 400, 500, 600, 700, 800, 900, 1000, 1100, 1200, or 1300 contiguous nucleotides, or up to the number of nucleotides present in a full-length nucleotide sequence disclosed herein.

"Variants" is intended to mean substantially similar sequences. For polynucleotides, a variant comprises a deletion and/or addition of one or more nucleotides at one or more internal sites within the reference polynucleotide and/or a substitution of one or more nucleotides at one or more sites in the mutant HPPD polynucleotide. As used herein, a "reference" polynucleotide or polypeptide comprises a mutant HPPD nucleotide sequence or amino acid sequence, respectively. As used herein, a "native" polynucleotide or polypeptide comprises a naturally occurring nucleotide sequence or amino acid sequence, respectively. One of skill in the art will recognize that variants of the nucleic acids of the invention will be constructed such that the open reading frame is maintained. For polynucleotides, conservative variants include those sequences that, because of the degeneracy of the genetic code, encode the amino acid sequence of one of the mutant HPPD polypeptides of the invention. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotide, such as those generated, for example, by using site-directed mutagenesis but which still encode a mutant HPPD protein of the invention. Generally, variants of a particular polynucleotide of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, a polynucleotide that encodes a polypeptide with a given percent sequence identity to the polypeptides of SEQ ID NOs: 1, 2, 3, 4, 5, 6, 7, 8, 9, 10, 11, 12, 20, 21, 22, 23, 24, 25, 26, 27, 28, 29, 30, 31, 32, 33, 34, 35, 36, 37, 38, 39, 40, 41, 49 and 50 are disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity across the entirety of the HPPD sequences described herein.

"Variant" protein is intended to mean a protein derived from the reference protein by deletion or addition of one or more amino acids at one or more internal sites in the mutant HPPD protein and/or substitution of one or more amino acids at one or more sites in the mutant HPPD protein. Variant proteins encompassed by the present invention are biologically active, that is they continue to possess the desired biological activity of the mutant HPPD protein, that is, HPPD enzymatic activity and/or herbicide tolerance as described herein. Such variants may result from, for example, genetic polymorphism or from human manipulation. Biologically active variants of a mutant HPPD protein of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity across the entirety of the amino acid sequence for the mutant HPPD protein as determined by sequence alignment programs and parameters described elsewhere herein. A biologically active variant of a protein of the invention may differ from that protein by as few as 1-15 amino acid residues, as few as 1-10, such as 6-10, as few as 5, as few as 4, 3, 2, or even 1 amino acid residue.

Methods of alignment of sequences for comparison are well known in the art and can be accomplished using mathematical algorithms such as the algorithm of Myers and Miller (1988) *CABIOS* 4:11-17; the local alignment algorithm of Smith et al. (1981) *Adv. Appl. Math.* 2:482; the global alignment algorithm of Needleman and Wunsch (1970) *J Mol. Biol.* 48:443-453; and the algorithm of Karlin and Altschul (1990) *Proc. Natl. Acad. Sci. USA* 872264, modified as in Karlin and Altschul (1993) *Proc. Natl. Acad. Sci. USA* 90:5873-5877. Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package, Version 10 (available from Accelrys Inc., 9685 Scranton Road, San Diego, Calif., USA).

Gene Stacking

In certain embodiments the polynucleotides of the invention encoding native or mutant HPPD polypeptides or variants thereof that retain HPPD enzymatic activity (e.g., a polynucleotide sequence encoding an amino acid sequence selected from the group consisting of SEQ ID NOs: 1, 2, 3, 4, 5, 6, 7, 8, 20, 21, 22, 23, 24, 25, 26, 27, 28, 29, 30, 31, 32, 33, 34, 35, 36, 37, 38, 39, 40, 41, 49 and 50) can be stacked with any combination of polynucleotide sequences of interest in order to create plants with a desired trait. A trait, as used herein, refers to the phenotype derived from a particular sequence or groups of sequences. For example, the polynucleotides encoding a mutant HPPD polypeptide or variant thereof that retains HPPD enzymatic activity may be stacked with any other polynucleotides encoding polypeptides that confer a desirable trait, including but not limited to resistance to diseases, insects, and herbicides, tolerance to heat and drought, reduced time to crop maturity, improved industrial processing, such as for the conversion of starch or biomass to fermentable sugars, and improved agronomic quality, such as high oil content and high protein content.

In a particular embodiment of the invention polynucleotides may be stacked (or, alternatively, expression cassettes may be stacked on a single polynucleotide) so as to express more than one type of HPPD polypeptide within a plant. This is a particular advantage where, for example, one HPPD is particularly suitable for providing resistance to one class of HPPD herbicide while the other provides better tolerance to a different class of HPPD herbicide. Stacking HPPD polypeptides is also an advantage where one polypeptide expresses inherent herbicide-resistance but is somewhat labile. This herbicide-resistant HPPD can then be stabilised in mixed expression with, for example, similar but less temperature-labile HPPDs through the formation of mixed enzyme dimers.

Exemplary polynucleotides that may be stacked with polynucleotides of the invention encoding a mutant HPPD polypeptide or variant thereof that retains HPPD enzymatic activity include polynucleotides encoding polypeptides conferring resistance to pests/pathogens such as viruses, nematodes, insects or fungi, and the like. Exemplary polynucleotides that may be stacked with polynucleotides of the invention include polynucleotides encoding: polypeptides having pesticidal and/or insecticidal activity, such as other *Bacillus thuringiensis* toxic proteins (described in U.S. Pat. Nos. 5,366,892; 5,747,450; 5,737,514; 5,723,756; 5,593, 881; and Geiser et al. (1986) *Gene* 48:109), lectins (Van Damme et al. (1994) *Plant Mol. Biol.* 24:825, pentin (described in U.S. Pat. No. 5,981,722), and the like; traits desirable for disease or herbicide resistance (e.g., fumonisin detoxification genes (U.S. Pat. No. 5,792,931); avirulence and disease resistance genes (Jones et al. (1994) *Science* 266:789; Martin et al. (1993) *Science* 262:1432; Mindrinos et al. (1994) *Cell* 78:1089); a gene encoding an aryloxyalkanoate dioxygenase conferring resistance to certain classes of auxin and acetylCoA carboxylase herbicides (e.g. in PCT Publication Nos. WO 2008/141154, WO 2007/053482 or a tfdA gene giving resistance to 2,4 Din U.S. Pat. No. 6,153, 401); a gene encoding a dicamba monoxygenase (Behrens et al. (2007) *Science*, 316, 1185) conferring resistance to dicamba; a gene encoding a homogentisate solanesyltransferase (HST) conferring resistance to HST-inhibiting herbicides (PCT Publication No. WO 2010/029311); a gene encoding a nitrilase conferring resistance to a nitrile-containing herbicide (e.g. the bxnA bromoxynil nitrilase); acetolactate synthase (ALS) mutants that lead to herbicide resistance such as the S4 and/or Hra mutations; glyphosate resistance (e.g., 5-enol-pyrovyl-shikimate-3-phosphate-synthase (EPSPS) gene, described in U.S. Pat. Nos. 4,940,935 and 5,188,642; or the glyphosate N-acetyltransferase (GAT) gene, described in Castle et al. (2004) *Science*, 304:1151-1154; and in U.S. Patent Application Publication Nos. 20070004912, 20050246798, and 20050060767)); glufosinate resistance (e.g., phosphinothricin acetyl transferase genes PAT and BAR, described in U.S. Pat. Nos. 5,561,236 and 5,276,268); a cytochrome P450 or variant thereof that confers herbicide resistance or tolerance to, inter alia, HPPD herbicides (U.S. Patent Application Publication No. 20090011936; U.S. Pat. Nos. 6,380,465; 6,121,512; 5,349, 127; 6,649,814; and 6,300,544; and PCT Publication No. WO 2007/000077); and traits desirable for processing or process products such as high oil (e.g., U.S. Pat. No. 6,232,529); modified oils (e.g., fatty acid desaturase genes (U.S. Pat. No. 5,952,544; PCT Publication No. WO 94/11516)); modified starches (e.g., ADPG pyrophosphorylases (AGPase), starch synthases (SS), starch branching enzymes (SBE), and starch debranching enzymes (SDBE)); and polymers or bioplastics (e.g., U.S. Pat. No. 5,602,321; beta-ketothiolase, polyhydroxybutyrate synthase, and acetoacetyl-CoA reductase (Schubert et al. (1988) *J. Bacteriol.* 170:5837-5847) facilitate expression of polyhydroxyalkanoates (PHAs)).

Thus, in one embodiment, the polynucleotides encoding a native or mutant HPPD polypeptide or variant thereof that retains HPPD enzymatic activity are stacked with one or more polynucleotides encoding polypeptides that confer resistance or tolerance to an herbicide. In one embodiment, the desirable trait is resistance or tolerance to an HPPD inhibitor. In another embodiment, the desirable trait is resistance or tolerance to glyphosate. In another embodiment, the desirable trait is resistance or tolerance to glufosinate. In further embodiments the desirable trait is resistance or tolerance to an HST inhibitor herbicide, an auxin herbicide or a PSII herbicide.

These stacked combinations can be created by any method including, but not limited to, cross-breeding plants by any conventional or TopCross methodology, or genetic transformation. If the sequences are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, PCT Publication Nos. WO 99/25821, WO 99/25854, WO 99/25840, WO 99/25855, and WO 99/25853.

Plant Expression Cassettes

The compositions of the invention may additionally contain nucleic acid sequences for transformation and expression in a plant of interest. The nucleic acid sequences may be present in DNA constructs or expression cassettes. "Expression cassette" as used herein means a nucleic acid molecule capable of directing expression of a particular nucleotide sequence in an appropriate host cell, comprising a promoter operatively linked to the nucleotide sequence of interest (i.e., a polynucleotide encoding a mutant HPPD polypeptide or variant thereof that retains HPPD enzymatic activity, alone or in combination with one or more additional nucleic acid molecules encoding polypeptides that confer desirable traits) which is operatively linked to termination signals. It also typically comprises sequences required for proper translation of the nucleotide sequence. The coding region usually codes for a protein of interest but may also code for a functional RNA of interest, for example antisense RNA or a nontranslated RNA, in the sense or antisense direction. The expression cassette comprising the nucleotide sequence of interest may be chimeric, meaning that at least one of its components is heterologous with respect to at least one of its other components. The expression cassette may also be one that is naturally occurring but has been obtained in a recombinant form useful for heterologous expression. Typically, however, the expression cassette is heterologous with respect to the host, i.e., the particular DNA sequence of the expression cassette does not occur naturally in the host cell and must have been introduced into the host cell or an ancestor of the host cell by a transformation event. The expression of the nucleotide sequence in the expression cassette may be under the control of a constitutive promoter or of an inducible promoter that initiates transcription only when the host cell is exposed to some particular external stimulus. Additionally, the promoter can also be specific to a particular tissue or organ or stage of development.

The present invention encompasses the transformation of plants with expression cassettes capable of expressing a polynucleotide of interest, i.e., a polynucleotide encoding a mutant HPPD polypeptide or variant thereof that retains HPPD enzymatic activity, alone or in combination with one or more additional nucleic acid molecules encoding polypeptides that confer desirable traits. The expression cassette will include in the 5'-3' direction of transcription, a transcriptional and translational initiation region (i.e., a promoter) and a polynucleotide open reading frame. The expression cassette may optionally comprise a transcriptional and translational termination region (i.e., termination region) functional in plants. In some embodiments, the expression cassette comprises a selectable marker gene to allow for selection for stable transformants. Expression constructs of the invention may also comprise a leader sequence and/or a sequence allowing for inducible expression of the polynucleotide of interest. See, Guo et al. (2003) *Plant J.* 34:383-92 and Chen et al. (2003) *Plant J.* 36:731-40 for examples of sequences allowing for inducible expression.

The regulatory sequences of the expression construct are operably linked to the polynucleotide of interest. By "operably linked" is intended a functional linkage between a promoter and a second sequence wherein the promoter sequence initiates and mediates transcription of the DNA sequence corresponding to the second sequence. Generally, operably linked means that the nucleotide sequences being linked are contiguous.

Any promoter capable of driving expression in the plant of interest may be used in the practice of the invention. The promoter may be native or analogous or foreign or heterologous to the plant host. The terms "heterologous" and "exogenous" when used herein to refer to a nucleic acid sequence (e.g. a DNA or RNA sequence) or a gene, refer to a sequence that originates from a source foreign to the particular host cell or, if from the same source, is modified from its original form. Thus, a heterologous gene in a host cell includes a gene that is endogenous to the particular host cell but has been modified through, for example, the use of DNA shuffling. The terms also include non-naturally occurring multiple copies of a naturally occurring DNA sequence. Thus, the terms refer to a DNA segment that is foreign or heterologous to the cell, or homologous to the cell but in a position within the host cell nucleic acid in which the element is not ordinarily found. Exogenous DNA segments are expressed to yield exogenous polypeptides.

A "homologous" nucleic acid (e.g., DNA) sequence is a nucleic acid (e.g., DNA or RNA) sequence naturally associated with a host cell into which it is introduced.

The choice of promoters to be included depends upon several factors, including, but not limited to, efficiency, selectability, inducibility, desired expression level, and cell- or tissue-preferential expression. It is a routine matter for one of skill in the art to modulate the expression of a sequence by appropriately selecting and positioning promoters and other regulatory regions relative to that sequence. The promoters that are used for expression of the transgene(s) can be a strong plant promoter, a viral promoter, or a chimeric promoters composed of elements such as: TATA box from any gene (or synthetic, based on analysis of plant gene TATA boxes), optionally fused to the region 5' to the TATA box of plant promoters (which direct tissue and temporally appropriate gene expression), optionally fused to 1 or more enhancers (such as the 35S enhancer, FMV enhancer, CMP enhancer, RUBISCO SMALL SUBUNIT enhancer, PLASTOCYANIN enhancer).

Exemplary constitutive promoters include, for example, the core promoter of the Rsyn7 promoter and other constitutive promoters disclosed in WO 99/43838 and U.S. Pat. No. 6,072,050; the core CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); MAS (Velten et al. (1984) *EMBO J.* 3:2723-2730); ALS promoter (U.S. Pat. No. 5,659,026), and the like. Other constitutive promoters are included in, for example, U.S. Pat. Nos. 5,608,149; 5,608,144; 5,604,121; 5,569,597; 5,466,785; 5,399,680; 5,268,463; 5,608,142; and 6,177,611.

Appropriate plant or chimeric promoters are useful for applications such as expression of transgenes in certain tissues, while minimizing expression in other tissues, such as seeds, or reproductive tissues. Exemplary cell type- or tissue-preferential promoters drive expression preferentially in the target tissue, but may also lead to some expression in other cell types or tissues as well. Methods for identifying and characterizing promoter regions in plant genomic DNA include, for example, those described in the following references: Jordano, et al., *Plant Cell*, 1:855-866 (1989); Bustos, et al., *Plant Cell*, 1:839-854 (1989); Green, et al., *EMBO J.* 7, 4035-4044 (1988); Meier, et al., *Plant Cell*, 3, 309-316 (1991); and Zhang, et al., *Plant Physiology* 110: 1069-1079 (1996).

In other embodiments of the present invention, inducible promoters may be desired. Inducible promoters drive transcription in response to external stimuli such as chemical agents or environmental stimuli. For example, inducible promoters can confer transcription in response to hormones such as giberellic acid or ethylene, or in response to light or drought.

A variety of transcriptional terminators are available for use in expression cassettes. These are responsible for the termination of transcription beyond the transgene and correct mRNA polyadenylation. The termination region may be native with the transcriptional initiation region, may be native with the operably linked DNA sequence of interest, may be native with the plant host, or may be derived from another source (i.e., foreign or heterologous to the promoter, the DNA sequence of interest, the plant host, or any combination thereof). Appropriate transcriptional terminators are those that are known to function in plants and include the CAMV 35S terminator, the tml terminator, the nopaline synthase terminator and the pea rbcs E9 terminator. These can be used in both monocotyledons and dicotyledons. In addition, a gene's native transcription terminator may be used.

Generally, the expression cassette will comprise a selectable marker gene for the selection of transformed cells. Selectable marker genes are utilized for the selection of transformed cells or tissues.

Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. For example, the introns of the maize Adh1 gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., *Genes Develop.* 1:1183-1200 (1987)). In the same experimental system, the intron from the maize bronze 1 gene had a similar effect in enhancing expression. Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from tobacco mosaic virus (TMV, the "W-sequence"), maize chlorotic mottle virus (MCMV), and alfalfa mosaic virus (AMV) have been shown to be effective in enhancing expression (e.g., Gallie et al. *Nucl. Acids Res.* 15: 8693-8711 (1987); Skuzeski et al. *Plant Molec. Biol.* 15: 65-79 (1990)). Other leader sequences known in the art include but are not limited to: picornavirus leaders, for example, EMCV leader (encephalomyocarditis 5' noncoding region) (Elroy-Stein, O., Fuerst, T. R., and Moss, B. *PNAS USA* 86:6126-6130 (1989)); potyvirus leaders, for example, tobacco etch virus (TEV) leader (Allison et al., 1986); maize dwarf mosaic virus (MDMV) leader; *Virology* 154:9-20); human immunoglobulin heavy-chain binding protein (BiP) leader, (Macejak, D. G., and Sarnow, P., *Nature* 353: 90-94 (1991); untranslated leader from the coat protein mRNA of alfalfa mosaic virus (AMV RNA 4), (Jobling, S. A., and Gehrke, L., *Nature* 325:622-625 (1987); tobacco mosaic virus leader (TMV), (Gallie, D. R. et al., *Molecular Biology of RNA*, 237-256 (1989); and maize chlorotic mottle virus leader (MCMV) (Lommel, S. A. et al., *Virology* 81:382-385 (1991). See also, Della-Cioppa et al., *Plant Physiology* 84:965-968 (1987).

The present invention also relates to nucleic acid constructs comprising one or more of the expression cassettes described above. The construct can be a vector, such as a plant transformation vector. In one embodiment, the vector is a plant transformation vector comprising a polynucleotide comprising the sequence set forth in SEQ ID NO: 51 or SEQ ID NO: 52.

Plants

As used herein, the term "plant part" or "plant tissue" includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. The aforementioned term also includes plant products, such as grain, fruits, and nuts.

Plants useful in the present invention include plants that are transgenic for at least a polynucleotide encoding a mutant HPPD polypeptide or variant thereof that retains HPPD enzymatic activity, alone or in combination with one or more additional nucleic acid molecules encoding polypeptides that confer desirable traits. The type of plant selected depends on a variety of factors, including for example, the downstream use of the harvested plant material, amenability of the plant species to transformation, and the conditions under which the plants will be grown, harvested, and/or processed. One of skill will further recognize that additional factors for selecting appropriate plant varieties for use in the present invention include high yield potential, good stalk strength, resistance to specific diseases, drought tolerance, rapid dry down and grain quality sufficient to allow storage and shipment to market with minimum loss.

Plants according to the present invention include any plant that is cultivated for the purpose of producing plant material that is sought after by man or animal for either oral consumption, or for utilization in an industrial, pharmaceutical, or commercial process. The invention may be applied to any of a variety of plants, including, but not limited to maize, wheat, rice, barley, soybean, cotton, *sorghum*, beans in general, rape/canola, alfalfa, flax, sunflower, safflower, millet, rye, sugarcane, sugar beet, cocoa, tea, *Brassica*, cotton, coffee, sweet potato, flax, peanut, clover; vegetables such as lettuce, tomato, cucurbits, cassava, potato, carrot, radish, pea, lentils, cabbage, cauliflower, broccoli, Brussels sprouts, peppers, and pineapple; tree fruits such as citrus, apples, pears, peaches, apricots, walnuts, avocado, banana, and coconut; and flowers such as orchids, carnations and roses. Other plants useful in the practice of the invention include perennial grasses, such as switchgrass, prairie grasses, indiangrass, big bluestem grass and the like. It is recognized that mixtures of plants may be used.

In addition, the term "crops" is to be understood as also including crops that have been rendered tolerant to herbicides or classes of herbicides (such as, for example, ALS inhibitors, for example primisulfuron, prosulfuron and trifloxysulfuron, EPSPS (5-enol-pyrovyl-shikimate-3-phosphate-synthase) inhibitors, GS (glutamine synthetase) inhibitors) as a result of conventional methods of breeding or genetic engineering. Examples of crops that have been rendered tolerant to herbicides or classes of herbicides by genetic engineering methods include glyphosate- and glufosinate-resistant crop varieties commercially available under the trade names RoundupReady® and LibertyLink®. The method according to the present invention is especially suitable for the protection of soybean crops which have also been rendered tolerant to glyphosate and/or glufosinate and where HPPD herbicides are used in a weed control programme along with other such herbicides (glufosinate and/or glyphosate) for weed control.

It is further contemplated that the constructs of the invention may be introduced into plant varieties having improved properties suitable or optimal for a particular downstream use. For example, naturally-occurring genetic variability results in plants with resistance or tolerance to HPPD inhibitors or other herbicides, and such plants are also useful in the methods of the invention. The method according to the present invention can be further optimized by crossing the transgenes that provide a level of tolerance, with soybean cultivars that exhibit an enhanced level of tolerance to HPPD inhibitors that is found in a small percentage of soybean lines.

Plant Transformation

Once an herbicide resistant or tolerant mutant HPPD polynucleotide, alone or in combination with one or more additional nucleic acid molecules encoding polypeptides that confer desirable traits, has been cloned into an expression system, it is transformed into a plant cell. The expression cassettes of the present invention can be introduced into the plant cell in a number of art-recognized ways. The term "introducing" in the context of a polynucleotide, for example, a nucleotide construct of interest, is intended to mean presenting to the plant the polynucleotide in such a manner that the polynucleotide gains access to the interior of a cell of the plant. Where more than one polynucleotide is to be introduced, these polynucleotides can be assembled as part of a single nucleotide construct, or as separate nucleotide constructs, and can be located on the same or different transformation vectors. Accordingly, these polynucleotides can be introduced into the host cell of interest in a single transformation event, in separate transformation events, or, for example, in plants, as part of a breeding protocol. The methods of the invention do not depend on a particular method for introducing one or more polynucleotides into a plant, only that the polynucleotide(s) gains access to the interior of at least one cell of the plant. Methods for introducing polynucleotides into plants are known in the art including, but not limited to, transient transformation methods, stable transformation methods, and virus-mediated methods.

"Transient transformation" in the context of a polynucleotide is intended to mean that a polynucleotide is introduced into the plant and does not integrate into the genome of the plant.

By "stably introducing" or "stably introduced" in the context of a polynucleotide introduced into a plant is intended the introduced polynucleotide is stably incorporated into the plant genome, and thus the plant is stably transformed with the polynucleotide.

"Stable transformation" or "stably transformed" is intended to mean that a polynucleotide, for example, a nucleotide construct described herein, introduced into a plant integrates into the genome of the plant and is capable of being inherited by the progeny thereof, more particularly, by the progeny of multiple successive generations.

Numerous transformation vectors available for plant transformation are known to those of ordinary skill in the plant transformation arts, and the genes pertinent to this invention can be used in conjunction with any such vectors. The selection of vector will depend upon the preferred transformation technique and the target species for transformation. For certain target species, different antibiotic or herbicide selection markers may be preferred. Selection markers used routinely in transformation include the nptll gene, which confers resistance to kanamycin and related antibiotics (Messing & Vierra *Gene* 19: 259-268 (1982); Bevan et al., *Nature* 304:184-187 (1983)), the pat and bar genes, which confer resistance to the herbicide glufosinate (also called phosphinothricin; see White et al., *Nucl. Acids Res* 18: 1062 (1990), Spencer et al. *Theor. Appl. Genet* 79: 625-631 (1990) and U.S. Pat. Nos. 5,561,236 and 5,276,268), the hph gene, which confers resistance to the antibiotic hygromycin (Blochinger & Diggelmann, *Mol. Cell Biol.* 4: 2929-2931), and the dhfr gene, which confers resistance to methatrexate (Bourouis et al., *EMBO J.* 2(7): 1099-1104 (1983)), the EPSPS gene, which confers resistance to glyphosate (U.S. Pat. Nos. 4,940,935 and 5,188,642), the glyphosate N-acetyltransferase (GAT) gene, which also confers resistance to glyphosate (Castle et al. (2004) *Science*, 304: 1151-1154; U.S. Patent App. Pub. Nos. 20070004912, 20050246798, and 20050060767); and the mannose-6-phosphate isomerase gene, which provides the ability to metabolize mannose (U.S. Pat. Nos. 5,767,378 and 5,994,629). Alternatively, and in one preferred embodiment the HPPD gene of the current invention is, in combination with the use of an HPPD herbicide as selection agent, itself used as the selectable marker.

Methods for regeneration of plants are also well known in the art. For example, Ti plasmid vectors have been utilized for the delivery of foreign DNA, as well as direct DNA uptake, liposomes, electroporation, microinjection, and microprojectiles. In addition, bacteria from the genus *Agrobacterium* can be utilized to transform plant cells. Below are descriptions of representative techniques for transforming both dicotyledonous and monocotyledonous plants, as well as a representative plastid transformation technique.

Many vectors are available for transformation using *Agrobacterium tumefaciens*. These typically carry at least one T-DNA border sequence and include vectors such as pBIN19 (Bevan, Nucl. Acids Res. (1984)). For the construction of vectors useful in *Agrobacterium* transformation, see, for example, U.S. Patent Application Publication No. 2006/0260011.

Transformation without the use of *Agrobacterium tumefaciens* circumvents the requirement for T-DNA sequences in the chosen transformation vector and consequently vectors lacking these sequences can be utilized in addition to vectors such as the ones described above which contain T-DNA sequences. Transformation techniques that do not rely on *Agrobacterium* include transformation via particle bombardment, protoplast uptake (e.g., PEG and electroporation) and microinjection. The choice of vector depends largely on the preferred selection for the species being transformed. For the construction of such vectors, see, e.g., U.S. Patent Application Publication No. 20060260011.

For expression of a nucleotide sequence of the present invention in plant plastids, plastid transformation vector pPH143 (see PCT Publication No. WO 97/32011, Example 36) is used. The nucleotide sequence is inserted into pPH143 thereby replacing the PROTOX coding sequence. This vector is then used for plastid transformation and selection of transformants for spectinomycin resistance. Alternatively, the nucleotide sequence is inserted in pPH143 so that it replaces the aadH gene. In this case, transformants are selected for resistance to PROTOX inhibitors.

Transformation techniques for dicotyledons are well known in the art and include *Agrobacterium*-based techniques and techniques that do not require *Agrobacterium*. Non-*Agrobacterium* techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al., *EMBO J.* 3: 2717-2722 (1984), Potrykus et al., *Mol. Gen. Genet.* 199: 169-177 (1985), Reich et al., *Biotechnology* 4: 1001-1004 (1986), and Klein et al., *Nature* 327: 70-73 (1987). In each case the transformed cells are regenerated to whole plants using standard techniques known in the art.

*Agrobacterium*-mediated transformation is a preferred technique for transformation of dicotyledons because of its high efficiency of transformation and its broad utility with many different species. *Agrobacterium* transformation typically involves the transfer of the binary vector carrying the foreign DNA of interest (e.g., pCIB200 or pCIB2001) to an appropriate *Agrobacterium* strain which may depend of the complement of vir genes carried by the host *Agrobacterium* strain either on a co-resident Ti plasmid or chromosomally (e.g., strain CIB542 for pCIB200 and pCIB2001 (Uknes et al. *Plant Cell* 5: 159-169 (1993)). The transfer of the recombinant binary vector to *Agrobacterium* is accomplished by a triparental mating procedure using *E. coli* carrying the recombinant binary vector, a helper *E. coli* strain which carries a plasmid such as pRK2013 and which is able to mobilize the recombinant binary vector to the target *Agrobacterium* strain. Alternatively, the recombinant binary vector can be transferred to *Agrobacterium* by DNA transformation (Hofgen & Willmitzer, *Nucl. Acids Res.* 16: 9877 (1988)).

Transformation of the target plant species by recombinant *Agrobacterium* usually involves co-cultivation of the *Agrobacterium* with explants from the plant and follows protocols well known in the art. Transformed tissue is regenerated on selectable medium carrying the antibiotic or herbicide resistance marker present between the binary plasmid T-DNA borders.

Another approach to transforming plant cells with a gene involves propelling inert or biologically active particles at plant tissues and cells. This technique is disclosed in U.S. Pat. Nos. 4,945,050, 5,036,006, and 5,100,792 all to Sanford et al. Generally, this procedure involves propelling inert or biologically active particles at the cells under conditions effective to penetrate the outer surface of the cell and afford incorporation within the interior thereof. When inert particles are utilized, the vector can be introduced into the cell by coating the particles with the vector containing the desired gene. Alternatively, the target cell can be surrounded by the vector so that the vector is carried into the cell by the wake of the particle. Biologically active particles (e.g., dried yeast cells, dried bacterium or a bacteriophage, each containing DNA sought to be introduced) can also be propelled into plant cell tissue.

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (i.e., co-transformation) and both of these techniques are suitable for use with this invention. Co-transformation may have the advantage of avoiding complete vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. *Biotechnology* 4: 1093-1096 (1986)).

European patents EP 0 292 435 and EP 0 392 225, and PCT Publication No. WO 93/07278 describe techniques for the preparation of callus and protoplasts from an elite inbred line of maize, transformation of protoplasts using PEG or electroporation, and the regeneration of maize plants from transformed protoplasts. Gordon-Kamm et al. (*Plant Cell* 2: 603-618 (1990)) and Fromm et al. (*Biotechnology* 8: 833-839 (1990)) have published techniques for transformation of A188-derived maize line using particle bombardment. Furthermore, PCT Publication No. WO 93/07278 and Koziel et al. (*Biotechnology* 11: 194-200 (1993)) describe techniques for the transformation of elite inbred lines of maize by particle bombardment. This technique utilizes immature maize embryos of 1.5-2.5 mm length excised from a maize ear 14-15 days after pollination and a PDS-1000He Biolistics device for bombardment.

Transformation of rice can also be undertaken by direct gene transfer techniques utilizing protoplasts or particle bombardment. Protoplast-mediated transformation has been described for *Japonica*-types and Indica-types (Zhang et al. *Plant Cell Rep* 7: 379-384 (1988); Shimamoto et al. *Nature* 338: 274-277 (1989); Datta et al. *Biotechnology* 8:736-740 (1990)). Both types are also routinely transformable using particle bombardment (Christou et al. *Biotechnology* 9: 957-962 (1991)). Furthermore, PCT Publication No. WO 93/21335 describes techniques for the transformation of rice via electroporation.

European patent EP 0 332 581 describes techniques for the generation, transformation and regeneration of Pooideae protoplasts. These techniques allow the transformation of Dactyl's and wheat. Furthermore, wheat transformation has been described by Vasil et al. (*Biotechnology* 10: 667-674 (1992)) using particle bombardment into cells of type C long-term regenerable callus, and also by Vasil et al. (*Biotechnology* 11:1553-1558 (1993)) and Weeks et al. (*Plant Physiol.* 102:1077-1084 (1993)) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75-1 mm in length) are plated onto MS medium with 3% sucrose (Murashiga & Skoog, *Physiologia Plantarum* 15: 473-497 (1962)) and 3 mg/l 2,4-D for induction of somatic embryos, which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2-3 hours and are then bombarded. Twenty embryos per target plate is typical, although not critical. An appropriate gene-carrying plasmid (such as pCIB3064 or pSOG35) is precipitated onto micrometer size gold particles using standard procedures. Each plate of embryos is shot with the DuPont BIOLISTICS® helium device using a burst pressure of about 1000 psi using a standard 80 mesh screen. After bombardment, the embryos are placed back into the dark to recover for about 24 hours (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/l NAA, 5 mg/l GA), further containing the appropriate selection agent (10 mg/l basta in the case of pCIB3064 and 2 mg/l methotrexate in the case of pSOG35). After approximately one month, developed shoots are transferred to larger sterile containers known as "GA7s" which contain half-strength MS, 2% sucrose, and the same concentration of selection agent.

Transformation of monocotyledons using *Agrobacterium* has also been described. See, PCT Publication No. WO 94/00977, U.S. Pat. No. 5,591,616, and Negrotto et al., *Plant Cell Reports* 19: 798-803 (2000). For example, rice (*Oryza*

*sativa*) can be used for generating transgenic plants. Various rice cultivars can be used (Hiei et al., 1994, *Plant Journal* 6:271-282; Dong et al., 1996, *Molecular Breeding* 2:267-276; Hiei et al., 1997, *Plant Molecular Biology*, 35:205-218). Also, the various media constituents described below may be either varied in quantity or substituted. Embryogenic responses are initiated and/or cultures are established from mature embryos by culturing on MS-CIM medium (MS basal salts, 4.3 g/l; B5 vitamins (200×), 5 ml/l; sucrose, 30 g/l; proline, 500 mg/l; glutamine, 500 mg/l; casein hydrolysate, 300 mg/1; 2,4-D (1 mg/ml), 2 ml/l; adjust pH to 5.8 with 1 N KOH; phytagel, 3 g/l). Either mature embryos at the initial stages of culture response or established culture lines are inoculated and co-cultivated with the *Agrobacterium tumefaciens* strain LBA4404 (*Agrobacterium*) containing the desired vector construction. *Agrobacterium* is cultured from glycerol stocks on solid YPC medium (100 mg/l spectinomycin and any other appropriate antibiotic) for about 2 days at 28° C. *Agrobacterium* is re-suspended in liquid MS-CIM medium. The *Agrobacterium* culture is diluted to an $OD^{600}$ of 0.2-0.3 and acetosyringone is added to a final concentration of 200 μM. Acetosyringone is added before mixing the solution with the rice cultures to induce *Agrobacterium* for DNA transfer to the plant cells. For inoculation, the plant cultures are immersed in the bacterial suspension. The liquid bacterial suspension is removed and the inoculated cultures are placed on co-cultivation medium and incubated at 22° C. for two days. The cultures are then transferred to MS-CIM medium with ticarcillin (400 mg/l) to inhibit the growth of *Agrobacterium*. For constructs utilizing the PMI selectable marker gene (Reed et al., *In Vitro Cell. Dev. Biol.-Plant* 37:127-132), cultures are transferred to selection medium containing mannose as a carbohydrate source (MS with 2% mannose, 300 mg/l ticarcillin) after 7 days, and cultured for 3-4 weeks in the dark. Resistant colonies are then transferred to regeneration induction medium (MS with no 2,4-D, 0.5 mg/l IAA, 1 mg/l zeatin, 200 mg/l timentin 2% mannose and 3% sorbitol) and grown in the dark for 14 days. Proliferating colonies are then transferred to another round of regeneration induction media and moved to the light growth room. Regenerated shoots are transferred to GA7 containers with GA7-1 medium (MS with no hormones and 2% sorbitol) for 2 weeks and then moved to the greenhouse when they are large enough and have adequate roots. Plants are transplanted to soil in the greenhouse ($T_0$ generation) grown to maturity, and the $T_1$ seed is harvested.

The plants obtained via transformation with a nucleic acid sequence of interest in the present invention can be any of a wide variety of plant species, including those of monocots and dicots; however, the plants used in the method of the invention are preferably selected from the list of agronomically important target crops set forth elsewhere herein. The expression of a gene of the present invention in combination with other characteristics important for production and quality can be incorporated into plant lines through breeding. Breeding approaches and techniques are known in the art. See, for example, Welsh J. R., *Fundamentals of Plant Genetics and Breeding*, John Wiley & Sons, NY (1981); *Crop Breeding*, Wood D. R. (Ed.) American Society of Agronomy Madison, Wis. (1983); Mayo O., *The Theory of Plant Breeding*, Second Edition, Clarendon Press, Oxford (1987); Singh, D. P., *Breeding for Resistance to Diseases and Insect Pests*, Springer-Verlag, NY (1986); and Wricke and Weber, *Quantitative Genetics and Selection Plant Breeding*, Walter de Gruyter and Co., Berlin (1986).

For the transformation of plastids, seeds of *Nicotiana tabacum* c.v. "Xanthienc" are germinated seven per plate in a 1" circular array on T agar medium and bombarded 12-14 days after sowing with 1 μm tungsten particles (M10, Biorad, Hercules, Calif.) coated with DNA from plasmids pPH143 and pPH145 essentially as described (Svab, Z. and Maliga, P. (1993) *PNAS* 90, 913-917). Bombarded seedlings are incubated on T medium for two days after which leaves are excised and placed abaxial side up in bright light (350-500 μmol photons/m$^2$/s) on plates of RMOP medium (Svab, Z., Hajdukiewicz, P. and Maliga, P. (1990) *PNAS* 87, 8526-8530) containing 500 μg/ml spectinomycin dihydrochloride (Sigma, St. Louis, Mo.). Resistant shoots appearing underneath the bleached leaves three to eight weeks after bombardment are subcloned onto the same selective medium, allowed to form callus, and secondary shoots isolated and subcloned. Complete segregation of transformed plastid genome copies (homoplasmicity) in independent subclones is assessed by standard techniques of Southern blotting (Sambrook et al., (1989) *Molecular Cloning: A Laboratory Manual*, Cold Spring Harbor Laboratory, Cold Spring Harbor). BamHI/EcoRI-digested total cellular DNA (Mettler, I. J. (1987) *Plant Mol Biol Reporter* 5, 346349) is separated on 1% Tris-borate (TBE) agarose gels, transferred to nylon membranes (Amersham) and probed with $^{32}$P-labeled random primed DNA sequences corresponding to a 0.7 kb BamHI/HindIII DNA fragment from pC8 containing a portion of the rps 7/12 plastid targeting sequence. Homoplasmic shoots are rooted aseptically on spectinomycin-containing MS/IBA medium (McBride, K. E. et al. (1994) *PNAS* 91, 7301-7305) and transferred to the greenhouse.

The genetic properties engineered into the transgenic seeds and plants described above are passed on by sexual reproduction or vegetative growth and can thus be maintained and propagated in progeny plants. Generally, maintenance and propagation make use of known agricultural methods developed to fit specific purposes such as tilling, sowing or harvesting.

Use of the advantageous genetic properties of the transgenic plants and seeds according to the invention can further be made in plant breeding. Depending on the desired properties, different breeding measures are taken. The relevant techniques are well known in the art and include but are not limited to hybridization, inbreeding, backcross breeding, multi-line breeding, variety blend, interspecific hybridization, aneuploid techniques, etc. Thus, the transgenic seeds and plants according to the invention can be used for the breeding of improved plant lines that, for example, increase the effectiveness of conventional methods such as herbicide or pesticide treatment or allow one to dispense with said methods due to their modified genetic properties.

Many suitable methods for transformation using suitable selection markers such as kanamycin, binary vectors such as from *Agrobacterium* and plant regeneration as, for example, from tobacco leaf discs are well known in the art. Optionally, a control population of plants are likewise transformed with a polynucleotide expressing the control HPPD. Alternatively, an untransformed dicot plant such as *Arabidopsis* or tobacco can be used as a control since this, in any case, expresses its own endogenous HPPD.

Herbicide Resistance

The present invention provides transgenic plants, plant cells, tissues, and seeds that have been transformed with a nucleic acid molecule encoding a mutant HPPD or variant thereof that confers resistance or tolerance to herbicides, alone or in combination with one or more additional nucleic acid molecules encoding polypeptides that confer desirable traits.

In one embodiment, the transgenic plants of the invention exhibit resistance or tolerance to application of herbicide in an amount of from about 5 to about 2,000 grams per hectare (g/ha), including, for example, about 5 g/ha, about 10 g/ha, about 15 g/ha, about 20 g/ha, about 25 g/ha, about 30 g/ha, about 35 g/ha, about 40 g/ha, about 45 g/ha, about 50 g/ha, about 55 g/ha, about 60 g/ha, about 65 g/ha, about 70 g/ha, about 75 g/ha, about 80 g/ha, about 85 g/ha, about 90 g/ha, about 95 g/ha, about 100 g/ha, about 110 g/ha, about 120 g/ha, about 130 g/ha, about 140 g/ha, about 150 g/ha, about 160 g/ha, about 170 g/ha, about 180 g/ha, about 190 g/ha, about 200 g/ha, about 210 g/ha, about 220 g/ha, about 230 g/ha, about 240 g/ha, about 250 g/ha, about 260 g/ha, about 270 g/ha, about 280 g/ha, about 290 g/ha, about 300 g/ha, about 310 g/ha, about 320 g/ha, about 330 g/ha, about 340 g/ha, about 350 g/ha, about 360 g/ha, about 370 g/ha, about 380 g/ha, about 390 g/ha, about 400 g/ha, about 410 g/ha, about 420 g/ha, about 430 g/ha, about 440 g/ha, about 450 g/ha, about 460 g/ha, about 470 g/ha, about 480 g/ha, about 490 g/ha, about 500 g/ha, about 510 g/ha, about 520 g/ha, about 530 g/ha, about 540 g/ha, about 550 g/ha, about 560 g/ha, about 570 g/ha, about 580 g/ha, about 590 g/ha, about 600 g/ha, about 610 g/ha, about 620 g/ha, about 630 g/ha, about 640 g/ha, about 650 g/ha, about 660 g/ha, about 670 g/ha, about 680 g/ha, about 690 g/ha, about 700 g/ha, about 710 g/ha, about 720 g/ha, about 730 g/ha, about 740 g/ha, about 750 g/ha, about 760 g/ha, about 770 g/ha, about 780 g/ha, about 790 g/ha, about 800 g/ha, about 810 g/ha, about 820 g/ha, about 830 g/ha, about 840 g/ha, about 850 g/ha, about 860 g/ha, about 870 g/ha, about 880 g/ha, about 890 g/ha, about 900 g/ha, about 910 g/ha, about 920 g/ha, about 930 g/ha, about 940 g/ha, about 950 g/ha, about 960 g/ha, about 970 g/ha, about 980 g/ha, about 990 g/ha, about 1,000, g/ha, about 1,010 g/ha, about 1,020 g/ha, about 1,030 g/ha, about 1,040 g/ha, about 1,050 g/ha, about 1,060 g/ha, about 1,070 g/ha, about 1,080 g/ha, about 1,090 g/ha, about 1,100 g/ha, about 1,110 g/ha, about 1,120 g/ha, about 1,130 g/ha, about 1,140 g/ha, about 1,150 g/ha, about 1,160 g/ha, about 1,170 g/ha, about 1,180 g/ha, about 1,190 g/ha, about 1,200 g/ha, about 1,210 g/ha, about 1,220 g/ha, about 1,230 g/ha, about 1,240 g/ha, about 1,250 g/ha, about 1,260 g/ha, about 1,270 g/ha, about 1,280 g/ha, about 1,290 g/ha, about 1,300 g/ha, about 1,310 g/ha, about 1,320 g/ha, about 1,330 g/ha, about 1,340 g/ha, about 1,350 g/ha, about 360 g/ha, about 1,370 g/ha, about 1,380 g/ha, about 1,390 g/ha, about 1,400 g/ha, about 1,410 g/ha, about 1,420 g/ha, about 1,430 g/ha, about 1,440 g/ha, about 1,450 g/ha, about 1,460 g/ha, about 1,470 g/ha, about 1,480 g/ha, about 1,490 g/ha, about 1,500 g/ha, about 1,510 g/ha, about 1,520 g/ha, about 1,530 g/ha, about 1,540 g/ha, about 1,550 g/ha, about 1,560 g/ha, about 1,570 g/ha, about 1,580 g/ha, about 1,590 g/ha, about 1,600 g/ha, about 1,610 g/ha, about 1,620 g/ha, about 1,630 g/ha, about 1,640 g/ha, about 1,650 g/ha, about 1,660 g/ha, about 1,670 g/ha, about 1,680 g/ha, about 1,690 g/ha, about 1,700 g/ha, about 1,710 g/ha, about 1,720 g/ha, about 1,730 g/ha, about 1,740 g/ha, about 1,750 g/ha, about 1,760 g/ha, about 1,770 g/ha, about 1,780 g/ha, about 1,790 g/ha, about 1,800 g/ha, about 1,810 g/ha, about 1,820 g/ha, about 1,830 g/ha, about 1,840 g/ha, about 1,850 g/ha, about 1,860 g/ha, about 1,870 g/ha, about 1,880 g/ha, about 1,890 g/ha, about 1,900 g/ha, about 1,910 g/ha, about 1,920 g/ha, about 1,930 g/ha, about 1,940 g/ha, about 1,950 g/ha, about 1,960 g/ha, about 1,970 g/ha, about 1,980 g/ha, about 1,990 g/ha, or about 2,000.

The average and distribution of herbicide tolerance or resistance levels of a range of primary plant transformation events are evaluated in the normal manner based upon plant damage, meristematic bleaching symptoms etc. at a range of different concentrations of herbicides. These data can be expressed in terms of, for example, $GR_{50}$ values derived from dose/response curves having "dose" plotted on the x-axis and "percentage kill", "herbicidal effect", "numbers of emerging green plants" etc. plotted on the y-axis where increased $GR_{50}$ values correspond to increased levels of inherent inhibitor-tolerance (e.g., increased $k_{off}/K_{mHPP}$ value) and/or level of expression of the expressed HPPD polypeptide.

The methods of the present invention are especially useful to protect crops from the herbicidal injury of HPPD inhibitor herbicides. For example, the HPPD inhibiting herbicide is suitably selected from the group consisting of bicyclopyrone (CAS RN 352010-68-5), benzobicyclon (CAS RN 156963-66-5), benzofenap (CAS RN 82692-44-2), ketospiradox (CAS RN 192708-91-1) or its free acid (CAS RN 187270-87-7), isoxachlortole (CAS RN 141112-06-3), isoxaflutole (CAS RN 141112-29-0), mesotrione (CAS RN 104206-82-8), pyrasulfotole (CAS RN 365400-11-9), pyrazolynate (CAS RN 58011-68-0), pyrazoxyfen (CAS RN 71561-11-0), sulcotrione (CAS RN 99105-77-8), tefuryltrione (CAS RN 473278-76-1), tembotrione (CAS RN 335104-84-2) and topramezone (CAS RN 210631-68-8); including, where applicable, agrochemically acceptable salts thereof.

Methods of Use

The present invention further provides a method of selectively controlling weeds at a locus comprising crop plants and weeds, wherein the plants are obtained by any of the methods of the current invention described above, wherein the method comprises application to the locus of a weed controlling amount of one or more herbicides. Any of the transgenic plants described herein may be used within these methods of the invention. The term "locus" may include soil, seeds, and seedlings, as well as established vegetation. Herbicides can suitably be applied pre-emergence or post-emergence of the crop or weeds.

The term "weed controlling amount" is meant to include functionally, an amount of herbicide which is capable of affecting the growth or development of a given weed. Thus, the amount may be small enough to simply retard or suppress the growth or development of a given weed, or the amount may be large enough to irreversibly destroy a given weed.

Thus, the present invention provides a method of controlling weeds at a locus comprising applying to the locus a weed-controlling amount of one or more herbicides, where the locus comprises a transgenic plant that has been transformed with a nucleic acid molecule encoding a mutant HPPD polypeptide or variant thereof that confers resistance or tolerance to HPPD herbicides, alone or in combination with one or more additional nucleic acid molecules encoding polypeptides that confer desirable traits. In one embodiment, the desirable trait is resistance or tolerance to an herbicide, including, for example, herbicides selected from the group consisting of an HPPD inhibitor, glyphosate, and glufosinate. In another embodiment, the locus comprises a transgenic plant that has been transformed with any combination of nucleic acid molecules described above, including one or more nucleic acid molecules encoding a mutant HPPD polypeptide or variant thereof that confers resistance or tolerance to an herbicide in combination with at least one, at least two, at least three, or at least four additional nucleic acid molecules encoding polypeptides that confer desirable traits.

In one embodiment, the present invention provides transgenic plants and methods useful for the control of unwanted plant species in crop fields, wherein the crop plants are made resistant to HPPD chemistry by transformation to express genes encoding mutant HPPD polypeptides, and where an HPPD herbicide is applied as an over-the-top application in amounts capable of killing or impairing the growth of unwanted plant species (weed species, or, for example, carry-over or "rogue" or "volunteer" crop plants in a field of desirable crop plants). The application may be pre- or post emergence of the crop plants or of the unwanted species, and may be combined with the application of other herbicides to which the crop is naturally tolerant, or to which it is resistant via expression of one or more other herbicide resistance transgenes. See, e.g., U.S. Patent Application Publication No. 2004/0058427 and PCT Publication No. WO 98/20144.

In another embodiment, the invention also relates to a method of protecting crop plants from herbicidal injury. In the cultivation of crop plants, especially on a commercial scale, correct crop rotation is crucially important for yield stability (the achievement of high yields of good quality over a long period) and for the economic success of an agronomic business. For example, across large areas of the main maize-growing regions of the USA (the "central corn belt"), soya is grown as the subsequent crop to maize in over 75% of cases. Selective weed control in maize crops is increasingly being carried out using HPPD inhibitor herbicides. Although that class of herbicides has excellent suitability for that purpose, it can result in agronomically unacceptable phytotoxic damage to the crop plants in subsequent crops ("carry-over" damage). For example, certain soya varieties are sensitive to even very small residues of such HPPD inhibitor herbicides. Accordingly, the herbicide resistant or tolerant plants of the invention are also useful for planting in a locus of any short term carry-over of herbicide from a previous application (e.g., by planting a transgenic plant of the invention in the year following application of an herbicide to reduce the risk of damage from soil residues of the herbicide).

EXAMPLES

The invention is now described with reference to the following Examples. These Examples are provided for the purpose of illustration only, and the invention is not limited to these Examples, but rather encompasses all variations which are evident as a result of the teachings provided herein.

Example 1

Cloning, expression and assay of Avena-derived HPPD SEQ ID NO: 1 and determination of $k_{cat}$, $K_{mHPP}$ and koff values versus various HPPD herbicides A DNA sequence, codon-optimised for expression in E. coli, was synthesised by GeneArt (Regensburg, Germany) to encode an HPPD derived from Avena sativa (SEQ ID NO: 1), cloned into pET24a and expressed in E. coli BL21(DE3) with 50 µg/ml kanamycin selection as described in PCT Publication No. WO 02/46387. Overnight cultures grown at 30° C. were used to inoculate 3×1 liter LB in shake flasks at a ratio of 1:100. Cultures were grown at 37° C., 220 rpm, until an $A^{1cm}600$ nm of 0.6-0.8 was reached. The temperature was decreased to 15° C. and induced with 0.1 mM IPTG. Cultures were grown overnight, and cells harvested after 15 min centrifugation at 10,000 g. Cells were stored at −20° C. until extraction. A cell pellet from 3 liters of shake flask culture (~12 g) was thawed in extraction buffer (50 mM Tris, 10 mM sodium ascorbate, 2 mM DTT, 2 mM AEBSF, 10 µM trypsin inhibitor, 1 mM EDTA, pH 7.66) at a ratio of 1 ml buffer: 1 g cell paste.

The extract was passed through the cell disrupter at 30,000 psi, and centrifuged at 50,000 g for 25 minutes at 4° C. The extract may be optionally buffer exchanged down Sephadex® G25. Supernatants were beaded in liquid nitrogen and stored at −80° C. Levels of HPPD expression were estimated by Western blot analysis and using purified Avena (1-10 ng) as standard. Extracts were diluted 1:6000 and 1-10 µl were loaded onto 12% SDS PAGE. In addition, expression was quantified by comparing induced and uninduced SDS PAGE with Coomassie® (Imperial Chemicals Industries, Ltd., London UK) staining. Gels were blotted onto PVDF membrane and Western blots carried out using rabbit anti-wheat HPPD (1:6600) serum as primary antibody and goat anti-rabbit FITC-linked antibodies (1:600) as secondary antibody. Detection of bands was carried out by scanning on a Fluorimager™ 595 (GE Healthcare Ltd, Buckinghamshire UK) and peak quantification was carried out by using ImageQuant™ (GE Healthcare Ltd, Buckinghamshire UK). Plasmid DNA was reisolated from all transformed strains and the DNA sequence across the coding region confirmed.

From Western blots, the expression level of SEQ ID NO: 1 polypeptide expressed in the E. coli extract was estimated to be about 10-14 mg/ml out of a total soluble protein concentration of 33.5 mg/ml.

The concentration of active HPPD in the extract was also more accurately estimated by active site titration. For example a range of volumes of extract (typically 0-20 µl) were added to 50 mM BisTrisPropane buffer at pH 7.0 and at 25° C. containing 25 mM Na ascorbate, 4 µg/ml bovine catalase and 3 nmoles of $^{14}$C-labelled Compound A (1.81 GBq/mmol), in a total final assay volume of 425 µl.

Compound A

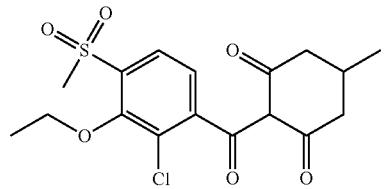 [SMILES: CCOc1c(S(C)(=O)=O)ccc(C(=O)C2C(=O)CC(C)CC2=O)c1Cl]

The radiolabel protein binding reaction was quenched after 3 minutes by the addition of 100 µl of 1 mM 'cold' Structure A. Protein was exchanged into 50 mM BisTris-Propane buffer at pH 7.0 containing 0.1M KCl by rapid chromatography down a NAP5 G25 Sephadex® column (GE Healthcare Ltd, Buckinghamshire UK) and $^{14}$C bound to protein fractions measured in Optiphase scintillant using a Tri-Carb 2900TR scintillation counter (Perkin Elmer, Wellesley, Mass.). The HPPD binding site concentration in the extract was calculated from the titration as described in PCT Publication No. WO 02/46387 and was estimated as 94.9, 78.3, and 82.3 (average 85.2) µM in one extract and 47.2 µM in another example.

The $K_{mHPP}$ and $k_{cat}$ values of the expressed HPPD were estimated on the basis of assays carried out at 25° C. in solutions of 50 mM BisTrisPropane buffer at pH 7.0 containing 25 mM Na ascorbate, 4 µg/ml bovine catalase (Sigma, St. Louis, Mo.), and a range of concentrations (typically 0.5×-10×$K_m$) of 4-hydroxyphenylpyruvate. Typically assays in a final volume of 110 µl were started with the addition of enzyme and accurately stopped after 20 or preferably 10 or 15 seconds with whirlimixed addition of 20 µl 25% perchloric acid. The assay solution was transferred to Chromacol 03-CVG HPLC vials, sealed and the amount of homogentisate formed in a 40 µl aliquot determined by injection onto a reverse phase Aqua C18 5µ 75×4.6 mm HPLC column running 5.5% acetonitrile 0.1% TFA (Buffer A) at 1.5 ml/min. The column was eluted at 1.5 ml/minute using a 2 minute wash in buffer A, followed by a 2 minute wash in a 30/70 mixture of buffer A and 100% acetonitrile, and a further 3.5 minute wash in buffer A. The elution of homogentisate was monitored by UV at 292 nm and the amount formed in each reaction quantified by comparison with a standard calibration curve.

$K_m$ and $V_{max}$ values were determined (for example FIG. 1) using a non linear least squares fit using Grafit 4™ software (Erithacus Software, Middlesex, UK). $K_{cat}$ values were determined by dividing the maximum rate, $V_{max}$ expressed in nmol/s by the number of nmoles of HPPD enzyme (based on the concentration determined by active-site titration).

From one set of separate experiments similar to those that produced the data shown in FIG. 1, on one extract of HPPD SEQ ID NO: 1 the $K_m$ value was estimated as 6.17, 4.51, 6.09, 6.13, 4.37, 4.62, 5.41, 5.13 and 6 µM ($K_m$ average=5.38 µM). The corresponding $k_{cat}$ values were 4.92, 6.25, 7.08, 6.26, 5.5, 6.77, 6.89, 7.12 and 7.39 s$^{-1}$ (kcat average=6.46 s$^{-1}$). Note that for this calculation and, standardly herein, Mr was taken to be ~94 kD and one active-site per dimer was assumed (i.e., half sites activity as well as inhibitor binding; see Garcia et al. (2000) *Biochemistry*, 39:7501-7507; Hawkes "Hydroxyphenylpyruvate Dioxygenase (HPPD)—The Herbicide Target." In *Modern Crop Protection Compounds*. Eds. Krämer and Schirmer. Weinheim, Germany: Wiley-VCH, 2007. Ch. 4.2, pp. 211-220). For the alternative assumption of one active site per monomer then calculated $k_{cat}$ values should simply be correspondingly and systematically halved.

On rates (governed by an association rate constant, $k_{on}$) for the formation of the enzyme:inhibitor complexes, EI and off rates (governed by a dissociation rate constant, $k_{off}$) were determined by methods known in the art and essentially as described in Hawkes et al. (2001) *Proc. Bright. Crop. Prot. Conf. Weeds*, 2:563-568 and in PCT Publication No. WO 02/46387).

For example, on rates were measured by, at zero time, adding ~60 pmoles HPPD to 50 mM BisTrisPropane buffer at pH 7.0 and at 25° C. containing 25 mM Na ascorbate, 4 µg/ml bovine catalase (Sigma, St. Louis, Mo.) and an excess (~300 pmoles) of $^{14}$C inhibitor in a total assay volume of 425 µl and, at various time points (0-180 s), quenching the radiolabel binding reaction by addition and rapid mixing of 100 µl 'cold' 1 mM structure A. Protein samples quenched at different times were then exchanged into 50 mM BisTris-Propane buffer at pH 7.0 containing 0.1M KCl by rapid chromatography down a NAP5 G25 Sephadex® column (GE Healthcare Ltd, Buckinghamshire UK) and the amount of $^{14}$C bound to protein fractions quantified in Optiphase scintillant using a Tri-Carb® 2900TR scintillation counter (Perkin Elmer, Wellesley, Mass.). The data were fit according to the scheme below in order to derive the value of the apparent second order rate constant, k2, governing the association rate of enzyme and radiolabelled inhibitor. A range of enzyme and inhibitor concentrations were used.

Optionally, the rate constant may be derived from similar experiments where enzyme (at ~0.05-0.2 µM binding sites) and, in this case, unlabelled, inhibitor (at ~0.5 to 2 µM) are reacted for a range of short times (0-60 s) in 50 mM BisTrisPropane buffer at pH 7.0 and at 25° C. containing 25 mM Na ascorbate, 4 µg/ml bovine catalase (Sigma, St. Louis, Mo.) and then quenched by rapid dilution into assay solution containing 100-200 µM HPP for immediate assay by HPLC/UV quantitation of homogentisate formation after 30-40 s (i.e., a time sufficiently short that inhibitor dissociation and association does not significantly occur on the timescale of the assay) as described above. Further example methods are described in PCT Publication No. WO 02/46387.

Off rates (k1 in the scheme below) were derived from exchange rate studies where either the test inhibitor, I, or its exchange partner, J were radiolabelled and the data fit according to the scheme below. As noted in Hawkes et al. (2001) *Proc. Bright. Crop. Prot. Conf. Weeds*, 2:563-568, HPPD preparations typically appear, at least in respect of the dissociation of certain inhibitors, to comprise 5-40% of a more rapidly exchanging (weaker binding) fraction of inhibitor binding sites. A small amount of this effect is due to non-specific binding, which can easily be subtracted or allowed for. For most inhibitors, the effect is small; with respect to structures like Compound A, such an effect is likely due to pro-chirality. Where fast and slow exchanging fractions are distinguished at all by inhibitors, here the measured off rates always refer only to the major slower exchanging fraction that represents 60-95% bulk of the HPPD inhibitor binding sites present in the extracts tested.

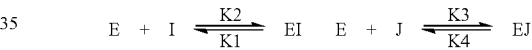

Off rates were determined by preincubating, for example, ~200 pmoles of HPPD binding sites (determined as described above by active site titration in a 3 min reaction with structure A) in 50 mM BisTrisPropane buffer at pH 7.0 and at 25° C. containing 25 mM Na ascorbate, 4 µg/ml bovine catalase (Sigma, St. Louis, Mo.) containing ~1.0 nmole $^{14}$C inhibitor at 25° C. in a total assay volume of 1.3 ml. After 30 minutes the exchange reaction was initiated with addition of 100 µl 1 mM 'cold' structure A with thorough mixing, and, immediately, 150 µl were withdrawn and loaded onto a NAP5 column, the protein exchanged into 50 mM BisTrisPropane buffer at pH 7.0 containing 0.1M KCl by rapid (<2 min) chromatography down a NAP5 G25 Sephadex® column (GE Healthcare Ltd, Buckinghamshire UK) and the amount of $^{14}$C bound to protein measured by Optiphase scintillant using a Tri-Carb® 2900TR scintillation counter (Perkin Elmer, Wellesley, Mass.). Further aliquots were removed and measured in the same way at various times over minutes or hours as required in order to determine the exchange kinetics.

In one variant of the method useful to better distinguish between off rates that were relatively rapid (e.g., where t½<15 min at 25° C.) the temperature of the experiment was reduced from 25° C. to ice temperature. In this case, off rates were determined by preincubating ~200 pmoles HPPD in reaction buffer (50 mM BTP pH 7, 25 mM Na ascorbate, 4 µg/ml bovine catalase, and 10% glycerol) containing ~1.0 nmoles $^{14}$C inhibitor at 25° C. in a total assay volume of 1.3 ml. After 30 minutes the reaction vessel was transferred to ice. After a further 10 minutes at ice temperature the exchange reaction was initiated by addition of 100 µl 1 mM Structure A, with thorough mixing, and 150 µl was withdrawn, loaded and quickly exchanged down a NAP5 column in a cold room at ~5-8° C. in order to quantify the amount of radiolabel remaining bound to the protein at various time from the start of exchange at ice temperature.

Off rates (k1) of HPPD inhibitors that are not readily available radiolabelled or that present other measurement problems (for example high levels of background non-specific protein-binding which can be measured as radiolabel binding that persists in the presence of high concentrations of 'cold' inhibitor) may be measured indirectly. In this case the enzyme complex (~0.1-0.2 µM) is first formed with the unlabelled inhibitor and then the exchange kinetics derived by chasing it off with high a concentration of $^{14}C$-labelled structure A (or radiolabelled D) and monitoring the rate at which the label becomes bound to protein. Structure A is a particularly potent inhibitor with known kinetics. In a 20 fold or more excess Structure A will, in equilibrium, >90% occupy the binding sites in exchange competition with the other inhibitors tested here and indeed most other inhibitors (those skilled in the art will of course design the experiment/relative concentrations and fit the data accordingly). Exemplary methods are also described in PCT Publication No. WO 02/46387.

Exemplary on and off rate data (and derived $K_i$ values) were obtained for the *Avena*-derived HPPD SEQ ID NO: 1 for the following compounds as follows.

Compound A ($^{14}C$ at 1.81 GBq/mmol)

Off rate k1=1.67E-05 $s^{-1}$ as determined at 25° C. using the direct, radiochemical method.

On rate k2=8.50E+04 $M^{-1}$ $s^{-1}$ as determined at 25° C. using the direct, radiochemical method.

$K_d$=1.96E-10 M.
$K_d/K_m$ ratio=0.000036
Thus $k_{off}$ was estimated as =1.67E-05 $s^{-1}$
Compound B ($^{14}C$ at 1.425 GBq/mmol)

Off rate k1(av)=8.1 E-04 $s^{-1}$ at 25° C. (individual experiments yielded k1=8.00E-04, 8.88E-04, 7.50E-04 and 8.00E-04 $s^{-1}$ as determined by the direct, radiochemical method).

Measured at ice temperature k1=1.58E-05 $s^{-1}$ (initial individual experiments yielded 1.16E-05 $s^{-1}$, 1.0E-05 $s^{-1}$, 1.2E-05 $s^{-1}$, 1.5E-05 $s^{-1}$. Later, more extensive experiments making better allowance for non-specific binding values came out consistently near and averaging around 1.58 E-05 $s^{-1}$ (1.58E-05 $s^{-1}$, 1.5-05 $s^{-1}$, 1.67-05 $s^{-1}$, 1.5-05 $s^{-1}$. 1.58-05 $s^{-1}$. 1.58-05 $s^{-1}$, 1.5-05 $s^{-1}$).

On rate k2(av)=6.7E+04 $s^{-1}$ $M^{-1}$ at 25° C. (individual experiments yielded k2=6.35E+04, 7.50E+04, 6.2E+04 as determined by the direct radiochemical method). For mesotrione which has a relatively fast off rate estimates for on rate based on the activity-based method were more variable ranging from 4.2E+04 $s^{-1}$ $M^{-1}$, 4.9E+04 $s^{-1}$ $M^{-1}$ to 7.5 E+04 $s^{-1}$ $M^{-1}$ at 25° C.

$K_d$ was thus estimated from the radiochemical data as 1.16E-08 $M^{-1}$ corresponding to a $Kd/K_m$ ratio of 0.00217.

Thus $k_{off}$ was estimated as 8.1 E-04 $s^{-1}$ at 25° C. and 1.58 E-05 $s^{-1}$ at 0° C.

Compound C ($^{14}C$ at 0.774 GBq/mmol)

Off rate k1(av)=5.3 E-05 $s^{-1}$ at 25° C. (initial experiments yielded k1=7.80E-05 $s^{-1}$, 9.17E-05 $s^{-1}$, 4.5E-05 $s^{-1}$, 6E-05 $s^{-1}$, 7 E-05 $s^{-1}$ and 7.80E-05 $s^{-1}$; however a subsequent set of experiments making more accurate allowance for non specific binding effects makes it likely that the former high values were outliers). Based on later more consistent values, off rate k1(av)=5.3 E-05 $s^{-1}$ based on individual experimental values of 6.5-05 $s^{-1}$, 5.0-05 $s^{-1}$, 5.67-05 $s^{-1}$, 4.67-05 $s^{-1}$, 5.17-05 $s^{-1}$, 4.67-05 $s^{-1}$, 4.67-05 $s^{-1}$, and 6.0-05 $s^{-1}$.

The on rate k2, which was estimated to be 7.50E+03 $s^{-1}$ $M^{-1}$ at 25° C. using the direct radiochemical method is in good agreement with estimates from the enzyme activity-based method of 7.50E+03 $s^{-1}$ $M^{-1}$, 7.80E+03 $s^{-1}$ $M^{-1}$, 7.60E+03 $s^{-1}$ $M^{-1}$, 7.20E+03 $s^{-1}$ $M^{-1}$ and 1.0E+04 $s^{-1}$ $M^{-1}$ at 25° C.

Based on the radiochemical method the estimate of Kd=7.1 E-09M.

Therefore the estimate of Kd/Km ratio=0.0013.

Thus $k_{off}$ was estimated as 5.3 E-05 $s^{-1}$.

Compound D ($^{14}C$ at 1.036 GBq/mmol)

Off rate k1=3.96E-05 $s^{-1}$ at 25° C. as determined using the direct, radiochemical method (individual measurements of 4.17E-05 $s^{-1}$ and 3.75E-05 $s^{-1}$). Off rate as determined in a series of indirect off rate experiments was 4.25-05 $s^{-1}$, 4.66-05 $s^{-1}$, 4.5-05 $s^{-1}$, 4.83-05 $s^{-1}$, 3.83-05 $s^{-1}$, 4.5-05 $s^{-1}$, 4.5-05 s⁻¹, 4.33-05 s⁻¹, 5.0-05 s⁻. Average value for off rate is taken to be 4.39E-05 s⁻¹ from all of the data.

On rate $k_2$=3.20E+04 $M^{-1}$ $s^{-1}$ at 25° C. as determined by the direct radiochemical method. This is in fair agreement with estimates from the activity based method for on rate of 3.20E+04 $M^{-1}$ $s^{-1}$ and 5.7E+04 $M^{-1}$ $s^{-1}$.

Based on the radiochemical methods the estimate of $K_d$=1.36E-9 M.

The estimate of $K_d/K_m$ ratio=0.00025.

Thus $k_{off}$ was estimated as 4.39E-05 $s^{-1}$.

Compound E

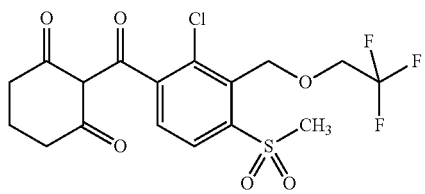 [SMILES: CS(=O)(=O)c1ccc(C(=O)C2C(=O)CCCC2=O)c(Cl)c1COCC(F)(F)F]

Off rate $k_1$=4.17E-05 $s^{-1}$ at 25° C. as initially determined by the indirect, radiochemical method based on individual measurements of 5.50E-05 $s^{-1}$ and 2.85E-05 $s^{-1}$). From a series of further measurements the initial higher value would appear to be an outlier with values obtained of 3.67E-05 $s^{-1}$, 3.17E-05 $s^{-1}$, 2.67E-05 $s^{-1}$, 3.17E-05 $s^{-1}$, 2.67E-05 $s^{-1}$, 3.33E-05 $s^{-1}$, 3.08E-05 $s^{-1}$, 2.02E-05 $s^{-1}$, 3.00E-05 $s^{-1}$ and a new average koff value estimated as 2.96 E-05 $s^{-1}$.

On rate $k_2$=1.30E+05 $M^{-1}$ $s^{-1}$ at 25° C. as determined by the direct non-radiochemical method.

The estimate of $K_d$=2.28E-10M.

The estimate of $K_d/K_m$ ratio=0.000042.

Thus $k_{off}$ was estimated as 2.96 E-05 $s^{-1}$.

Compound F

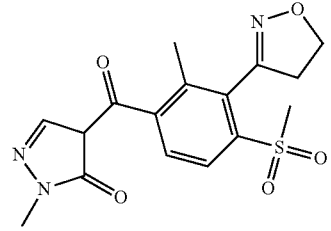 [SMILES: Cc1c(C(=O)C2C=NN(C)C2=O)ccc(S(C)(=O)=O)c1C1=NOCC1]

From a series of indirect off rate measurements (7.08E-05 $s^{-1}$, 6.00E-05 $s^{-1}$, 7.00E-05 $s^{-1}$ and 6.83E-05 $s^{-1}$) the average $k_{off}$ value was estimated as 6.72 E-05 $s^{-1}$.

Example 2

Cloning, expression and assay of HPPDs SEQ ID NOs: 1-14 from various plants and determination of $k_{cat}$, $Km_{HPP}$ and koff values versus various HPPD herbicides DNA sequences optimized for *E. coli* codon usage and encoding HPPD polypeptides corresponding to SEQ ID NOs: 1-14 derived from various plants were synthesized by GeneArt (Regensburg, Germany), cloned into pET24a, and expressed in *E. coli* BL21(DE3) with 50 µg/ml kanamycin selection as described in PCT App. Pub. No. WO 02/46387. Cells were grown, protein extracts prepared, and HPPD active site titres and kinetic measurements (of $k_{cat}$, $K_{mHPP}$ and $k_{off}$ values versus various different herbicides) carried out as described in Example 1.

The HPPD corresponding to SEQ ID NO: 1 was included as an internal control in experiments. The average absolute values of the various kinetic parameters for SEQ ID NO: 1 are listed above in detail in Example 1. The data in Table 2 below provide data from these measurements for SEQ ID NOs: 2-14 expressed as a ratio versus the corresponding control value for SEQ ID NO: 1. Thus all the parameter values for SEQ ID NO: 1 are given as 1.0 and all values in the table are comparative to those for SEQ ID NO: 1.

TABLE 2

| Kinetic parameters of HPPDs of SEQ ID NOs: 2-14 | | | | | | | | |
|---|---|---|---|---|---|---|---|---|
| SEQ ID NO: | $K_{cat}/K_{cat}$ SEQ ID NO: 1 | $K_{mHPP}/K_m$ SEQ ID NO: 1 | $(K_{cat}/K_m)/(K_{cat}/K_m)$ SEQ ID NO: 1 | $K_{off}B/K_{off}B$ SEQ ID NO: 1 | $K_{off}C/K_{off}C$ SEQ ID NO: 1 | $K_{off}D/K_{off}D$ SEQ ID NO: 1 | $K_{off}E/K_{off}E$ SEQ ID NO: 1 | $K_{off}F/K_{off}F$ SEQ ID NO: 1 |
| 1 | 1.0 | 1.0 | 1.0 | 1.0 | 1.0 | 1.0 | 1.0 | 1.0 |
| 2 | | | | 2.0 | | | | |
| 3 | 1.1 | 1.1 | 0.9 | 2.1 | 1.3 | 1.3 | 1.5 | 1.6 |
|  | 1.3 | 1.2 | 1.1 | 2.2 | 1.1 | 1.2 | 1.5 | |
| 4 | 1.3 | 1.6 | 0.8 | 0.5 | | 0.6 | 1.6 | |
|  | 1.3 | 1.6 | 0.8 | | | | | |
| 5 | 1.5 | 1.4 | 1.1 | 0.5 | | 0.7 | 1.5 | |
|  | 1.7 | 1.8 | 0.9 | | | | | |
| 6 | 1.0 | 1.1 | 0.9 | 1.0 | | 1.8 | 1.0 | |
| 7 | 1.1 | 0.9 | 1.2 | 1.1 | | 2.1 | 1.7 | 1.3 |
|  | 0.9 | 0.8 | 1.1 | 1.3 | | 1.7 | 1.7 | |
| 8 | 1.1 | 0.8 | 1.3 | 1.3 | | 1.4 | 1.1 | |
|  | 1.2 | 0.8 | 1.4 | | | | | |
| 9 | 1.2 | 1.1 | 1.1 | 0.1 | | 0.2 | 0.5 | |
| 10 | 1.4 | | | <0.05 | | 0.2 | 0.1 | |
| 11 | | | | <0.1 | | 0.3 | 0.3 | 0.3 |
| 12 | | | | 0.1 | | 0.1 | 0.2 | 0.2 |
| 13 | 0.7 | 0.7 | 1.0 | <0.05 | | 0.2 | | |
| 14 | 0.8 | 6.0 | 0.2 | <0.05 | | 4.0 | | |

'$k_{off}$ B', '$k_{off}$ C', etc. refer to off rates measured by radiolabel exchange with the HPPD-inhibitor herbicides B-F described in Example 1.

It is apparent from the data in Table 2 that, relative to SEQ ID NO: 1, some HPPDs are more and others are less inherently resistant to the various herbicides B-F and therefore more or less suitable for conferring resistance in transgenic plants. In addition some exhibit greater or smaller values of $k_{cat}/K_m$ relative to the HPPD of SEQ ID NO: 1. For each herbicide the relevant comparative parameter that determines the suitability or otherwise of the given HPPD sequence is the multiple of the $k_{cat}/K_m$ (relative to that for SEQ ID NO: 1) value and the corresponding $k_{off}$ rate for the herbicide (relative to that for SEQ ID NO: 1).

Thus, for example, the HPPD of SEQ ID NO: 3 derived from *Alopecurus* gives a value for this multiple of 2.3 for mesotrione (B) meaning that it is effectively about 2.3 fold more resistant to mesotrione than is SEQ ID NO: 1 and, all being equal, will confer a higher (probably about two fold) level of tolerance to mesotrione when likewise expressed in transgenic plants.

Similarly, the same sequence also provides enhanced (albeit to a lesser degree) tolerance over SEQ ID NO: 1 to the other herbicides tested (topramezone, tembotrione and the diketonitrile derived from isoxaflutole etc). Likewise it can be seen that the HPPDs of SEQ ID NOs: 6, 7 and 8 also confer advantages. On the other hand, of the range of other HPPDs tested, some appear significantly less effective than the HPPD of SEQ ID NO: 1 for providing tolerance to any herbicide. Thus, for example, the HPPDs from *Erichola*, *Arabidopsis* and *Bidens* appear to be of similar catalytic activity to the HPPD of SEQ ID NO: 1 but are >20 fold more sensitive to mesotrione whilst the *Pseudomonas* enzyme is both less catalytically efficient ($k_{cat}/K_m$~0.2 of that for SEQ ID NO: 1) and more sensitive to mesotrione. Thus, a number of the new HPPD sequences described herein (e.g., SEQ ID NOs: 2-8) offer significant improvements over the prior art in respect of providing better options for providing tolerance to HPPD herbicides and especially in respect of the chemical classes exemplified.

Example 3

Cloning, expression and assay of mutant variants of HPPDs and determination of $k_{cat}$, $K_{mHPP}$ and $k_{off}$ values versus various HPPD herbicides DNA sequences optimized for *E. coli* codon usage and encoding HPPD polypeptides corresponding to SEQ ID NO: S:20-47, encoding HPPD polypeptides derived from *Avena sativa*, *Alopecurus mysoides* and *Poa annua* were synthesized by GeneArt (Regensburg, Germany), cloned into pET24a, and expressed in *E. coli* BL21(DE3) with 50 µg/ml kanamycin selection as described in PCT Publication No. WO 02/46387. Cells were grown, protein extracts were prepared, and HPPD active site titres and kinetic measurements of $k_{cat}$, $K_{mHPP}$, and $k_{off}$ values were carried out as described in Example 1.

Within the present example, the following HPPD sequences derived from SEQ ID NO: 1 were used:

HPPD SEQ ID NO: 20 was changed relative to SEQ ID NO: 1 by the substitution of M for L at position 358.

HPPD SEQ ID NO: 21 was changed relative to SEQ ID NO: 1 by the substitution of I for the V at position 217.

HPPD SEQ ID NO: 22 was changed relative to SEQ ID NO: 1 by the substitution of L for the V at position 217.

HPPD SEQ ID NO: 23 was changed relative to SEQ ID NO: 1 by the substitution of R for the A at position 326.

HPPD SEQ ID NO: 24 was changed relative to SEQ ID NO: 1 by the substitution of K for the A at position 326.

HPPD SEQ ID NO: 25 was changed relative to SEQ ID NO: 1 by the substitution of I for the A at position 326.

HPPD SEQ ID NO: 26 was changed relative to SEQ ID NO: 1 by the substitution of E for the I at position 339.

HPPD SEQ ID NO: 27 was changed relative to SEQ ID NO: 1 by the substitution of D for the I at position 339.

HPPD SEQ ID NO: 28 was changed relative to SEQ ID NO: 1 by the substitution of C for the I at position 339.

HPPD SEQ ID NO: 29 was changed relative to SEQ ID NO: 1 by the substitution of R for the G at position 408.

HPPD SEQ ID NO: 30 was changed relative to SEQ ID NO: 1 by the substitution of M for L at position 358 and by the substitution of R for the A at position 326.

HPPD SEQ ID NO: 31 was changed relative to SEQ ID NO: 1 by the substitution of M for L at position 358, by the substitution of R for the A at position 326, and by the substitution of I for the V at position 217.

HPPD SEQ ID NO: 32 was changed relative to SEQ ID NO: 1 by the substitution of M for L at position 358 and by the substitution of I for the V at position 217.

HPPD SEQ ID NO: 33 was changed relative to SEQ ID NO: 1 by the substitution of R for the A at position 326 and by the substitution of I for the V at position 217.

HPPD SEQ ID NO: 34 was changed relative to SEQ ID NO: 1 by the substitution of M for L at position 358, by the substitution of K for the A at position 326, and by the substitution of I for the V at position 217.

HPPD SEQ ID NO: 35 was changed relative to SEQ ID NO: 1 by the substitution of M for L at position 358, by the substitution of R for the A at position 326, and by the substitution of L for the V at position 217.

HPPD SEQ ID NO: 36 was changed relative to SEQ ID NO: 1 by the substitution of M for L at position 358, by the substitution of R for the A at position 326, by the substitution of I for the V at position 217, and by the substitution of E for the I at position 339.

HPPD SEQ ID NO: 37 was changed relative to SEQ ID NO: 1 by the substitution of M for L at position 358, by the substitution of R for the A at position 326, by the substitution of L for the V at position 217, and by the substitution of E for the I at position 339.

HPPD SEQ ID NO: 42 was changed relative to SEQ ID NO: 1 by the substitution of H for the G at position 412.

HPPD SEQ ID NO: 43 was changed relative to SEQ ID NO: 1 by the substitution of C for the G at position 412.

HPPD SEQ ID NO: 44 was changed relative to SEQ ID NO: 1 by the substitution of A for the Q at position 297.

HPPD SEQ ID NO: 45 was changed relative to SEQ ID NO: 1 by the substitution of N for the Q at position 283.

HPPD SEQ ID NO: 46 was changed relative to SEQ ID NO: 1 by the substitution of G for the Q at position 297.

HPPD SEQ ID NO: 47 was changed relative to SEQ ID NO: 1 by the substitution of A for L at position 358.

Within the present example, the following HPPD sequences derived from SEQ ID NO: 3 were used:

HPPD SEQ ID NO: 40 was changed relative to SEQ ID NO: 3 by the substitution of M for L at position 359 and by the substitution of R for the A at position 327.

HPPD SEQ ID NO: 41 was changed relative to SEQ ID NO: 3 by the substitution of M for L at position 359, by the substitution of R for the A at position 327, and by the substitution of I for the V at position 218.

Within the present example, the following HPPD sequences derived from SEQ ID NO: 7 were used:

HPPD SEQ ID NO: 38 was changed relative to SEQ ID NO: 7 by the substitution of M for L at position 353 and by the substitution of R for the A at position 321.

HPPD SEQ ID NO: 39 was changed relative to SEQ ID NO: 7 by the substitution of M for L at position 353, by the substitution of R for the A at position 321, and by the substitution of I for the first V at position 213.

The HPPD corresponding to SEQ ID NO: 1 was included as an internal control in experiments. The average absolute values of the various kinetic parameters for the HPPD of SEQ ID NO: 1 are listed above in detail in Example 1. The data in Tables 3-5 below provide data from these measurements for SEQ ID NOs: 20-47 and 50 expressed as a ratio versus the corresponding control value for SEQ ID NO: 1. Thus all the parameter values for SEQ ID NO: 1 are given as 1.0.

TABLE 3

Kinetic parameters of HPPDs of SEQ ID NOs: 20-29

| SEQ ID NO: | $K_{cat}/K_{cat}$ SEQ ID NO: 1 | $K_{mHPP}/K_m$ SEQ ID NO: 1 | $(K_{cat}/K_m)/(K_{cat}/K_m)$ SEQ ID NO: 1 | $K_{off}B/K_{off}B$ SEQ ID NO: 1 | $K_{off}C/K_{off}C$ SEQ ID NO: 1 | $K_{off}D/K_{off}D$ SEQ ID NO: 1 | $K_{off}E/K_{off}E$ SEQ ID NO: 1 | $K_{off}F/K_{off}F$ SEQ ID NO: 1 |
|---|---|---|---|---|---|---|---|---|
| 1 | 1.0 | 1.0 | 1.0 | 1.0 | 1.0 | 1.0 | 1.0 | 1.0 |
| 20 | 0.7 | 0.9 | 0.8 | 2.0 | 1.1 | 2.3 | 1.2 | 2.1 |
|  | 0.8 | 0.9 | 0.8 | 1.9 |  | 1.9 |  |  |
| 21 | 1.1 | 1.4 | 0.8 | 1.5 | 1.1 | 1.0 | 1.0 | 1.1 |
|  | 0.9 | 0.9 | 1.0 | 1.5 |  |  |  |  |
| 22 | 0.8 | 0.8 | 1.0 | 2.0 | 1.0 | 1.2 | 1.0 | 1.0 |
|  | 0.7 | 0.7 | 1.1 |  |  |  |  |  |
| 23 | 1.5 | 1.0 | 1.6 | 1.7 |  | 1.4 | 1.2 | 1.3 |
|  | 1.3 | 0.6 | 2.2 | 1.7 | 0.9 | 1.4 | 1.3 |  |
| 24 | 0.8 | 1.0 | 0.8 | 1.4 | 1.1 | 1.5 | 1.2 | 1.3 |
|  | 0.7 | 0.6 | 1.2 |  |  |  |  |  |
| 25 | 0.9 |  |  | 1.6 |  | 1.1 | 1.3 |  |
| 26 | 0.6 | 0.5 | 1.2 | 1.5 | 1.0 | 1.4 | 1.6 | 1.5 |
|  | 0.6 | 0.6 | 1.0 |  |  |  |  |  |
| 27 | 0.8 | 0.9 | 0.9 | 1.7 |  | 1.1 | 1.5 |  |
|  | 0.7 | 0.7 | 1.1 |  |  |  |  |  |
| 28 |  |  |  | 1.2 |  | 1.0 | 1.6 |  |
| 29 | 0.1 | 0.6 | 0.2 | 8.1 |  | 1.7 | 11.3 |  |
|  | 0.1 | 0.3 | 0.4 |  |  |  |  |  |

TABLE 4

Kinetic parameters of HPPDs of SEQ ID NOs: 30-36

| SEQ ID NO: | $K_{cat}/K_{cat}$ SEQ ID NO: 1 | $K_{mHPP}/K_m$ SEQ ID NO: 1 | $(K_{cat}/K_m)/(K_{cat}/K_m)$ SEQ ID NO: 1 | $K_{off}B/K_{off}B$ SEQ ID NO: 1 | $K_{off}C/K_{off}C$ SEQ ID NO: 1 | $K_{off}D/K_{off}D$ SEQ ID NO: 1 | $K_{off}E/K_{off}E$ SEQ ID NO: 1 | $K_{off}F/K_{off}F$ SEQ ID NO: 1 |
|---|---|---|---|---|---|---|---|---|
| 1 | 1.0 | 1.0 | 1.0 | 1.0 | 1.0 | 1.0 | 1.0 | 1.0 |
| 30 | 0.6 | 0.6 | 1.1 | 3.4 |  | 2.8 | 1.6 | 3.2 |
|  | 0.6 | 0.5 | 1.1 | 3.3 |  | 2.7 | 1.6 | 3.1 |
|  | 0.8 | 0.8 | 1.1 | 3.5 | 1.1 | 3.1 | 1.9 |  |
|  | 0.8 | 0.7 | 1.1 | 3.6 | 0.9 | 2.8 | 2.2 |  |
|  | 0.8 | 0.7 | 1.0 |  |  |  |  |  |
| 31 | 0.6 | 0.5 | 1.1 | 5.3 | 1.1 | 3.2 | 2.4 | 3.8 |
|  | 0.6 | 0.5 | 1.1 | 5.3 |  | 2.6 | 2.3 |  |
|  | 0.8 | 0.7 | 1.2 |  |  |  |  |  |
| 32 | 1.0 | 1.1 | 0.8 | 3.1 | 1.0 | 2.1 | 1.6 | 2.7 |
|  | 0.9 | 0.9 | 0.9 | 3.2 |  | 2.3 |  |  |
| 33 | 0.6 | 0.5 | 0.8 | 2.5 | 1.3 | 1.4 | 1.5 | 1.3 |
|  | 0.6 | 0.7 | 0.7 |  |  |  |  |  |
| 34 | 0.7 | 0.8 | 0.9 | 5.0 |  | 3.2 | 2.9 |  |
|  | 0.7 | 0.9 | 0.8 |  |  |  |  |  |
| 35 | 0.8 | 1.2 | 0.7 | 6.3 |  | 3.0 | 2.5 |  |
|  | 0.7 | 0.8 | 0.9 |  |  |  |  |  |
| 36 | 0.7 | 0.7 | 1.0 | 8.5 |  | 3.6 | 5.1 |  |
|  | 0.7 | 0.5 | 1.3 |  |  |  |  |  |

TABLE 5

Kinetic parameters of HPPDs of SEQ ID NOs: 37-47 and 50

| SEQ ID NO: | $K_{cat}/K_{cat}$ SEQ ID NO: 1 | $K_{mHPP}/K_m$ SEQ ID NO: 1 | $(K_{cat}/K_m)/(K_{cat}/K_m)$ SEQ ID NO: 1 | $K_{off}B/K_{off}B$ SEQ ID NO: 1 | $K_{off}C/K_{off}C$ SEQ ID NO: 1 | $K_{off}D/K_{off}D$ SEQ ID NO: 1 | $K_{off}E/K_{off}E$ SEQ ID NO: 1 | $K_{off}F/K_{off}F$ SEQ ID NO: 1 |
|---|---|---|---|---|---|---|---|---|
| 1 | 1.0 | 1.0 | 1.0 | 1.0 | 1.0 | 1.0 | 1.0 | 1.0 |
| 37 | 0.7 | 0.5 | 1.3 | 8.6 | | 3.4 | 3.7 | |
|  | 0.7 | 0.4 | 1.6 | | | | | |
| 38 | 0.5 | 0.8 | 0.7 | 3.9 | | 3.1 | 2.8 | |
|  | 0.6 | 0.5 | 1.2 | | | | | |
| 39 | 0.8 | 0.7 | 1.2 | 6.4 | | 4.3 | 4.8 | |
|  | 0.9 | 0.8 | 1.0 | | | | | |
| 40 | 0.6 | 0.5 | 1.0 | 8.4 | | 2.1 | 2.5 | |
|  | 0.8 | 0.6 | 1.3 | | | | | |
| 41 | 0.9 | 0.7 | 1.2 | 12.5 | | 3.6 | 5.3 | |
|  | 0.9 | 1.0 | 1.0 | | | | | |
| 42 | 2.0 | 8.1 | 0.2 | 1.4 | 0.7 | 0.6 | 1.0 | 1.9 |
|  | 1.1 | 4.6 | 0.2 | | | | | |
| 43 | 0.7 | 10.5 | <0.1 | 2.0 | 1.4 | 1.0 | 2.7 | 0.7 |
|  | 0.5 | 8.5 | <0.1 | | | | | |
| 44 | 0.4 | 22 | <0.1 | | 1.6 | 0.6 | | |
| 45 | <0.05 | >2 | <<0.1 | | | 2.0 | | |
| 46 | 0.1 | 49 | <<0.1 | 2.7 | 1.8 | | | |
| 47 | 0.2 | 2 | 0.1 | 1.0 | 1.7 | | | |
| 50 | 1.1 | 2 | 1.1 | 15.3 | | 3.2 | 4.7 | |
|  | | | | | | 3.4 | 3.7 | 4.1 |

It is apparent from the data depicted in Tables 3-5 that, relative to SEQ ID NO: 1, some mutant HPPDs are more and others are less inherently resistant to the various herbicides B-F and therefore more or less suitable for conferring resistance in transgenic plants. Again, for each herbicide the relevant comparative parameter that determines the suitability or otherwise of the given HPPD sequence is the multiple of the $k_{cat}/K_m$ (relative to that for SEQ ID NO: 1) value and the corresponding $k_{off}$ rate for the herbicide (relative to that for SEQ ID NO: 1). Thus, those sequences, for example SEQ ID NOs: 20-29, having single amino acid changes relative to SEQ ID NO: 1 at positions L358, V217, I339 and A326 of SEQ ID NO: 1 not only show significant increases in off rate ($k_{off}$) to one or more of the test herbicides (B-F) but also remain catalytically efficient (i.e. $k_{cat}/K_m$ remains about the same or is improved over that for SEQ ID NO: 1). Thus, for example, the HPPD of SEQ ID NO: 26, which has an I339E amino acid substitution relative to SEQ ID NO: 1 exhibits a significant (~1.5 fold) improvement in inherent tolerance to herbicides B, D, E and F relative to SEQ ID NO: 1. Similarly, the various other single amino acid substitutions (L358M, V217I, V217L, G408R, I339D, I339C, A326R, A326I and A326K of SEQ ID NOs: 20-29) also provided improvements in inherent tolerance to one or more of the herbicides.

SEQ ID NO: 29, with a G408R change relative to SEQ ID NO: 1, exhibits only about a quarter to a third of the catalytic activity of the HPPD of SEQ ID NO: 1. However this shortfall in catalytic activity is more than made up by the 8× or more increase in the value of $k_{off}$ governing the rate of dissociation of compounds B and E from the enzyme. Further evidence demonstrates that mutating G408 confers advantageous properties on the mutant enzyme. For example, a G408A substitution has similar catalytic activity to the HPPD of SEQ ID NO: 1 ($k_{cat}/K_m$) and exhibits, compared to SEQ ID NO: 1, a 1.45 fold increase in the rate of dissociation ($k_{off}$) of the enzyme:inhibitor complex with mesotrione. The G408A mutant HPPD also exhibits, relative to SEQ ID NO: 1, a greater than 1.5× increase in the value of $k_{off}$ in respect of inhibitor D and a greater than 3.5× increase in the value of $K_{off}$ in respect of inhibitor E. As such, commercial levels of tolerance to HPPD herbicides, and particularly to the structural classes exemplified herein, is more readily attained through the additional improvements conferred by these disclosed mutations.

In order to provide any degree of useful tolerance, a mutation must provide an decrease in herbicide binding (here measured as an increase in the rate of dissociation of herbicide from the enzyme) that, in numerical magnitude, more than outweighs any catalytic deficit (here measured as $k_{cat}/K_m$). Even more valuable are those mutations that can be combined together with each other and incorporated into a variety of HPPD sequences (for example, the HPPDs set forth in Table 2) so as to work in combination and provide additive, or more preferably, synergistic levels of herbicide tolerance relative to native HPPDs.

Thus, for example, the variant HPPD of SEQ ID NO: 30 derived from Avena which combines the A326R substitution of SEQ ID NO: 23 with the L358M substitution of SEQ ID NO: 20 provides a level of HPPD herbicide resistance that exceeds that of either the two single mutations and, indeed, provides a near multiplicative increase. So for example the HPPD of SEQ ID NO: 30 is about 3.5 fold more resistant to mesotrione than is SEQ ID NO: 1 and thus, all things being equal, will confer a higher (probably about three or more fold) level of tolerance to mesotrione when likewise expressed in transgenic plants. The same HPPD sequence (i.e., SEQ ID NO: 30) also provides enhanced tolerance over SEQ ID NO: 1 in respect of the other herbicides tested and, notably, for example, is about 3 fold more tolerant to topramezone and isoxaflutole (diketonitrile) than is SEQ ID NO: 1. The HPPD of SEQ ID NO: 31, which combines the V217I substitution of SEQ ID NO: 21 with the L358M substitution of SEQ ID NO: 20 and the A326R substitution of SEQ ID NO: 23 correspondingly shows even yet further (~5.8 fold) enhancement in resistance to mesotrione and other herbicides over the HPPD of SEQ ID NO: 1. Similarly, the HPPD of SEQ ID NO: 36 which yet further adds the I339E change of SEQ ID NO: 26 to those of SEQ ID NO: 31 is yet even more tolerant to mesotrione (~9.8 fold) than is the HPPD of SEQ ID NO: 1. This demonstrates that the changes at all of these amino acid positions can be combined to provide enhanced levels of inherent enzyme herbicide tolerance.

In addition the same mutational changes also function and beneficially alter the characteristics of HPPDs other than the SEQ ID NO: 1 from *Avena*. Thus, for example, SEQ ID NO: 40 combines the equivalent amino acid changes as in SEQ ID NO: 30 but this time in the *Alopecurus* HPPD of SEQ ID NO: 3. The benefits of the two mutational changes and of the *Alopecurus* HPPD enzyme over *Avena* work about multiplicatively so that, taking into account the values of $k_{cat}/K_m$ and of $k_{off}$, the HPPD of SEQ ID NO: 40 exhibits a more than 10 fold improvement in inherent tolerance to mesotrione relative to SEQ ID NO: 1. Similarly, SEQ ID NO: 39 combines the equivalent amino acid changes as in SEQ ID NO: 31 but this time into the *Poa* HPPD of SEQ ID NO: 7. Accordingly, SEQ ID NO: 39 exhibits significantly better tolerance to compound D (~4.7 fold better than the HPPD of SEQ ID NO: 1) than does the HPPD of SEQ ID NO: 31 (~3.2 fold better than the HPPD of SEQ ID NO: 1). SEQ ID NO: 41 also combines the equivalent amino acid changes as in SEQ ID NO: 31 but this time into the *Alopecurus* HPPD of SEQ ID NO: 3. The HPPD of SEQ ID NO: 41 exhibits a high level of inherent tolerance to both compound E (~5.8 fold higher than the HPPD of SEQ ID NO: 1) and also to mesotrione (~13.8 fold higher than the HPPD of SEQ ID NO: 1).

Example 4

Preparation and Evaluation of Herbicide Tolerance Conferred by Heterologous HPPD Enzymes Expressed in Tobacco In the present example, native and mutant HPPDs are, for example, SEQ ID NOs: 1-14 and 20-47. DNA sequences that encode these (optimized for tobacco or, optionally, codon optimized according to a target crop such as soybean) are prepared synthetically and obtained commercially from GeneArt (Regensburg, Germany). Each sequence is designed to have 5' NdeI and 3'BamH1 sites to facilitate direct cloning and then cloned into a suitable binary vector for *Agrobacterium*-based plant transformation.

In a particular embodiment, tobacco-optimized genes encoding N-terminal fusions of the *petunia* EPSPS chloroplast transit peptide (SEQ ID NO: 48) to HPPD SEQ ID NOs: 13 and 14 and the wheat HPPD (SEQ ID NO: 5 in PCT Publication No. WO 02/46387; UNIPROT:A7WK82) are cloned into expression constructs and transformed into tobacco. The CTP/HPPD encoding nucleotide sequence is edited by PCR (or initially synthesized) to include a 5' XhoI site, a TMV omega enhancer (SEQ ID NO: 86) and a 3' KpnI site (and to remove any such internal sites).

The expression cassette, comprising the TMV omega 5' leader, CTP and 4-HPPD gene is excised using XhoI/KpnI and cloned into similarly digested pBIN 19 (Bevan, *Nucl. Acids Res.* (1984) behind a double enhanced 35S promoter (SEQ ID NO: 87) and ahead of a NOS 3' transcription terminator (SEQ ID NO: 88) and then transformed into *E. coli* TOP 10 competent cells. DNA recovered from the *E. coli* is used to transform *Agrobacterium tumefaciens* LBA4404, and transformed bacteria are selected on media contain rifampicin and kanamycin. Tobacco tissue is subjected to *Agrobacterium*-mediated transformation using methods known in the art or as described herein. For example, a master plate of *Agrobacterium tumefaciens* containing the HPPD expressing binary vector is used to inoculate 10 ml LB (L broth) containing 100 mg/l rifampicin plus 50 mg/l kanamycin using a single bacterial colony. This is incubated overnight at 28° C. shaking at 200 rpm. This entire overnight culture is used to inoculate a 50 ml volume of LB containing the same antibiotics. Again this is cultured overnight at 28° C. shaking at 200 rpm. The *Agrobacterium* cells are pelleted by centrifuging at 3000 rpm for 15 minutes and then resuspended in MS (Murashige and Skoog) medium containing 30 g/l sucrose, pH 5.9 to an OD (600 nM)=0.6. This suspension is dispensed in 25 ml aliquots into petri dishes.

Clonally micro-propagated tobacco shoot cultures are used to excise young (not yet fully expanded) leaves. The mid rib and outer leaf margins are removed and discarded, and the remaining lamina cut into 1 cm squares. These are transferred to the *Agrobacterium* suspension for 20 minutes. Explants are then removed, dabbed on sterile filter paper to remove excess suspension, then transferred onto solid NBM medium (MS medium containing 30 g/l sucrose, 1 mg/l BAP (benzylaminopurine) and 0.1 mg/l NAA (napthalene acetic acid) at pH 5.9 and solidified with 8 g/l plantagar), with the abaxial surface of each explant in contact with the medium. Approximately 7 explants are transferred per plate, which are then sealed and maintained in a lit incubator at 25° C. for a 16 hour photoperiod for 3 days.

Explants are then transferred onto NBM medium containing 100 mg/l kanamycin plus antibiotics to prevent further growth of *Agrobacterium* (200 mg/l timentin with 250 mg/l carbenicillin). Further subculture onto this same medium was then performed every 2 weeks.

As shoots start to regenerate from the callusing leaf explants, these are removed to Shoot elongation medium (MS medium, 30 g/l sucrose, 8 g/l plantagar, 100 mg/l kanamycin, 200 mg/l timentin, 250 mg/l carbenicillin, pH 5.9). Stable transgenic plants readily root within 2 weeks. To provide multiple plants per event to ultimately allow more than one herbicide test per transgenic plant, all rooting shoots are micropropagated to generate 3 or more rooted clones.

Putative transgenic plants that are rooting and showing vigorous shoot growth on the medium incorporating kanamycin are analysed by PCR using primers that amplified a 500 bp fragment within the HPPD transgene. Evaluation of this same primer set on untransformed tobacco showed conclusively that these primers would not amplify sequences from the native tobacco HPPD gene.

Transformed shoots are divided into 2 or 3 clones and regenerated from kanamycin resistant callus. Shoots are rooted on MS agar containing kanamycin. Surviving rooted explants are re-rooted to provide approximately 40-50 kanamycin resistant and PCR positive events from each event.

Once rooted, plantlets are transferred from agar and potted into 50% peat, 50% John Innes Soil No. 3 with slow-release fertilizer in 3 inch round pots and left regularly watered to establish for 8-12 days in the glass house. Glass house conditions were adjusted to about 24-27° C. day, 18-21° C. night and approximately a 14 hour photoperiod. Humidity was adjusted to ~65% and light levels were up to 2000 μmol/m² at bench level.

Three transgenic populations each of about forty tobacco plants and comprising, alternatively, an HPPD gene encoding the wheat HPPD (A7WK82), HPPD SEQ ID NO: 12 or HPPD SEQ ID NO: 13 were thus produced. A sub-set of about 30 plants were then selected on the basis of similar size from each population for spray testing. All the plants were then sprayed with 600 g/ha of mesotrione. Callisto® was mixed in water with 0.2-0.25% X-77® surfactant and sprayed from a boom on a suitable track sprayer moving at 2 mph with the nozzle about 2 inches from the plant tops. Spray volume was 200 l/ha. Plants were assessed for damage and scored at 14 days after treatment (DAT). The results are depicted in Table 6.

From the data depicted in Table 6 it is clear that, of the like-expressed HPPDs, only the wheat HPPD(A7WK82) had conferred a useful level of tolerance to mesotrione (i.e., normally robust to at least 2-4× of a normal field application rate). In contrast, the HPPDs of SEQ ID NO: 13 (from *Arabidopsis*) and SEQ ID NO: 14 (from *Pseudomonas fluorescens*) provided no effective tolerance at the rate sprayed. Five out of 33 wheat HPPD events exhibited < or equal to 10% damage (zero to slight stunting). This differential in the mesotrione tolerance according to which HPPD is expressed is entirely consistent both with the in vitro data depicted in Table 2 (indicating that neither the *Arabidopsis* nor *Pseudomonas* HPPDs have much inherent tolerance to mesotrione) and also with the published data describing the relative significant superiority of the wheat HPPD (both in vitro and in planta) to either of these (Hawkes et al (2001) in *Proc. Brit Crop Prot. Conf.* (Weeds), p 563. British Crop Protection Council and PCT Publication No. WO 02/46387).

TABLE 6

| Arabidopsis | | | Wheat | | | Pseudomonas | | |
|---|---|---|---|---|---|---|---|---|
| Event | Score | Bleaching | Event | Score | Bleaching | Event | Score | Bleaching |
| 987 | 90 | Full | 1605 | 90 | Full | 1897 | 85 | Full |
| 1988 | 90 | Full | 1607 | 0 | Green | 1898 | 80 | Full |
| 1990 | 80 | Full | 1608 | 15 | Green | 1899 | 80 | Full |
| 1993 | 85 | Full | 1609 | 30 | Green | 1905 | 85 | Full |
| 1995 | 85 | Full | 1610 | 80 | Full | 1908 | 85 | Full |
| 1996 | 90 | Full | 1612 | 75 | Full | 1909 | 90 | Full |
| 1997 | 85 | Full | 1613 | 80 | Full | 1918 | 85 | Full |
| 1999 | 90 | Full | 1616 | 50 | Partly | 1920 | 100 | Full |
| 2009 | 85 | Full | 1617 | 65 | Full | 1927 | 85 | Full |
| 2011 | 90 | Full | 1618 | 70 | Full | 1928 | 90 | Full |
| 2012 | 90 | Full | 1620 | 0 | Green | 1929 | 85 | Full |
| 2013 | 95 | Full | 1622 | 20 | Green | 1930 | 85 | Full |
| 2015 | 90 | Full | 1623 | 30 | Green | 1931 | 85 | Full |
| 2016 | 90 | Full | 1626 | 75 | Full | 1934 | 85 | Full |
| 2021 | 90 | Full | 1636 | 85 | Full | 1936 | 80 | Full |
| 2022 | 90 | Full | 1701 | 70 | Full | 1937 | 80 | Full |
| 2029 | 90 | Full | 1704 | 75 | Full | 1938 | 75 | Full |
| 2031 | 85 | Full | 1705 | 75 | Full | 1939 | 90 | Full |
| 2033 | 85 | Full | 1706 | 10 | Green | 1940 | 85 | Full |
| 2035 | 85 | Full | 1708 | 15 | Green | 1943 | 85 | Full |
| 2036 | 90 | Full | 1709 | 90 | Full | 1944 | 80 | Full |
| 2038 | 85 | Full | 1710 | 5 | Green | 1945 | 80 | Full |
| 2039 | 90 | Full | 1711 | 85 | Full | 1951 | 90 | Full |
| 2040 | 90 | Full | 1713 | 70 | Full | 1952 | 90 | Full |
| 2044 | 90 | Full | 1717 | 75 | Full | 1953 | 90 | Full |
| 2049 | 85 | Full | 1718 | 80 | Full | 1954 | 95 | Full |
| 2051 | 90 | Full | 1719 | 5 | Green | 1955 | 95 | Full |
| 2052 | 85 | Full | 1720 | 70 | Full | 1956 | 95 | Full |
| 2053 | 90 | Full | 1721 | 15 | Green | 1957 | 95 | Full |
| 2059 | 0 | Full | 1722 | 90 | Full | 1958 | 95 | Full |
| 2061 | 90 | Full | 1723 | 15 | Green | 1965 | 85 | Full |
| 2062 | 90 | Full | 1727 | 35 | Green | 1966 | 95 | Full |
| | | | 1728 | 40 | Partly | | | |

Table 7 depicts an assessment of damage 14 DAT with 600 g/ha isoxaflutole of clonal plants of the same events as depicted in Table 6 from an experiment carried out in parallel at the same time.

TABLE 7

| Arabidopsis | | | Wheat | | | Pseudomonas | | |
|---|---|---|---|---|---|---|---|---|
| Event | Score | Bleaching | Event | Score | Bleaching | Event | Score | Bleaching |
| 987 | 65 | Full | 1605 | 85 | Full | 1897 | 70 | Full |
| 1988 | 75 | Full | 1607 | 60 | Partly | 1898 | 50 | Partly |
| 1990 | 80 | Full | 1608 | 15 | Green | 1899 | 50 | Partly |
| 1993 | 10 | Full | 1609 | 70 | Full | 1905 | 65 | Full |
| 1995 | 80 | Full | 1610 | 80 | Full | 1908 | 90 | Full |
| 1996 | 65 | Full | 1612 | 85 | Full | 1909 | 95 | Full |
| 1997 | 70 | Full | 1613 | 30 | Green | 1918 | 70 | Full |
| 1999 | 85 | Full | 1616 | 70 | Full | 1920 | Full | |
| 2009 | 70 | Full | 1617 | 80 | Full | 1927 | 70 | Full |
| 2011 | 70 | Full | 1618 | 10 | Green | 1928 | 75 | Full |
| 2012 | 70 | Full | 1620 | 65 | Full | 1929 | 60 | Partly |
| 2013 | 90 | Full | 1622 | 80 | Full | 1930 | 75 | Full |
| 2015 | 80 | Full | 1623 | 65 | Full | 1931 | 60 | Partly |
| 2016 | 70 | Full | 1626 | 90 | Full | 1934 | 70 | Full |
| 2021 | 70 | Full | 1636 | 35 | Green | 1936 | 60 | Partly |
| 2022 | 65 | Full | 1701 | 65 | Full | 1937 | 65 | Full |
| 2029 | 70 | Full | 1704 | 90 | Full | 1938 | 30 | Full |
| 2031 | 80 | Full | 1705 | 65 | Full | 1939 | 80 | Full |
| 2033 | 70 | Full | 1706 | 25 | Green | 1940 | 70 | Full |
| 2035 | 80 | Full | 1708 | 25 | Green | 1943 | 75 | Full |
| 2036 | 80 | Full | 1709 | 90 | Full | 1944 | 75 | Full |
| 2038 | 80 | Full | 1710 | 40 | Partly | 1945 | 50 | Partly |
| 2039 | | Full | 1711 | 95 | Full | 1951 | 68 | Full |
| 2040 | 85 | Full | 1713 | 65 | Full | 1952 | 75 | Full |
| 2044 | 90 | Full | 1717 | 85 | Full | 1953 | 68 | Full |
| 2049 | 75 | Full | 1718 | 75 | Full | 1954 | 68 | Full |
| 2051 | 75 | Full | 1719 | 25 | Green | 1955 | 55 | Partly |
| 2052 | 68 | Full | 1720 | 80 | Full | 1956 | 55 | Partly |
| 2053 | 68 | Full | 1721 | 65 | Full | 1957 | 70 | Full |
| 2059 | 70 | Full | 1722 | 95 | Full | 1958 | 68 | Full |
| 2061 | 75 | Full | 1723 | 15 | Green | 1965 | 80 | Full |
| 2062 | 90 | Full | 1727 | 50 | Partly | 1966 | 75 | Full |
| | | | 1728 | 68 | Full | | | |

All of the isoxaflutole-sprayed plants were damaged with only 3/33 wheat HPPD-expressing events showing less than 20% damage. Again, none of the *Arabidopsis* HPPD expressing plants appeared appreciably resistant whereas the *Pseudomonas* HPPD did confer some degree of resistance with 4/32 plants showing 50% damage or less. Again this is broadly consistent with the in vitro kinetic data (Table 2 and PCT Publication No. WO 02/46387), showing that while exhibiting a high $K_m$ value for HPP and therefore exhibiting a relatively poor value of $k_{cat}/K_m$ the *Pseudomonas* HPPD does exhibit a relatively high value of $k_{off}$ for the diketonitrile of isoxaflutole (i.e., Compound D).

The foregoing data broadly establish the predictive power of determining the in vitro enzyme kinetics, as determined by the relative value of $(k_{cat}/K_m) \times k_{off}$, to anticipate how much tolerance a given HPPD will confer to a given HPPD herbicide when expressed in a crop plant.

In further examples, tobacco-optimized genes encoding HPPD SEQ ID NOs. 1 to 14 and HPPD SEQ NOs: 20-47 are cloned (this time without any CTP) into expression constructs, as described below, and transformed into tobacco. The HPPD encoding nucleotide sequence is edited by PCR (or initially synthesized) to include 5' XhoI site, a TMV omega enhancer and a 3' KpnI site (and to remove any such internal sites). The expression cassette, comprising the TMV omega leader and 4-HPPD gene is excised using XhoI/KpnI and cloned into similarly digested pBIN 19 (Bevan, *Nucl. Acids Res.* (1984) behind a double 35S promoter and ahead of a Nos gene transcriptional terminator and then transformed into *E. coli* TOP 10 competent cells. Again, transgenic populations of tobacco plants are generated and assessed in the glass-house as described above.

Example 5

Construction of Soybean Transformation Vectors

Binary vectors for dicot (soybean) transformation were constructed with a promoter, such as a synthetic promoter containing CaMV 35S and FMV transcriptional enhancers driving the expression of HPPD coding sequence, such as SEQ ID NOs: 1-8 and 20-41, followed by a Nos gene 3' terminator. The HPPD gene was codon-optimized for soybean expression based upon the predicted amino acid sequence of the HPPD gene coding region. In the case that HPPD itself is not used as the selectable marker, *Agrobacterium* binary transformation vectors containing an HPPD expression cassette are constructed by adding a transformation selectable marker gene. For example, binary transformation vector 17900 (SEQ ID NO: 51) contains an expression cassette encoding an HPPD variant (SEQ ID NO: 49) linked with two PAT gene cassettes (one with the 35S promoter and one with the CMP promoter, and where both PAT genes are followed by the nos terminator) for glufosinate based selection during the transformation process. Another binary transformation vector (17901; SEQ ID NO: 52) contains an expression cassette encoding the HPPD variant (SEQ ID NO: 50) and also an EPSPS selectable marker cassette. Vector 17901 is transformed into soybean and transgenic plants are obtained using glyphosate selection using *Agrobacterium*-mediated transformation of immature seed targets. The DNA sequences encoding the HPPD genes are codon-optimized for expression in dicot plants.

The example binary vectors described above are constructed using a combination of methods well known to those skilled in the art such as overlap PCR, DNA synthesis, restriction fragment sub-cloning and ligation. Their unique structures are made explicit in FIG. 3 (vector 17900) and FIG. 4 (vector 17901) and in the sequence listings SEQ ID NOs: 51 and 52. Additional information regarding the vectors is provided below.

Figure 3:
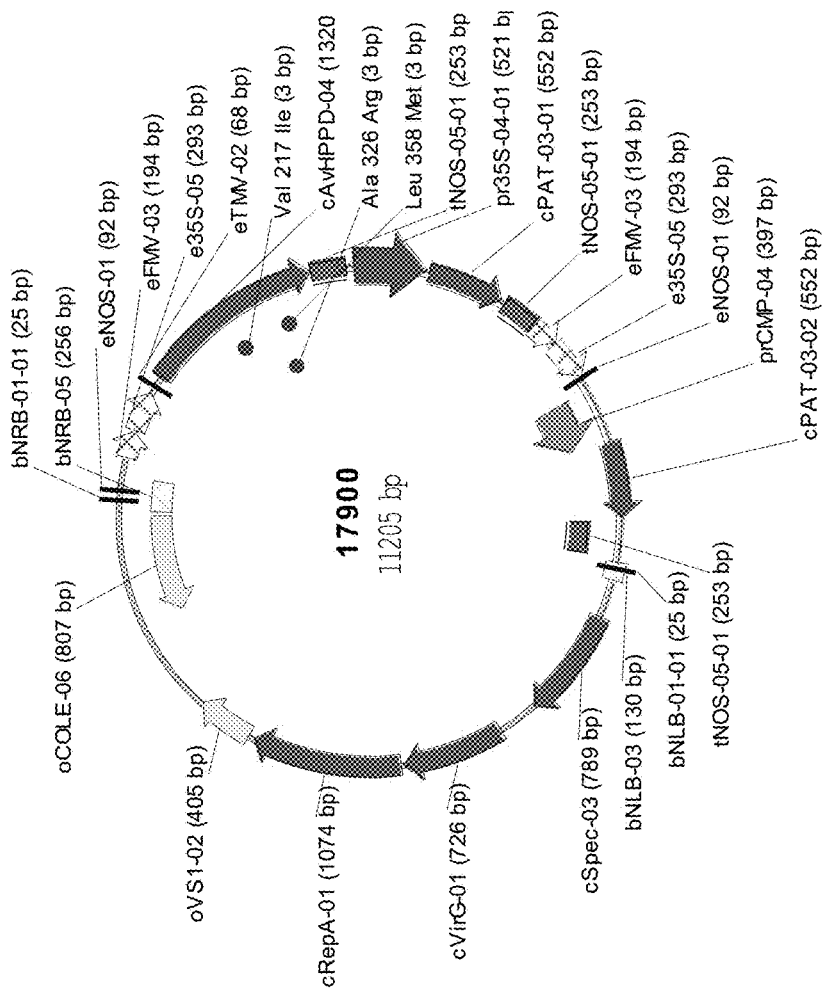
FIG. 3 shows a representation of binary vector 17900 for soybean transformation, conferring HPPD resistance with a dicot codon optimized oat HPPD gene encoding SEQ ID NO: 49. This binary vector also contains double PAT selectable markers for glufosinate selection.
Figure 4:
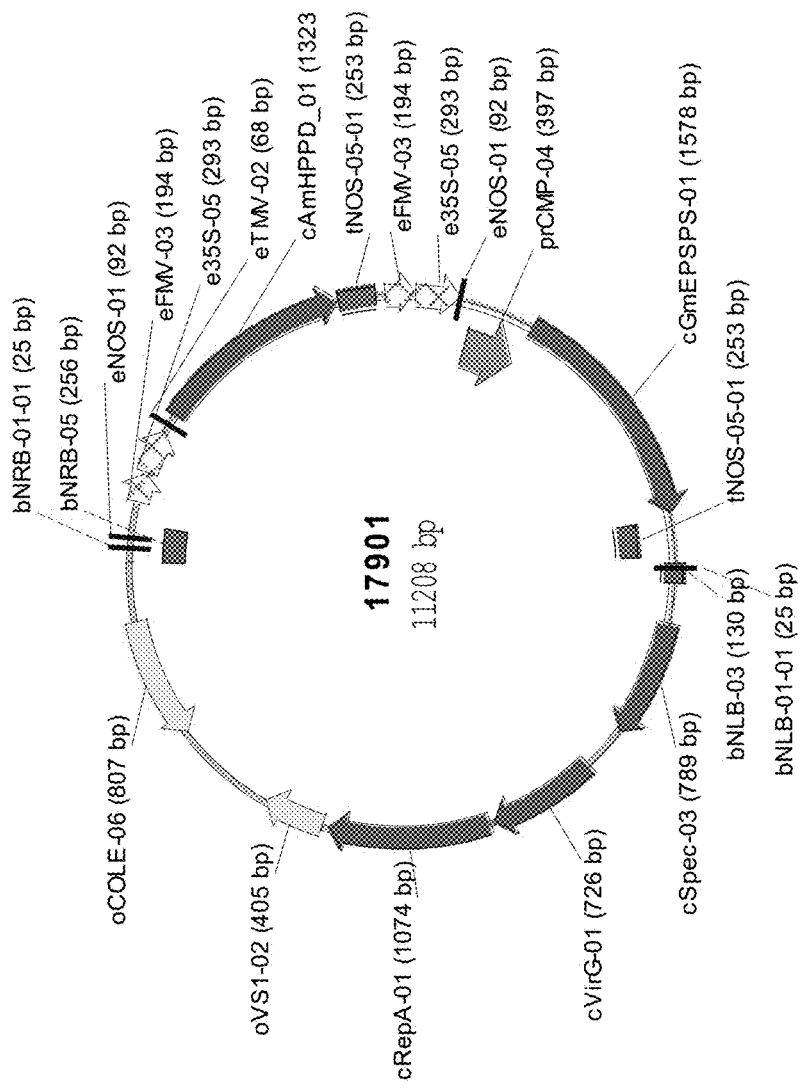
FIG. 4 shows a representation of binary vector 17901 for soybean transformation conferring HPPD resistance with a dicot codon optimized oat HPPD gene encoding SEQ ID NO: 50 and also conferring tolerance to glyphosate (selectable marker).

The abbreviations used in FIG. 3 (vector 17900) are defined as follows:

cAvHPPD-04
Start: 1024 End: 2343
Soybean codon optimized oat HPPD gene encoding SEQ ID NO: 49
cPAT-03-01
Start: 3209 End: 3760
PAT Hoescht A02774 synthetic *S. viridochromogenes*, plant codons; identical to Q57146 phosphinothricin acetyl transferase protein
cPAT-03-02
Start: 5062 End: 5613
PAT Q57146 *S. viridochromogenes* phosphinothricin acetyl transferase protein, cPAT-03-01 DNA, with mutated BamH1, Bgl2 sites
cSpec-03
Start: 6346 End: 7134
Also called aadA; gene encoding the enzyme aminoglycoside 3'adenyltransferase that confers resistance to spectinomycin and streptomycin for maintenance of the vector in *E. coli* and *Agrobacterium*.
cVirG-01
Start: 7434 End: 8159
virG (putative) from pAD1289 with TTG start codon. virGN54D came from pAD1289 described in Hansen et al. 1994, *PNAS* 91:7603-7607
cRepA-01
Start: 8189 End: 9262
RepA, pVS1 replication protein
eNOS-01
Start: 168 End: 259
Putative NOS enhancer sequence from 15235 as found in the right border of certain binary vectors.
eFMV-03
Start: 396 End: 589
Enhancer region from figwort mosaic virus (FMV)
e35S-05
Start: 596 End: 888
C to T & C to A by changes in CMV 35S enhancer region
eTMV-02
Start: 953 End: 1020
TMV Omega 5'UTR leader seq thought to enhance expression. EMBL: TOTMV6
eFMV-03
Start: 4054 End: 4247
Enhancer region from figwort mosaic virus (FMV)
e35S-05
Start: 4254 End: 4546
C to T & C to A by changes in CMV 35S enhancer region
eNOS-01
Start: 4557 End: 4648
Putative NOS enhancer sequence from 15235 as found in the right border of certain binary vectors.
bNRB-05
Start: 4 End: 259 (complementary)
Right border/NOS T-DNA region; may influence promoters. EMBL Nos: J01826, V00087, AF485783.
bNRB-01-01
Start: 101 End: 125 (complementary)
Right Border Repeat of T-DNA of *Agrobacterium tumefaciens* nopaline ti-plasmid
bNLB-03
Start: 5937 End: 6066 (complementary)
Left border region of T-DNA of *Agrobacterium tumefaciens* nopaline ti-plasmid
Start: 5972 End: 5996 (complementary)
25 bp Left border repeat region of T-DNA of *Agrobacterium tumefaciens* nopaline ti-plasmid
prCMP-04
Start: 4655 End: 5051
Cestrum yellow leaf curl virus promoter & leader. Genbank® Accession No. AF364175. See also U.S. Patent Application Publication No. 20040086447. prCMP-01 with 1 base pair truncation on 5' end and 2 base pair truncation on 3' end
pr35S-04-01
Start: 2664 End: 3184
35S promoter from CMV. EMBL: CAMVG2
oVS1-02
Start: 9305 End: 9709
Origin of replication and partitioning region from plasmid pVS1 of *Pseudomonas* (Itoh et al. 1984, *Plasmid* 11: 206-220); similar to GenBank® Accession Number U10487; serves as origin of replication in *Agrobacterium tumefaciens* host
oCOLE-06
Start: 10387 End: 11193 (complementary)
The ColE1 origin of replication functional in *E. coli* derived from pUC19
tNOS-05-01
Start: 2360 End: 2612
Synthetic nopaline synthetase terminator tNOS-05-01
Start: 3794 End: 4046
Synthetic nopaline synthetase terminator
tNOS-05-01
Start: 5642 End: 5894
Synthetic nopaline synthetase terminator The abbreviations used in FIG. 4 (vector 17901) are defined as follows:
cAmHPPD-01
Start: 1024 End: 2346
tobacco codon optimized *Alopecurus mycosuroides* HPPD gene encoding SEQ ID NO: 50
cGmEPSPS-01
Start: 3675 End: 5252
Soybean codon-optimized version of double mutant soybean EPSPS cDNA
cSpec-03
Start: 6346 End: 7134
Also called aadA; gene encoding the enzyme aminoglycoside 3'adenyltransferase that confers resistance to spectinomycin and streptomycin for maintenance of the vector in *E. coli* and *Agrobacterium*.
cVirG-01
Start: 7434 End: 8159
virG (putative) from pAD1289 with TTG start codon. virGN54D came from pAD1289 described in Hansen et al. 1994, *PNAS* 91:7603-7607
cRepA-01
Start: 8189 End: 9262
RepA, pVS1 replication protein
eNOS-01
Start: 168 End: 259
Putative NOS enhancer sequence from 15235 as found in the right border of certain binary vectors.
eFMV-03
Start: 396 End: 589
Enhancer region from figwort mosaic virus (FMV)
e35S-05
Start: 596 End: 888
C to T & C to A by changes in CMV 35S enhancer region
eTMV-02
Start: 953 End: 1020
TMV Omega 5'UTR leader seq thought to enhance expression. EMBL: TOTMV6
eFMV-03
Start: 4054 End: 4247
Enhancer region from figwort mosaic virus (FMV)
e35S-05
Start: 4254 End: 4546
C to T & C to A by changes in CMV 35S enhancer region
eNOS-01
Start: 4557 End: 4648
Putative NOS enhancer sequence from 15235 as found in the right border of certain binary vectors.
bNRB-05
Start: 4 End: 259 (complementary)
Right border/NOS T-DNA region; may influence promoters. EMBL Nos: J01826, V00087, AF485783.
bNRB-01-01
Start: 101 End: 125 (complementary)
Right Border Repeat of T-DNA of *Agrobacterium tumefaciens* nopaline ti-plasmid
bNLB-03
Start: 5937 End: 6066 (complementary)
Left border region of T-DNA of *Agrobacterium tumefaciens* nopaline ti-plasmid
Start: 5972 End: 5996 (complementary)
25 bp Left border repeat region of T-DNA of *Agrobacterium tumefaciens* nopaline ti-plasmid
prCMP-04
Start: 4655 End: 5051
Cestrum yellow leaf curl virus promoter & leader. Genbank® Accession No. AF364175. See also U.S. Patent Application Publication No. 20040086447. prCMP-01 with 1 base pair truncation on 5' end and 2 base pair truncation on 3' end
oVS1-02
Start: 9305 End: 9709
Origin of replication and partitioning region from plasmid pVS1 of *Pseudomonas* (Itoh et al. 1984, *Plasmid* 11: 206-220); similar to GenBank® Accession Number U10487; serves as origin of replication in *Agrobacterium tumefaciens* host
oCOLE-06
Start: 10387 End: 11193 (complementary)
The ColE1 origin of replication functional in *E. coli* derived from pUC19
tNOS-05-01
Start: 2360 End: 2612
Synthetic nopaline synthetase terminator
tNOS-05-01
Start: 3794 End: 4046
Synthetic nopaline synthetase terminator Example 6

Transformation of Soybean and Selection of Herbicide-Resistant Plants

Soybean plant material can be suitably transformed and fertile plants regenerated by many methods which are well known to one of skill in the art. For example, fertile morphologically normal transgenic soybean plants may be obtained by: 1) production of somatic embryogenic tissue from, e.g., immature cotyledon, hypocotyl or other suitable tissue; 2) transformation by particle bombardment or infection with *Agrobacterium*; and 3) regeneration of plants. In one example, as described in U.S. Pat. No. 5,024,944, cotyledon tissue is excised from immature embryos of soybean, preferably with the embryonic axis removed, and cultured on hormone-containing medium so as to form somatic embryogenic plant material. This material is transformed using, for example, direct DNA methods, DNA coated microprojectile bombardment or infection with *Agrobacterium*, cultured on a suitable selection medium and regenerated, optionally also in the continued presence of selecting agent, into fertile transgenic soybean plants. Selection agents may be antibiotics such as kanamycin, hygromycin, or herbicides such as phosphonothricin or glyphosate or, alternatively, selection may be based upon expression of a visualisable marker gene such as GUS. Alternatively, target tissues for transformation comprise meristematic rather than somaclonal embryogenic tissue or, optionally, is flower or flower-forming tissue. Other examples of soybean transforamtions can be found, e.g. by physical DNA delivery method, such as particle bombardment (Finer and McMullen (1991) *In Vitro Cell Dev. Biol.* 27P:175-182; McCabe et al. (1988) *Bio/technology* 6:923-926), whisker (Khalafalla et al. (2006) *African J. of Biotechnology* 5:1594-1599), aerosol bean injection (U.S. Pat. No. 7,001,754), or by *Agrobacterium*-mediated delivery methods (Hinchee et al. (1988) *Bio/Technology* 6:915-922; U.S. Pat. No. 7,002,058; U.S. Patent Application Publication No. 20040034889; U.S. Patent Application Publication No. 20080229447; Paz et al. (2006) *Plant Cell Report* 25:206-213). The HPPD gene can also be delivered into organelle such as plastid to confer increased herbicide resistance (see U.S. Patent Application Publication No. 20070039075).

Soybean transgenic plants can be generated with the heretofore described binary vectors containing HPPD gene variants with different transformation methods. Optionally, the HPPD gene can provide the means of selection and identification of transgenic tissue. For example, a vector was used to transform immature seed targets as described (see e.g., U.S. Patent Application Publication No. 20080229447) to generate transgenic HPPD soybean plants directly using HPPD inhibitor, such as mesotrione, as selection agent. Optionally, HPPD genes can be present in the polynucleotide alongside other sequences which provide additional means of selection/identification of transformed tissue including, for example, the known genes which provide resistance to kanamycin, hygromycin, phosphinothricin, butafenacil, or glyphosate. For example, different binary vectors containing PAT or EPSPS selectable marker genes as described in Example 4 were transformed into immature soybean seed target to generate HPPD herbicide tolerant plants using *Agrobacterium*-mediated transformation and glufosinate or glyphosate selection as described (see e.g., U.S. Patent Application Publication No. 20080229447).

Alternatively selectable marker sequences may be present on separate polynucleotides and a process of, for example, co-transformation and co-selection is used. Alternatively, rather than a selectable marker gene, a scorable marker gene such as GUS may be used to identify transformed tissue.

An *Agrobacterium*-based method for soybean transformation can be used to generate transgenic plants using glufosinate, glyphosate or HPPD inhibitor mesotrione as selection agent using immature soybean seeds as described (U.S. Patent Application Publication No. 20080229447).

Example 7

Soybean T$_0$ Transgenic Plant Growth, Analysis and Herbicide Tolerance Evaluation T$_0$ plants were taken from tissue culture to the greenhouse where they were transplanted into water-saturated soil (Redi-Earth® Plug and Seedling Mix, Sun Gro Horticulture, Bellevue, Wash.) mixed with 1% granular Marathon® (Olympic Horticultural Products, Co., Mainland, Pa.) at 5-10 g/gal Redi-Earth® Mix in 2" square pots. The plants were covered with humidity domes and placed in a Conviron chamber (Pembina, N. Dak.) with the following environmental conditions: 24° C. day; 18° C. night; 16 hr light-8 hrs dark photoperiod; and 80% relative humidity.

After plants become established in the soil and new growth appears (~1-2 weeks), plants are sampled and tested for the presence of desired transgene by Taqman™ analysis using appropriate probes for the HPPD genes, or promoters (for example prCMP and prUBq3). All positive plants and several negative plants are transplanted into 4" square pots containing MetroMix® 380 soil (Sun Gro Horticulture, Bellevue, Wash.). Sierra 17-6-12 slow release fertilizer is incorporated into the soil at the recommended rate. The negative plants serve as controls for the spray experiment. The plants are then relocated into a standard greenhouse to acclimatize (~1 week). The environmental conditions are typically: 27° C. day; 21° C. night; 16 hr photoperiod (with ambient light); ambient humidity. After acclimatizing (~1 week), the plants are ready to be sprayed with the desired herbicides. Herbicide tolerant transgenic soybean plants are grown to maturity for seed production. Transgenic seeds and progeny plants are used to further evaluate their herbicide tolerance performance and molecular characteristics.

Thus T1 soybean plants of vector 17900 (FIG. 3) and of vector 17901 (FIG. 4) expressing, alternatively, SEQ ID NO: 49 and SEQ ID NO: 50 from identical expression cassettes are grown and tested for tolerance to a range of HPPD herbicides in comparison with like plants, likewise expressing HPPD SEQ ID NO: 1.

All patents, patent applications and publications mentioned in the specification are indicative of the level of those skilled in the art to which this invention pertains. All patents, patent applications and publications are herein incorporated by reference to the same extent as if each individual publication or patent application was specifically and individually indicated to be incorporated by reference.

While this invention has been disclosed with reference to specific embodiments, it is apparent that other embodiments and variations of this invention can be devised by others skilled in the art without departing from the true spirit and scope of the invention. The appended claims include all such embodiments and equivalent variations.

What is claimed is:

1. An expression cassette comprising a polynucleotide encoding a polypeptide operably linked to a heterologous promoter that drives expression in a plant or plant cell, wherein said polypeptide is plant-derived and has 4-hydroyxyphenylpyruvate dioxygenase (HPPD) enzymatic activity and comprises an A, G, S, L, M, C, T or I at the position relative to position 259 of SEQ ID NO:1 and comprises at least one of the following amino acid sequences:

a) (L,I,R)(V,A)(G,A)DVL(S,T) (SEQ ID NO: 15), wherein the first L, the I, or the R is replaced with any other amino acid;
   b) G(I,V)LVD(R,K) (SEQ ID NO: 16,) wherein the L is replaced with any other amino acid;
   c) DH(V,I,M)VGN (SEQ ID NO: 17), wherein the first V, the I or the M is replaced with any other amino acid; and
   d) GGF(E,D)F(M,L)(A,P) (SEQ ID NO: 18), wherein the A or P is replaced with any other amino acid.

2. The expression cassette of claim 1, wherein the nucleotide sequence of the polynucleotide is optimized for expression in a plant.

3. The expression cassette of claim 1, further comprising an operably linked isolated polynucleotide sequence encoding a polypeptide that confers a desirable trait.

4. The expression cassette of claim 3, wherein the desirable trait is resistance or tolerance to an herbicide.

5. The expression cassette of claim 4, wherein said desirable trait is resistance or tolerance to an HPPD inhibitor, glyphosate, or glufosinate.

6. The expression cassette of claim 5, wherein said polypeptide that confers a desirable trait is a cytochrome P450 or variant thereof.

7. The expression cassette of claim 5, wherein said polypeptide that confers a desirable trait is an EPSPS (5-enol-pyrovyl-shikimate-3-phosphate-synthase).

8. The expression cassette of claim 5, wherein said polypeptide that confers a desirable trait is a phosphinothricin acetyl transferase (PAT).

9. A vector comprising the expression cassette of claim 8.

10. A method for conferring resistance or tolerance to an HPPD inhibitor in a plant, the method comprising introducing the expression cassette of claim 8 into the plant.

11. A transformed plant cell comprising the expression cassette of claim 1.

12. The transformed plant cell of claim 11, wherein the transformed plant cell is from a plant selected from the group consisting of rice, barley, potato, sweet potato, canola, sunflower, rye, oats, wheat, corn, soybean, sugar beet, tobacco, *Miscanthus* grass, Switch grass, safflower, trees, cotton, cassava, tomato, *sorghum*, alfalfa, sugar beet, and sugarcane.

13. The transformed plant cell of claim 11, wherein the transformed plant cell is a soybean plant cell.

14. A plant, plant part, or seed comprising the plant cell of claim 11.

15. A method of controlling weeds at a locus comprising crop plants and weeds, wherein the crop plants comprise a plant according to claim 14, the method comprising applying to the locus a weed-controlling amount of one or more HPPD inhibitors.

16. The method of claim 15, wherein the one or more HPPD inhibitors are selected from the group consisting of bicyclopyrone, benzobicyclon, benzofenap, ketospiradox or its free acid, isoxachlortole, isoxaflutole, mesotrione, pyrasulfotole, pyrazolynate, pyrazoxyfen, sulcotrione, tefuryltrione, tembotrione, topramezone, and agrochemically acceptable salts thereof.

17. The method of claim 15, wherein the one or more HPPD inhibitors is mesotrione.

18. The expression cassette of claim 1, wherein the first L, the I, or the R of SEQ ID NO: 15 is replaced with E, C, A or D.

19. The expression cassette of claim 1, wherein the L of SEQ ID NO: 16 is replaced with M.

20. The expression cassette of claim 1, wherein the A or P of SEQ ID NO: 18 is replaced with R, I, L, H or K.

21. The expression cassette of claim 1, wherein the first V, the I or the M is replaced with L or I.

22. The expression cassette of claim 1, wherein the polypeptide comprises at least two of the amino acid sequences found in sub-parts a-d.

23. The expression cassette of claim 1, wherein the polypeptide comprises at least three of the amino acid sequences found in sub-parts a-d.

24. The expression cassette of claim 1, wherein the polypeptide comprises all four of the amino acid sequences found in sub-parts a-d.

25. The expression cassette of claim 1, wherein the polypeptide comprises an A, T or I at the position relative to position 259 of SEQ ID NO:1.

26. The expression cassette of claim 1, wherein the polypeptide comprises an A at the position relative to position 259 of SEQ ID NO:1.

27. The expression cassette of claim 1, wherein the polypeptide comprises a T at the position relative to position 259 of SEQ ID NO:1.

28. The expression cassette of claim 1, wherein the polypeptide comprises an I at the position relative to position 259 of SEQ ID NO:1.

\* \* \* \* \*